US006514964B1

(12) United States Patent
Chen et al.

(10) Patent No.: US 6,514,964 B1
(45) Date of Patent: Feb. 4, 2003

(54) FUSED CYCLOHEPTANE AND FUSED AZACYCLOHEPTANE COMPOUNDS AND THEIR METHODS OF USE

(75) Inventors: Zhidong Chen, Thousand Oaks, CA (US); Celia Dominguez, Thousands Oaks, CA (US); Ellen Grenzer-Laber, Ventura, CA (US); Nianhe Han, Thousand Oaks, CA (US); Longbing Liu, Thousand Oaks, CA (US); Ofir A. Moreno, Del Mar, CA (US); Melvin C. Rutledge, Westlake Village, CA (US); Andrew S. Tasker, Simi Valley, CA (US)

(73) Assignee: Amgen Inc., Thousand Oaks, CA (US)

( * ) Notice: Subject to any disclaimer, the term of this patent is extended or adjusted under 35 U.S.C. 154(b) by 0 days.

(21) Appl. No.: 09/671,025

(22) Filed: Sep. 26, 2000

Related U.S. Application Data

(60) Provisional application No. 60/156,174, filed on Sep. 27, 1999.

(51) Int. Cl.[7] .................... C07D 223/16; C07D 401/12; C07D 403/12; C07D 471/04; A61K 31/55
(52) U.S. Cl. .................... 514/212.06; 514/212.07; 514/213.01; 540/521; 540/522; 540/523; 540/593
(58) Field of Search .................... 514/213.01, 212.06, 514/212.07; 540/593, 521, 522, 523

(56) References Cited

U.S. PATENT DOCUMENTS

| | | | | |
|---|---|---|---|---|
| 5,250,679 A | * | 10/1993 | Blackburn | 540/490 |
| 5,374,722 A | | 12/1994 | Berger | 540/581 |
| 5,565,449 A | | 10/1996 | Blackburn | 514/219 |
| 5,674,865 A | | 10/1997 | Blackburn | 514/213 |
| 5,705,890 A | | 1/1998 | Blackburn | 514/220 |
| 6,232,308 B1 | * | 5/2001 | Askew | 514/221 |

FOREIGN PATENT DOCUMENTS

| | | |
|---|---|---|
| EP | 039051 | 11/1981 |
| EP | 528 587 | 2/1995 |
| WO | WO 96/26190 | 8/1996 |
| WO | WO 97/01540 | 1/1997 |
| WO | WO 97/35615 | 10/1997 |
| WO | WO 98/14192 | 4/1998 |
| WO | WO 98/18460 | 5/1998 |
| WO | WO 98/18461 | 5/1998 |
| WO | WO 99/05107 | 2/1999 |
| WO | WO 99/06049 | 2/1999 |
| WO | WO 99/11626 | 3/1999 |
| WO | WO 99/15170 | 4/1999 |
| WO | WO 99/15178 | 4/1999 |
| WO | WO 99/15506 | 4/1999 |
| WO | WO 99/15507 | 4/1999 |
| WO | WO 99/15508 | 4/1999 |
| WO | WO 99/30709 | 6/1999 |
| WO | WO 99/30713 | 6/1999 |
| WO | WO 99/58139 | 11/1999 |

OTHER PUBLICATIONS

Orita, Kazuhiko et al., Alkylation of 1,2,4,5–tetrahydro–3–methyl–3H–3–benzazepin–2–one with sodium hydride and alkyl halide, "*Tetrahedron*" V. 36, No. 8, (1980), pp. 1017–1021, Elsevier Science Publishers, Amsterdam, NL.

Miller et al. (1995) 'enantiospecific Synthesis of SB214857, a Potent, Orally Active, Nonpeptide Fibrinogen Receptor Antagonist.

Agrez et al. (1994), "The $\alpha v\beta 6$ Integrin Promotes Proliferation of Colon Carcinoma Cells through a Unique Region of the $\beta 6$ Cytoplasmic Domain," *J. Biol. Chem.* 127(2):547–556.

Agrez et al. (1999), "The $\alpha v\beta 6$ Integrin Induces Gelatinase B Secretion in Colon Cancer Cells," *Int. J. Cancer* 81:90–97.

Albericio et al. (1998), "Use of Onium Salt–Base Coupling Reagents in Peptide Synthesis," *J. Org. Chem.* 63:9678–9683.

Arner et al. (1995), "Signal Transduction Through Chondrocyte Integrin Receptors Induces Matrix Metalloproteinase Synthesis and Synergizes with Interleukin–1," *Arthritis Rheumatism* 38:1304–1314.

Baati et al. (1999), "An Improved Method for the Preparation of Amidines via Thiophenylimidic Esters," *Synthesis* 6:927–929.

Berge et al. (1977), "Pharmaceutical Salts", *J. Pharm. Sci.* 66(1):1–19.

Brooks et al. (1997), "Insulin–like Growth Factor Receptor Cooperates with Integrin $\alpha v\beta 5$ to Promote Tumor Cell Dissemination in Vivo," *J. Clin. Invest.* 99(6):1390–1398.

Brooks (1997), "Integrin $\alpha v\beta 3$: A Therapeutic Target," *DN&P* 10(8):456–461.

Bungaard et al. (1989), "A Novel Solution–Stable, Water–Soluble Prodrug Type for Drugs Containing a Hydroxyor an NH–Acidic Group," *J. Medicinal Chemistry* vol. 32, No. 12 pp. 2503–2509.

(List continued on next page.)

*Primary Examiner*—Bruck Kifle
(74) *Attorney, Agent, or Firm*—MarySusan Howard; Ron K. Levy; Steven M. Odre

(57) ABSTRACT

The invention comprises novel compounds that are effective in the prophylaxis and treatment of diseases, such as integrin receptors mediated diseases, in particular, diseases or conditions mediated by integrin receptors, such as $\alpha_v\beta_3$, $\alpha_v\beta_5$, $\alpha_v\beta_6$ and the like. The invention encompasses novel compounds, pharmaceutically acceptable salts thereof, pharmaceutical compositions and methods for prophylaxis and treatment of such diseases and disorders. The subject invention also relates to processes for making such compounds as well as to intermediates useful in such processes.

8 Claims, No Drawings

OTHER PUBLICATIONS

Busk et al. (1992), "Characterization of the Integrin αvβ6 as a Fibronectin–binding Protein," *J. Biol. Chem.* 267:5790–5796.

Carpino et al. (1999), "The Diisopropylcarbodiimide/1–Hydroxy–7–azabenzotriazole System: Segment Coupling and Stepwise Peptide Assembly," *Tetrahedron* 55:6813–6830.

Carreiras et al. (1999), "Migration Properties of the Human Ovarian Adenocarcinoma Cell Line IGROV1: Importance of αvβ3 Integrins and Vitronectin," *Int. J. Cancer* 80:285–294.

Carron, et al. (1998), "A Peptidomimetic Antagonist of the Integrin αvβ3 Inhibits Leydig Cell Tumor Growth and the Development of Hypercalcemia of Malignancy," *Cancer Res.* 58:1930–1935.

Gautier et al., The Chemistry of Amidines Imidates, Patai (Ed), Wiley, (1975), pp. 283–348 (Table of Contents).

Cheresh (1991), "Structure, function and biological properties of integrin αvβ$_3$ on human melanoma cells," *Cancer Metastasis Rev.* 10:3–10.

Clark et al. (1991), "Aryl Radical Cyclisations: Quinoline, Isoquinolone, and 1–Benzazepin–2–one Rings via 6– and 7–Exo Cyclisations," *Tetrahedron Letters* (24):2829–2832.

Clark et al. (1996), "Transient Functional Expression of αvβ$_3$ on Vascular Cells during Wound Repair," *Am. J. Pathol.* 148(5):1407–1421.

Dunn (1995), Compr. Org. Funct. Group Transform. 5:741–782 and pp. 1161–1308.

Gladson et al. (1997), "Vitronectin Expression in Differentiating Neuroblastic Tumors," *Am. J. Pathol.* 150(5):1631–1646.

Haapasalmi et al. (1996), "Ketatinocytes in Human Wounds Express αvβ6 Integrin," *J. Invest. Dermatol.* 106:42–48.

Hermann et al. (1999), "The Vitronectin Receptor and its Associated CD47 Molecule Mediates Proinflammatory Cytokine Synthesis in Human Monocytes by Interaction with Soluble CD23," *J. Cell Biol.* 144(4):767–775.

Horton (1997), "The αvμ3 Integrin 'Vitronectin Receptor'," *Int. J. Biochem. Cell Biol.* 29 (5):721–725.

Huang et al. (1996), "Inactivation of the Integrin β6 Subunit Gene Reveals a Role of Epithelial Integrins in Regulating Inflammation in the Lungs and Skin," *J. Cell Biol.* 133(4):921–928.

Keenan et al. (1997), "Discovery of Potent Nonpeptide Vitronectin Receptor (αvβ3) Antagonist," *J. Med.Chem.* 40:2289–92.

Kim et al. (1994), "Vitronectin–driven Human Keratinocyte Locomotion is Mediated by the αvβ$_5$ Integrin Receptor," *J. Biol. Chem.* 269(43):26926–326932.

Liaw et al. (1995), "The Adhesive and Migratory Effects of Osteopontin are Mediated via Distinct Cell Surface Integrins," *J. Clin. Invest.* 95:713–724.

Maryanoff et al. (1989), "The Wittig Olefination Reaction and Modifications Involving Phosphoryl–Stabilizated Carbanions. Stereochemistry, Mechanism, and Selected Synthetic Aspects," *Chem. Rev.* 89:863–927.

Marcinkiewicz et al. (1996), "One–Step Affinity Purification of ecombinant αvβ3 Integrin from Transfected Cells," *Protein Expression Purification* 8:68–74.

Munger et al. (1999), "The Integrin αvβ6 Binds and Activates Latent TGFβ1: A Mechanism for Regulating Pulmonary Inflammation and Fibrosis," *Cell* 96:319–328.

Natali et al. (1997), "Clinical Significance of αvβ3 Integrin and Intercellular Adhesion Molecule–1 Expression in Cutaneous Malignant Melanoma Lesions," *Cancer Research* 57:1554–60.

Neff et al. (1998), "Foot–and–Mouth Disease Virus Virulent for Cattle Utilizes the Integrin αvβ$_3$ as its Receptor," Journal of Virology, 72(5):3587–3594.

Niu et al. (1998), "Integrin–Mediated Signalling of Gelatinase B Secretion in Colon Cancer Cells," *Biochemical Biophysical. Research. Communications* 249:287–291.

Panetti et al. (1993), "The αvβ$_5$ Integrin Receptor Regulates Receptor–mediated Endocytosis of Vitronectin," *Journal of Biological Chemistry.* 268(16):11492–11495.

Passaniti et al. (1992), "Methods in Laboratory Investigation," *Laboratory Investigation.* 67(4):519–528.

Pytela et al. (1987), "Arginine–Glycine–Aspartic Acid Adhesion Receptors," *Methods in Enzymol.* 144:475–489.

Raeburn et al. (1992), "Techniques for Drug Delivery to the Airways, and the Assessment of Lung Function in Animal Models," *J. Pharmacol. Toxicol. Methods.* 27(3):143–159.

Ramadas et al. (1995), "An Expedient Synthesis of Substituted Guanidines," *Tet. Lett.* 36(16):2841–2844.

Ramadas et al. (1997), "A Short and Concise Synthesis of Guanidines," *Synlett* pp. 1053–1054.

Raynal et al. (1996), "Bone Sialoprotein Stimulates in Vitro Bone Resorption," *Endocrinology* 137(6):2347–54.

Rodan et al. (1997), "Integrin function in osteoclasts," *J. Endocrinol.* 154(Suppl.):S47–S56.

Roivainen et al. (1994), "Entry of Coxsackievirus A9 into Host Cells: Specific Interactions with αvβ$_3$ Integrins, the Vitronectin Receptor," *Virology* 203:357–365.

Schwartz et al. (1992), "Restenosis and the Proportional Neointimal Response to Artery Injury: Results in a Porcine Mode," *JACC* 19(2):267–274.

Schvartz et al. (1999), "Molecules in Focus: Vitronectin," *Int. J. Biochem.& Cell Biol.* 31:539–544.

Smith et al. (1990), "Purification and Functional Characterization of Integrin αvβ5," *J. Biol. Chem.* 265(19):11008–11013.

Smith et al. (1994), "Oxygen–Induced Retinopathy in the Mouse," *Invest. Ophthal. & Vis. Sci.* 35(1):101–111.

Still et al. (1993), "Direct Synthesis of Z–Unsaturated Esters. A Useful Modification of the Homer–Emmons Olefination," *Tet. Lett.* 24(41):4405–4408.

Novak et al. (1999), "A Convenient Route to Cyanoguanidines" *Synthetic Communications* 29(10):1757–1766.

Summerford et al. (1999), "αvβ$_5$ integrins: a co–receptor for adeno–associated virus type 2 infection," *Nat. Med. (N.Y.)* 5(1):78–82.

Utsumi et al. (1999), "Urinary excretion of the vitronectin receptor (integrin αvβ3) in patients with Fabry disease," *Clin. Chim. Acta* 279:55–68.

Wickham et al. (1994), "Integrin αvβ$_5$ Selectively Promotes Adenovirus Mediated Cell Membrane Permeabilization," *J. Cell. Biol.* 127(1):257–264.

Woo et al. (1996), "Suppressive effect of N–(benzyloxycarbonyl)–L–phenylalanyl–L–tyrosinal on bone resorption in vitro and in vivo," *Eurpean J. Pharmacology* 300:131–135.

Yatohogo et al. (1988), "Novel Purification of Vitronectin from Human Plasma by Heparin Affinity Chromatography," *Cell Structure and Function* 13:281–292.

Wronski et al. (1991), "The Ovariectomized Rat as an Animal Model for Postmenopausal Bone Loss," *Cells and Materials, Supplement* 1, 1991 pp. 69–74.

Gonda (1990), "Aerosois for Delivery of Therapeutic and Diagnostic Agents to the Respiratory Tract," *Critical Reviews in Therapeutic Drug Carrier Systems* 6(4):273–313.

Beller et al (1998), "Palladium–catalyzed Olefinations of Aryl Halides (Heck Reaction) and Related Transformations," *Transition Metals for Organic Synthesis* 1:208–240.

Svensson et al, (1998) *"The Design and Bioactivation of Presystemically Stable Prodrugs"* Drug Metabolism Review 19(2):165–194.

Nip, (1995) *"The Role of the Integrin Vitronectin Receptor, •ᵥ108₃ in Melanoma Metastasis"* Cancer Metatasis Review 14:241–252.

Agrez, (1997), Virology 239:71–77.

Duggan, (2000), Exp. Opin. Ther. Patents 10(9): 1367–1383, "Ligands to the Integrin Receptor •ᵥ•₃".

* cited by examiner

FUSED CYCLOHEPTANE AND FUSED AZACYCLOHEPTANE COMPOUNDS AND THEIR METHODS OF USE

This application claims the benefit of U.S. Provisional Application No. 60/156,174 filed Sep. 27, 1999, which is hereby incorporated by reference in its entirety.

BACKGROUND OF THE INVENTION

The present invention comprises a new class of compounds useful in treating diseases, such as diseases, conditions or disorders mediated by integrin receptors, such as vitronectin and fibronectin receptors. In particular, the compounds of the invention and pharmaceutical compositions thereof are useful for the prophylaxis and treatment of diseases, conditions or disorders involving atherosclerosis, restenosis, inflammation, cancer, osteoporosis and the like. This invention also relates to intermediates and processes useful in the preparation of such compounds.

Integrins are heteromeric cell surface receptors many of which have extracellular domains that bind to an Arg-Gly-Asp tripeptide (RDG) found in extracellular (plasma and matrix) proteins, such as fibronectin, vitronectin, fibrinogen and osteopontin. The fibrinogen receptor, gpIIb/IIIa integrin, is a platelet surface receptor that is thought to mediate platelet aggregation and the formation of hemostatic clot at bleeding wound sites (Blood. 71:831, 1988).

Vitronectin receptors, $\alpha_v\beta_3$ and $\alpha_v\beta_5$ integrin, are expressed by a number of cells, such as endothelial, smooth muscle, osteoclast, bone resorbing, tumor and epithelial cells. Integrin $\alpha_v\beta_3$ has been reported to be involved in bone resorption (Endocrinology 137:2347–54, 1996; J. Endocrinol. 154(Suppl.):S47–S56, 1997), in cell attachment, spreading and migration (Int. J. Biochem. Cell Biol. 31:539–544, 1999; Carreitas et al., Int. J. Cancer 80:285–294, 1999), in signal transduction, cell to cell interactions and is upregulated in response to vascular damage (Int. J. Biochem. Cell Biol. 29:721–725, 1997), in tumor cell invasion, angiogenesis, wound healing, phagocytosis of apototic cells and inflammation (J. Cell Biol. 144:767–775, 1999; Drug News Perspect. 10:456–461, 1997; Am. J. Pathol. 148:1407–1421, 1996), in tumor growth and hypercalcemia of malignancy (Cancer Res. 58:1930–1935, 1998), in tumorigenicity of human melanoma cells (Natali et al., Cancer Res. 57:1554–60, 1997), in melanoma metastasis (Cancer Metastasis Rev. 14:241–245, 1995; Cancer Metastasis Rev. 10:3–10, 1991), in the chondrocyte synthesis of matrix metalloproteinases (such as stromelysin, collagenase and gelatinase) which are involved in diseases such as rheumatoid arthritis and osteoarthritis (Arthritis Rheum. 38:1304–1314, 1995), in the progression of the renal injury in Fabry disease (Clin. Chim. Acta 279:55–68, 1999), and in viral infections (J. Virol. 72:3587–3594, 1998; Virology 203:357–65, 1994). Keenan et al. (J. Med. Chem. 40:2289–92, 1997) disclose examples of $\alpha_v\beta_3$ inhibitors which are selective for $\alpha_v\beta_3$ over platelet fibrinogen receptor ($\alpha_{IIb}\beta_3$).

Integrin $\alpha_v\beta_5$ (Smith et al., J. Biol. Chem. 265:11008–13, 1990) is thought to be involved in endocytosis and degradation of vitronectin (J. Biol. Chem. 268:11492–5, 1993), cellular locomotion of human keratinocytes (J. Biol. Chem. 269:26926–32, 1994), tumor cell metastasis (J. Clin. Invest. 99:1390–1398, 1997), differentiation of neuroblastoma metastasis (Am. J. Pathol. 150:1631–1646, 1997), and viral infections (Nat. Med. (N.Y.) 5:78–82, 1999; J. Cell Biol. 127:257-64, 1994).

Integrin $\alpha_v\beta_6$ is an RGD, tenascin and fibronectin binding protein (J. Biol. Chem. 267:5790–6, 1992) which is expressed by a number of cells, such as carcinoma and epithelial cells, and is thought to be involved in carcinoma cell proliferation (J. Cell Biol. 127:547–56, 1994), in wound healing and cell attachment (J. Invest. Dermatol. 106:42–8, 1996), in epithelial inflammation, such as asthma (J. Cell Biol. 133:921–928, 1996), in inducing gelatinase B secretion, activation of the protein kinase-C pathway, tumor cell spreading and proliferation in colon cancer cells (Biochem. Biophys. Res. Commun. 249:287–291, 1998; Int. J. Cancer 81:90–97, 1999), in regulation of pulmonary inflammation and fibrosis and binding and activating transforming growth factor $\beta 1$ (Munger et al., Cell (Cambridge, Mass.) 96:319–328, 1999), and in viral infections (Virology 239:71–77, 1997).

Antagonists of vitronectin receptors $\alpha_v\beta_3$, $\alpha_v\beta_5$ and/or $\alpha_v\beta_6$ have been reported to be useful in the treatment and prevention of atherosclerosis, restenosis, inflammation, wound healing, cancer (e.g., tumor regression by inducing apoptosis), metastasis, bone resorption related diseases (e.g., osteoporosis), diabetic retinopathy, macular degeneration, angiogenesis and viral disease (e.g., WO 99/30713; WO 99/30709).

WO 99/05107 discloses benzocycloheptenylacetic acid compounds useful as vitronectin receptor antagonists.

WO 98/14192 discloses benzazepin-3-on-4-ylacetic acid compounds as vitronectin receptor antagonists.

WO 96/26190 discloses benzodiazepine-3-one and benzazepin-3-one compounds as integrin receptor inhibitors.

WO 99/11626 discloses compounds of the formula

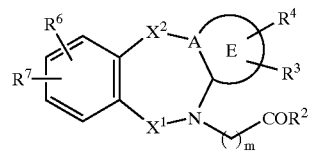

wherein m, A, E, $X^1$, $X^2$, $R^2$, $R^3$, $R^4$, $R^6$ and $R^7$ are as defined therein, are useful as integrin receptor inhibitors, in particular fibrinogen ($\alpha_{IIb}\beta_3$) or vitronectin ($\alpha_v\beta_3$) receptor inhibitors.

WO 97/01540 discloses compounds of the formula

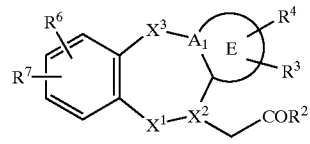

wherein $A_1$, E, $X^1$, $X^2$, $X^3$, $R^2$, $R^3$, $R^4$, $R^6$ and $R^7$ are as defined therein, are useful as integrin receptor inhibitors, in particular fibrinogen ($\alpha_{IIb}\beta_3$) or vitronectin ($\alpha_v\beta_3$) receptor inhibitors.

U.S. Pat. No. 5,565,449 discloses compounds of the formula

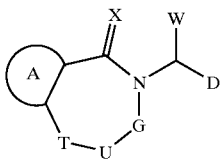

wherein A, D, G, T, U, W and X are as defined therein, are useful as integrin inhibitors of fibrinogen GPII$_b$III$_a$.

U.S. Pat. No. 5,705,890 discloses tricyclic benzodiazepine compounds useful as platelet aggregation (fibrinogen binding) inhibitors.

U.S. Pat. No. 5,674,865 discloses benzodiazepinedione compounds useful as platelet aggregation (fibrinogen binding) inhibitors.

WO 99/15178 and WO 99/15170 disclose benzazepineacetic acid compounds useful as vitronectin receptor antagonists.

WO 99/11626 and WO 99/06049 disclose tricyclic benzazepine, benzodiazepineacetate and benzazepineacetate compounds useful as fibrinogen and vitronectin receptor antagonists.

WO 99/15508 discloses dibenzo[a,d]cycloheptene-10-acetic acid compounds useful as vitronectin receptor antagonists.

WO 99/15506 and WO 99/15507 disclose iminobenzazulene compounds useful as vitronectin receptor antagonists.

WO 98/18461 discloses 4–10 membered mono- or polycyclic aromatic or nonaromatic ring system (containing 0–4 oxygen, sulfur and/or nitrogen heteroatoms) compounds useful as integrin receptor antagonists.

WO 97/01540 discloses dibenzocycloheptene compounds useful as integrin receptor antagonists.

WO 96/26190 discloses benzodiazepine-3-one and benzazepin-3-one compounds as integrin receptor inhibitors.

SUMMARY OF THE INVENTION

The present invention comprises a new class of compounds useful in the prophylaxis and treatment of diseases, such as integrin receptors mediated diseases. In particular, the compounds of the invention are useful for the prophylaxis and treatment of diseases or conditions mediated by integrin receptors, such as $\alpha_v\beta_3$, $\alpha_v\beta_5$, $\alpha_v\beta_6$ and the like. Accordingly, the invention also comprises pharmaceutical compositions comprising the compounds, methods for the prophylaxis and treatment of integrin receptors mediated diseases, such as cancer, tumor growth, metastasis, diabetic retinopathy, macular degeneration, angiogenesis, restenosis, bone resorption, atherosclerosis, inflammation, viral infection, wound healing and the like, using the compounds and compositions of the invention, and intermediates and processes useful for the preparation of the compounds of the invention.

The compounds of the invention are represented by the following general structure:

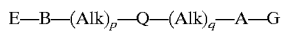

wherein E, B, Alk, Q, A, G, p and q are defined below.

The foregoing merely summarizes certain aspects of the invention and is not intended, nor should it be construed, as limiting the invention in any way. All patents and other publications recited herein are hereby incorporated by reference in their entirety.

DETAILED DESCRIPTION OF THE INVENTION

The present invention provides novel compounds which are useful for treating disease states involving cancer, tumor growth, metastasis, diabetic retinopathy, macular degeneration, angiogenesis, restenosis, bone resorption, atherosclerosis, inflammation, viral disease, wound healing and the like, as well as other disease states associated with the same pathways effecting the noted disease states, especially those modulated by integrin receptors and related pathways, such as the integrin receptors $\alpha_v\beta_3$, $\alpha_v\beta_5$, $\alpha_v\beta_6$ and the like.

In accordance with the present invention, there is provided compounds of the formula:

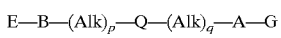

or a pharmaceutically acceptable salt thereof, wherein p and q are each independently 0 or 1;

each Alk is independently an alkyl radical; preferably, a $C_1$–$C_{12}$ alkyl radical; more preferably, a $C_1$–$C_8$ alkyl radical; and most preferably, a $C_1$–$C_6$ alkyl radical;

A and Q each independently represent a bond, —C(X)—, —S(O)$_t$—, —S—, —O—, —N(R$_1$)—, —C(Y)—N(R$_1$)—, —N(R$_1$)—C(Y)—, —S(O)$_t$—N(R$_1$)—, —N(R$_1$)—S(O)$_t$—, —N(R$_1$)—C(Y)—N (R$_1$)— or —N(R$_1$)—S(O)$_t$—N(R$_1$)—, or a radical of cycloalkyl, aryl, heterocyclyl or heteroaryl each of which is optionally substituted by 1–3 radicals of R$_2$;

preferably, A and Q each independently represent a bond, —C(X)—, —S(O)$_t$—, —S—, —O—, —N(R$_1$)—, —C(Y)—N(R$_1$)—, —N(R$_1$)—C(Y)—, —S(O)$_t$—N (R$_1$)—, —N(R$_1$)—S(O)$_t$—, —N(R$_1$)—C(Y)—N (R$_1$)— or —N(R$_1$)—S(O)$_t$—N(R$_1$)—, or a radical of $C_3$–$C_8$ cycloalkyl, aryl, heterocyclyl of 5–8 ring members or heteroaryl of 5–10 ring members each of which is optionally substituted by 1–3 radicals of R$_2$; and more preferably, A and Q each independently represent a bond, —C(O)—, —S(O)$_t$—, —O—, —N(R$_1$)—, —C(Y)—N(R$_1$)—, —N(R$_1$)—C(Y)—, —S(O)$_t$—N (R$_1$)— or —N(R$_1$)—S(O)$_t$—, or a radical of $C_3$–$C_6$ cycloalkyl, phenyl, heterocyclyl of 5–6 ring members or heteroaryl of 5–6 ring members each of which is optionally substituted by 1–3 radicals of R$_2$; and B represents a bond, —C(Y)—, —S(O)$_t$—, —S—, —O—, —N(R$_1$)—, —C(Y)—N(R$_1$)—, —N(R$_1$)—C (Y)—, —S(O)$_t$—N(R$_1$)—, —N(R$_1$)—S(O)$_t$—, —N(R$_1$)—C(Y)—N(R$_1$)— or —N(R$_1$)—S(O)$_t$—N (R$_1$)—, or a radical of cycloalkyl, aryl, heterocyclyl or heteroaryl each of which is optionally substituted by 1–3 radicals of R$_2$;

preferably, B represents a bond, —C(Y)—, —S(O)$_t$—, —S—, —O—, —N(R$_1$)—, —C(Y)—N(R$_1$)—, —N(R$_1$)—C(Y)—, —S(O)$_t$—N(R$_1$)—, —N(R$_1$)—S (O)$_t$—, —N(R$_1$)—C(Y)—N(R$_1$)— or —N(R$_1$)—S(O)$_t$—N(R$_1$)—, or a radical of $C_3$–$C_8$ cycloalkyl, aryl, heterocyclyl of 5–8 ring members or heteroaryl of 5–10 ring members each of which is optionally substituted by 1–3 radicals of R$_2$;

more preferably, B represents a bond, —C(Y)—, —S(O)$_t$—, —O— or —N(R$_1$)—, or a radical of phenyl, heterocyclyl of 5–6 ring members or heteroaryl of 5–6 ring members each of which is optionally substituted by 1–3 radicals of R$_2$; and most preferably, B represents a bond, —S(O)$_t$—, —O— or —N(R$_1$)—, or a phenyl radical which is optionally substituted by 1–3 radicals of R$_2$;

provided the total number of atoms that directly connect E to G via the shortest sequence is 3–12, preferably 4–9, more preferably 4–7;

each X is independently O or S; and preferably, O;

each Y is independently O, S, N(R$_1$) or N(CN); and preferably, O, N(R$_1$) or N(CN);

each t is independently 1 or 2; and preferably, 2;

each R$_1$ is independently a hydrogen or alkyl radical; preferably, each R$_1$ is independently a hydrogen or C$_1$–C$_4$ alkyl radical; and most preferably, each R$_1$ is independently a hydrogen or methyl radical;

radicals of R$_2$ are each independently a halo, alkyl, alkoxy, alkylthio, haloalkyl, haloalkoxy, hydroxy, carboxy, cyano, azido, amidino, guanidino, nitro, amino, alkylamino or dialkylamino radical or two adjacent R$_2$ radicals represent a methylenedioxy, ethylenedioxy or propylenedioxy radical;

preferably, radicals of R$_2$ are each independently a halo, C$_1$–C$_4$ alkyl, C$_1$–C$_4$ alkoxy, C$_1$–C$_4$ alkylthio, C$_1$–C$_4$ haloalkyl of 1–3 halo radicals, C$_1$–C$_4$ haloalkoxy of 1–3 halo radicals, hydroxy, carboxy, cyano, azido, amidino, guanidino, nitro, amino, C$_1$–C$_4$ alkylamino or di(C$_1$–C$_4$ alkyl)amino radical or two adjacent R$_2$ radicals represent a methylenedioxy, ethylenedioxy or propylenedioxy radical;

more preferably, radicals of R$_2$ are each independently a halo, C$_1$–C$_3$ alkyl, C$_1$–C$_3$ alkoxy, C$_1$–C$_3$ alkylthio, —CF$_3$, —OCF$_3$, hydroxy, cyano, nitro, amino, C$_1$–C$_4$ alkylamino or di (C$_1$–C$_4$ alkyl)amino radical; and most preferably, radicals of R$_2$ are each independently a halo, methyl, methoxy, —CF$_3$, —OCF$_3$, hydroxy, cyano, nitro, amino, C$_1$–C$_4$ alkylamino or di (C$_1$–C$_2$ alkyl)amino radical;

E represents —R$_3$, —NH—R$_3$, —NH—C(Y)—R$_3$, —C(Y)—NH—R$_3$, —NH—S(O)$_t$—R$_3$, —S(O)$_t$—NH—R$_3$, —NH—C(Y)—NH—R$_3$, —NH—C(Y)—O—R$_3$, —NH—S(O)$_t$—NH—R$_3$, —NH-alkyl-C(Y)—R$_3$, —NH-alkyl-S(O)$_t$—R$_3$, —NH-alkyl-C(Y)—NH—R$_3$ or —NH-alkyl-S(O)$_t$—NH—R$_3$ radical;

preferably, E represents —R$_3$, —NH—R$_3$, —NH—C(Y)—R$_3$, —C(Y)—NH—R$_3$, —NH—S(O)$_t$—R$_3$, —S(O)$_t$—NH—R$_3$, —NH—C(Y)—NH—R$_3$, —NH—C(Y)—O—R$_3$, —NH—S(O)$_t$—NH—R$_3$, —NH—(C$_1$-C$_4$ alkyl)-C(Y)—R$_3$, —NH—(C$_1$-C$_4$ alkyl)-S(O)$_t$—R$_3$, —NH—(C$_1$-C$_4$ alkyl)-C(Y)—NH—R$_3$ or —NH— (C$_1$-C$_4$ alkyl)-S(O)$_t$—NH—R$_3$ radical;

more preferably, E represents —R$_3$, —NH—R$_3$, —NH—C(Y)—R$_3$, —C(Y)—NH—R$_3$, —S(O)$_t$—NH—R$_3$, —NH—C(Y)—NH—R$_3$, —NH—C(Y)—O—R$_3$ or —NH— (C$_1$-C$_4$ alkyl)-C(Y)—NH—R$_3$ radical;

more preferably, E represents —R$_3$, —NH—R$_3$, —NH—C(Y)—R$_3$, —C(Y)—NH—R$_3$, —NH—C(Y)13 NH—R$_3$ or —NH—C(Y)—O—R$_3$ radical; and most preferably, E represents —R$_3$, —NH—R$_3$, —NH—C(NR$_1$)—R$_1$, —C(NR$_1$)—NH—R$_1$, —NH—C(NR$_1$)—NH—R, or —NH—C (NR$_1$)—O—CH$_3$ radical; or alternatively preferably, E represents —NH—C(NR$_1$)—R$_3$, —C(NR$_1$)—NH—R$_3$, —NH—C(NR$_1$)—NH—R$_3$ or a radical of the formula

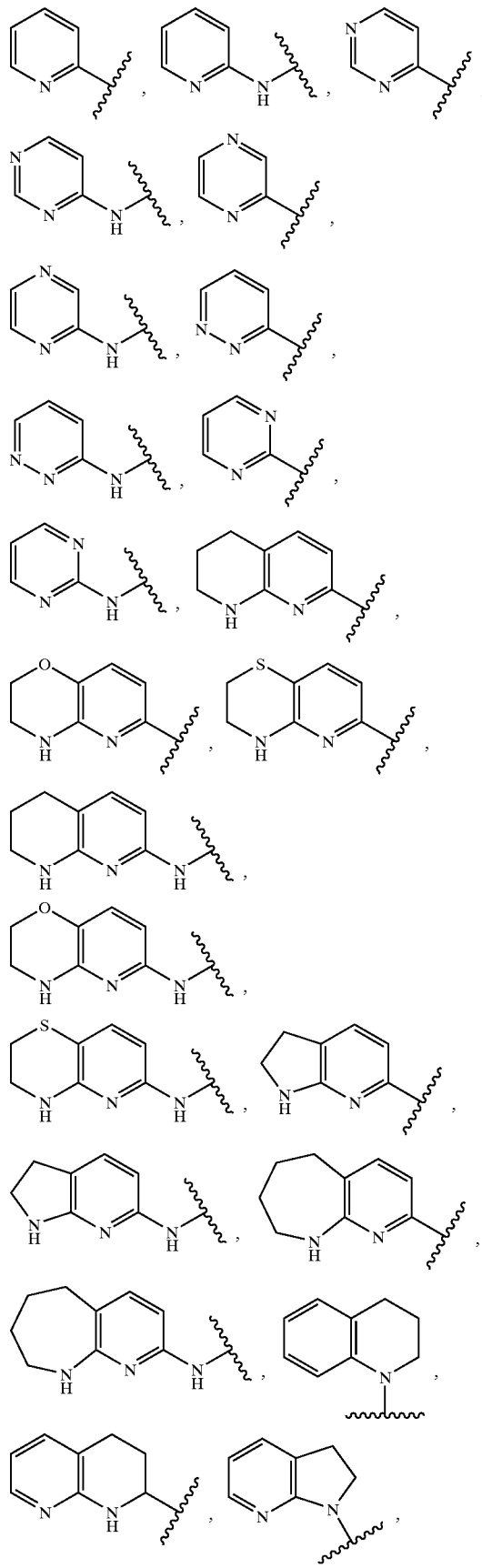

each of which formula is optionally substituted by 1–2 radicals of $R_2$; wherein n is 1–4, preferably, 1–3; more preferably, 1–2; and more preferably, E represents —NH—C($NR_1$)—$R_3$, —C($NR_1$)—NH—$R_3$, —NH—C($NR_1$)—NH—$R_3$ or a radical of the formula each of which formula is optionally substituted by 1–2 radicals of $R_2$;

$R_3$ is a radical of hydrogen, alkyl, aryl, aryl-alkyl, heteroaryl, heteroaryl-alkyl, heterocyclyl or heterocyclyl-alkyl, wherein the aryl, heteroaryl and heterocyclyl radicals are optionally substituted by 1–3 radicals of $R_2$;

preferably, $R_3$ is hydrogen, $C_1$–$C_{10}$ alkyl, aryl, aryl-$C_1$–$C_{10}$ alkyl, heteroaryl, heteroaryl-$C_1$–$C_{10}$ alkyl, heterocyclyl or heterocyclyl-$C_1$–$C_{10}$ alkyl radical, wherein the heteroaryl and heterocyclyl radicals have 5–15 ring members and the aryl, heteroaryl and heterocyclyl radicals are optionally substituted by 1–3 radicals of $R_2$;

more preferably, $R_3$ is hydrogen, $C_1$–$C_4$ alkyl, aryl, aryl-$C_1$–$C_4$ alkyl, heteroaryl, heteroaryl-$C_1$–$C_4$ alkyl, heterocyclyl or heterocyclyl-$C_1$–$C_4$ alkyl radical, wherein the heteroaryl and heterocyclyl radicals have 5–15 ring members and the aryl, heteroaryl and heterocyclyl radicals are optionally substituted by 1–3 radicals of $R_2$;

more preferably, $R_3$ is hydrogen, $C_1$–$C_4$ alkyl, aryl, aryl-$C_1$–$C_4$ alkyl, heteroaryl or heteroaryl-$C_1$–$C_4$ alkyl radical, wherein the heteroaryl radical has 5–15 ring members and the aryl and heteroaryl radicals are optionally substituted by 1–3 radicals of $R_2$;

more preferably, $R_3$ is a heteroaryl radical of 5–15 ring members and is optionally substituted by 1–3 radicals of $R_2$;

most preferably, $R_3$ is a heteroaryl radical of 5–10 ring members and is optionally substituted by 1–3 radicals of $R_2$;

G is a radical of formula

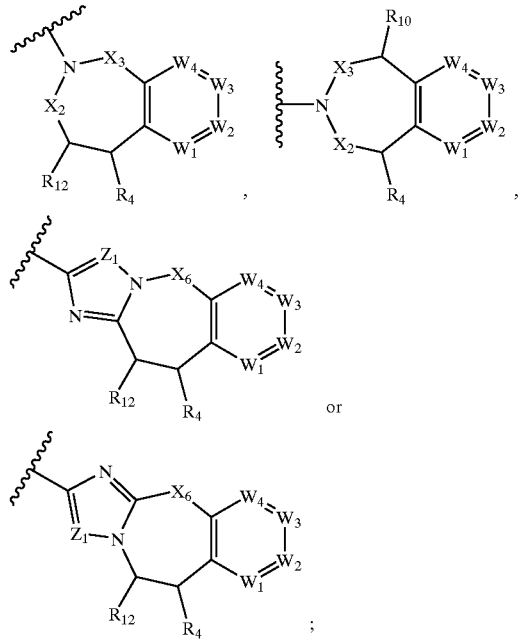

preferably, G is a radical of formula

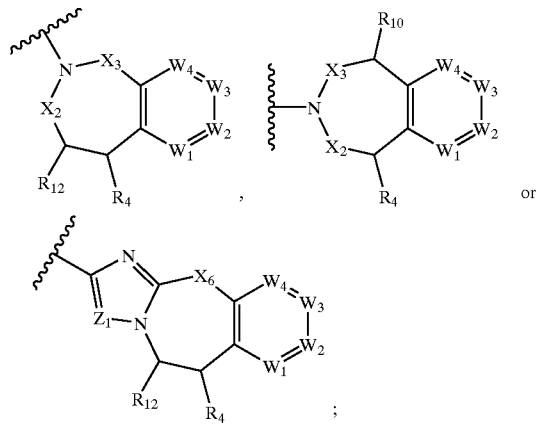

more preferably, G is a radical of formula

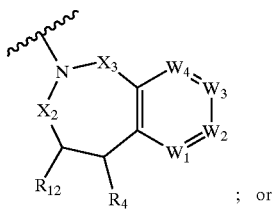

; or alternatively more preferably, G is a radical of formula

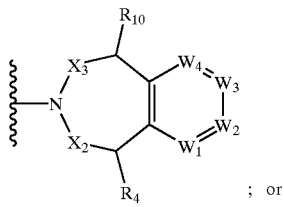

; or alternatively more preferably, G is a radical of formula

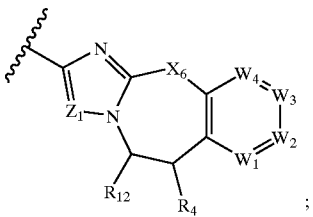

;

$W_1$ is C—$R_{15}$ or N; $W_2$ is C—$R_{16}$ or N; $W_3$ is C—$R_{17}$ or N; and $W_4$ is C—$R_{18}$ or N; or $W_1$ and $W_2$, $W_2$ and $W_3$, or $W_3$ and $W_4$ taken together represent a fused phenyl, fused $C_5$–$C_7$ cycloalkyl, fused heteroaryl of 5–6 ring members or fused heterocyclyl of 5–7 ring members, each of which is optionally substituted by 1–3 radicals of $R_2$; preferably, $W_1$ is C—$R_{15}$ or N; $W_2$ is C—$R_{16}$ or N; $W_3$ is C—$R_{17}$ or N; and $W_4$ is C—$R_{18}$ or N; and more preferably, $W_1$ is C—$R_{15}$; $W_2$ is C—$R_{16}$; $W_3$ is C—$R_{17}$; and $W_4$ is C—$R_{18}$; provided not more than 2 of $W_1$, $W_2$, $W_3$ or $W_4$ represent N; preferably, not more than 2 of $W_1$, $W_2$, $W_3$ or $W_4$ represent N;

radicals of $R_{15}$, $R_{17}$ and $R_{18}$ are each independently a radical of hydrogen, halo, hydroxy, carboxy, cyano, azido, amidino, nitro, amino, —$R_9$, —C(Y)—$R_9$, —S(O)$_t$—$R_9$, —S—$R_9$, —O—$R_9$, —N($R_1$)—$R_9$, —C(Y)—N($R_1$)—$R_9$, —N($R_1$)—C(Y)—H, —N($R_1$)—C(Y)—$R_9$, —O—C(Y)—N($R_1$)—$R_9$, —N($R_1$)—C(Y)—O—$R_9$, —S(O)$_t$—N($R_1$)—$R_9$, —N($R_1$)—S(O)$_t$—$R_9$, —N($R_1$)—C(Y)—N($R_1$)—$R_9$ or —N($R_1$)—S(O)$_t$—N($R_1$)—$R_9$;

preferably, radicals of $R_{15}$, $R_{17}$ and $R_{18}$ are each independently a radical of hydrogen, halo, hydroxy, carboxy, cyano, azido, amidino, nitro, amino, —$R_9$, —C(O)—$R_9$, —S(O)$_t$—$R_9$, —S—$R_9$, —O—$R_9$, —N($R_1$)—$R_9$, —C(O)—N($R_1$)—$R_9$, —N($R_1$)—C(O)—H, —N($R_1$)—C(O)—$R_9$, —S(O)$_t$—N($R_1$)—$R_9$ or —N($R_1$)—S(O)$_t$—$R_9$;

more preferably, radicals of $R_{15}$, $R_{17}$ and $R_{18}$ are each independently a radical of hydrogen, halo, hydroxy, cyano, $C_1$–$C_3$ alkyl, $C_1$$C_3$ alkoxy, —$CF_3$ or —$OCF_3$; and most preferably, $R_{15}$, $R_{17}$ and $R_{18}$ are each independently a radical of hydrogen, fluoro, chloro, bromo, hydroxy, cyano, methyl, methoxy, —$CF_3$ or —$OCF_3$; and $R_{16}$ is a radical of hydrogen, halo, hydroxy, carboxy, cyano, azido, amidino, nitro, amino, —$R_9$, —C(Y)—$R_9$, —S(O)$_t$—$R_9$, —S—$R_9$, —O—$R_9$, —N($R_1$)—$R_9$, —C(Y)—N($R_1$)—$R_9$, —N($R_1$)—C(Y)—H, —N($R_1$)—C(Y)—$R_9$, —O—C(Y)—N($R_1$)—$R_9$, —N($R_1$)—C(Y)—O—$R_9$, —S(O)$_t$—N($R_1$)—$R_9$, —N($R_1$)—S(O)$_t$—$R_9$, —N($R_1$)—C(Y)—N($R_1$)—$R_9$ or —N($R_1$)—S(O)$_t$—N($R_1$)—$R_9$;

preferably, $R_{16}$ is a radical of hydrogen, halo, hydroxy, carboxy, cyano, azido, amidino, nitro, amino, —$R_9$, —C(O)—$R_9$, —S(O)$_t$—$R_9$, —S—$R_9$, —O—$R_9$, —N($R_1$)—$R_9$, —C(O)—N($R_1$)—$R_9$, —N($R_1$)—C(O)—H, —N($R_1$)—C(O)—$R_9$, —S(O)$_t$—N($R_1$)—$R_9$ or —N($R_1$)—S(O)$_t$—$R_9$;

more preferably, $R_{16}$ is a radical of hydrogen, halo, hydroxy, carboxy, cyano, amino, —$R_9$, —S(O)$_t$—$R_9$, —O—$R_9$, —N($R_1$)—$R_9$, —C(O)—N($R_1$)—$R_9$, —N($R_1$)—C(O)—H, —N($R_1$)—C(O)—$R_9$, —S(O)$_t$—N($R_1$)—$R_9$ or —N($R_1$)—S(O)$_t$—$R_9$; and most preferably, $R_{16}$ is a radical of hydrogen, fluoro, chloro, bromo, hydroxy, cyano, amino, —$R_9$, —S(O)$_t$—$R_9$, —O—$R_9$, —N($R_1$)—$R_9$, —C(O)—N($R_1$)—$R_9$, —N($R_1$)—C(O)—H, —N($R_1$)—C(O)—$R_9$, —S(O)$_t$—N($R_1$)—$R_9$ or —N($R_1$)—S(O)$_t$—$R_9$; or alternatively, $R_{15}$ and $R_{16}$, $R_{16}$ and $R_{17}$, or $R_{17}$ and $R_{18}$ taken together represent a methylenedioxy, ethylenedioxy or propylenedioxy radical; and provided the combined total number of aryl, cycloalkyl, heteroaryl and heterocyclyl radicals in $R_{15}$, $R_{16}$, $R_{17}$ and $R_{18}$ is 0–1;

wherein each $R_9$ is independently a radical of alkyl, haloalkyl, arylalkyl, heteroarylalkyl, heterocyclylalkyl, aryl, cycloalkyl, heteroaryl or heterocyclyl, wherein the aryl, cycloalkyl, heteroaryl and heterocyclyl radicals are optionally substituted by 1–3 radicals of $R_2$;

preferably, each $R_9$ is independently a radical of $C_1$–$C_4$ alkyl, $C_1$–$C_4$ haloalkyl of 1–3 halo radicals, aryl—$C_1$–$C_4$ alkyl, heteroaryl—$C_3$–$C_4$ alkyl, heterocyclyl-$C_1$–$C_4$ alkyl, aryl, cycloalkyl, heteroaryl or heterocyclyl, wherein the aryl, cycloalkyl, heteroaryl and heterocyclyl radicals are optionally substituted by 1–3 radicals of $R_2$;

more preferably, each $R_9$ is independently a radical of $C_1$–$C_4$ alkyl, —$CF_3$, phenyl-$C_1$–$C_4$ alkyl or phenyl, wherein each phenyl radical is optionally substituted by 1–3 radicals of $R_2$; and most preferably, each $R_9$ is independently a radical of $C_1$–$C_4$ alkyl, —$CF_3$, phenyl-$C_1$–$C_2$ alkyl or phenyl, wherein each phenyl radical is optionally substituted by 1–3 radicals of $R_2$;

$X_2$, $X_3$ and $X_6$ are each independently a —C(X)—, —S(O)$_t$—, —CHR$_6$— or —CHR$_7$— radical; preferably, $X_2$, $X_3$ and $X_6$ are each independently a —CHR$_6$— or —CHR$_7$— radical; and more preferably $X_2$, $X_3$ and $X_6$ are each independently a —CHR$_6$— radical;

$Z_1$ is N or C—$R_6$; preferably, $Z_1$ is C—$R_6$;

$R_{10}$ and $R_{12}$ are each independently an —$R_6$, —$R_7$ or —OR$_7$ radical; preferably, $R_{10}$ and $R_{12}$ are each independently a hydrogen, hydroxy or $C_1$–$C_4$ alkyl radical; more preferably, $R_{10}$ and $R_{12}$ are each independently a hydrogen, hydroxy or $C_1$–$C_2$ alkyl radical; most preferably, $R_{10}$ and $R_{12}$ are each a hydrogen radical;

provided the combined total number of aryl, heteroaryl and heterocyclyl radicals in $X_2$, $X_3$, $X_6$, $R_{10}$ and $R_{12}$ is 0–2; preferably, 0–1;

wherein each $R_6$ is independently a hydrogen, hydroxy, alkyl, haloalkyl, alkoxy, haloalkoxy, halo or cyano radical; preferably, each $R_6$ is independently a hydrogen, hydroxy, $C_1$–$C_4$ alkyl, $C_1$–$C_4$ haloalkyl of 1–3 halo radicals, $C_1$–$C_4$ alkoxy, $C_1$–$C_4$ haloalkoxy, halo or cyano radical; more preferably, each $R_6$ is independently a hydrogen, hydroxy or $C_1$–$C_2$ alkyl radical; and most preferably, each $R_6$ is a hydrogen radical; and each $R_7$ is independently a radical of aryl, aryl-alkyl, heteroaryl, heteroaryl-alkyl, heterocyclyl or heterocyclyl-alkyl, each of which is optionally substituted by 1–3 radicals of $R_2$; preferably, each $R_7$ is independently a radical of aryl, aryl-$C_1$–$C_4$ alkyl, heteroaryl, heteroaryl-$C_1$–$C_4$ alkyl, heterocyclyl or heterocyclyl-$C_1$–$C_4$ alkyl, each of which is optionally substituted by 1–3 radicals of $R_2$, and wherein the heteroaryl and heterocyclyl radicals have 5–10 ring members; more preferably, each $R_7$ is independently a radical of phenyl, phenyl-$C_1$–$C_2$ alkyl, heteroaryl, heteroaryl-$C_1$–$C_2$ alkyl, heterocyclyl or heterocyclyl-$C_1$–$C_2$ alkyl, each of which is optionally substituted by 1–3 radicals of $R_2$, and wherein the heteroaryl and heterocyclyl radicals have 5–6 ring members; and $R_4$ is an alkyl radical substituted by a radical of carboxy, tetrazolyl, —CO$_2$R$_8$, —C(O)—NH—S(O)$_t$—R$_8$, —C(O)—NH—C(O)—R$_6$ or —C(O)—NH—R$_8$, and optionally substituted by a radical of aryl, heteroaryl or heterocyclyl, each of which is optionally substituted by 1–3 radicals of $R_2$;

preferably, $R_4$ is a $C_1$–$C_{10}$ alkyl radical substituted by a radical of carboxy, tetrazolyl, —CO$_2$R$_8$, —C(O)—NH—S(O)$_t$—R$_8$, —C(O)—NH—C(O)—R$_8$ or —C(O)—NH—R$_8$, and optionally substituted by a radical of aryl, heteroaryl or heterocyclyl, each of which is optionally substituted by 1–3 radicals of $R_2$;

more preferably, $R_4$ is a $C_1$–$C_4$ alkyl radical substituted by a radical of carboxy, tetrazolyl, or —CO$_2$R$_8$, and optionally substituted by a radical of aryl, heteroaryl or heterocyclyl, each of which is optionally substituted by 1–3 radicals of $R_2$;

more preferably, $R_4$ is a $C_1$–$C_4$ alkyl radical substituted by a radical of carboxy or —CO$_2$R$_8$; and most preferably, $R_4$ is a $C_1$–$C_2$ alkyl radical substituted by a radical of carboxy or —CO$_2$R$_8$;

wherein $R_8$ is an alkyl radical substituted by 1–2 radicals of hydroxy, carboxy, amino, aryl or heteroaryl, wherein the aryl and heteroaryl radicals are optionally substituted by 1–3 radicals of $R_2$;

preferably, $R_8$ is a $C_1$–$C_{10}$ alkyl radical substituted by 1–2 radicals of hydroxy, carboxy, amino, aryl or heteroaryl of 5–10 ring members, wherein the aryl and heteroaryl radicals are optionally substituted by 1–3 radicals of $R_2$;

more preferably, $R_8$ is a $C_1$–$C_4$ alkyl radical optionally substituted by a radical of aryl or heteroaryl of 5–10 ring members, wherein the aryl and heteroaryl radicals are optionally substituted by 1–3 radicals of $R_2$;

more preferably, $R_8$ is a $C_1$–$C_4$ alkyl radical optionally substituted by a phenyl radical, wherein the phenyl radical is optionally substituted by 1–3 radicals of $R_2$; and most preferably, $R_8$ is a $C_1$–$C_2$ alkyl radical.

In another aspect of the invention, there is provided a method for the therapeutic or prophylactic treatment of disease states involving tumor growth, metastasis, diabetic retinopathy, macular degeneration, angiogenesis, restenosis, bone resorption, atherosclerosis, inflammation, viral disease, wound healing or the like in a warm-blooded animal which comprises administering to a warm blooded animal in need thereof a therapeutically or prophylactically effective amount of a compound or pharmaceutical composition of the invention.

In a further embodiment of the invention, there is provided a method for modulation, preferably inhibition, of one or more integrin receptors which comprises administering to a warm blooded animal in need thereof an effective amount of a compound or pharmacutical composition of the invention.

In a further embodiment of the invention, there is provided a method for modulation, preferably inhibition, of one or more vitronectin receptors which comprises administering to a warm blooded animal in need thereof an effective amount of a compound or pharmacutical composition of the invention.

In a related embodiment, there is provided a method for modulation, preferably inhibition, of $\alpha_v\beta_3$ and/or $\alpha_v\beta_5$ and/or $\alpha_v\beta$ receptors which comprises administering to a warm blooded animal in need thereof an effective amount of a compound or pharmacutical composition of the invention.

An additionally preferred embodiment of the invention includes a method for the therapeutic or prophylactic treatment of an integrin receptor mediated disease state in a warm-blooded animal which comprises administering to said animal a therapeutically or prophylactically effective amount of a compound or pharmacutical composition of the invention. For example, the compounds of the invention may modulate an integrin receptor mediated response, for example, by antagonizing one or more vitronectin receptors response. Especially preferred in this embodiment is the inhibition of the $\alpha_v\beta_3$ and/or $\alpha_v\beta_5$ and/or $\alpha_v\beta_6$ receptor response.

The compounds and pharmacutical compositions of this invention are useful in the prophylaxis and/or treatment (comprising administering to a warm blooded animal, such as a mammal (e.g., a human, horse, sheep, pig, mouse, rat, bovine and the like) an effective amount of such compound or composition) of (1) diseases and disorders which can be effected or facilitated by modulating one or more integrin receptors, such as by antagonizing one or more integrin receptors, including but not limited to disorders induced or facilitated by one or more integrin receptors; (2) diseases and disorders which can be effected or facilitated by modulating one or more vitronectin receptors, such as by antagonizing one or more vitronectin receptors, including but not limited to disorders induced or facilitated by one or more vitronectin receptors; (3) diseases and disorders which can be effected or facilitated by modulating the $\alpha_v\beta_3$ and/or $\alpha_v\beta_5$ and/or $\alpha_v\beta_6$ receptor response, such as by inhibition of the $\alpha_v\beta_3$ and/or $\alpha_v\beta_5$ and/or $\alpha_v\beta_6$ receptor response, including but not limited to disorders induced or facilitated by the $\alpha_v\beta_3$ and/or $\alpha_v\beta_5$ and/or $\alpha_v\beta_6$ receptor response; or (4) disease states involving cancer, such as tumor growth; metastasis; diabetic retinopathy; macular degeneration; angiogenesis; restenosis; bone resorption, such as osteoporosis, osteoarthritis, bone formation, bone loss, hyperparathyroidism, Paget's disease, hypercalcemia of malignancy, osteolytic lesions, In Behcet's disease, osteomalacia, hyperostosis or osteopetrosis; atherosclerosis; inflammation, such as rheumatoid arthritis, pain, psoriasis or allergies; viral disease; wound healing; or the like.

As utilized herein, the following terms shall have the following meanings:

"Alkyl", alone or in combination, means a saturated or partially unsaturated (provided there are at least two carbon atoms) straight-chain or branched-chain alkyl radical containing the designated number of carbon atoms; preferably 1–18 carbon atoms ($C_1$–$C_{18}$), more preferably 1–12 carbon atoms ($C_1$–$C_{12}$), more preferably 1–8 carbon atoms ($C_1$–$C_8$), more preferably 1–6 carbon atoms ($C_1$–$C_6$), more preferably 1–4 carbon atoms ($C_1$–$C_4$), more preferably 1–3 carbon atoms ($C_1$–$C_3$), and most preferably 1–2 carbon atoms ($C_1$–$C_2$). Examples of such radicals include methyl, ethyl, vinyl, n-propyl, allyl, isopropyl, n-butyl, 1-butenyl, 2-butenyl, 3-butenyl, sec-butyl, sec-butenyl, t-butyl, n-pentyl, 2-methylbutyl, 3-methylbutyl, 3-methylbutenyl, n-hexyl, 2-methylpentyl, 3-methylpentyl, 4-methylpentyl, 2,2-dimethylbutyl, 2,3-dimethylbutyl, and the like. A partially unsaturated alkyl preferably has at least one double or triple bond, more preferably 1–3 double or triple bonds , more preferably 1–2 double or triple bonds, and most preferably 1 double bond or 1 triple bond. "Alkyl" may also represent a divalent alkyl radical, such as aryl-alkyl-.

"Alkoxy", alone or in combination, means a radical of the type "R—O—" wherein "R" is an alkyl radical as defined above and "O" is an oxygen atom. Examples of such alkoxy radicals include methoxy, ethoxy, n-propoxy, isopropoxy, n-butoxy, iso-butoxy, sec-butoxy, tert-butoxy, allyloxy and the like.

"Alkylthio", alone or in combination, means a radical of the type "R—S—" wherein "R" is an alkyl radical as defined above and "S" is a sulfur atom. Examples of such alkylthio radicals include methylthio, ethylthio, n-propylthio, isopropylthio, n-butylthio, iso-butylthio, sec-butylthio, tert-butylthio, allylthio and the like.

The term "carbocyclic", alone or in combination, refers to an organic cyclic moiety in which the cyclic skeleton is comprised of only carbon atoms whereas the term "heterocyclic", alone or in combination, refers to an organic cyclic moiety in which the cyclic skeleton contains one or more, preferably 1–4, more preferably 1–3, most preferably 1–2, heteroatoms selected from nitrogen, oxygen, or sulfur and which may or may not include carbon atoms.

The term "cycloalkyl", alone or in combination, refers to a saturated or partially unsaturated (preferably 1–2 double bonds, more preferably 1 double bond) carbocyclic moiety containing the indicated number of carbon atoms, preferably 3–12 ring members, more preferably 3–8 ring members, and most preferably, 3–6 ring members. For example, the term "$C_3$–$C_{10}$ cycloalkyl" refers to an organic cyclic substituent in which three to ten carbon atoms form a three, four, five, six, seven, eight, nine or ten-membered ring, including, for example, a cyclopropyl, cyclobutyl, cyclopentyl, cyclopentenyl, cyclohexenyl, cyclohexyl, cycloheptyl, cyclooctyl and the like ring. As used herein, "cycloalkyl" may also refer to two or more cyclic ring systems which are fused to form, for example, bicyclic, tricyclic, or other similar bridged compounds (e.g. norbornanyl, norbornenyl, adamantanyl, etc.).

"Aryl" refers to an aromatic carbocyclic group having a single ring, for example, a phenyl ring, multiple rings, for example, biphenyl, or multiple condensed rings in which at least one ring is aromatic, for example, naphthyl, 1,2,3,4,-tetrahydronaphthyl, anthryl, or phenanthryl, which can be unsubstituted or substituted with one or more (preferably 1–5, more preferably 1–4, more preferably 1–3, most preferably 1–2) other substituents as defined above. The substituents attached to a phenyl ring portion of an aryl moiety in the compounds of this invention may be configured in the ortho-, meta- or para-orientations. Examples of typical aryl moieties included in the scope of the present invention may include, but are not limited to, the following:

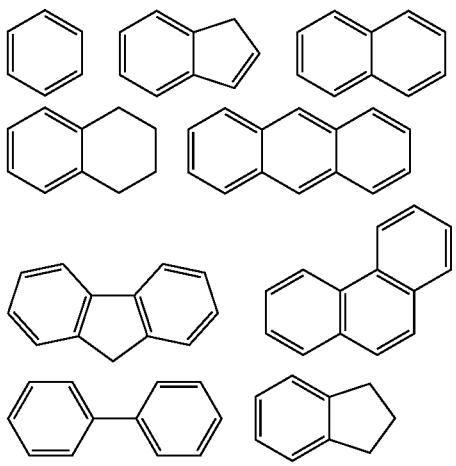

"Aryl-alkyl", alone or in combination, means an alkyl radical as defined above wherein a hydrogen radical is replaced with an aryl radical, such as benzyl, and for example, "aryl-$C_1$–$C_4$ alkyl", alone or in combination, means a $C_1$–$C_4$ alkyl radical as defined above wherein a hydrogen radical is replaced with an aryl radical.

"Heterocycle" refers to a saturated, unsaturated or aromatic carbocyclic group having a single ring, multiple rings or multiple condensed rings, and having at least one hetero atom such as nitrogen, oxygen or sulfur within at least one of the rings. "Heteroaryl" refers to a heterocycle in which at least one ring is aromatic. Further, bi- or tri-cyclic heteroaryl moieties may comprise at least one ring which is either completely or partially saturated. Any of the heteroaryl groups can be unsubstituted or optionally substituted with one or more groups as defined above and one or more, preferably 1–2, more preferably one, "oxo" group. "Heterocyclyl" refers to a saturated or partially unsaturated, preferably one double bond, monocyclic or bicyclic, preferably monocyclic, heterocycle radical containing at least one, preferably 1 to 4, more preferably 1 to 3, even more preferably 1–2, nitrogen, oxygen or sulfur atom ring member and having preferably 3–8 ring members in each ring, more preferably 5–8 ring members in each ring and even more preferably 5–6 ring members in each ring. "Heterocyclyl" is intended to include sulfone and sulfoxide derivatives of sulfur ring members and N-oxides of tertiary nitrogen ring members, and carbocyclic fused, preferably 3–6 ring carbon atoms and more preferably 5–6 ring carbon atoms. Any of the heterocyclyl groups can be unsubstituted or optionally substituted with one or more groups as defined above and one or more, preferably 1–2, more preferably one, "oxo" group.

As one skilled in the art will appreciate such heterocycle moieties may exist in several isomeric forms, all of which are to be encompassed by the present invention. For example, a 1,3,5-triazine moiety is isomeric to a 1,2,4-triazine group. Such positional isomers are to be considered within the scope of the present invention. Likewise, the heterocyclyl or heteroaryl groups can be bonded to other moieties in the compounds of the invention. The point(s) of attachment to these other moieties is not to be construed as limiting on the scope of the invention. Thus, by way of example, a pyridyl moiety may be bound to other groups through the 2-, 3-, or 4-position of the pyridyl group and a piperidinyl may be bound to other groups through the nitogen or carbon atoms of the piperidinyl group. All such configurations are to be construed as within the scope of the present invention.

Examples of heterocyclic or heteroaryl moieties included in the scope of the present invention may include, but are not limited to, the following:

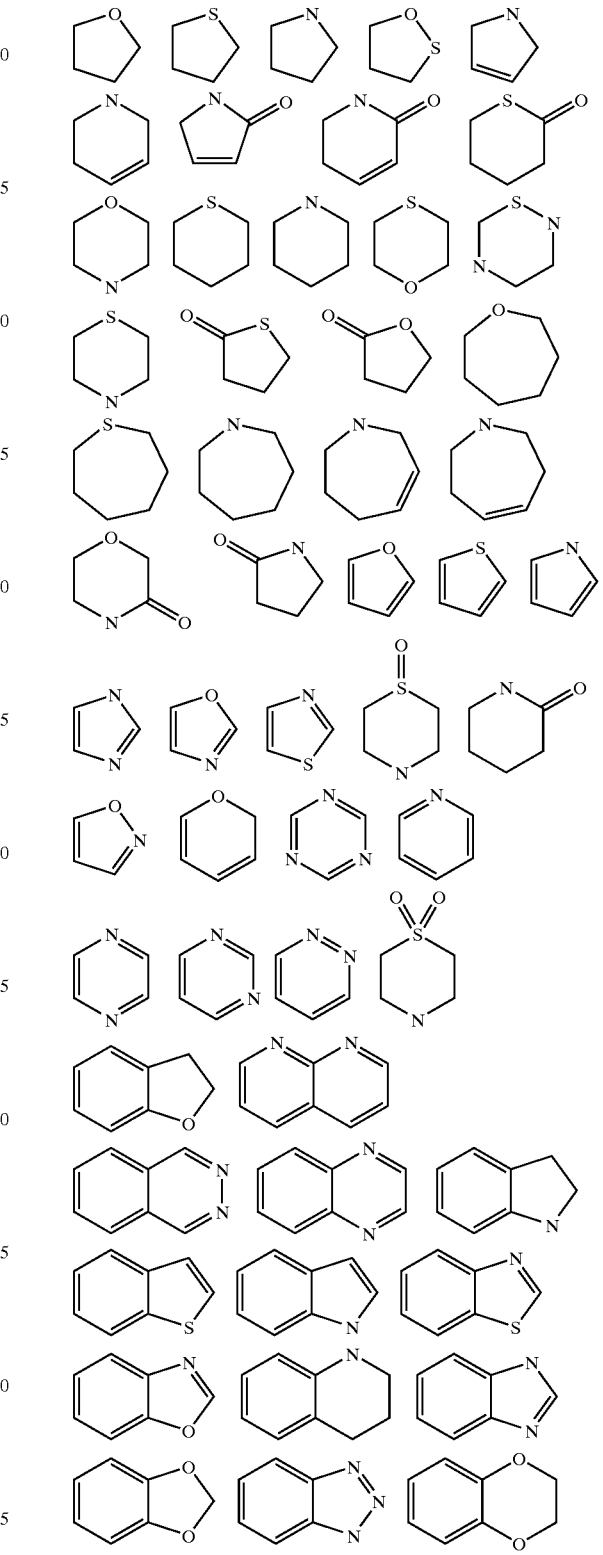

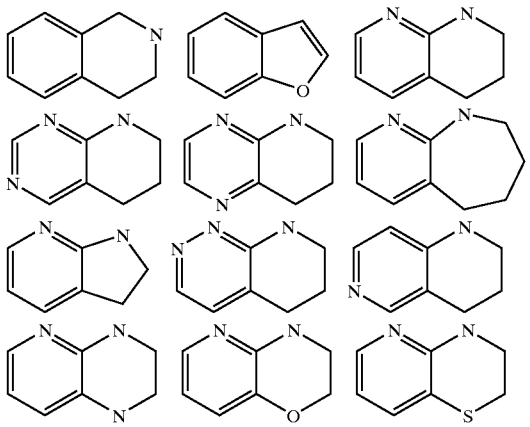

Heterocycle "fused" forms a ring system in which a heterocyclyl or heteroaryl group and a cycloalkyl or aryl group have two carbons in common, for example indole, isoquinoline, tetrahydroquinoline, methylenedioxybenzene and the like.

"Benzo", alone or in combination, means the divalent radical $C_6H_4$=derived from benzene. "Benzo fused" forms a ring system in which benzene and a cycloalkyl or aryl group have two carbons in common, for example tetrahydronaphthylene and the like.

The term "halo" or "halogen" refers to a halogen atom which may include fluoro, chloro, bromo and iodo. Preferred halo groups include chloro, bromo and fluoro with chloro and fluoro being especially preferred.

"Haloalkyl", alone or in combination, means an alkyl radical as defined above in which at least one hydrogen atom, preferably 1–3, is replaced by a halogen radical, more preferably fluoro or chloro radicals. Examples of such haloalkyl radicals include 1,1,1-trifluoroethyl, chloromethyl, 1-bromoethyl, fluoromethyl, difluoromethyl, trifluoromethyl, bis(trifluoromethyl)methyl and the like.

The following table defines by example certain ring structure abbreviations used herein:

| Abbreviation | Structure/Name |
|---|---|
| B[2]A-2-yl | 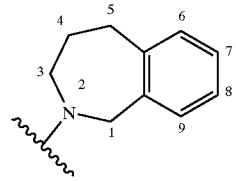<br>2,3,4,5-tetrahydro-1H-2-benzazepin-2-yl |
| 8-aza-B[2]A-2-yl | 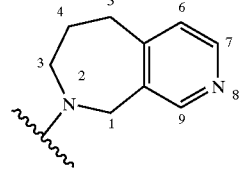<br>8-aza-2,3,4,5-tetrahydro-1H-2-benzazepin-2-yl |
| B[3]A-3-yl | {} <br>2,3,4,5-tetrahydro-1H-3-benzazepin-3-yl |
| 7-aza-B[3]A-3-yl | <br>7-aza-2,3,4,5-tetrahydro-1H-3-benzazepin-3-yl |
| 6,8-diaza-B[3]A-3-yl | <br>6,8-diaza-2,3,4,5-tetrahydro-1H-3-benzazepin-3-yl |
| IBA(I)-2-yl | 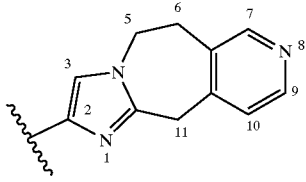<br>6,11-dihydro-5H-imidazo [2,1-b] [3] benzazepin-2-yl |
| IBA(II)-2-yl | 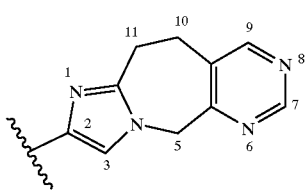<br>10,11-dihydro-5H-imidazo [1,2-b] [2] benzazepin-2-yl |
| 8-aza-IBA(I)-2-yl | <br>8-aza-6,11-dihydro-5H-imidazo [2,1-b] [3] benezazepin-2-yl |
| 6,8-diaza-IBA(II)-2-yl | <br>6,8-diaza-10,11-dihydro-5H-imidazo [1,2-b] [2] benzazepin-2-yl |

-continued

| Abbreviation | Structure/Name |
|---|---|
| TBA(I)-2-yl | 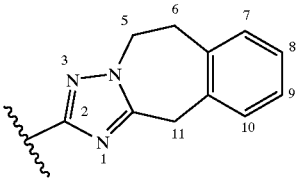<br>6,11-dihydro-5H-[1,2,4] triazolo [5,1-b] [3] benzazepin-2-yl] |
| TBA(III)-2-yl | 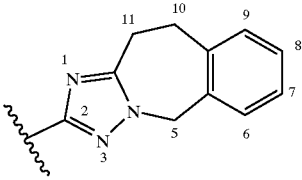<br>10,11-dihydro-5H-[1,2,4] triazolo [2,3-b] [2] benzazepin-2-yl |

Certain symbols used herein are indended to have the following meanings:

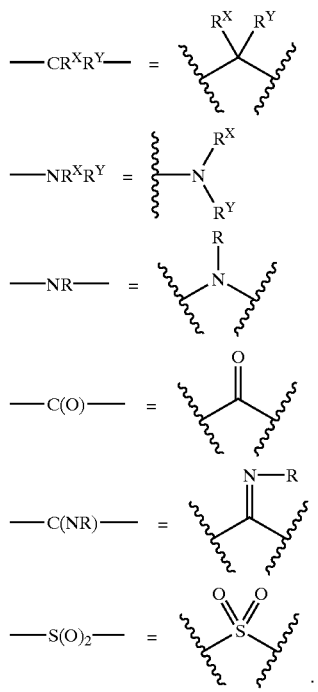

It should be noted that compounds of the invention may contain groups that may exist in tautomeric forms, such as cyclic and acyclic amidine and guanidine groups, heteroatom substituted heteroaryl groups (Y'=O, S, NR), and the like

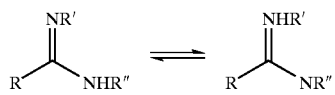

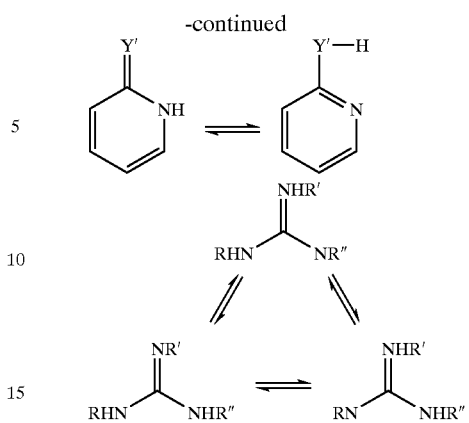

and though one form is named, described, displayed and/or claimed herein, all the tautomeric forms are intended to be inherently included in such name, description, display and/or claim.

"Modulate" as used herein refers to the ability of a compound of this invention to interact with a receptor, target gene or other gene product to (a) up-regulate the activity of that receptor, target gene or other gene product or biological effect (for example, as an agonist) or (b) down-regulating the receptor, target gene or other gene product or other biological effect, particularly by acting as an antagonist for the receptor, target gene or other gene product. Additionally, encompassed by "modulate" is the ability of a compound of the invention to effect a desired biological response, even if that response occurs upstream or downstream one or more steps in a signaling pathway from the receptor, target gene or other gene product in question. Thus, by way of example, the compounds of the invention may provide the desired effect by interacting with an integrin receptor, particularly a vitronectin receptor, such as the $\alpha_v\beta_3$ and/or $\alpha_v\beta_5$ and/or $\alpha_v\beta_6$ receptor, to act as an agonist or antagonist to that receptor or at some point, either upstream or downstream, in the signaling pathway for the receptor to effect the desired therapeutic or prophylactic response.

"Pharmaceutically acceptable salt", as used herein, refers to an organic or inorganic salt which is useful in the treatment of a warm-blooded animal. Such salts can be acid or basic addition salts, depending on the nature of the compound of this invention. For examples of "pharmacologically acceptable salts," see Berge et al., J. Pharm. Sci. 66:1 (1977). As used herein, "warm blooded animal" includes a mammal, including a member of the human, equine, porcine, bovine, murine, canine, feline and the like species.

In the case of an acidic moiety in a compound of this invention, a salt may be formed by treatment of a compound of this invention with a basic compound, particularly an inorganic base. Preferred inorganic salts are those formed with alkali and alkaline earth metals such as lithium, sodium, potassium, barium and calcium. Preferred organic base salts include, for example, ammonium, dibenzylammonium, benzylammonium, 2-hydroxyethylammonium, bis(2-hydroxyethyl)ammonium, phenylethylbenzylamine, dibenzyl-ethylenediamine, and the like salts. Other salts of acidic moieties may include, for example, those salts formed with procaine, quinine and N-methylglucosamine, plus salts formed with basic amino acids such as glycine, ornithine, histidine, phenylglycine, lysine and arginine. An especially preferred salt is a sodium or potassium salt of a compound of this invention.

With respect to basic moieties, a salt is formed by the treatment of a compound of this invention with an acidic compound, particularly an inorganic acid. Preferred inorganic salts of this type may include, for example, the hydrochloric, hydrobromic, hydroiodic, sulfuric, phosphoric or the like salts. Preferred organic salts of this type, may include, for example, salts formed with formic, acetic, succinic, citric, lactic, maleic, fumaric, palmitic, cholic, pamoic, mucic, d-glutamic, d-camphoric, glutaric, glycolic, phthalic, tartaric, lauric, stearic, salicyclic, methanesulfonic, benzenesulfonic, para-toluenesulfonic, sorbic, puric, benzoic, cinnamic and the like organic acids. An especially preferred salt of this type is a hydrochloride or sulfate salt of a compound of this invention.

Also encompassed in the scope of the present invention are pharmaceutically acceptable esters of a carboxylic acid or hydroxyl containing group, including a metabolically labile ester or a prodrug form of a compound of this invention. A metabolically labile ester is one which may produce, for example, an increase in blood levels and prolong the efficacy of the corresponding non-esterified form of the compound. A prodrug form is one which is not in an active form of the molecule as administered but which becomes therapeutically active after some in vivo activity or biotransformation, such as metabolism, for example, enzymatic or hydrolytic cleavage. For a general discussion of prodrugs involving esters see Svensson and Tunek Drug Metabolism Reviews 165 (1988) and Bundgaard Design of Prodrugs, Elsevier (1985). Examples of a masked carboxylate anion include a variety of esters, such as alkyl (for example, methyl, ethyl), cycloalkyl (for example, cyclohexyl), aralkyl (for example, benzyl, p-methoxybenzyl), and alkylcarbonyloxyalkyl (for example, pivaloyloxymethyl). Amines have been masked as arylcarbonyloxymethyl substituted derivatives which are cleaved by esterases in vivo releasing the free drug and formaldehyde (Bungaard J. Med. Chem. 2503 (1989)). Also, drugs containing an acidic NH group, such as imidazole, imide, indole and the like, have been masked with N-acyloxymethyl groups (Bundgaard Design of Prodrugs, Elsevier (1985)). Hydroxy groups have been masked as esters and ethers. EP 039,051 (Sloan and Little, Apr. 11, 1981) discloses Mannich-base hydroxamic acid prodrugs, their preparation and use. Esters of a compound of this invention, may include, for example, the methyl, ethyl, propyl, and butyl esters, as well as other suitable esters formed between an acidic moiety and a hydroxyl containing moiety. Metabolically labile esters, may include, for example, methoxymethyl, ethoxymethyl, isopropoxymethyl, α-methoxyethyl, groups such as α-(($C_1$–$C_4$)alkyloxy)ethyl; for example, methoxyethyl, ethoxyethyl, propoxyethyl, iso-propoxyethyl, etc.; 2-oxo-1,3-dioxolen-4-ylmethyl groups, such as 5-methyl-2-oxo-1,3, dioxolen-4-ylmethyl, etc.; $C_1$–$C_3$ alkylthiomethyl groups, for example, methylthiomethyl, ethylthiomethyl, isopropylthiomethyl, etc.; acyloxymethyl groups, for example, pivaloyloxymethyl, α-acetoxymethyl, etc.; ethoxycarbonyl-1-methyl; or α-acyloxy-α-substituted methyl groups, for example α-acetoxyethyl.

Additionally, the compounds of the invention may have one or more asymmetric carbon atoms and, therefore, may exist in stereoisomeric forms. All stereoisomers are intended to be included within the scope of the present invention. As used, "stereoisomer" or "stereoisomeric" refers to a compound which has the same molecular weight, chemical composition, and constitution as another, but with the atoms grouped such that their orientation in three-dimensional space is different. Such stereoisomers may exist as enantiomeric mixtures, diastereomers or may be resolved into individual stereoisomeric components (e.g. specific enantiomers) by methods familiar to one skilled in the art.

Likewise, the compounds of this invention may exist as isomers, that is compounds of the same molecular formula but in which the atoms, relative to one another, are arranged differently. One skilled in the art will appreciate that it is possible to prepare compounds of this invention in which one or more of the substituents are reversed in orientation relative to the other atoms in the molecule. That is, the substituent to be inserted may be the same as that noted except that it is inserted into the molecule in the reverse orientation. One skilled in the art will appreciate that these isomeric forms of the compounds of this invention are to be construed as encompassed within the scope of the present invention.

Further, the compounds of the invention may exist as crystalline solids which can be crystallized from common solvents such as ethanol, N,N-dimethyl-formamide, water, or the like. Thus, crystalline forms of the compounds of the invention may exist as solvates and/or hydrates of the parent compounds or their pharmaceutically acceptable salts. All of such forms likewise are to be construed as falling within the scope of the invention.

While it may be possible to administer a compound of the invention alone, in the methods described, the compound administered normally will be present as an active ingredient in a pharmaceutical formulation. Thus, in one another embodiment of the invention, there is provided a formulation comprising a compound of this invention in combination with a pharmaceutically acceptable carrier, diluent or excipient therefor.

The composition used in the noted therapeutic methods can be in a variety of forms. These include, for example, solid, semi-solid and liquid dosage forms, such as tablets, pills, powders, liquid solutions or suspensions, liposomes, injectable and infusible solutions. The preferred form depends on the intended mode of administration and therapeutic application. Considerations for preparing appropriate formulations will be familiar to one skilled in the art and are described, for example, in Goodman and Gilman's: "The Pharmacological Basis of Therapeutics", 8th Ed., Pergamon Press, Gilman et al. eds. (1990); and "Remington's Pharmaceutical Sciences", 18th Ed., Mack Publishing Co., A. Gennaro, ed. (1990). Methods for administration are discussed therein, e.g. for oral, topical, intravenous, intraperitoneal, or intramuscular administration. Pharmaceutically acceptable carriers, diluents, and excipients, likewise, are discussed therein. Typical carriers, diluents, and excipients may include water (for example, water for injection), buffers, lactose, starch, sucrose, and the like.

As noted, a compound of the invention can be administered orally, topically or parenterally (e.g. intravenously, intraperitoneally, intramuscularly, subcutaneously, etc.), or inhaled as a dry powder, aerosol, or mist, for pulmonary delivery. Such forms of the compounds of the invention may be administered by conventional means for creating aerosols or administering dry powder medications using devices such as for example, metered dose inhalers, nasal sprayers, dry powder inhaler, jet nebulizers, or ultrasonic nebulizers. Such devices optionally may be include a mouthpiece fitted around an orifice. In certain circumstances, it may be desirable to administer the desired compound of the invention by continuous infusion, such as through a continuous infusion pump, or using a transdermal delivery device, such as a patch.

The compounds of the invention may also be administered as an aerosol. The term "aerosol" includes any gas-borne suspended phase of a compound of the invention which is capable of being inhaled into the bronchioles or nasal passages. Specifically, aerosol includes a gas-borne suspension of droplets of the desired compound, as may be produced in a metered dose inhaler or nebulizer, or in a mist sprayer. Aerosol also includes a dry powder composition of a compound of the instant invention suspended in air or other carrier gas, which may be delivered by insufflation from an inhaler device, for example.

For solutions used in making aerosols of the invention, the preferred range of concentration of the compounds of the invention is 0.1–100 milligrams (mg)/milliliter (mL), more preferably 0.1–30 mg/mL, and most preferably 1–10 mg/mL. Usually the solutions are buffered with a physiologically compatible buffer such as phosphate or bicarbonate. The usual pH range is from about 5 to about 9, preferably from about 6.5 to about 7.8, and more preferably from about 7.0 to about 7.6. Typically, sodium chloride is added to adjust the osmolarity to the physiological range, preferably within 10% of isotonic. Formulation of such solutions for creating aerosol inhalants is discussed, for example, in Remington's, supra; See, also, Ganderton and Johens, "Drug Delivery to the Respiratory Tract, Ellis Horwood (1987); Gonda, "Critical Review in Therapeutic Drug Carrier Systems" 6 273–313 (1990); and Raeburn et al. J. Pharmacol. Toxicol. Methods. 27 143–159 (1992).

Solutions of a compound of the invention may be converted into aerosols by any of the known means routinely used for making aerosol inhalant pharmaceuticals. In general, such methods comprise pressurizing or providing a means of pressurizing a container of the solution, usually with an inert carrier gas, and passing the pressurized gas through a small orifice, thereby pulling droplets of the solution into the mouth and trachea of the animal to which the drug is to be administered. Typically, a mouthpiece is fitted to the outlet of the orifice to facilitate delivery into the mouth and trachea.

In one embodiment, devices of the present invention comprise solutions of the compounds of the invention connected to or contained within any of the conventional means for creating aerosols in asthma medication, such as metered dose inhalers, jet nebulizers, or ultrasonic nebulizers. Optionally such devices may include a mouthpiece fitted around the orifice.

Further, there are provided a device which may comprise a solution of a compound of the instant invention in a nasal sprayer.

A dry powder comprising a compound of the invention, optionally with an excipient is another embodiment. This may be administered by a drug powder inhaler containing the described powder.

Powders may be formed with the aid of any suitable powder bases, for example, talc, lactose, starch and the like. Drops may be formulated with an aqueous base or non-aqueous base also comprising one or more dispersing agents, suspending agents solubilizing agents, and the like.

Any of the formulations of the invention may also include one or more preservatives or bacteriostatic agents, for example, methyl hydroxybenzoate, ethyl hydroxybenzoate, propyl hydroxybenzoate, chlorocresol, benzalkonium chlorides, and the like. Additionally, the formulations may contain other active ingredients.

The pharmaceutical formulations of the invention may be administered by parenteral or oral administration for prophylactic and/or therapeutic treatment. The pharmaceutical compositions can be administered in a variety of unit dosage forms depending on the method of administration. For example, unit dosage forms suitable for oral administration may include, powders, tablets, pills, capsules and dragees.

The pharmaceutical formulations can be administered intravenously. Therefore, the invention further provides formulations for intravenous administration which comprise a compound of the invention dissolved or suspended in a pharmaceutically acceptable carrier or diluent therefor. A variety of aqueous carriers can be used, for example, water, buffered water or other buffer solutions, saline, and the like. The resulting aqueous solutions can be packaged for use as is, or lyophilized, the lyophilized preparation being combined with a sterile aqueous solution prior to administration. The sterile aqueous solution for the lyophilized product can be packaged as a kit for use with the lyophilized formulation. The compositions can contain pharmaceutically acceptable substances to aid in administration and more closely mimic physiological conditions. Such substances, can include, for example, pH adjusting substances such as acids, bases or buffering agents, tonicity adjusting agents, wetting agents and the like. Such substances may include but are not limited to, for example, sodium hydroxide, hydrochloric acid, sulfuric acid, sodium acetate, sodium lactate, sodium chloride, potassium chloride, calcium chloride, sorbitan monolaurate, triethanolamine oleate, and the like or any other means familiar to one skilled in the art for maintaining pH at a desired level.

For solid formulations, carriers, diluents, and excipients known to one skilled in the art may be used. Such carriers, diluents and excipients may include, for example, mannitol, lactose, starch magnesium stearate, sodium saccharin, talcum, cellulose, glucose, sucrose, or other solid polyol sugar, magnesium carbonate, and the like. For oral administration, a pharmaceutically acceptable formulation is prepared by admixing any of the usual carrier, diluents, and excipients, such as those noted, with from about 0.1 to about 95% of a compound of the invention.

The preferred dosage for use in the methods of the invention, however, is in the range of about 0.01 mg/kg to about 100 mg/kg of body weight, preferably from about 0.1 mg/kg to about 50 mg/kg, up to 4 times per day. Whatever the dosage form, one skilled in the art will recognize that the dosage administered will be adjusted to factors such as the age, weight, and condition of the patient involved. The skilled practitioner will be familiar with how to adjust the dosage to accommodate these and other factors.

While the compounds of the invention can be administered as the sole active pharmaceutical agent, the compounds can also be used in combination with one or more agents such as anti-platelet agents, anti-inflammatory agents, matrix metalloproteinase inhibitors, cancer treatment agents, antiinfective agents and the like. For example, the compounds of the invention can be administered in combination with glycoprotein IIb/IIIa receptor antagonists for the prophylaxis and/or treatment of acute coronary ischemic syndrome and the like (WO 97/35615, incorporated herein by reference in its entirety), or in combination with IL-1 antagonists, such as, p38 inhibitors, TNF-α inhibitors, IL-1 inhibitors, IL-1 receptor antagonist (IL-1Ra) and the like, for the prophylaxis and/or treatment of rheumatoid arthritis, osteoarthritis and the like (Arner et al., Arthritis & Rheumatism 38:1304–14, 1995). When administered as a combination, the therapeutic agents can be formulated as separate compositions which are given at the same time or different times, or the therapeutic agents can be given as a single composition.

Compound Synthesis

Compounds of the invention can be synthesized according to one or more of the following methods. It should be noted that the general procedures are shown as it relates to preparation of compounds having unspecified stereochemistry. However, such procedures are generally applicable to those compounds of a specific stereochemistry, e.g., where the stereochemistry about a group is (S) or (R). In addition, the compounds having one stereochemistry (e.g., (R)) can often be utilized to produce those having opposite stereochemistry (i.e., (S)) using well-known methods, for example, by inversion. Because compounds of the invention can possess one or more asymmetric carbon atoms, the compounds are thus capable of existing in the form of optical isomers as well as in the form of racemic or nonracemic mixtures thereof. The optical isomers can be obtained by resolution of the racemic mixtures according to conventional processes, for example by formation of diastereoisomeric salts by treatment with an optically active acid or base. Examples of appropriate acids are tartaric acid, diacetyltartaric acid, dibenzoyltartaric acid, ditoluoyltartaric acid, camphorsulfonic acid and the like. Examples of appropriate bases are brucine, ephedrine, strychnine, morphine and the like. The separation of the mixture of diastereoisomers by crystallization is followed by liberation of the optically active bases from these salts. A alternative process for separation of optical isomers involves the use of a chiral chromatography column optimally chosen to maximize the separation of the enantiomers. Another available method involves synthesis of covalent diastereoisomeric molecules by reacting compounds of the invention with an optically pure acid in an activated form or an optically pure isocyanate. The synthesized diastereoisomers can be separated by conventional means such as chromatography, distillation, crystallization or sublimation, and then hydrolyzed to deliver the enantiomerically pure compound. The optically active compounds of the invention can likewise be obtained by utilizing optically active starting materials or alternatively, by generating optically active synthetic intermediates either by chiral reactions, such as using a chiral reagent, chiral catalyst and the like, or by isolating the desired chiral synthetic intermediate isomer using the methods described above. These isomers may be in the form of a free acid, a free base, an ester or a salt.

"Leaving group" (L) generally refers to groups readily displaceable by a nucleophile, such as an amine, a carbon, a thiol or an alcohol nucleophile. Such leaving groups are well known in the art. Examples of such leaving groups include, but are not limited to, N-hydroxysuccinimide, N-hydroxybenzotriazole, halides, triflates, tosylates and the like. Preferred leaving groups are indicated herein where appropriate.

"Protecting group" generally refers to groups well known in the art which are used to prevent selected reactive groups, such as carboxy, amino, hydroxy, mercapto and the like, from undergoing undesired reactions, such as nucleophilic, electrophilic, oxidation, reduction and the like (see Greene, T. W. and Wuts, P. G. M., Protective Groups in Organic Synthesis, Wiley, 1991). Preferred protecting groups are indicated herein where appropriate. Examples of amino protecting groups include, but are not limited to, aralkyl, substituted aralkyl, cycloalkenylalkyl and substituted cycloalkenyl alkyl, allyl, substituted allyl, acyl, alkoxycarbonyl, aralkoxycarbonyl, silyl and the like. Examples of aralkyl include, but are not limited to, benzyl, ortho-methylbenzyl, trityl and benzhydryl, which can be optionally substituted with halogen, alkyl, alkoxy, hydroxy, nitro, acylamino, acyl and the like, and salts, such as phosphonium and ammonium salts. Examples of aryl groups include phenyl, naphthyl, indanyl, anthracenyl, 9-(9-phenylfluorenyl), phenanthrenyl and the like. Examples of cycloalkenylalkyl or substituted cycloalkylenylalkyl radicals, preferably have 6–10 carbon atoms, include, but are not limited to, cyclohexenyl methyl and the like. Suitable acyl, alkoxycarbonyl and aralkoxycarbonyl groups include benzyloxycarbonyl, t-butoxycarbonyl, iso-butoxycarbonyl, benzoyl, substituted benzoyl, butyryl, acetyl, trifluoroacetyl, tri-chloro acetyl, phthaloyl and the like. A mixture of protecting groups can be used to protect the same amino group, such as a primary amino group can be protected by both an aralkyl group and an aralkoxycarbonyl group. Amino protecting groups can also form a heterocyclic ring with the nitrogen to which they are attached, for example, 1,2-bis(methylene)benzene, phthalimidyl, succinimidyl, maleimidyl and the like and where these heterocyclic groups can further include adjoining aryl and cycloalkyl rings. In addition, the heterocyclic groups can be mono-, di- or tri-substituted, such as nitrophthalimidyl. Amino groups may also be protected against undesired reactions, such as oxidation, through the formation of an addition salt, such as hydrochloride, toluenesulfonic acid, trifluoroacetic acid and the like. Many of the amino protecting groups are also suitable for protecting carboxy, hydroxy and nmercapto groups. For example, aralkyl groups. Alkyl groups are also sutiable groups for protecting hydroxy and mercapto groups, such as tert-butyl.

Silyl protecting groups are silicon atoms optionally substituted by one or more alkyl, aryl and aralkyl groups. Suitable silyl protecting groups ainclude, but are not limited to, trimethylsilyl, triethylsilyl, tri-isopropylsilyl, tert-butyldimethylsilyl, dimethylphenylsilyl, 1,2-bis(dimethylsilyl)benzene, 1,2-bis(dimethylsilyl)ethane and diphenylmethylsilyl. Silylation of an amino groups provide mono- or di-silylamino groups. Silylation of aminoalcohol compounds can lead to a N,N,O-tri-silyl derivative. Removal of the silyl function from a silyl ether function is readily accomplished by treatment with, for example, a metal hydroxide or ammonium flouride reagent, either as a discrete reaction step or in situ during a reaction with the alcohol group. Suitable silylating agents are, for example, trimethylsilyl chloride, tert-buty-dimethylsilyl chloride, phenyldimethylsilyl chloride, diphenylmethyl silyl chloride or their combination products with imidazole or DMF. Methods for silylation of amines and removal of silyl protecting groups are well known to those skilled in the art. Methods of preparation of these amine derivatives from corresponding amino acids, amino acid amides or amino acid esters are also well known to those skilled in the art of organic chemistry including amino acid/amino acid ester or aminoalcohol chemistry.

Protecting groups are removed under conditions which will not affect the remaining portion of the molecule. These methods are well known in the art and include acid hydrolysis, hydrogenolysis and the like. A preferred method involves removal of a protecting group, such as removal of a benzyloxycarbonyl group by hydrogenolysis utilizing palladium on carbon in a suitable solvent system such as an alcohol, acetic acid, and the like or mixtures thereof. A t-butoxy carbonyl protecting group can be removed utilizing an inorganic or organic acid, such as HCl or trifluoro-acetic acid, in a suitable solvent system, such as dioxane or methylene chloride. The resulting amino salt can readily be neutralized to yield the free amine. Carboxy protecting group, such as methyl, ethyl, benzyl, tert-butyl, 4-methoxyphenylmethyl and the like, can be removed under hydroylsis and hydrogenolysis conditions well known to those skilled in the art.

Compounds of the invention may be prepared as described in the following schemes and synthetic examples.

Compounds of the invention, E—B-(Alk)$_p$-Q-(Alk)$_q$-A—G, can be prepared by one or more of the following coupling reactions using reagents, reaction conditions and solvents typical for such coupling reactions:

1. E+L-(Alk)$_p$-Q-(Alk)$_q$-A—G
2. E—OH+L-(Alk)$_p$-Q-(Alk)$_q$-A—G
3. E—SH+L-(Alk)$_p$-Q-(Alk)$_q$-A—G
4. E—NHR$_1$+L-(Alk)$_p$-Q-(Alk)$_q$-A—G
5. E—NHR$_1$+L—C(Y)-(Alk)$_p$-Q-(Alk)$_q$-A—G
6. E—NHR$_1$+L—C(Y)-NR$_1$-(Alk)$_p$-Q-(Alk)$_q$-A—G
7. E—NHR$_1$+L—S(O)$_t$-(Alk)$_p$-Q-(Alk)$_q$-A—G
8. E—NHR$_1$+L—S(O)$_t$—NR$_1$-(Alk)$_p$-Q-(Alk)$_q$-A—G
9. E—L+HO-(Alk)$_p$-Q-(Alk)$_q$-A—G
10. E—L+HS-(Alk)$_p$-Q-(Alk)$_q$-A—G
11. E—L+HNR$_1$-(Alk)$_p$—Q-(Alk)$_q$-A—G
12. E—C(Y)—L+HNR$_1$-(Alk)$_p$-Q-(Alk)$_q$-A—G
13. E—NR$_1$—C(Y)—L+HNR$_1$-(Alk)$_p$-Q-(Alk)$_q$-A—G
14. E—S(O)$_t$—L+HNR$_1$-(Alk)$_p$-Q-(Alk)$_q$-A—G
15. E—NR$_1$—S(O)$_t$—L+HNR$_1$-(Alk)$_p$-Q-(Alk)$_q$-A—G
16. E—B-(Alk)$_p$-OH+L-(Alk)$_q$-A—G
17. E—B-(Alk)$_p$-SH+L-(Alk)$_q$-A—G
18. E—B-(Alk)$_p$-NHR$_1$+L-(Alk)$_q$-A—G
19. E—B-(Alk)$_p$-NHR$_1$+L—C(X)-(Alk)$_q$-A—G
20. E—B-(Alk)$_p$-NHR$_1$+L—C(X)—NR$_1$-(Alk)$_q$-A—G
21. E—B-(Alk)$_p$-NHR$_1$+L—S(O)$_t$—(Alk)$_q$-A—G
22. E—B-(Alk)$_p$-NHR$_1$+L—S(O)$_t$—NR$_1$-(Alk)$_q$-A—G
23. E—B-(Alk)$_p$-L+HO-(Alk)$_q$-A—G
24. E—B-(Alk)$_p$-L+HS-(Alk)$_q$-A—G
25. E—B-(Alk)$_p$-L+HNR$_1$-(Alk)$_q$-A—G
26. E—B-(Alk)$_p$—C(X)-L+HNR$_1$-(Alk)$_q$-A—G
27. E—B-(Alk)$_p$-NR$_1$—C(X)—L+HNR$_1$-(Alk)$_q$-A—G
28. E—B-(Alk)$_p$-S(O)$_t$—L+HNR$_1$-(Alk)$_q$-A—G
29. E—B-(Alk)$_p$-NR$_1$—S(O)$_t$—L+HNR$_1$-(Alk)$_q$-A—G
30. E—B-(Alk)$_p$-Q-(Alk)$_q$-L+G
31. E—B-(Alk)$_p$-Q-(Alk)$_q$-OH+L—G
32. E—B-(Alk)$_p$-Q-(Alk)$_q$-SH+L—G
33. E—B-(Alk)$_p$-Q-(Alk)$_q$-NHR$_1$+L—G
34. E—B-(Alk)$_p$-Q-(Alk)$_q$-NHR$_1$+L—C(X)—G
35. E—B-(Alk)$_p$-Q-(Alk)$_q$-NHR$_1$+L—C(X)—NR$_1$—G
36. E—B-(Alk)$_p$-Q-(Alk)$_q$-NHR$_1$+L—S(O)$_t$—G
37. E—B-(Alk)$_p$-Q-(Alk)$_q$-NHR$_1$+L—S(O)$_t$—NR$_1$—G
38. E—B-(Alk)$_p$-Q-(Alk)$_q$-L+HO—G
39. E—B-(Alk)$_p$-Q-(Alk)$_q$-L+HS—G
40. E—B-(Alk)$_p$-Q-(Alk)$_q$-L+HNR$_1$—G
41. E—B-(Alk)$_p$-Q-(Alk)$_q$-C(X)—L+HNR$_1$—G
42. E—B-(Alk)$_p$-Q-(Alk)$_q$-NR$_1$—C(X)—L+HNR$_1$—G
43. E—B-(Alk)$_p$-Q-(Alk)$_q$-S(O)$_t$—L+HNR$_1$—G
44. E—B-(Alk)$_p$-Q-(Alk)$_q$-NR$_1$—S(O)$_t$—L+HNR$_1$—G wherein L is a leaving group, such as chloro, bromo, iodo, triflyate, N-hydroxysuccinimide, N-hydroxybenzotriazole, tosylate, mesylate, methoxy, methylthiol, phenoxy, thiophenoxy and the like. Thioethers may be oxidized to the corresponding sulfinyl groups by oxidation with an oxidizing agent, such as hydrogen peroxide, sodium periodate and the like. Thioethers and sulfinyl groups may be oxidized to the corresponding sulfonyl groups by oxidation with an oxidizing agent, such as potassium peroxymonosulfate, potassium permanganate, hydrogen peroxide and the like.

The preparation of amidine groups, such as when B represents a —C(Y)—N(R$_1$)— or —N(R$_1$)—C(Y)— radical, is well known to those skilled in the art (see Baati et al., Synthesis 1999:927–929; Dunn, Compr. Org. funct. Group Transform. 5:741–82 and 1161–308, 1995; and Gautier et al., Chem. Amidines Imidates, Patai (Ed.), Wiley (1975), pp. 283–348). Guanidine groups, such as when B represents —N(R$_1$)—C(Y)—N(R$_1$)— radical, can be prepared from urea groups (e.g., by reaction with POCl$_3$ and a substituted amine in an organic solvent, such as toluene), from thiourea groups (e.g., by reaction with a substituted amine in the presence of CuSO$_4$, SiO$_2$ and a base, such as triethylamine, in an organic solvent such as tetrahydrofuran (Tet. Lett. 36:2841–4, 1995) or sodium periodate in the presence of base in dimethylformaide and water (Synlett 1997:1053–4)), from substituted cyanamide groups, —N(R)—CN (e.g., by reaction with a substituted amine), from imino ester amine groups, R'O—C(NR)—N(R)— (e.g., by reaction with a substituted amine), or from imino thioester amine groups, R'S—C(NR)—N(R)— (by reaction with a substituted amine (Synth. Commun. 29:1757–66, 1999).

Schemes 1 and 2 illustrate the preparation of compounds of the invention wherein G is a benzazepine type ring system. Compounds (21) and (22), wherein A$_1$— represents the radical E—B-(Alk)$_p$-Q-(Alk)$_q$-A— or an intermediate radical (such as, M—B-(Alk)$_p$-Q-(Alk)$_q$-A—, M-(Alk)$_p$-Q-(Alk)$_q$-A—, M—Q-(Alk)$_q$-A—, M-(Alk)$_q$-A—, M—A— and the like wherein M is a reactive moiety such as an electrophile, nucleophile, leaving group or the like or a group that can be converted into an electrophile, nucleophile, leaving group or the like) that can be readily converted into the radical E—B-(Alk)$_p$-Q-(Alk)$_q$-A—, can be prepared from the corresponding amines (23) and (25), respectively, by alkylation, acylation, sulfonylation and the like, with A$_1$—L, wherein L is a leaving group such as halide, tosylate, mesylate, carboxylic acid activating group (such as N-hydroxysuccinimide, carbodiimide (Tetrahedron 55:6813–6830, 1999), BOP (J. Org. Chem. 63:9678–9683, 1998) and the like) and the like. Alternatively, compounds (21) and (22) can be prepared by (a) nucleophilic displacement by A$_1$—NH$_2$ of leaving groups (L) on compounds (24) and (26), respectively, (b) reductive amination of compounds (24) and (26), respectively, wherein L—X$_2$— and L—X$_3$— represents a ketone or aldehyde, using A$_1$—NH$_2$ and a reducing agent (such as sodium cyanoborohydride, PtO$_2$/H$_2$ and the like), or (c) a mixture of both (a) and (b).

Reaction of $A_1$—$NH_2$ with L—$X_2$— and L—$X_3$— can be simultaneous (one pot) or sequencial stepwise reactions.

Scheme 1

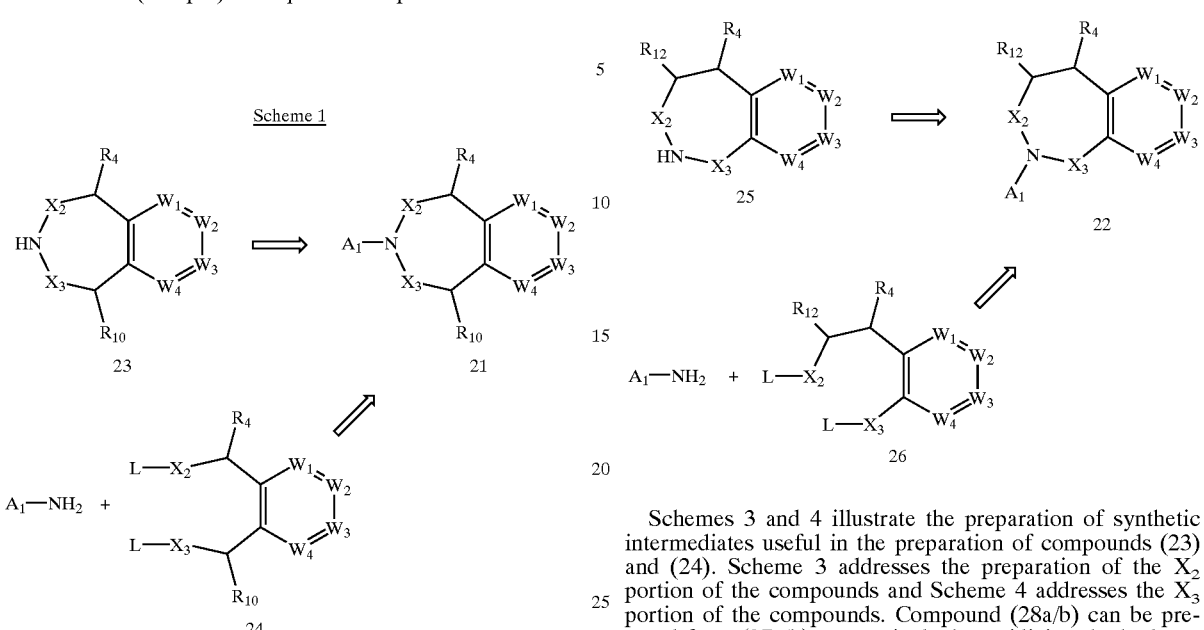

Scheme 2

Schemes 3 and 4 illustrate the preparation of synthetic intermediates useful in the preparation of compounds (23) and (24). Scheme 3 addresses the preparation of the $X_2$ portion of the compounds and Scheme 4 addresses the $X_3$ portion of the compounds. Compound (28a/b) can be prepared from (27a/b), respectively, by oxidizing the hydroxy group to an aldehyde, such as by Swern oxidation or the like, and reacting the aldehyde with a nucleophile of $R_4$ or $R_{10}$, respectively, such as with organometallic agents (such Scheme 3

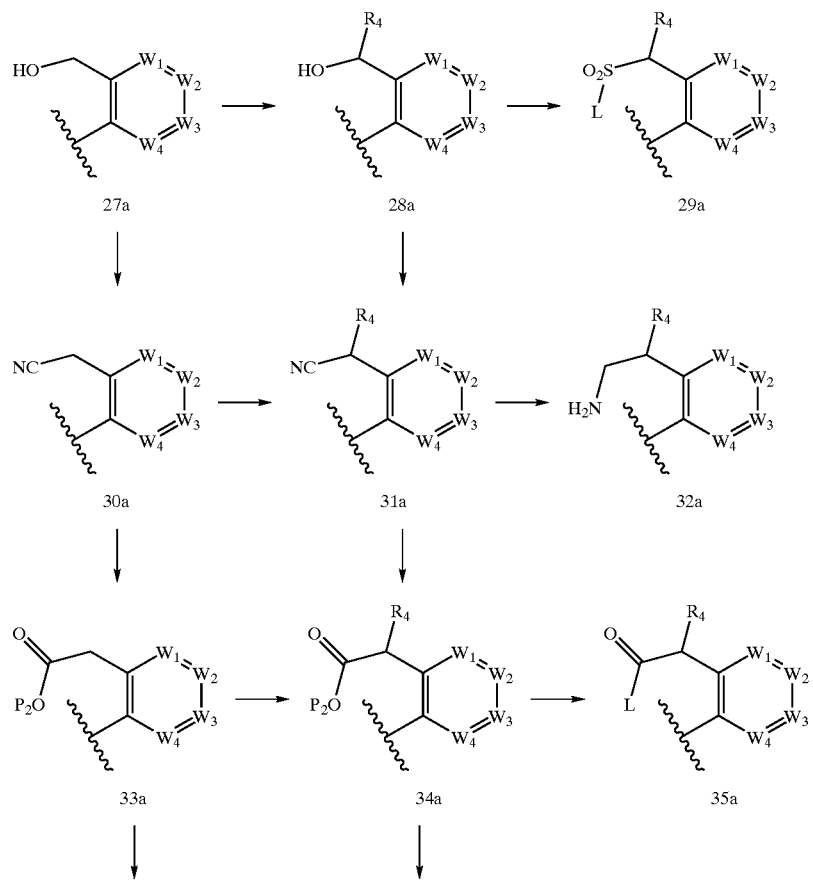

-continued

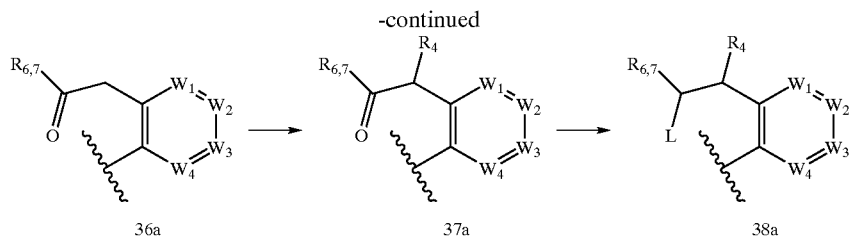

as $(R_4)_2CuLi$, $R_{10}$—Li or the like), or alternatively, oxidizing the hydroxy group to a carboxylic acid, reacting the acid with a nucleophile of $R_4$ or $R_{10}$, respectively, such as $R_4$—Li, $R_{10}$—MgBr or the like, and then reducing the resulting ketone to the hydroxy group, such as with sodium cyanoborohydride. Alcohol (28a/b) can be converted into sulfonyl compound (29a/b) by converting the hydroxy group into a leaving group (such as a halide, tosylate, mesylate, triflate or the like), nucleophilic displacement of the leaving group with a thiol salt (such as sodium sulfide or the like) and then coversion of the resulting thiol to a sulfonyl halide (such as $Cl_2/H_2O$ oxidation or the like). Alcohols (27a/b) and (28a/b) can be converted into cyano compounds (30a/b) and (31a/b), respectively, by converting the hydroxy group into a leaving group as before followed by nucleophilic displacement of the leaving group with a cyanide salt (such as sodium cyanide or the like). Cyano compound (31a/b) can be prepared from cyano compound (30a/b) by nucleophilic displacement reaction with $R_4$—L and $R_{10}$—L, respectively, in the presence of base. Cyano compound (31a/b) can be reduced to the amine (32a/b), such as with $BH_3$—$Me_2S$ or the like. Cyano compounds (30a/b) and (31a/b) can be hydrolyzed to a carboxylic acid which can then be esterified ($P_2$) to form esters (33a/b) and (34a/b) respectively, or the acid of (34a/b) can be converted into an active ester (35a/b). As in the case of the cyano compound (30a/b), the ester compound (33a/b) can undergo a nucleophilic displacement reaction with $R_4$—L and $R_{10}$—L, respectively, in the presence of base (such as sodium hydride or the like) to prepare ester (34a/b). Esters (33a/b) and (34a/b) can undergo a condensation reaction with $R_{6,7}$—C(O)—L, wherein $R_{6,7}$— represents radicals $R_6$— or $R_7$— as defined herein, in the presence of base, such as sodium hydride or the like, followed by hydroylsis and decarboxylation to yield ketones (36a/b) and (37a/b), respectively. Ketone (36a/b) can also undergo nucleophilc displacement of $R_4$—L and $R_{10}$—L, respectively, in the presence of base to yield ketone (37a/b). Ketone (37a/b) can undergo reductive amination with $A_1$—$NH_2$ or $P_N$—$NH_2$ (wherein $P_N$— is a nitrogen protecting group, such as benzyl, BOC or the like) or alternatively, can be reduced and the corresponding alcohol can be converted into a leaving group to yield compound (38a/b). The selection of which combination of moieties for $X_2$ and $X_3$ to be used in the preparation of compound (21) is well within the skill of one skilled in the art.

Scheme 4

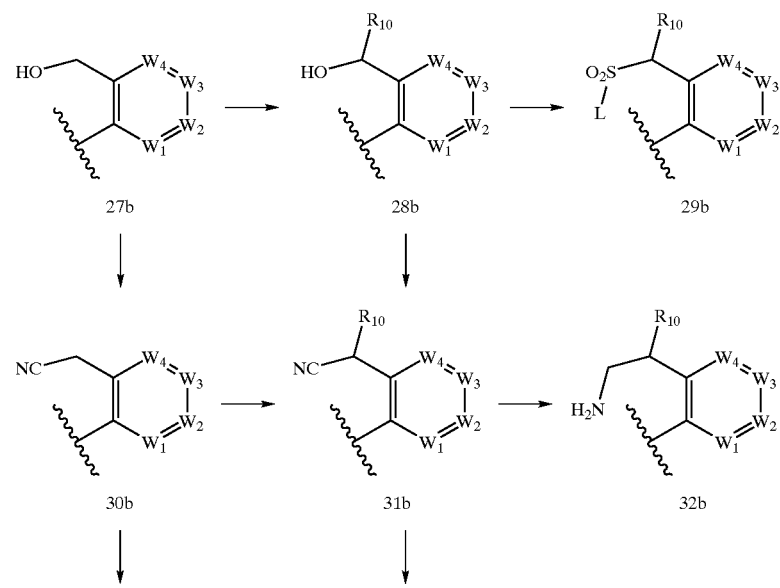

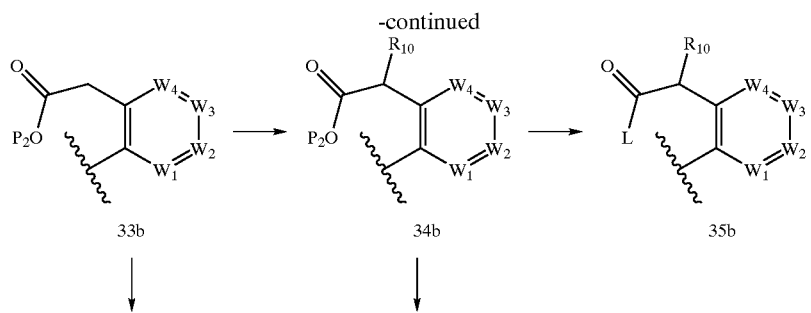
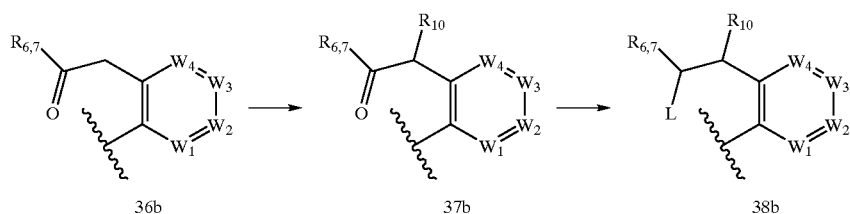

Schemes 5, 6 and 7 illustrate the preparation of compounds (25) and (26). Schemes 5 and 6 address the preparation of the $X_2$ portion of the compounds and Scheme 7 addresses the $X_3$ portion of the compounds. Compound (40) can be prepared from aldehyde (39) as described above for compound (28). In Scheme 5, condensation of $P_2O_2CCH_2R_{12}$ (or alternatively, the corresponding Wittig reagent (Chem. Rev. 89:863–927, 1989) or Horner-Wadsworth-Emmons condensation (Tet. Lett. 24:4405–4408, 1983)) with compound (39) in the Scheme 5

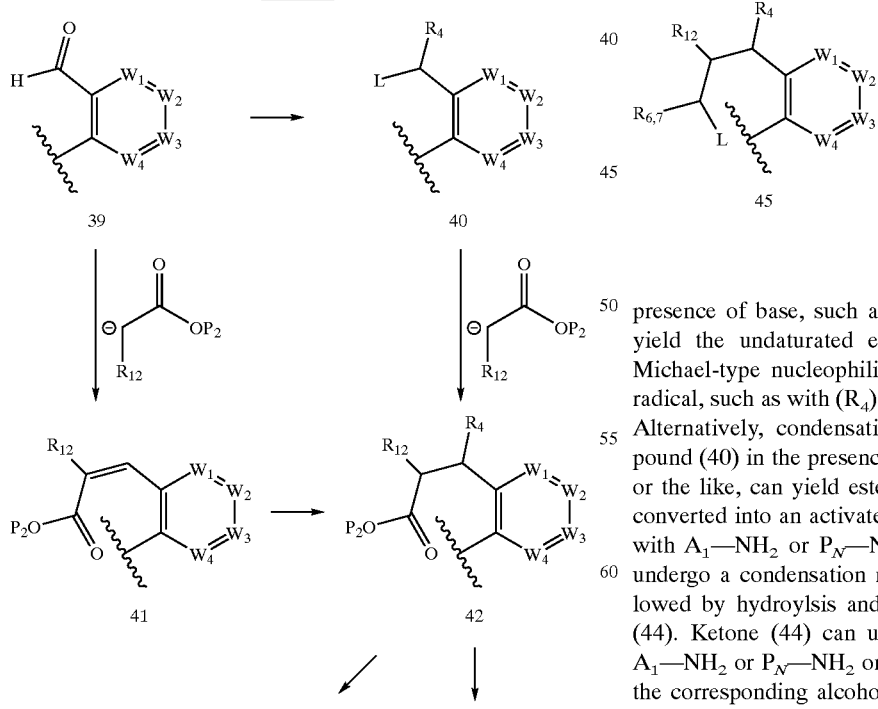

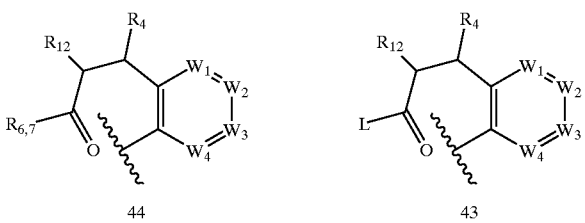

presence of base, such as sodium hydride or the like can yield the undaturated ester (41) which can undergo a Michael-type nucleophilic reaction to introduce the $R_4$— radical, such as with $(R_4)_2Cu$ or the like, to yield ester (42). Alternatively, condensation of $P_2O_2CCH_2R_{12}$ with compound (40) in the presence of base, such as sodium hydride or the like, can yield ester (42) directly. Ester (42) can be converted into an activated ester (43) which can be reacted with $A_1$—$NH_2$ or $P_N$—$NH_2$. Alternatively, ester (42) can undergo a condensation reaction with $R_{6,7}$—C(O)—L followed by hydroylsis and decarboxylation to yield ketone (44). Ketone (44) can undergo reductive amination with $A_1$—$NH_2$ or $P_N$—$NH_2$ or alternatively, can be reduced and the corresponding alcohol can be converted into a leaving group to yield compound (45).

Scheme 6

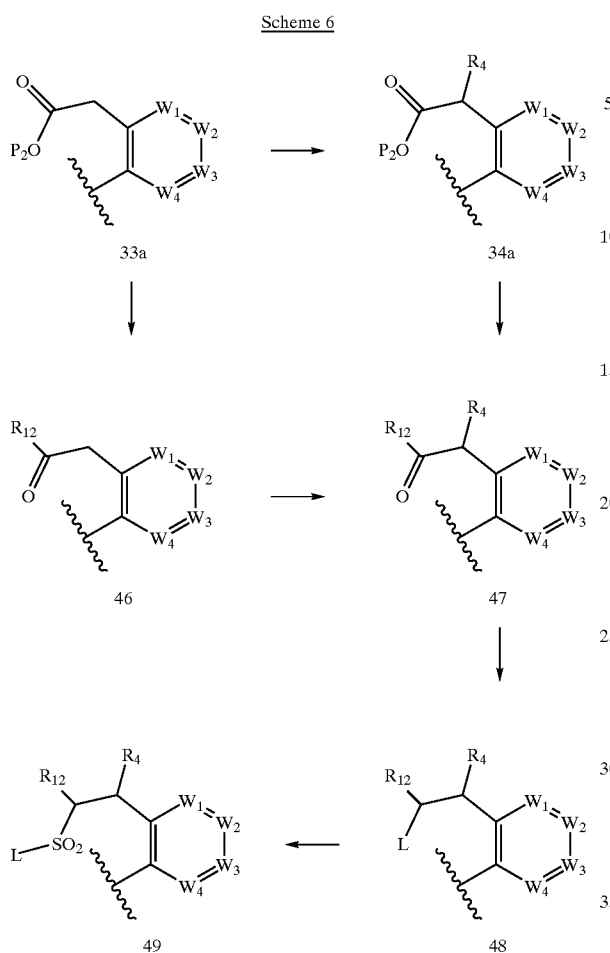

Scheme 7

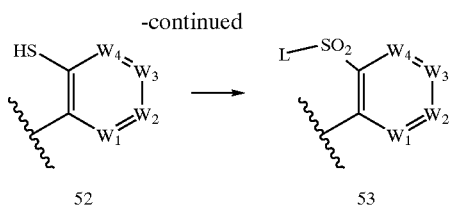

In Scheme 6, esters (33a) and (34a) can undergo a condensation reaction with $R_{12}$—C(O)—L in the presence of base, such as sodium hydride or the like, followed by hydroylsis and decarboxylation to yield ketones (46) and (47), respectively. Ketone (46) can also undergo nucleophilc displacement of $R_4$—L in the presence of base to yield ketone (47). Reduction of ketone (47) and conversion of the resulting alcohol to a leaving group (such as a halide, tosylate, mesylate, triflate or the like) as described above can yield compound (48). Nucleophilic displacement of the leaving group of compound (48) with a thiol salt (such as sodium sulfide or the like) and then coversion of the resulting thiol to a sulfonyl halide (such as $Cl_2/H_2O$ oxidation or the like) can yield compound (49).

In Scheme 7, ketone (50) can be prepared from the corresponding carboxylic acid by reacting the acid with a nucleophile of $R_{6,7}$, such as $R_{6,7}$—Li, $R_{6,7}$—MgBr or the like, or alternatively, by acylation of the aromatic ring with $R_{6,7}$—C(O)—L in the presence of a Friedel-Crafts catalyst, such as $AlCl_3$ or the like, or alternatively, nucleophilic reaction of $R_{6,7}$—C(O)—L or $R_{6,7}$—$CO_2H$ with the corresponding organometallic salt of the aromatic ring. Ketone (50) can undergo reductive amination with $A_1$—$NH_2$ or $P_N$—$NH_2$ or alternatively, can be reduced and the corresponding alcohol can be converted into a leaving group to yield compound (51). Sulfonyl compound (53) can be prepared from the corresponding thiol (52) (such as by $Cl_2/H_2O$ oxidation or the like) which can be prepared by nucleophilic displacement of the corresponding halide with a thiol salt (such as sodium sulfide or the like).

Scheme 8

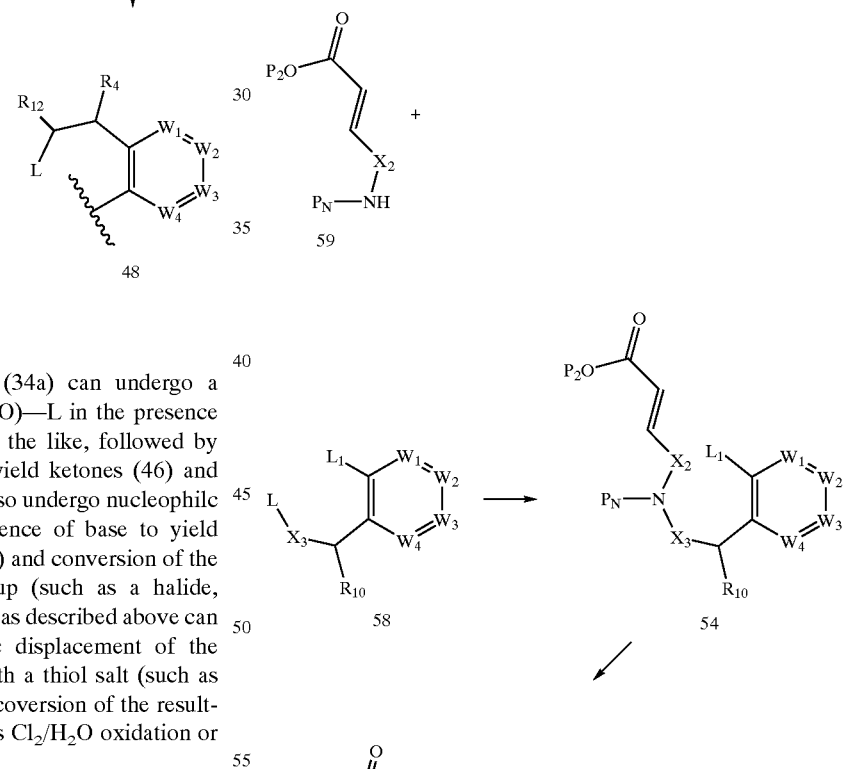

Alternatively, compounds (21) and (22) can be prepared by Heck Cyclization (Trans. Met. Org. Synth. 1:208–240, 1998) as shown in Schemes 8 and 9, respectively. Unsaturated esters (54) and (55), wherein $L_1$ is a leaving group, such as halide, triflate or the like, can be cyclized in the presence of $Pd(PPh_3)_4$ to yield compounds (56) and (57), respectively. The double bond of compounds (56) and (57) can be reduced (such as by hydrogenation in the presence of Pd/C catalyst, magnesium in methanol or the like) and the ester groups can be readily converted into groups represented by $R_4$— radical using methods described above and standard methods well known to those skilled in the art. Unsaturated esters (54) and (55) can be prepared by nucleophilic displacement of the leaving group L of compounds (58) and (60), respectively, with amino compounds (59) and (61), respectively, which are commerically available or can be readily prepared from commerically available starting materials. In leu of the nitrogen protecting group $P_N$—, $A_1$— or hydrogen atom may be used.

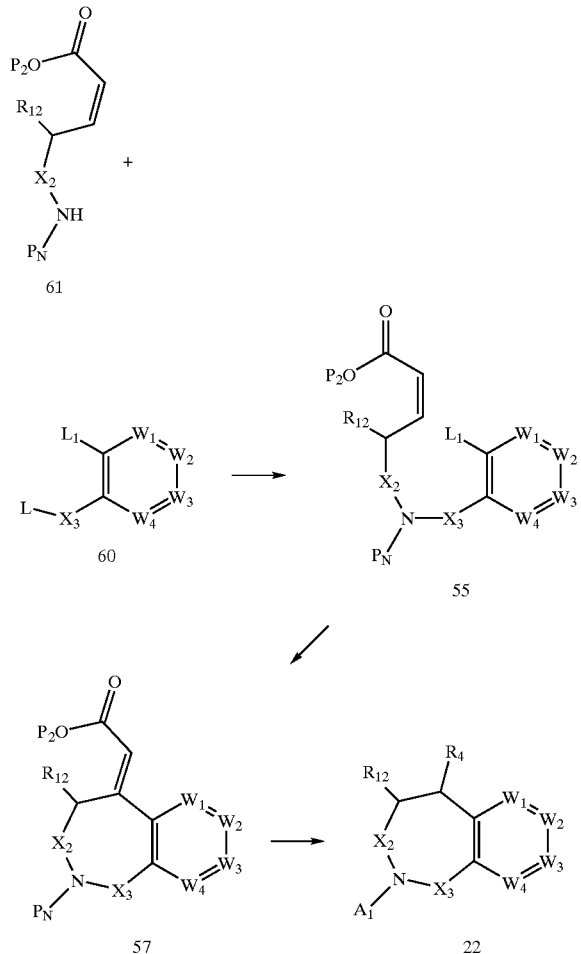

Scheme 9

Alternatively, compounds (54) and (55) can be cyclized by radical chain reaction utilizing an appropriate initiator, such as AIBN (Tet. Lett. 32:2829–2832, 1991), to esters (56) and (57), respectively, wherein the double bond is saturated.

Schemes 10 and 11 illustrate the preparation of compounds of the invention wherein G is a imidazolo-fused or triazolo-fused benzazepine type ring system. In Schemes 10 and 11, imidazolo-fused or triazolo-fused benzazepine type ring system (80) and (83) can be prepared from substituted imidazoles and triazoles (which are commercially available or readily prepared from commercially available starting materials) by alkylation of the imidazole or triazole nitrogen with alkylating agents (79) and (81). Cyclization can be effected by coversion of the hydroxy group of the alkylating agent into a leaving group which undergoes nucleophilic displacement upon metalation of the bromo (alternatively, chloro or iodo) group of the imidazole or triazole. One skilled in the art will recognize that other known processes, conditions and methods can be employed to effect the cyclization. Alkylating agents (79) and (81) can be prepared according to the processes described above.

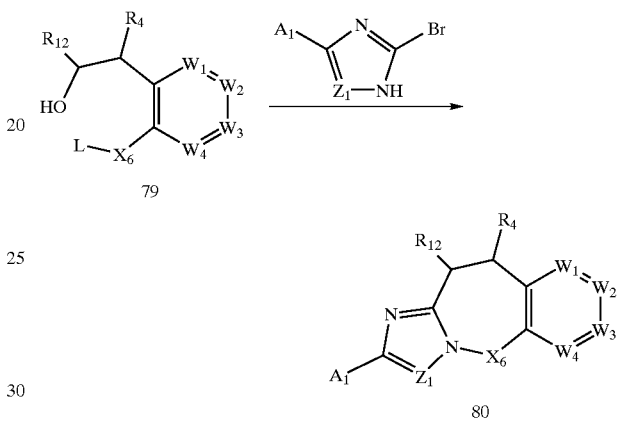

Scheme 10

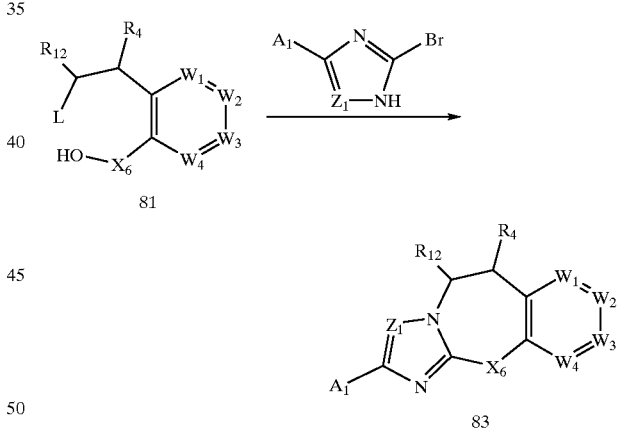

Scheme 11

The reactions described above may be carried out in any number of solvents in which the reactants may be mutually soluble, including, for example, tetrahydrofuran, benzene, toluene, chloroform, dichloromethane, N,N-dimethylformamide, ethyl ether, dioxane, water, acetonitrile, or the like. Generally the reaction is carried out at a temperature of between −80° C. and 150° C., preferably, however, at room temperature. In certain cases, as noted in the examples provided herein, however, the temperature of the reaction may reach as high as or exceed about 360 °C.

The product and intermediates may be isolated or purified using one or more standard purification techniques, including, for example, one or more of simple solvent evaporation, recrystallization, distillation, sublimation, filtration, chromatography, including thin-layer chromatography, HPLC (e.g., reverse phase HPLC using, for example, dilute trifluoroacetic acid in water, acetonitrile, or methanol mixtures as eluent), column chromatography, flash chromatography, radial chromatography, trituration, and the like.

In the preparation of the compounds of the invention, one skilled in the art will understand that one may need to protect or block various reactive functionalities on the starting compounds or intermediates while a desired reaction is carried out on other portions of the molecule. After the desired reactions are complete, or at any desired time, normally such protecting groups will be removed by, for example, hydrolytic or hydrogenolytic means. Such protection and deprotection steps are conventional in organic chemistry. One skilled in the art is referred to "Protective Groups in Organic Chemistry," McOmie, Ed., Plenum Press, New York, N.Y.; and "Protective Groups in Organic Synthesis," Greene, Ed., John Wiley & Sons, New York, N.Y. (1981) for the teaching of protective groups which may be useful in the preparation of compounds of the present invention.

Alternate means beyond those described above for preparing the compounds of the invention will be apparent to one skilled in the art and the noted general procedures are not to be construed as limiting the invention. To more fully understand the invention, including methods of preparing compounds of the invention, the following non-limiting examples are provided. The reader will appreciate that starting materials not otherwise described herein are either available commercially or can be prepared from commercially available compounds by methods generally known in the art.

Unless otherwise noted, all materials were obtained from commercial suppliers and used without further purification. Anhydrous solvents such as dimethylformamide (DMF), tetrahydrofuran (THF), dichloromethane ($CH_2Cl_2$), and toluene, dioxane were obtained from Aldrich Chemical Company in Sure/Seal bottles. All reactions involving air- or moisture-sensitive compounds were performed under a $N_2$ atmosphere. Flash chromatography was performed using ICN Biomedicals (SiliTech 32–63D 60A). Thin-layer chromatography (TLC) was performed with Analtech or Whatman silica gel TLC plates (250 μm). Preparatory TLC was performed with Whatman silica gel TLC plates (2000 μm). $^1$H NMR spectra were determined with superconducting FT NMR spectrometers operating at 400 and 500 MHz. Chemical shifts are expressed in ppm downfield from internal tetramethylsilane. Significant $^1$H NMR data are reported in the following order: multiplicity (s, singlet; d, doublet; t, triplet; q, quartet; m, multiplet; quin, quintet), number of protons, and coupling constants in Hz. Elemental analyses were performed by Atlantic Microlab, Inc., Norcross, Ga. Melting points were determined with a Buchi 535 capillary melting point apparatus and are uncorrected. Low resolution mass spectra (MS) were determined on a Perkin Elmer-SCIEX API 165 mass spectrometer using APCI or ES ionization modes (positive or negative). High resolution mass spectra (HRMS) were performed by Mass Consortium, San Diego, Calif. using FAB ionization.

EXAMPLE 1

Preparation of Methyl 2-(1H,2H,3H,4H,5H-benzo[e]azaperhydroepin-5-yl)acetate Hydrochloride Step A: 3-(((2-bromoohenyl)methyl)amino)propan-1-ol To a stirring solution of 2-bromobenzaldehyde in dichloroethane (0.4 M) at RT under nitrogen was added 3-aminopropanol (1.5 eq), sodium triacetoxyborohydride (2 eq), and acetic acid (4 eq). After 5 hr the reaction was carefully quenched with 2M sodium carbonate and extracted with methylene chloride. The organic phase was extracted with 1N hydrochloric acid. The aqueous phase was neutralized with 1N sodium hydroxide and extracted with methylene chloride. The organic phase was dried over sodium sulfate, filtered and concentrated in vacuo to afford the product. EI-MS m/z 245 (M+H)$^+$ Step B: (Tert-butoxy)-N-((2-bromohenyl)methyl)-N-(3-hydroxyoroyl)carboxamide To a stirring solution of 3-(((2-bromophenyl)methyl)amino)propan-1-ol in methylene chloride (0.1 M) was added di-tert-butyl dicarbonate (1.1 eq). After 1 hr, the solvent was removed by rotary evaporation, and the residue partitioned between ether and 1N HCl. The ethereal portion was dried over sodium sulfate filtered and concentrated in vacuo to afford the product. EI-MS m/z 344 (M+H)$^+$ Step C: Methyl (2E)-5-(N-(tert-butoxycarbonyl)-N-((2-bromohenyl)methyl)amino)pent-2-enoate To a stirring solution of dimethyl sulfoxide (3.8 eq) in methylene chloride (0.1 M) at −78° C. was added oxalyl chloride (1.8 eq). After 10 min., (tert-butoxy)-N-((2-bromophenyl)methyl)-N-(3-hydroxypropyl)carboxamide (1 eq) was added. After stirring for 30 min., diisopropylethylamine (4 eq) was added, and the reaction was allowed to warm to RT. After 30 min, methyl (triphenylphosphoranylidene) acetate (1.2 eq) was added, and stirring was continued for 18 hr. The mixture was poured into water and extracted with ethyl acetate. The organic phase was washed with water and brine, dried over sodium Asulfate, filtered and concentrated in vacuo to afford the product. EI-MS m/z 398 (M+H)$^+$ Step D: Methyl 2-(2-(tert-butoxycarbonyl)-1H,3H,4H-benzo[e]azaverhydroepin-5-ylidene)acetate To a stirring solution of methyl (2E)-5-(N-(tert-butoxycarbonyl)-N-((2-bromophenyl)methyl)amino)pent-2-enoate in toluene (0.1 M) was added triethylamine (1.5 eq) and tetrakis(triphenylphosphine)p alladium (0.05 eq). The reaction was refluxed for 48 hr under nitrogen cooled to RT. The solvent was removed by rotary evaporation and the product was purified by flash chromatograpy (10% EtOAc/Hexane). EI-MS m/z 326 (M−H)$^-$ Step E: Methyl 2-(2-(tert-butoxycarbonyl)-1H,3H,4H,5H-benzo[e]azaperhydroepin-5-yl)acetate To a stirring solution of methyl 2-(2-(tert-butoxy carbonyl)-1H,3H,4H-benzo[e]azaperhydroepin-5-ylidene) acetate in methanol (0.1 M) was added magnesium turnings (10 eq) and the mixture was refluxed for 18 hr. The mixture was filtered through celite and concentrated by rotary evaporation. The product was purified by flash chromatography (25% EtOAc/Hexane). EI-MS m/z 318 (M+H)$^+$ Step F: Methyl 2-(1H,2H,3H,4H,5H-benzo[e]azaperhydroepin-5-yl)acetate Hydrochloride Methyl 2-(2-(tert-butoxycarbonyl)-1H,3H,4H,5H-benzo[e]azaperhydroepin-5-yl)acetate was dissolved in 4M HCl in dioxane (0.2 M). After 18 hrs, removal of solvent in vacuo, followed by trituration with ether afforded the product. EI-MS m/z 220 (M+H)$^+$

EXAMPLE 2

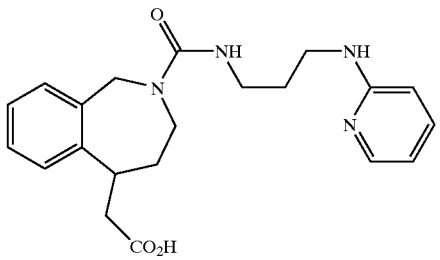

Preparation of 2-(2-(N-(3-(2-pyridylamino)propyl) carbamoyl)-1H,3H,4H,5H-benzo[e]azain-5-yl)acetic acid Step A: 2-(N-(3-aminoprop-1-yl)amino)pyridine To a stirring solution of 2-fluoropyridine in pyridine (0.5 M) was added 1,3-propanediamine (5 eq), and the solution was refluxed overnight. The solution was then concentrated in vacuo and the residue was partitioned between ethyl acetate and 10% sodium carbonate. The phases were separated, and the organic phase was washed with brine, dried over magnesium sulfate, filtered and concentrated in vacuo. The residue was chromatographed (silica; 10:1:1 EtOH/NH$_4$OH/H$_2$O) to afford a viscous pale yellow oil. EI-MS m/z 152 (M+H)$^+$ Step B: Methyl 2-(2-(N-(3-(2-pyridylamino)prop-1-yl)carbamoyl)-1H,3H,4H-5H-benzo[e]azapin-5-yl)acetate Methyl 2-(1H,2H,3H,4H,5H-benzo[e]azaperhydroepin-5-yl)acetate Hydrochloride was dissolved in methylene chloride and washed with 1N NaOH. The organic layer was separated, dried over sodium sulfate and concentrated by rotary evaporation. The residue was stirred under nitrogen with 20% phosgene in toluene (0.1 M) for 10 mins. After concentration by rotary evaporation, the residue was dissolved in THF (0.1 M), followed by addition of diisopropylethylamine (1.5 eq) and 2-(N-(3-aminoprop-1-yl)amino)pyridine (1.2 eq). The reaction was stirred for 18 hr under nitrogen, followed by concentration by rotary evaporation and the product was purified by flash chromatograpy (5% MeOH/CH$_2$Cl$_2$). EI-MS m/z 397 (M+H)$^+$ Step C: 2-(2-(N-(3-(2-pyridylamino)prop-1-yl) carbamoyl)-1H,3H,4H,5H-benzo[e]azain-5-yl)acetic acid To a stirring solution of methyl-2-(2-(N-(3-(2-pyridylamino)propyl)carbamoyl)-1H,3H,4H-5H-benzo[e]azapin-5-yl)acetate in methanol (0.1 M) was added 1N NaOH (3 eq). After 18 hrs, the reaction was neutralized with 10% HCl, concentrated by rotary evaporation and purified by recrystalization from 2% MeOH/CH$_2$Cl$_2$. EI-MS m/z 383 (M+H)$^+$; $^1$H—NMR (400 MHz, d6-DMSO): δ7.90 (d, J=4.4Hz, 1H), 7.31 (m, 2H), 7.25 (m, 2H), 7.06 (m, 1H), 6.48 (m, 4H), 4.48 (q, J=30 Hz, 2H), 3.53 (dd, J=6 Hz, 2H), 3.39 (d, J=7 Hz, 1H), 3.30 (m, 1H), 3.12 (m, 2H), 3.00 (m, 2H), 2.45 (d, J=5.5 Hz, 2H), 1.83 (m, 1H), 1.60 (m, 2H), 1.49 (m, 1H).

EXAMPLE 3

2-(2-(N-(4-(2-pyridylamino)butyl)carbamoyl)-1H, 3H,4H,5H-benzo[e]azapin-5-yl)acetic acid

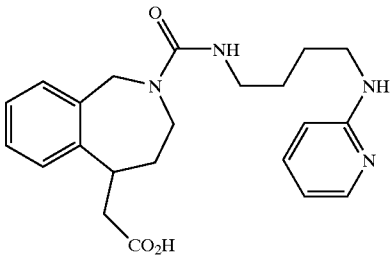

2-(2-(N-(4-(2-pyridylamino)but-1-yl)carbamoyl)-1H,3H,4H,5H-benzo[e]azapin-5-yl)acetic acid was prepared from 2-(N-(4-aminobut-1-yl)amino)pyridine and methyl 2-(1H,2H,3H,4H,5H-benzo[e]azaperhydroepin-5-yl)acetate according to the procedure of Example 2. EI-MS m/z 397 (M+H)$^+$; $^1$H-NMR (400 MHz, d6-DMSO): δ7.91 (d, J=4 Hz, 1H), 7.43(m, 2H), 7.19 (m, 3H), 6.48 (m, 3H), 6.32 (t, J=10 Hz, 1H), 4.48 (s, 2H), 3.52 (m, 2H), 3.41 (m, 2H), 3.17(d, J=5.4 Hz, 2H), 2.96 (m, 2H), 2.68 (m, 2H), 1.81 (m, 1H), 1.48 (m, 2H), 1.41 (m, 2H).

EXAMPLE 4

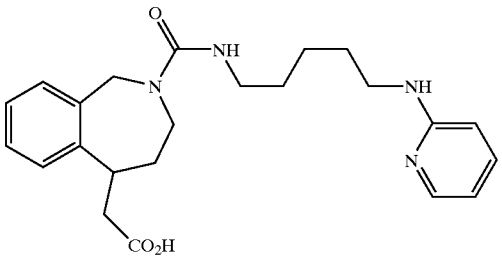

2-(2-(N-(5-(2-pyridylamino)pent-1-yl)carbamoyl)-1H,3H,4H,5H-benzo[e]azapin-5-yl)acetic acid 2-(2-(N-(5-(2-pyridylamino)pent-1-yl)carbamoyl)-1H, 3H,4H,5H-benzo[e]azapin-5-yl)acetic acid was prepared from 2-(N-(5-aminopent-1-yl)amino)pyridine and methyl 2-(1H,2H,3H,4H,5H-benzo[e]azaperhydroepin-5-yl)acetate according to the procedure of Example 2. EI-MS m/z 411 (M+H)$^+$; $^1$H-NMR (400 MHz, d6-DMSO): δ7.89 (d, J=1.4 Hz, 1H), 7.28 (m, 2H), 7.13–7.10 (m, 4H), 6.37 (m, 2H), 6.25 (t, J=5.3 Hz, 1H), 4.38 (s, 2H), 3.41 (m, 2H), 3.34 (m, 2H), 3.25(m, 2H), 3.09 (t, J=17 Hz, 2H), 2.61 (m, 2H), 1.75 (m, 1H), 1.40 (m, 2H), 1.29 (m, 2H), 1.03 (m, 2H).

EXAMPLE 5

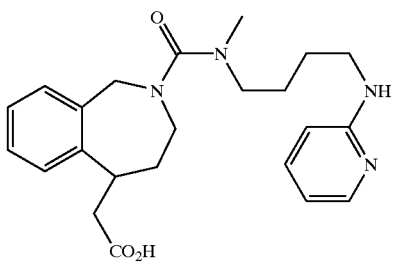

2-(2-(N-methyl—N-(4-(2-pyridylamino)but-1-yl)carbamoyl)-1H,3H,4H,5H-benzo[e]azapin-5-yl)acetic acid 2-(2-(N-methyl—N-(4-(2-pyridylamino)butyl)carbamoyl)-1H,3H,4H,5H-benzo[e]azapin-5-yl)acetic acid was prepared from 2-(N-(4-(methylamino)but-1-yl)amino) pyridine and methyl 2-(1H,2H,3H,4H,5H-benzo[e]azaperhydroepin-5-yl)acetate according to the procedure of Example 2. EI-MS m/z 411 (M+H)$^+$; $^1$H-NMR (400 MHz, d6-DMSO): δ8.08 (d, J=5 Hz, 1H), 7.50 (m, 1H), 7.41–7.23 (m, 5H), 6.60 (m, 2H), 4.50 (q, J=34 Hz, 2H), 3.68 (m, 2H), 3.35 (m, 3H), 3.13 (m, 1H), 2.87 (d, J=7 Hz, 2H), 2.69 (m, 5H), 2.11 (m, 1H), 1.88 (m, 1H), 1.69 (m, 1H), 1.41 (m, 2H).

EXAMPLE 6

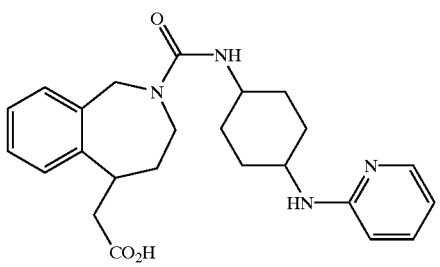

2-(2-(N-(4-(2-pyridylamino)-trans-cyclohexyl)carbamoyl)-1H,3H,4H,5H-benzo[e]azapin-5-yl)acetic acid 2-(2-(N-(4-(2-pyridylamino)-trans-cyclohexyl)carbamoyl)-1H,3H,4H,5H-benzo[e]azapin-5-yl)acetic acid was prepared from 2-(N-(trans-4-aminocyclohexyl)amino) pyridine and methyl 2-(1H,2H,3H,4H,5H-benzo[e]azaperhydroepin-5-yl)acetate according to the procedure of Example 2. EI-MS m/z 423 (M+H)$^+$; $^1$H-NMR (400 MHz, d4-D$_3$OD): δ7.70 (d, J=4.6 Hz, 1H), 7.50 (m, 1H), 7.20–6.85 (m, 6H), 6.42 (m, 2H), 4.45 (q, J=9 Hz, 2H), 4.38 (m, 1H), 3.52 (m, 1H), 3.41 (m, 4H), 2.61 (m, 3H), 1.91 (m, 3H), 1.76 (m, 2H), 1.50 (m, 1H), 1.39–1.11 (m, 3H).

EXAMPLE 7

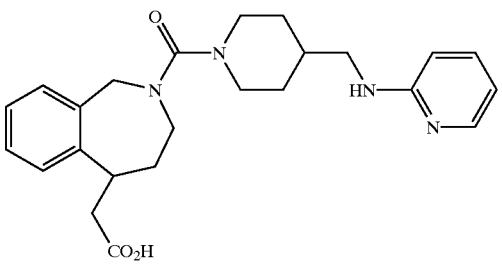

2-(2-(((4-(2-pyridylamino)methyl)piperid-1-yl)carbonyl)-1H,3H,4H,5H-benzo[e]azapin-5-yl)acetic acid 2-(2-(((4-(2-pyridylamino)methyl)piperid-1-yl)carbonyl)-1H,3H,4H,5H-benzo[e]azapin-5-yl)acetic acid was prepared from 2-(N-(piperid-4-ylmethyl)amino) pyridine and methyl 2-(1H,2H,3H,4H,5H-benzo[e]azaperhydroepin-5-yl)acetate according to the procedure of Example 2. EI-MS m/z 423 (M+H)$^+$; $^1$H-NMR (400 MHz, d6-DMSO): δ8.02 (d, J=4.5 Hz, 1H), 7.43 (t, J=16 Hz, 1H), 7.29 (d, J=7 Hz, 1H), 7.20–6.96 (m, 3H), 6.74 (d, J=12 Hz, 1H), 6.50 (t, J=8 Hz, 1H), 4.42 (q, J=24 Hz, 2H), 4.20 (d, J=12 Hz, 2H), 3.70–3.20 (m, 4H), 2.85 (m, 2H), 2.62 (t, J=24 Hz, 2H), 2.31 (d, J=7 Hz, 2H), 1.79 (m, 1H), 1.59 (m, 2H), 1.47 (m, 1H), 0.99 (q, J=11 Hz, 2H).

EXAMPLE 8

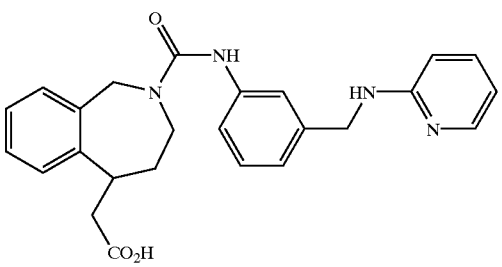

2-(2-(N-(3-(2-pyridylamino)methylphenyl)carbamoyl)-1H,3H,4H,5H-benzo[e]azapin-5-yl)acetic acid 2-(2-(N-(3-(2-pyridylamino)methylphenyl)carbamoyl)-1H,3H,4H,5H-benzo[e]azapin-5-yl)acetic acid was prepared from 2-(N-((3-aminophenyl)methyl)amino) pyridine and methyl 2-(1H,2H,3H,4H,5H-benzo[e]azaperhydroepin-5-yl)acetate according to the procedure of Example 2. EI-MS m/z 431 (M+H)$^+$; $^1$H-NMR (400 MHz, d6-DMSO): δ8.02 (s, 1H), 7.84 (m, 1H), 7.32 (s, 1H), 7.00 (m, 4H), 6.83 (m, 1H), 6.78 (d, J=7.5 Hz, 1H), 6.30 (m, 2H), 4.51 (q, J=8.5 Hz, 2H), 4.26 (s, 2H), 3.56 (s, 2H), 3.38 (m, 1H), 2.60 (m, 2H), 1.80 (m, 1H), 1.48 (m, 1H).

EXAMPLE 9

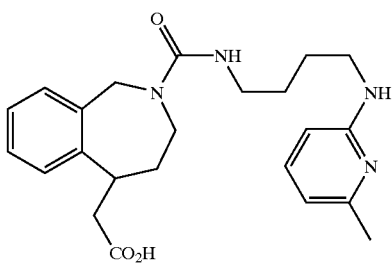

2-(2-(N-(4-((6-methyl-2-pyridyl)amino)but-1-yl)
carbamoyl)-1H,3H,4H,5H-benzo[e]azapin-5-yl)
acetic acid 2-(2-(N-(4-((6-methyl-2-pyridyl)amino)but-1-yl)
carbamoy)l-1H,3H,4H,5H-benzo[e]azapin-5-yl)acetic acid
was prepared from 6-methyl-2-(N-(4-aminobut-1-yl)amino)
pyridine and methyl 2-(1H,2H,3H,4H,5H-benzo[e]
azaperhydroepin-5-yl)acetate according to the procedure of
Example 2. EI-MS m/z 411 (M+H)$^+$; $^1$H-NMR (400 MHz,
d6-DMSO): δ7.52 (m, 1H), 7.32 (d, J=7 Hz, 1H), 7.14 (m,
4H), 6.41 (m, 2H), 6.32 (m, 1H), 4.48 (s, 2H), 3.59 (s, 2H),
3.41 (m, 2H), 3.20 (m, 2H), 2.99 (m, 2H), 2.70 (q, J=17 Hz,
2H), 2.34 (s, 3H), 1.82 (m, 1H), 1.47 (m, 4H).

EXAMPLE 10

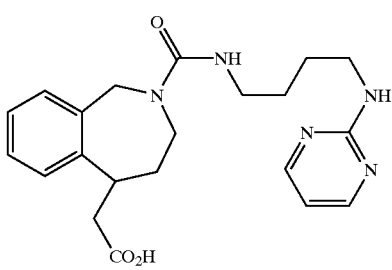

2-(2-(N-(4-(pyrimidin-2-ylamino)but-1-yl)
carbamoyl)-1H,3H,4H,5H-benzo[e]azapin-5-yl)
acetic acid 2-(2-(N-(4-(pyrimidin-2-ylamino)but-1-yl)carbamoyl)-
1H,3H,4H,5H-benzo[e]azapin-5-yl)acetic acid was prepared
from 6-methyl-2-(N-(4-aminobut-1-yl)amino)pyrimidine
and methyl 2-(1H,2H,3H,4H,5H-benzo[e]azaperhydroepin-
5-yl)acetate according to the procedure of Example 2.
EI-MS m/z 398 (M+H)$^+$; $^1$H-NMR (400 MHz, d6-DMSO):
δ8.07 (d, J=4.4 Hz, 1H), 7.25–6.82 (m, 5H), 6.36 (t, J=10
Hz, 1H), 6.12 (m, 1H), 4.26 (s, 2H), 3.31 (s, 2H), 3.21 (m,
2H), 3.00 (t, J=6 Hz, 2H), 2.78 (m, 2H), 2.50 (q, J=48 Hz,
2H), 1.62 (m, 1H), 1.22 (m, 4H).

EXAMPLE 11

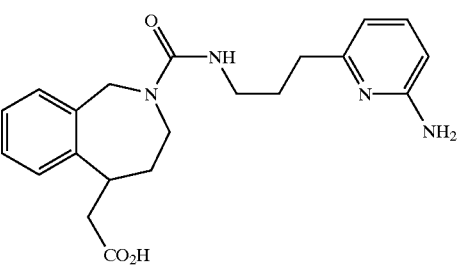

2-(2-(N-(3-(6-amino-2-pyridyl)prop-1-yl)
carbamoyl)-1H,3H,4H,5H-benzo[e]azapin-5-yl)
acetic acid Hydrochloride 2-(2-(N-(3-(6-amino-2-pyridyl)prop-1-yl)carbamoyl)-
1H,3H,4H,5H-benzo[e]azapin-5-y)acetic acid hydrochlo-
ride was prepared from 6-amino-2-(3-aminoprop-1-yl)
pyridine and methyl 2-(1H,2H,3H,4H,5H-benzo[e]
azaperhydroepin-5-yl)acetate according to the procedure of
Example 2. EI-MS m/z 383 (M+H)$^+$; $^1$H-NMR (400 MHz,
d4-CD$_3$OD): δ7.90 (t, J=8.7 Hz, 1H), 7.42 (d, J=7.1 Hz, 1H),
7.30 (m, 3H), 6.91 (d, J+8.1 Hz, 3H), 6.32 (d, J=7.2 Hz, 1H),
4.69 (q, J=30 Hz, 2H), 3.80 (m, 1H), 3.69 (m, 2H), 3.37 (t,
J=12 Hz, 2H), 2.91 (m, 2H), 2.72 (t, J=14 Hz, 2H), 2.17 (m,
1H), 1.92 (t, J=14 Hz, 2H), 1.70 (m, 1H).

EXAMPLE 12

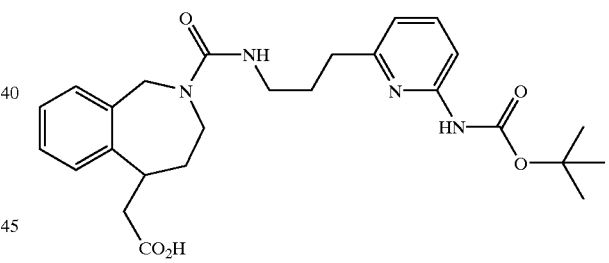

2-(2-(N-(3-(6-(tert-butoxycarbonylamino)-2-pyridyl)
proyl)carbamoyl)-1H,3H,4H,5H-benzo[e]azapin-5-
yl)acetic acid 2-(2-(N-(3-(6((tert-butoxy)carbonylamino)-2-pyridyl)
propyl)carbamoyl)-1H,3H,4H,5H-benzo[e]azapin-5-yl)
acetic acid was prepared from 6-(tert-
butoxycarbonylamino)-2-(3-aminoprop-1-yl)pyridine and
methyl 2-(1H,2H,3H,4H,5H-benzo[e]azaperhydroepin-5-
yl)acetate according to the procedure of Example 2. EI-MS
m/z 483 (M+H)$^+$; $^1$H-NMR (400 MHz, d4-CD$_3$OD): δ7.63
(m, 2H), 7.30 (d, J=7 Hz, 1H), 7.27–7.12 (m, 4H), 6.82 (d,
J=7. Hz, 1H), 4.55 (q, J=53 Hz, 2H), 3.68 (m, 1H), 3.56 (m,
2H), 3.20 (t, J=16 Hz, 2H), 2.76 (m, 2H), 2.63 (t, J=15 Hz,
2H), 2.04 (m, 1H), 1.86 (t, J=15 Hz, 2H), 1.59 (s, 9H), 1.32
(m, 1H).

EXAMPLE 13

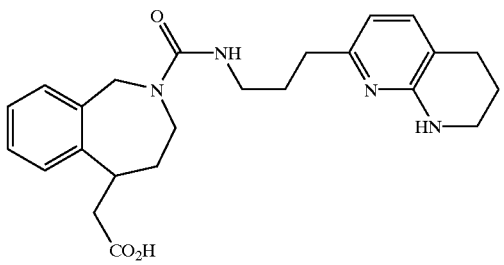

2-(2-(N-(3-(1,2,3,4-tetrahydropyridino(2,3-b)pyridin-7-yl)prop-1-yl)carbamoyl)-1H,3H,4H,5H-benzo[e]azapin-5-yl)acetic acid 2-(2-(N-(3-(1,2,3,4-tetrahydropyridino(2,3-b)pyridin-7-yl)prop-1-yl)carbamoyl)-1H,3H,4H,5H-benzo[e]azapin-5-yl)acetic acid was prepared from 3-(1,2,3,4-tetrahydropyridino[2,3-b]pyridin-7-yl)prop-1-ylamine and methyl 2-(1H,2H,3H,4H,5H-benzo[e]azaperhydroepin-5-yl)acetate according to the procedure of Example 2. 3-(1,2,3,4-tetrahydropyridino[2,3-b]pyridin-7-yl)prop-1-ylamine was prepared according to Duggan, M. E. WO 98/18460. EI-MS m/z 423 (M+H)+; $^1$H-NMR (400 MHz, d6-DMSO): δ7.30–6.98 (m, 5H), 6.30 (m, 1H), 6.20 (d, J=7 Hz, 1H), 4.41 (q, J=36 Hz, 2H), 3.60 (m, 1H), 3.40 (m, 2H), 3.24 (t, J=11 Hz, 2H), 2.94 (m, 2H), 2.61 (t, J=13 Hz, 2H), 2.36 (t, J=15 Hz, 2H), 2.28 (d, J=7 Hz, 2H), 1.80 (m, 3H), 1.64 (t, J=8 Hz, 2H), 1.40 (m, 1H).

EXAMPLE 14

Preparation of 2-(2-(((4-(2-pyridylamino)but-1-yl)amino)sulfonyl)-1H,3H,4H,5H-benzo[e]azapin-5-yl)acetic acid

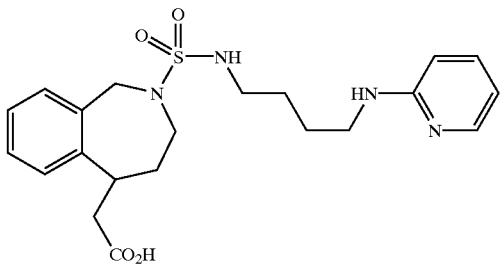

Step A: 2-Hydroxyohenyl ((4-(2-pyridylamino)butyl)amino)sulfonate

To a stirring solution of N-(2-pyridyl)-1,4 butanediamine and triethylamine (1.1 eq) in dimethylformamide (0.15 M) at 0° C. was added catechol sulfate (1.1 eq) in methylene chloride (0.15 M). After 3 hrs, the reaction was poured into water and extracted with diethyl ether. The ethereal extract was dried over magnesium sulfate, filtered and concentrated in vacuo to afford the product. EI-MS m/z 338 (M+H)+

Step B: Methyl 2-(((4-(2-pyridylamino)but-1-yl)amino)sulfonyl)-1H,3H,4H,5H-benzo[e]azapin-5-yl)acetate 2-Hydroxyphenyl ((4-(2-pyridylamino)but-1-yl)amino)sulfonate (1 eq) and methyl 2-(1H,2H,3H,4H,5H-benzo[e]azaperhydroepin-5-yl)acetate (1 eq) were dissolved in dioxane (0.1 M) and refluxed under nitrogen for 5 hr. Removal of solvent by rotary evaporation and flash chromatography (5% MeOH in CH$_2$Cl$_2$) afforded the product. EI-MS m/z 447 (M+H)+

Step C: 2-(2-(((4-(2-pyridylamino)but-1-yl)amino)sulfonyl)-1H,3H,4H,5H-benzo[e]azapin-5-yl)acetic acid Methyl 2-(2-(((4-(2-pyridylamino)but-1-yl)amino)sulfonyl)-1H,3H,4H,5H-benzo[e]azapin-5-yl)acetate was saponified according to the procedure of Example 2. EI-MS m/z 433 (M+H)+; $^1$H-NMR (400 MHz, d6-DMSO): δ7.80 (d, J=4 Hz, 1H), 7.19 (t, J=14 Hz, 1H), 7.13–6.92 (m, 5H), 6.38 (m,1H), 6.30 (m, 2H), 4.25 (q, J=32 Hz, 2H), 3.42 (m, 1H), 3.36 (m, 1H), 3.04 (m, 2H), 2.46 (m, 2H), 2.28 (m, 2H), 1.75 (m, 1H), 1.41 (m, 1H), 1.28 (m, 4H).

EXAMPLE 15

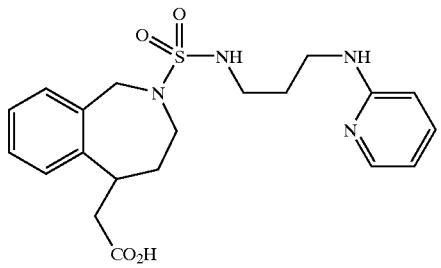

2-(2-(((3-(2-pyridylamino)prop-1-yl)amino)sulfonyl)-1H,3H,4H,5H-benzo[e]azapin-5-yl)acetic acid 2-(2-(((3-(2-pyridylamino)propyl)amino)sulfonyl)-1H,3H,4H,5H-benzo[e]azapin-5-yl)acetic acid was prepared from 2-hydroxyphenyl ((3-(2-pyridylamino) prop-1-yl)amino)sulfonate and methyl 2-(1H,2H,3H,4H,5H-benzo[e]azaperhydroepin-5-yl)acetate according to the procedure of Example 14. EI-MS m/z 419 (M+H)+; $^1$H-NMR (400 MHz, d6-DMSO): δ7.95 (d, J=4.3 Hz, 1H), 7.35 (t, J=14 Hz, 1H), 7.26–7.06 (m, 5H), 6.57 (m, 1H), 6.41 (t, J=13 Hz, 2H), 4.38 (q, J=41 Hz, 2H), 3.58 (m, 3H), 3.19 (t, J=3.5 Hz, 2H), 2.70 (t, J=3 Hz, 2H), 2.38 (d, J=7 Hz, 2H), 1.88 (m, 1H), 1.60 (m, 2H), 1.50 (m, 2H).

EXAMPLE 16

Preparation of 2-(2-(2-((2-(2-pyridylamino)ethyl)amino)acetyl)-1H,3H,4H,5H-benzo[e]azain-5-yl)acetic acid

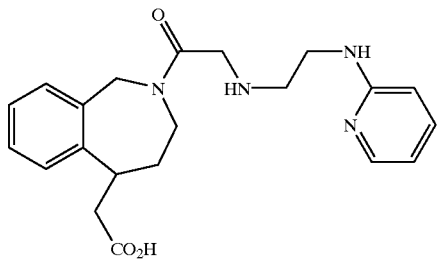

Step A: Methyl 2-(2-(2-Bromoacetyl)-1H,3H,4H,5H-benzo[e]azalin-5-yl)acetate

To a stirring solution of methyl 2-(1H,2H,3H,4H,5H-benzo[e]azaperhydroepin-5-yl)acetate hydrochloride in THF (0.1 M) was added diisopropylethylamine (1.5 eq). The reaction was stirred for 15 min, followed by addition of bromoacetyl bromide (1.1 eq). After 30 min, the reaction was diluted with methylene chloride and washed with 10% HCl, water and brine. The organic layer was separated, dried over sodium sulfate and concentrated by rotary evaporation.

The residue was purified by flash chromatography (50% EtOAc/Hexane).

Step B: Methyl 2-(2-(2-((2-(2-pyridylamino)ethyl) amino) acetyl)-1H,3H,4H,5H-benzo[e]azapin-5-yl)acetate To a stirring solution of methyl 2-(2-(2-bromoacetyl)-1H,3H,4H,5H-benzo[e]azapin-5-yl)acetate in THF (0.2 M), was added diisopropylethylamine (1.5 eq) and 2-(2-pyridylamino)-1-aminoethane (1.2 eq). The reaction was stirred for 18 hr, followed by concentration by rotary evaporation and the product was purified by flash chromatography (10% MeOH/CH$_2$Cl$_2$). EI-MS m/z 397 (M–H)$^-$ Step C: 2-(2-(2-((2-(2-pyridylamino)ethyl)amino) acetyl)-1H,3H,4H,5H-benzo[e]azapin-5-yl)acetic acid Methyl 2-(2-(2-((2-(2-pyridylamino)ethyl)amino) acetyl)-1H,3H,4H,5H-benzo[e]azapin-5-yl)acetate was saponified according to the procedure of Example 2. $^1$H-NMR (400 MHz, d4-CD$_3$OD): δ7.90 (m, 2H), 7.43–7.11 (m, 5H), 6.97 (m, 1H), 4.69 (q, J=18 Hz, 2H), 4.19 (m, 1H), 3.83 (m, 2H), 3.65 (m, 1H), 3.55 (m, 1H), 3.38 (m, 2H), 3.34 (s, 2H), 2.83 (m, 2H), 2.04 (m, 1H), 1.69 (m, 1H).

EXAMPLE 17

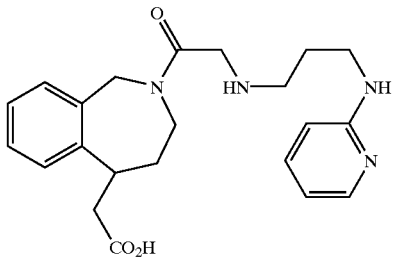

2-(2-(2-((3-(2-pyridylamino)prop-1-yl)amino)acetyl-1H,3H,4H,5H-benzo[e]azapin-5-yl)acetic acid 2-(2-(2-((3-(2-pyridylamino)prop-1-yl)amino)acetyl-(1H,3H,4H,5H-benzo[e]azapin-5-yl)acetic acid was prepared from 3-(2-pyridylamino)-1-aminopropane and methyl 2-(2-(2-bromoacetyl)-1H,3H,4H,5H-benzo[e]azepin-5-yl)acetate according to the procedure of Example 16. $^1$H-NMR (400 MHz, d4-CD$_3$OD): δ7.39–7.04 (m, 6H), 6.44 (m, 2H), 4.60 (m, 2H), 3.91 (m, 1H), 3.58 (m, 2H), 3.39 (m, 2H), 3.29 (s, 2H), 2.95 (m, 2H), 2.59 (m, 2H), 1.95 (m, 1H), 1.85 (m, 2H), 1.60 (m, 2H).

EXAMPLE 18

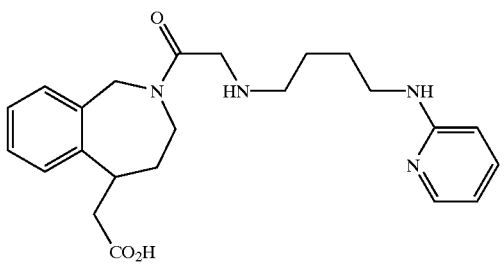

2-(2-(2-((4-(2-pyridylamino)but-1-yl)amino)acetyl-1H,3H,4H,5H-benzo[e]azapin-5-yl-acetic acid 2-(2-(2-((4-(2-pyridylamino)but-1-yl)amino)acetyl-1H,3H,4H,5H-benzo[e]azapin-5-yl)acetic acid was prepared from 4-(2-pyridylamino)-1-aminobutane and methyl 2-(2-(2-bromoacetyl)-1H,3H,4H,5H-benzo[e]azepin-5-yl)acetate according to the procedure of Example 16. $^1$H-NMR (400 MHz, d6-DMSO): δ7.96(m, 1H), 7.39–7.09 (m, 6H), 6.46 (m, 1H), 6.40 (m, 2H), 4.61 (m, 2H), 3.74 (s, 2H), 3.60 (m, 1H), 3.49 (m, 1H), 3.18 (m, 3H), 2.66 (m, 4H), 1.89 (m, 1H), 1.52 (m, 5H).

EXAMPLE 19

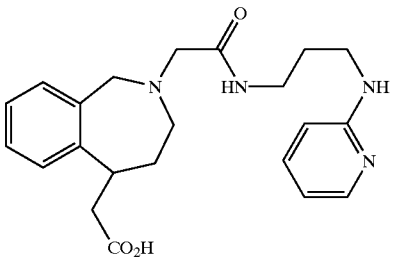

2-(2-((N-(3-(2-pyridylamino)prop-1-yl)carbamoyl) methyl)-1H,3H,4H,5H-benzo[e]azapin-5-yl)acetic acid 2-(2-((N-(3-(2-pyridylamino)propyl)carbamoyl)methyl)-1H,3H,4H,5H-benzo[e]azapin-5-yl)acetate was prepared from 3-(2-pyridylamino)-1-(2-bromoacetylamino)propane and methyl 2-(1H,2H,3H,4H,5H-benzo[e]azaperhydroepin-5-yl)acetate hydrochloride in a manner similar to the procedure of Example 16, Step B. 3-(2-pyridylamino)-1-(2-bromoacetylamino)propane was prepared from 3-(2-pyridylamino)-1-aminopropane and bromoacetyl bromide in a manner similar to the procedure of Example 16, Step A. $^1$H-NMR (400 MHz, d6-DMSO): δ7.90 (m, 1H), 7.82 (m, 1H), 7.30 (m, 1H), 7.16 (m, 1H), 7.08 (m, 3H), 6.44 (m, 1H), 6.39 (m, 2H), 3.86 (m, 2H), 3.43 (m, 1H), 3.24 (m, 2H), 3.18(m, 2H), 3.02 (s, 2H), 2.86 (m, 2H), 2.70 (m, 2H), 1.65 (m, 1H), 1.60 (m, 3H).

EXAMPLE 20

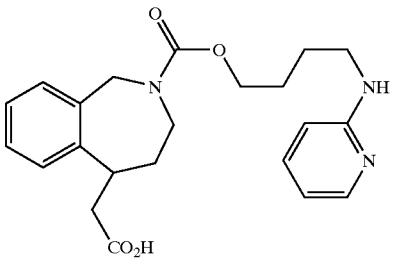

Preparation of 2-(2-(4-(2-pyridylamino)but-1-oxy carbonyl)-1H,3H,4H,5H-benzo[e]azapin-5-yl)acetic acid Step A: Methyl 2-(2-(4-(2-pyridylamino)but-1-oxycarbonyl)-1H,3H,4H,5H-benzo[e]azapin-5-yl)acetate To a stirring solution of methyl 2-(1H,2H,3H,4H,5H-benzo[e]azaperhydroepin-5-yl)acetate hydrochloride in methylene chloride (0.2 M), was added dimethylaminopyridine (2 eq) and 4-(2-pyridylamino)butyl 4-nitrophenyl carbonate (1.1 eq). The reaction was stirred for 18 hr under nitrogen, diluted with methylene chloride, washed with sodium carbonate, dried over sodium sulfate, filtered and concentrated in vacuo. Flash chromatograpy (4% MeOH/CH$_2$Cl$_2$) afforded the product. EI-MS m/z 412 (M+H)$^+$ Step B: 2-(2-(4-(2-pyridylamino)but-1-oxycarbonyl)-1H, 3H,4H,5H-benzo[e]azapin-5-yl)acetic acid Methyl 2-(2-(4-(2-pyridylamino)but-1-oxycarbonyl)-1H, 3H,4H,5H-benzo[e]azapin-5-yl)acetate was saponified according to the procedure of Example 2. EI-MS m/z 397 (M+H)⁺; ¹H-NMR (400 MHz, d6-DMSO): δ7.90 (m, 1H), 7.30 (m, 1H), 7.22–7.01 (m, 5H), 6.39 (m, 2H), 4.42 (q, J=30 Hz, 2H), 3.91 (m, 2H), 3.69 (m, 1H), 3.57 (m, 1H), 3.46 (m, 2H), 3.28 (m, 2H), 2.69 (m, 2H), 1.76 (m, 1H) 1.60 (m, 5H).

EXAMPLE 21

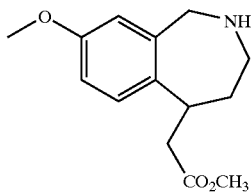

Preparation of Methyl 2-(8-methoxy-1H,2H,3H,4H, 5H-benzo[e]azaperhydroepin-5-yl) acetate Step A: Methyl 2-bromo-5-methoxybenzoate Sulfuric acid (2 eq) was added to a solution of 2-bromo-5-methoxybenzoic acid (1 eq) in methanol (0.30 M) at 0° C. under $N_2$. The solution was allowed to warm to RT and then refluxed for 5 h. After cooling to RT, the solution was concentrated in vacuo, the residue dissolved in ethyl acetate and washed with 1N NaOH solution (2×). The combined aqueous layers were extracted with ethyl acetate and the combined organics dried over $MgSO_4$. Concentration in vacuo gave methyl 2-bromo-5-methoxybenzoate as a clear oil. EI-MS m/z 245, 247 (M+H)⁺

Step B: 2-Bromo-5-methoxybenzyl alcohol

Lithium aluminum hydride (1.3 eq) was added in portions to a solution of methyl 2-bromo-5-methoxy benzoate (1 eq) in diethyl ether (0.35 M) at 0° C. under $N_2$ and the resulting mixture allowed to warm to RT with stirring for 5 h. Quenched with H2O (3×g LAH), followed sequentially by 15% NaOH solution (3×g LAH), and $H_2O$ (3×g LAH). The solution was filtered through a scintered glass funnel rinsing with diethyl ether and concentrated in vacuo to give 2-bromo-5-methoxybenzyl alcohol as a clear oil. EI-MS m/z 239, 241 (M+Na)⁺

Step C: 2-Bromo-5-methoxybenzaldehyde

Pyridinium Chlorochromate (1.2 eq) was added to a solution of 2-bromo-5-methoxybenzyl alcohol (1 eq) and Celite (1.2 eq) in methylene chloride (0.30 M) at RT and the resulting mixture was stirred under nitrogen for 3 h. The mixture was filtered through a plug of silica rinsing with methylene chloride and concentrated in vacuo to give 2-bromo-5-methoxy benzaldehyde as a white solid. EI-MS m/z 232, 234 (M+NH$_4$)⁺

Step D: 3-(((2-bromo-5-methoxyphenyl)methyl)amino) propan-1-ol

To a stirred solution of 2-bromo-5-methoxybenzaldehyde (1 eq) in dichloroethane was added 3-aminopropanol (1.5 eq) followed by NaBH(OAc)$_3$ (2 eq) and acetic acid (4 eq) and the resulting mixture was stirred at RT under nitrogen for 8 h. The reaction mixture was quenched by careful addition of 2M Na$_2$CO$_3$ solution and stirred 1 h. The mixture was concentrated in vacuo and poured into diethyl ether. The phases were separated and the organic phase washed with 1N HCl solution. The aqueous phase was then washed with diethyl ether and subsequently basified with 1N NaOH solution. The aqueous phase was extracted with diethyl ether, dried over Na$_2$SO$_4$ and concentrated in vacuo to give 3-(((2-bromo-5-methoxyphenyl)methyl) amino)propan-1-ol as a clear oil. EI-MS m/z 274, 276 (M+H)⁺

Step E: N-(tert-butoxycarbonyl)-N-((2-bromo-5-methoxyhenyl)methyl)-N-(3-hydroxwropyl)amine Di-tert-butyl dicarbonate (1.1 eq) was added to a solution of 3-(((2-bromo-5-methoxyphenyl)methyl)amino) propan-1-ol (1 eq) in methylene chloride (0.30M) at RT and the resulting mixture stirred under nitrogen 2 h. Concentration in vacuo and purification by flash chromatography (20–30% ethyl acetate/hexane) gave N-(tert-butoxycarbonyl)-N-((2-bromo-5-methoxyphenyl) methyl)-N-(3-hydroxypropyl)amine as a clear oil. EI-MS m/z 374, 376 (M+H)⁺

Step F: Methyl (2E)-5-((tert-butoxy)-N-((2-bromo-5-methoxyphenyl)methyl)carbonylamino)pent-2-enoate Oxalyl chloride (1.8 eq) was added to a stirred solution of dimethylsulfoxide (3.8 eq) in methylene chloride (0.25 M) at −78° C. maintaining the temperature<−65° C. After 20 min, a solution of N-(tert-butoxycarbonyl)-N-((2-bromo-5-methoxyphenyl)methyl)-N-(3-hydroxypropyl)amine (1 eq) was added and the resulting mixture stirred 30 minutes. Hunig's base (4 eq) was added and the reaction was allowed to warm to RT. The mixture was then cooled to 15° C. and methyl (triphenylphosphoranylidene)acetate was added. The resulting mixture was stirred 12 h and purified by flash chromatography on silica gel (10–20% ethyl acetate/hexane) to give methyl (2E)-5-((tert-butoxy)-N-((2-bromo-5-methoxyphenyl)methyl)carbonylamino)pent-2-enoate as a clear oil. EI-MS m/z 428, 430 (M+H)⁺

Step G: Methyl 2-(2-(tert-butoxycarbonyl)-8-methoxy-1H, 3H,4H-benzo[e]azaperhydroepin-5-ylidene)acetate Triethylamine (1.5 eq) was added to a solution of methyl (2E)-5-((tert-butoxy)-N-((2-bromo-5-methoxy phenyl) methyl)carbonylamino)pent-2-enoate (1 eq), palladium acetate (0.10 eq), and tri-o-tolylphosphine (0.20 eq) in acetonitrile (0.1 M) and the resulting mixture refluxed under argon for 48 h. Concentration in vacuo and purification by flash chromatography on silica gel (10–20% ethyl acetate/hexane) gave methyl 2-(2-(tert-butoxycarbonyl)-8-methoxy-1H,3H,4H-benzo[e]azaperhydroepin-5-ylidene) acetate as a clear oil. EI-MS m/z 348 (M+H)⁺

Step H: Methyl 2-(2-(tert-butoxycarbonyl)-8-methoxy-1H, 3H,4H,5H-benzo[e]azaperhydroepin-5-yl)acetate Magnesium turnings (10 eq) were added to a solution of methyl 2-(2-(tert-butoxycarbonyl)-8-methoxy-1H,3H,4H-benzo[e] azaperhydroepin-5-ylidene)acetate (1 eq) in methanol (0.1 M) and the mixture refluxed under nitrogen for 24 h. After cooling to RT, the mixture was poured into 1 N HCl and extracted with ethyl acetate. The organics were dried over magnesium sulfate and concentrated in vacuo to give methyl 2-(2-((tert-butyl)oxycarbonyl)-8-methoxy-1H,3H,4H,5H-benzo[e]azaperhydroepin-5-yl)acetate as a clear oil. EI-MS m/z 350 (M+H)⁺

Step I: Methyl 2-(8-methoxy-1H,2H,3H,4H,5H-benzo[e] azaTerhydroepin-5-yl)acetate Methyl 2-(2-(tert-butoxycarbonyl)-8-methoxy-1H,3H, 4H,5H-benzo[e]azaperhydroepin-5-yl)acetate (1 eq) and 4.0 M HCl/dioxane (12 eq) were stirred at RT under nitrogen for 3 h. The solvents were removed by rotary evaporation and the residue dissolved in methylene chloride and washed with 1N NaOH. The organics were dried over sodium sulfate and concentrated in vacuo to give methyl 2-(8-methoxy-1H,2H, 3H,4H,5H-benzo[e]azaperhydroepin-5-yl)acetate as a white solid. EI-MS m/z 250 (M+H)⁺

EXAMPLE 22

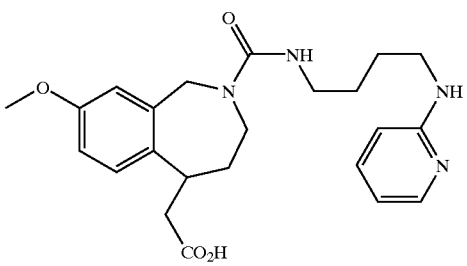

Preparation of 2-(8-methoxy-2-(N-(4-(2-pyridylamino)but-1-yl)carbamoyl)-1H,3H,4H,5H-benzo[e]azaerhydroepin-5-yl)acetic acid Step A: Methyl 2-(8-methoxy-2-(N-(4-(2-pyridylamino)but-1-yl)carbamoyl)-1H,3H,4H,5H-benzo[e]azaperhydroepin-5-yl)acetate Methyl 2-(8-methoxy-1H,2H,3H,4H,5H-benzo[e]azaperhydroepin-5-yl)acetate (1 eq) was stirred under nitrogen with 20% phosgene (1.1 eq) in toluene for 10 min. The excess phosgene was removed by rotary evaporation and the crude product was dissolved in THF (0.10 M), followed by addition of diisopropylethylamine (1.5 eq) and 2-(4-aminobut-1-ylamino)pyridine (1.5 eq). The reaction was stirred for 12 h at RT under nitrogen, concentrated in vacuo and the product was purified by flash chromatograpy (4–7% MeOH/CH$_2$Cl$_2$) to give methyl 2-(8-methoxy-2-(N-(4-(2-pyridylamino)but-1-yl)carbamoyl)-1H,3H,4H,5H-benzo[e]azaperhydroepin-5-yl)acetate as a clear oil. EI-MS m/z 441 (M+H)$^+$ Step B: 2-(8-methoxy-2-(N-(4-(2-pyridylamino)but-1-yl)carbamoyl)-1H,3H,4H,5H-benzo[e]azaperhydroepin-5-yl) acetic acid 1 N NaOH solution (2 eq) was added to a solution of methyl 2-(8-methoxy-2-(N-(4-(2-pyridylamino)but-1-yl)carbamoyl)-1H,3H,4H,5H-benzo[e]azaperhydroepin-5-yl) acetate (1 eq) in methanol (0.05 M) and the resulting mixture stirred under nitrogen for 12 h. The mixture was neutralized to pH=7 with 1N HCl solution and concentrated in vacuo. Purification by flash chromatography on silica gel (20% MeOH/80% CH$_3$Cl/1% AcOH) gave 2-(8-methoxy-2-(N-(4-(2-pyridylamino)but-1-yl)carbamoyl)-1H,3H,4H,5H-benzo[e]azaperhydroepin-5-yl)acetic acid as a white solid. EI-MS m/z 427 (M+H)$^+$; $^1$H NMR (400 MHz, D$_2$O) $\delta$7.76 (ddd, J 8.8, 7.2, 1.4 Hz, 1H), 7.64 (d, J=6.3 Hz, 1H), 6.98 (d, J=8.5 Hz, 1H), 6.81 (m, 3H), 6.58 (dd, J=8.4, 2.4 Hz, 1H), 4.38 (ABq, J=16.0 Hz, 2H), 3.67 (s, 3H), 3.57 (m, 2H), 3.33 (m, 1H), 3.07 (m, 4H), 2.63 (dd, J=14.8, 8.2 Hz, 1H), 2.53 (dd, J=14.8, 7.6 Hz, 1H), 1.81 (m, 1H), 1.55 (m, 1H), 1.40 (m, 2H), 1.27 (m, 2H).

EXAMPLE 23

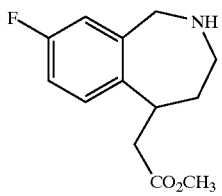

Preparation of Methyl 2-(8-fluoro-1H,2H,3H,4H,5H-benzo[e]azaperhydroeoin-5-yl)acetate Step A: 3-(((2-bromo-5-fluorophenyl)methyl)amino)propan-1-ol Hunig's base (1.3 eq) and 3-aminopropan-1-ol (1.3 eq) were added to a solution of 2-bromo-5-fluoro-benzyl bromide (1 eq) in acetonitrile (0.6 M) and the resulting mixture stirred at RT under nitrogen for 12 h. Concentrated in vacuo to give 3-(((2-bromo-5-fluorophenyl)methyl)amino)propan-1-ol as a clear oil. EI-MS m/z 262, 264 (M+H)$^+$ Step B: N-(tert-butoxycarbonyl)-N-((2-bromo-5-fluorophenyl)methyl)-N-(3-hydroxypronyl)amine Di-tert-butyl dicarbonate (1.1 eq) was added to a solution of 3-(((2-bromo-5-fluorophenyl)methyl)amino) propan-1-ol (1 eq) in methylene chloride (0.50M) at RT and the resulting mixture stirred under nitrogen 5 h. Concentration in vacuo and purification by flash chromatography on silica gel (20–30% ethyl acetate/hexane) gave N-(tert-butoxycarbonyl)-N-((2-bromo-5-fluorophenyl)methyl)-N-(3-hydroxypropyl)amine as a clear oil. EI-MS m/z 362, 364 (M+H)$^+$ Step C: Methyl (2E)-5-(N-(tert-butoxycarbonyl)-N-((2-bromo-5-fluorophenyl)methyl)amino)pent-2-enoate Oxalyl chloride (1.8 eq) was added to a stirred solution of dimethylsulfoxide (3.8 eq) in methylene chloride (0.25 M) at −78° C. maintaining the temperature<−65° C. After 20 min, a solution of N-(tert-butoxycarbonyl)-N-((2-bromo-5-fluorophenyl)methyl)-N-(3-hydroxypropyl)amine (1 eq) was added and the resulting mixture stirred 30 minutes. Hunig's base (4 eq) was added and the reaction allowed to warm to RT. The mixture was then cooled to 15° C. and methyl (triphenylphosphoranylidene)acetate was added. The resulting mixture was stirred 12 h and purified by flash chromatography on silica gel (10–20% ethyl acetate/hexane) to give methyl (2E)-5-(N-(tert-butoxycarbonyl)-N-((2-bromo-5-fluorophenyl)methyl) amino)pent-2-enoate as a clear oil. EI-MS m/z 474, 476 (M−H+HOAc)$^-$ Step D: Methyl 2-(2-(tert-butoxycarbonyl)-8-fluoro-1H,3H,4H-benzo[e]azaperhydroeoin-5-ylidene)acetate Triethylamine (1.5 eq) was added to a solution of methyl (2E)-5-(N-(tert-butoxycarbonyl)-N-((2-bromo-5-fluorophenyl)methyl)amino)pent-2-enoate (1 eq), palladium acetate (0.10 eq), and tri-o-tolylphosphine (0.20 eq) in acetonitrile (0.1 M) and the resulting mixture refluxed under argon for 48 h. Concentration in vacuo and purification by flash chromatography on silica gel (5–10% ethyl acetate/hexane) gave methyl 2-(2-(tert-butoxycarbonyl)-8-fluoro-1H,3H,4H-benzo[e]azaperhydroepin-5-ylidene)acetate as a clear oil. EI-MS m/z 336 (M+H)$^+$ Step E: Methyl 2-(2-(tert-butoxycarbonyl)-8-fluoro-1H,3H,4H,5H-benzo[e]azaperhydroepin-5-yl)acetate Magnesium turnings (10 eq) were added to a solution of methyl 2-(2-(tert-butoxycarbonyl)-8-flouro-1H,3H,4H-benzo[e]azaperhydroepin-5-ylidene)acetate (1 eq) in methanol (0.1 M) and the mixture refluxed under nitrogen for 24 h. After cooling to RT, the mixture was poured into 1 N HCl and extracted with ethyl acetate. The organics were dried over magnesium sulfate and concentrated in vacuo to give methyl 2-(2-(tert-butoxycarbonyl)-8-fluoro-1H,3H,4H,5H-benzo[e]azaperhydroepin-5-yl)acetate as a clear oil. EI-MS m/z 338 (M+H)$^+$ Step F: Methyl 2-(8-fluoro-1H,2H,3H,4H,5H-benzo[e]azaoerhydroepin-5-yl)acetate Methyl 2-(2-(tert-butoxycarbonyl)-8-fluoro-1H,3H,4H,5H-benzo[e]azaperhydroepin-5-yl)acetate (1 eq) and 4.0 M HCl/dioxane (12 eq) were stirred at RT under nitrogen for 3 h. The solvents were removed by rotary evaporation and the residue dissolved in methylene chloride and washed with 1N NaOH. The organics were dried over sodium sulfate and concentrated in vacuo to give methyl 2-(8-fluoro-1H,2H,3H,4H,5H-benzo[e]azaperhydroepin-5-yl)acetate as a clear oil. EI-MS m/z 238 (M+H)$^+$

EXAMPLE 24

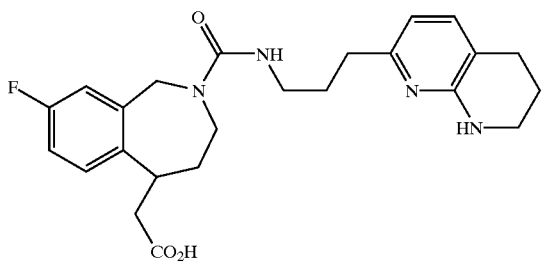

Preparation of 2-(8-fluoro-2-(N-(3-(1,2,3,4-tetrahydro pyridino [2,3,b]pyridin-7-yl)propyl) carbamoyl)-1H,3H,4H,5H-benzo[e]azaperhydroepin-5-yl)acetic acid Step A: Methyl 2-(8-fluoro-2-(N-(3-(1,2,3,4-tetrahydro pyridino[2,3,b]pyridin-7-yl)propyl)carbamoyl)-1H,3H,4H,5H-benzo[e]azaperhydroepin-5-yl)acetate Methyl 2-(8-fluoro-1H,2H,3H,4H,5H-benzo[e]azaperhydroepin-5-yl)acetate (1 eq) was stirred under nitrogen with 20% phosgene (1.1 eq) in toluene for 10 min. The excess phosgene was removed by rotary evaporation and the crude product was dissolved in 1:1 THF/DMF (0.25 M), followed by addition of diisopropylethylamine (1.1 eq) and 3-(1,2,3,4-tetrahydropyridino[2,3,b]pyridin-7-yl) propylamine (1.1 eq). The reaction was stirred for 12 h at RT under nitrogen, concentrated in vacuo and the product was purified by flash chromatograpy (2–5% MeOH/CH$_3$Cl) to give methyl 2-(8-fluoro-2-(N-(3-(1,2,3,4-tetrahydropyridino[2,3,b]pyridin-7-yl)propyl) carbamoyl)-1H,3H,4H,5H-benzo[e]azaperhydroepin-5-yl) acetate as a clear oil. EI-MS m/z 455 (M+H)$^+$ Step B: 2-(8-fluoro-2-(N-(3-(1,2,3,4-tetrahydro pyridino[2,3,b]pyridin-7-yl)proyl)carbamoyl)-1H,3H,4H,5H-benzo[e]azaperhydroepin-5-yl)acetic acid 1 N NaOH solution (3 eq) was added to a solution of methyl 2-(8-fluoro-2-(N-(3-(1,2,3,4-tetrahydropyridino [2,3,b]pyridin-7-yl)propyl) carbamoyl)-1H,3H,4H,5H-benzo[e]azaperhydroepin-5-yl) acetate (1 eq) in methanol (0.10 M) and the resulting mixture stirred under nitrogen for 12 h. The mixture was neutralized to pH=7 with 1N HCl solution and concentrated in vacuo. Purification by flash chromatography on silica gel (4–6% MeOH/CH$_2$Cl$_2$) gave 2-(8-fluoro-2-(N-(3-(1,2,3,4-tetrahydropyridino[2,3,b]pyridin-7-yl)propyl) carbamoyl)-1H,3H,4H,5H-benzo[e]azaperhydroepin-5-yl) acetic acid as a white solid. EI-MS m/z 441 (M+H)$^+$; $^1$H NMR (400 MHz, CDCl$_3$) δ10.56 (br s, 1H), 7.22 (d, J=7.3 Hz, 1H), 7.12 (dd, J=8.4, 5.8 Hz, 1H), 6.93 (dd, J=9.2, 2.2 Hz, 1H), 6.86 (t, J=8.4 Hz, 1H), 6.27 (d, J=7.3 Hz, 1H), 5.55 (br s, 1H), 4.90 (br s, 1H), 4.35 (d, J=15.2 Hz, 2H), 3.50 (m, 4H), 3.27 (m ,1H), 3.11 (m, 1H), 2.67 (m, 6H), 2.35 (m, 1H), 1.90 (m, 4H), 1.74 (m, 1H), 1.42 (m, 1H).

EXAMPLE 25

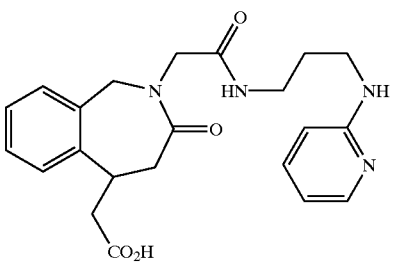

Preparation of 2-(2-({N-(4-(2-pyridylamino)prop-1-yl) carbamoyl}methyl)-3-oxo-1H,4H,5H-benzo(e) azepin-5-yl) acetic acid Step A: Trans-glutaconic Acid Methyl Ester To a stirring solution of glutaconic acid in DMF (0.1 M) at 0° C. was added NaH (1 eq). After 15 min, iodomethane (1.2 eq) was added, and the mixture was allowed to warm to room temperature overnight. The reaction was quenched with saturated ammonium chloride, and extracted with ethyl acetate. The organic phase was washed with water and brine, dried over magnesium sulfate, filtered and concentrated in vacuo. The residue was chromatographed (silica; 10% MeOH/CHCl$_3$) to afford a colorless viscous oil. EI-MS m/z 143 (M–H)$^-$ Step B: Benzyl 2-(N-(2-bromophenylmethyl)amino)acetate To a stirring solution of 2-bromobenzaldehyde in dichloromethane (0.2 M) was added glycine benzyl ester (1.2 eq), sodium triacetoxyborohydride (2 eq) and acetic acid (4 eq). After stirring overnight, the solution was washed with 10% sodium carbonate, dried over magnesium sulfate, filtered and concentrated in vacuo. The residue was chromatographed (silica; 30%–40% EtOAc/Hexanes) to afford a pale yellow oil. EI-MS m/z 334, 336 (M+H)$^+$ Step C: Benzyl 2-(N-((3-(methoxycarbonyl)propen-1-yl) carbonyl)-N-(2-bromophenylmethyl)amino)acetate Benzyl 2-(N-(2-bromophenylmethyl)amino)acetate was dissolved in dichloromethane (0.2 M), followed by addition of trans-glutaconic acid methyl ester (1.2 eq), triethylamine (2 eq), EDAC (1.2 eq), and HOAT (0.1 eq). After stirring for 2 hrs, the solution was washed with 10% HCl, 10% sodium carbonate, water and brine, dried over magnesium sulfate, filtered and concentrated in vacuo. Flash chromatography (50% EtOAc/Hex) afforded a viscous oil. EI-MS m/z 460, 462 (M+H)$^+$ Step D: Methyl 2-(2-((phenylmethoxycarbonyl)methyl)-3-oxo-1H,4H-benzo[e]azaperhydroepin-5-ylidene)acetate Benzyl 2-(N-((3-(methoxycarbonyl)propen-1-yl) carbonyl)-N-(2-bromophenylmethyl)amino)acetate was dissolved in toluene (0.1 M), followed by addition of triethylamine (1.2 eq) and tetrakis(triphenyl phosphine)palladium (0.05 eq), and the solution was stirred at reflux overnight. The reaction was washed with water and brine, dried over magnesium sulfate and concentrated in vacuo. Flash chromatography (silica; 50% EtOAc/Hex) afforded a viscous oil. EI-MS m/z 380 (M+H)$^+$ Step E: Methyl 2-(2-(carboxymethyl)-3-oxo-1H,4H,5H-benzo[e]azaperhydroelin-5-yl)acetate The olefin was dissolved in methanol, followed by addition of 10% palladium on carbon (10%/wt), and subjected to hydrogenation on a parr shaker at 50 psi. After 8 hrs, the mixture was filtered through celite and concentrated in vacuo to afford a viscous oil. EI-MS m/z 292 (M+H)$^+$ Step F: Methyl 2-(2-({N-(4-(2-pyridylamino)prop-1-yl) carbamoyl}methyl)-3-oxo-1H,4H,5H-benzo(e)azepin-5-yl) acetate Methyl 2-(2-(carboxymethyl)-3-oxo-1H,4H,5H-benzo[e]azaperhydroepin-5-yl)acetate was dissolved in dichloromethane (0.2 M) followed by addition of 2-(3-aminoprop-1-ylamino)pyridine (1.2 eq), Hunig's base (1.5 eq), and EDAC (1.2 eq). After 2 hours of stirring, the reaction was washed with 10% sodium carbonate, water and brine, dried over magnesium sulfate, filtered and concentrated. Flash chromatography (silica; 10% MeOH/CHCl3) afforded a colorless solid. EI-MS m/z 425 (M+H)+

Step G: 2-(2-({N-(4-(2-pyridylamino)prop-1-yl)carbamoyl}methyl)-3-oxo-1H,4H,5H-benzo(e)azepin-5-yl)acetic acid Methyl 2-(2-({N-(4-(2-pyridylamino)prop-1-yl)carbamoyl}methyl)-3-oxo-1H,4H,5H-benzo(e)azepin-5-yl)acetate was dissolved in MeOH, followed by addition of 1 N NaOH (5 eq), and solution was stirred overnight. 1 N HCl (5 eq) was added, and the reaction was concentrated in vacuo. Flash chromatography (silica; 10% MeOH/CHCl$_3$) afforded the title compound as a colorless solid. EI-MS m/z 411 (M+H); $^1$H NMR (400 MHz; D2O): 7.62 (1H, t, J=8.1 Hz), 7.53 (1H, d, J=6.0 Hz), 7.10 (4H, m), 6.74 (1H, d, J=9.1 Hz), 6.62 (1H, t, J=6.8 Hz), 4.67 (1H, d, J=16 Hz), 4.22 (1H, d, J=16 Hz), 3.95 (2H, m), 3.42 (1H, t, J=6.9 Hz), 3.12 (4H, m), 2.0–1.8 (4H, m), 1.65 (2H, m).

EXAMPLE 26

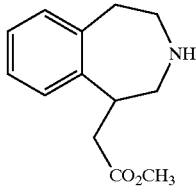

Preparation of Methyl 2-(1H,2H,3H,4H,5H-benzo[d]azepin-1-yl)acetate

Step A: 2-(2-Bromophenyl)-N-(phenylmethyl)acetamide

To a stirring solution of 2-bromophenylacetic acid in dichloromethane (0.2 M) was added benzylamine (1.2 eq), triethylamine (1.5 eq), and EDAC (1.5 eq). After 2 hrs, the solution was washed with water, 10% HCl, 10% sodium carbonate, and water, dried over magnesium sulfate, filtered and concentrated in vacuo to afford a colorless solid. EI-MS m/z 304/306 (M+H)+

Step B: N-(2-(2-Bromophenyl)ethyl)-N-(phenylmethyl)amine 2-(2-Bromophenyl)-N-(phenylmethyl)acetamide was dissolved THF (0.2 M), followed by addition of BH$_3$.DMS (3 eq), and the reaction was heated to reflux with stirring. After 2 hrs, the mixture was cooled to room temerature, and quenched with excess 10% HCl. The mixture was heated to reflux for 1 hr, and then cooled to room temperature. After washing with EtOAc, the aqueous phase was made alkaline with 10% sodium carbonate, and extracted with EtOAc. The organic phase was washed with brine, dried over magnesium sulfate, filtered and concentrated in vacuo. The residue was triturated with EtOAc to afford a colorless solid. EI-MS m/z 290/292 (M+H)+

Step C: Methyl 4-(N-(phenylmethyl)-N-((2-bromophenyl)methyl) amino)but-2-enoate

N-(2-(2-Bromophenyl)ethyl)-N-(phenylmethyl)amine was dissolved in acetonitrile (0.2 M), followed by addition of methyl 4-bromocrotonate (1.2 eq) and triethylamine (1.5 eq), and the reaction was refluxed overnight. After cooling to room temperature, the reaction was diluted with EtOAc, washed with 10% sodium carbonate, water, and brine, dried over magnesium sulfate, filtered and concentrated in vacuo. Flash chromatography (silica; 50% EtOAc/Hex) afforded a colorless oil. EI-MS m/z 388/390 (M+H)+

Step D: Methyl 2-(3-(Phenylmethyl)-2H,4H,5H-benzo[d]azaoerhydroepin-1-ylidene)acetate Methyl 4-(N-(phenylmethyl)-N-((2-bromophenyl)methyl) amino)but-2-enoate was dissolved in toluene (0.1M) followed by addition of triethylamine (1 eq), tetrakis(triphenylphosphine)palladium (0.05 eq), and 2M sodium carbonate (15%/v). The mixture was heated to reflux overnight with vigorous stirring. After cooling to room temperature, the phases were separated, and the organic phase was washed with water and brine, dried over magnesium sulfate, filtered and concentrated in vacuo. The residue was dissolved in EtOAc and extracted 5x with 6N HCl. The combined extracts were neutralized with 10% sodium carbonate, and extracted with EtOAc. The organic phase was washed with brine, dried over magnesium sulfate, filtered and concentrated to afford a yellow oil. EI-MS m/z 208 (M+H)+

Step E: Methyl 2-(1H,2H,3H,4H,5H-benzo[d]azepin-1-yl)acetate

Methyl 2-(3-(phenylmethyl)-2H,4H,5H-benzo[d]azaperhydroepin-1-ylidene)acetate was dissolved in MeOH (0.1M), followed by addition of p-toluenesulfonic acid (1 eq) and 10% palladium on carbon (50%/wt), and the mixture was subjected to hydrogenation on a parr shaker at 50 psi overnight. The reaction was filtered through celite and concentrated in vacuo. The residue was dissolved in EtOAc, washed with 10% sodium carbonate and brine, dried over magnesium sulfate, filtered and concentrated to afford the title compound as a colorless oil. EI-MS m/z 220 (M+H)+

EXAMPLE 27

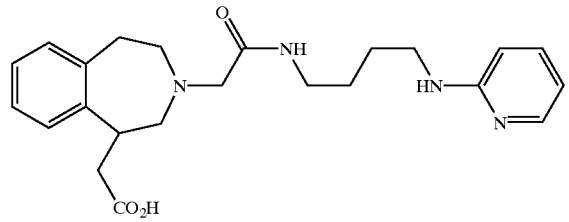

Preparation of 2-(3-({N-(4-(2-pyridylamino)but-1-yl) carbamoyl}methyl)-1H,2H,4H,5H-benzo[d]azepin-1-yl) acetic acid Step A: Methyl 2-(3-({N-(4-(2-pyridylamino)but-1-yl)carbamoyl}methyl)-1H,2H,4H,5H-benzo[d]azepin-1-yl)acetate To a stirring solution of methyl 2-(1H,2H,3H,4H,5H-benzo[d]azepin-1-yl)acetate in acetonitrile (0.2 M) was added Hunig's base (1.5 eq), followed by bromoacetic acid. After stirring for 2 hr, 2-((4-aminobut-1-yl)amino)pyridine (1.2 eq) was added, followed by Hunig's base (1.5 eq) and EDAC (1.5 eq), and stirring was continued for another 2 hr. The reaction was diluted with EtOAc, and washed with water and brine, dried over magnesium sulfate, filtered and concentrated in vacuo. Flash chromatography (silica; 10% MeOH/EtOAc) afforded a colorless solid. EI-MS m/z 425 (M+H)+

Step B: 2-(3-({N-(4-(2-pyridylamino)but-1-yl) carbamoyl}methyl)-1H,2H,4H,5H-benzo[d]azepin-1-yl) acetic acid Methyl 2-(3-({N-(4-(2-pyridylamino)but-1-yl) carbamoyl}methyl)-1H,2H,4H,5H-benzo[d]azepin-1-yl)

acetate was dissolved in MeOH (0.1M) followed by addition of 1N NaOH (5 eq). After stirring overnight, 1N HCl (5 eq) was added, and the solution was concentrated in vacuo. Flash chromatography (10% MeOH/CHCl$_3$) afforded a colorless solid. EI-MS m/z 411 (M+H)$^+$; $^1$H NMR (400 MHz; D$_2$O): 7.50 (2H, m), 6.93 (4H, m), 6.62 (1H, d, J=8.9 Hz), 6.51 (1H, t, J=6.7 Hz), 3.23 (1H, m), 3.01 (6H, m), 2.75 (2H, br), 2.57 (4H, m), 2.38 (2H, m), 1.36 (4H, br).

EXAMPLE 28

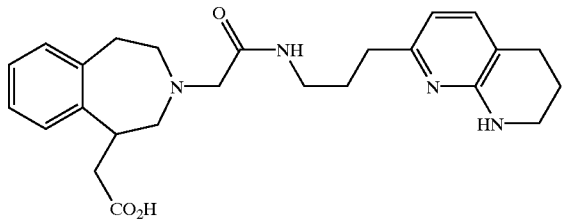

2-(3-{[N-(3-(1,2,3,4-tetrahydropyridino[2,3-b]pyridin-7-yl)propyl)carbamoyl]methyl}-1H,2H,4H, 5H-benzo[d]azepinyl)acetic acid 2-(3-{[N-(3-(1,2,3,4-tetrahydropyridino[2,3-b]pyridin-7-yl)propyl)carbamoyl]methyl}-1H,2H,4H,5H-benzo[d] azepinyl)acetic acid was prepared from bromoacetic acid, 3-(1,2,3,4-tetrahydropyridino[2,3-b]pyridin-7-yl) propylamine and methyl 2-(1H,2H,3H,4H,5H-benzo[d]azepin-1-yl)acetate according to the procedure of Example 27. EI-MS m/z 437 (M+H)$^+$; $^1$H NMR (400 MHz; CDCl$_3$): 9.61 (1H, br), 8.39 (1H, br), 7.15 (5H, m), 6.31 (1H, d, J=7.25 Hz), 3.64 (2H, m), 3.34 (6H, m), 2.99 (4H, m), 2.71 (4H, m), 1.93 (5H, m), 0.86 (2H, m).

EXAMPLE 29

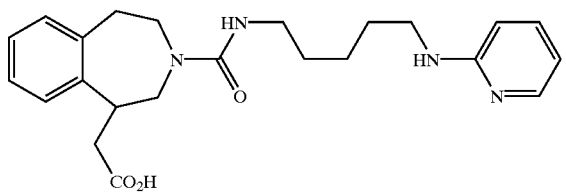

2-(3-{N-(5-(2-pyridylamino)pent-1-yl)carbamoyl}-1H,2H,4H,5H-benzo[d]azepinyl)acetic acid 2-(3-{N-(5-(2-pyridylamino)pent-1-yl)carbamoyl}-1H, 2H,4H,5H-benzo[d]azepinyl)acetic acid was prepared from methyl 2-(1H,2H,3H,4H,5H-benzo[d]azepin-1-yl) acetate and 2-((5-aminopent-1-yl)amino)pyridine according to the procedure of Example 2. EI-MS m/z 411 (M+H)$^+$; $^1$H NMR (400 MHz; D$_2$O): 7.42 (1H, d, J=6.02 Hz), 7.33 (1H, t, J=8.01 Hz), 6.82 (4H, m), 6.46 (1H, d, J=8.90 Hz), 6.40 (1H, t, J=6.9 Hz), 3.18 (5H, m), 2.90 (2H, t, J=6.80 Hz), 2.72 (3H, m), 2.51 (1H, dt, J=15.11 Hz, 4.42 Hz), 2.18 (2H, m), 1.23 (2H, m), 1.06 (2H, m), 0.94 (2H, m).

EXAMPLE 30

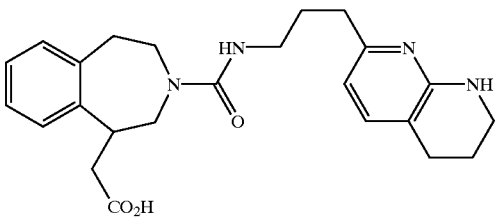

2-{3-(N-(3-(1,2,3,4-tetrahydropyridino[2,3-b] pyridin-7-yl)propyl)carbamoyl)-1H,2H,4H,5H-benzo[d]azepin-1-yl}acetic acid 2-{3-(N-(3-(1,2,3,4-tetrahydropyridino[2,3-b]pyridin-7-yl)propyl)carbamoyl)-1H,2H,4H,5H-benzo[d]azepin-1-yl}acetic acid was prepared from methyl 2-(1H,2H,3H,4H, 5H-benzo[d]azepin-1-yl)acetate and 3-(1,2,3,4-tetrahydropyridino[2,3-b]pyridin-7-yl) propylamine according to the procedure of Example 2. EI-MS m/z 423 (M+H)$^+$; $^1$H NMR (400 MHz, CDCl$_3$): 11.10 (1H, br), 7.86 (1H, br), 7.28–7.14 (5H, m), 6.32 (1H, d, J=7.18 Hz), 4.79 (1H, br), 4.10 (1H, br), 3.48 (5H, m), 3.2–2.6 (10H, m), 2.08 (1H, m), 1.90 (4H, m).

EXAMPLE 31

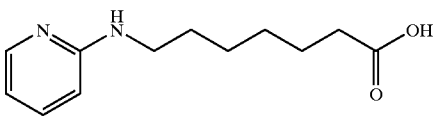

7-(2-pyridylamino)heptanoic acid

To a stirring solution of 7-aminoheptanoic acid in pyridine (0.5 M) was added 2-fluoropyridine (2 eq) and 2N NaOH (1 eq), and the reaction was refluxed overnight. The mixture was adjusted to neutral pH with 6N HCl and concentrated in vacuo. The residue was suspended in 10:1:1 EtOH/NH$_4$OH/H$_2$O, filtered through a plug of silica, and concentrated in vacuo to afford a colorless solid.

EXAMPLE 32

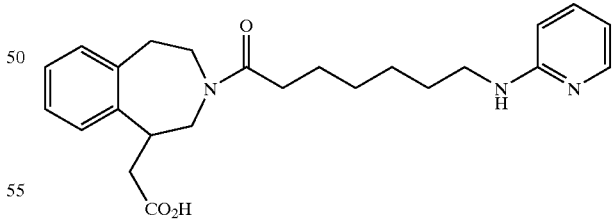

Preparation of 2-{3-(7-(2-pyridylamino)heptanoyl)-1H,2H,4H,5H-benzo[d]azepin-1-yl}acetic acid Step A: Methyl 2-{3-(7-(2-pyridylamino)heptanoyl)-1H,2H, 4H,5H-benzo[d]azepin-1-yl}acetate To a stirring solution of methyl 2-(1H,2H,3H,4H,5H-benzo[d]azepin-1-yl)acetate in dichloromethane (0.2 M) was added 7-(2-pyridylamino)heptanoic acid (1.2 eq), triethylamine (1.5 eq), and EDAC (2 eq). After 4 hrs, the reaction was washed with water, 10% sodium carbonate, dried over magnesium sulfate, filtered and concentrated in vacuo. Flash chromatography (silica; EtOAc) afforded a colorless oil.

Step B: 2-{3-(7-(2-pyridylamino)heptanoyl)-1H,2H,4H,5H-benzo[d]azepin-1-yl}acetic acid Methyl 2-{3-(7-(2-pyridylamino)heptanoyl)-1H,2H,4H,5H-benzo[d]azepin-1-yl}acetate was dissolved in MeOH, and 1N NaOH (5 eq) was added. After stirring overnight, 1N HCl (5 eq) was added, and the reaction was concentrated in vacuo. Flash chromatography (silica; 10% MeOH/CHCl$_3$) afforded a colorless solid. The sodium salt was prepared by dissolving the compound in MeOH (0.1 M), adding NaOMe (1.0 eq, 0.5 M in MeOH), and concentrating in vacuo to afford a colorless solid. ESI-MS m/z 432 (M+H)$^+$; $^1$H NMR (400 MHz, DMSO-d6): 7.98 (1H, m), 7.33 (1H, m), 7.2–7.10 (4H, m), 6.60 (1H, d, J=8.4 Hz), 6.43 (1H, m), 3.71 (2H, m), 3.49 (2H, m), 3.24 (2H, m), 2.90 (3H, m), 2.40 (2H, m), 2.24 (2H, m), 2.07 (1H, m), 1.53 (4H, m), 1.20 (4H, m).

EXAMPLE 33

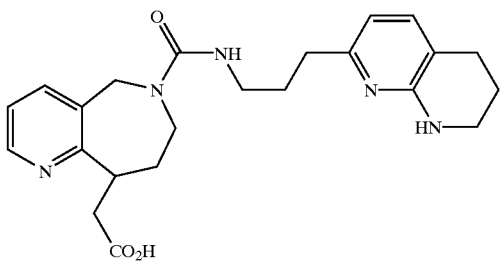

Preparation of 2-{6-(N-(3-(1,2,3,4-tetrahydrolyridino [2,3-b]yridin-7-yl)proyyl)carbamoyl)-5H,7H,8H,9H-=pyridino[2,3-e]azaperhydroepin-9-yl}acetic acid Step A: N-((2-Bromo(3-pyridyl))methyl)-2-(1,3-dioxolan-2-yl)ethylamine To a solution of 2-bromopyridine-3-carbaldehyde (3.53 g, 19.0 mmol, 1.0 eq) (Melnyk et al., Synthetic Commun. 23(19):2727–2730, 1993) in 1,2-dichloroethane (50 mL) was added 2-(1,3-dioxolan-2-yl)ethylamine (TCI-GR, 2.67 g, 22.8 mmol, 1.2 eq), sodium triacetoxyborohydride (Aldrich, 1.61 g, 76 mmol, 4.0 eq) and glacial acetic acid (1.14 g, 19 mmol, 1.0 eq). The reaction mixture was stirred under nitrogen at room temperature for 2 h. The reaction was quenched with 1.0 N aqueous NaOH to about pH 8 and the solution was extracted with EtOAc (200 mL×3). The organic extracts were washed with saturated NaCl, dried with MgSO$_4$, filtered and concentrated. Flash column chromatography (silica gel, 0–10% EtOAc-Hexane) afforded the title compound as a colorless oil. MS m/z 377 (Br=79, M+H), 379 (Br=81, M+H).

Step B: N-((2-Bromo(3-pyridyl)methyl)-N-(2-(1,3-dioxolan-2-yl)ethyl)(phenylmethoxy)carboxamide A biphasic mixture of N-((2-bromo(3-pyridyl))methyl)-2-(1,3-dioxolan-2-yl)ethylamine (4.15 g, 14.4 mmol, 1.0 eq), benzyl chloroformate (Aldrich, 3.70 g, 21.7 mmol, 1.5 eq) and Na$_2$CO$_3$ (3.05 g, 28.8 mmol, 2.0 eq) CH$_2$Cl$_2$ (20 ml) and H$_2$O (20 mL) was stirred at room temperature overnight. The reaction mixture was diluted with H$_2$O (50 mL), and extracted with CH$_2$Cl$_2$ (60 mL×3). The organic extracts were washed with brine, dried with Na$_2$SO$_4$, filtered, and concentrated. Flash column chromatography (silica gel, 0–50% EtOAc-Hexane) afforded the title compound as a colorless oil. MS m/z 421 (Br=79, M+H), 423 (Br=81, M+H).

Step C: N-((2-Bromo(3-pyridyl)methyl)-N-(3-oxobutyl)(phenylmethoxy)carboxamide

A solution of N-((2-bromo(3-pyridyl)methyl)-N-(2-(1,3-dioxolan-2-yl)ethyl)(phenylmethoxy)carboxamide in a mixture of 5% aqueous HCl (50 mL) and acetone (50 mL) was stirred at room temperature for 24 h. Acetone was removed under reduced pressure and the aqueous reaction mixture was extracted with EtOAc (70 mL×3). The organic extracts were washed with brine, dried with Na$_2$SO$_4$, filtered and concentrated. Flash column chromatography (silica gel, 0–50% EtOAc-Hexane) afforded the title compound as a colorless oil. MS m/z 376 (Br=79, M+H), 378 (Br=81, M+H).

Step D: Methyl (2E)-5-{N-((2-bromo(3-pyridyl)methyl)-N-(Phenylmethoxycarbonyl)amino}pent-2-enoate To a solution of N-((2-bromo(3-pyridyl)methyl)-N-(3-oxobutyl)(phenylmethoxy)carboxamide (4.83 g, 12.8 mmol, 1.0 eq) in CH$_2$Cl$_2$(20 mL) at room temperature was added a solution of carbomethoxymethylene triphenylphosphorane (Avocado, 4.92 g, 14.7 mmol, 1.15 eq) in CH$_2$Cl$_2$ (50 mL) by a canular. The reaction mixture was stirred under nitrogen at room temperature for 6 h. The solvent was removed under reduced pressure. Flash column chromatography (silica gel, 0–50% EtOAc-Hexane) afforded the title compound as a colorless oil. MS m/z 433 (Br=79, M+H), 435 (Br=81, M+H).

Step E: Methyl 2-{6-(benzyloxycarbonyl)-5H,7H,8H-pyrido[2,3-e]azaperhydroepin-9-ylidene}acetate A mixture of methyl (2E)-5-{N-((2-bromo(3-pyridyl)methyl)-N-(phenylmethoxycarbonyl)amino}pent-2-enoate (650 mg, 1.50 mmol, 1.0 eq), tetrakis(triphenyl phosphine)palladium(0) (Aldrich, 581 mg, 0.50 mmol, 0.33 eq), triethylamine (540 mg, 4.5 mmol, 3.0 eq), aqueous sodium carbonate (8 mL, 2.0 M) in toluene (23.0 mL) in a sealed vessel was stirred at 120° C. for 48 h. The reaction mixture was diluted with CH$_2$Cl$_2$ (40 mL) and was allowed to pass through a pad of celite. The organic layer was separated and aqueous layer was extracted with CH$_2$Cl$_2$ (40 mL×2). The combined organic layer was dried with Na$_2$SO$_4$, filtered and dried under reduced pressure. Reverse phase high performance liquid chromatography (0.1% TFA-H$_2$O/CH$_3$CN) afforded the title compound as a colorless semisolid. MS m/z 353 (M+H).

Step F: Methyl 2-(5H,6H,7H,8H-pyridino[2,3-e]azaperhydroein-9-ylidene)acetate

A mixture of methyl 2-{6-(benzyloxycarbonyl)-5H,7H,8H-pyrido[2,3-e] azaperhydroepin-9-ylidene}acetate (127 mg, 0.36 mmol, 1.0 eq), ammonium formate (Sigma, 192 mg, 2.72 mmol, 8.0 eq ) and 10% Pd/C (24 mg) in a mixture of solvents (10 mL of methanol and 5 mL of H$_2$O) was stirred at room temperature for 3 h. Methanol was removed under reduced pressure. The remaining aqueous layer was diluted with aqueous sodium carbonate (2.0 M, 20 mL) and extracted with CH$_2$Cl$_2$ (30 mL×3). The organic extractants were dried with Na$_2$SO$_4$, filtered and concentrated. Preparative thin layer chramotography (5% Methanol+0.5% ammonium hydroxide-CH$_2$Cl$_2$) afforded the title compound as a colorless semisolid. MS m/z 219 (M+H).

Step G: Methyl 2-(5H,6H,7H,8H,9H-pyridino[2,3-e]azaperhydroepin-9-yl)acetate

A mixture of methyl 2-(5H,6H,7H,8H-pyridino[2,3-e]azaperhydroepin-9-ylidene)acetate (35 mg, 0.16 mmol, 1.0 eq) and magnesium (Aldrich, powder, 42 mg, 1.73 mmol, 11 eq) in methanol (1.65 mL) was stirred for 20 h. Following the dilution of the reaction mixture with methanol, it was allowed to pass through a pad of celite and concentrated under reduced pressure. Preparative thin layer chromatography (5% Methanol+0.5% ammonium hydroxide-CH₂Cl₂) afforded the title compound as a colorless sticky solid. MS m/z 221 (M+H).

Step H: Methyl 2-{6-(N-(3-(1,2,3,4-tetrahydropyridino[2,3-b]pyridin-7-yl)propyl)carbamoyl)-5H,7H,8H,9H-pyridino[2,3-e]azaperhydroein-9-yl}acetate To a mixture of methyl 2-(5H,6H,7H,8H,9H-pyridino[2,3-e]azaperhydroepin-9-yl)acetate (16 mg, 0.073 mmol, 1.0 eq) in THF (0.5 mL) was added a solution of phosgene (Fluka, 1.0 mL, 20% in toluene) and diisopropylethyl amine (38 mg, 0.29 mmol, 4.0 eq). The reaction mixture was stirred at room temperature for 10 min. Solvents were removed under reduced pressure. The newly formed intermediate was dissolved in THF (1 mL), followed by the addition of a solution of 3-(1,2,3,4-tetrahydropyridino[2,3-b]pyridin-7-yl)propylamine (0.212 mL, 1.1 M in THF/DMF, 0.23 mmol, 3.2 eq) and diisopropylethylamine (38 mg, 0.29 mmol, 4.0 eq). The reaction mixture was stirred at room temperature overnight. Preparative thin layer chromatography (5% MeOH+0.25% triethylamine-CH₂-Cl₂) afforded the title compound as a colorless semisolid. MS m/z 438 (M+H).

Step I: 2-{6-(N-(3-(1,2,3,4-tetrahydroyridino[2,3-b]pyridin-7-yl)propyl)carbamoyl)-5H,7H,8H,9H-pyridin-[2,3-e]azaperhydroepin-9-yl}acetic acid To a solution of methyl 2-{6-(N-(3-(1,2,3,4-tetrahydro pyridino[2,3-b]pyridin-7-yl)propyl)carbamoyl)-5H,7H,8H,9H-pyridino[2,3-e]azaperhydroepin-9-yl}acetate (11.1 mg, 0.254 mmol, 1.0 eq) in ethanol (0.30 mL) was added a solution of NaOH (0.028 mL, 2.0 M, 0.0556 mmol, 2.2 eq) was stirred at 55° C. for 24 h. Following the neutralization of the reaction mixture with a solution of HCl (0.028 mL, 2.0 N), all the solvents were removed under reduced pressure. The crude product was triturated 10% MeOH—CH₂Cl₂, filtered and concentrated under reduced pressure to afford the title compound as colorless sticky solid. ¹H NMR (400 MHz, CD₃OD): δ8.32 (m, 1), 7.67 (d, 1, J=7.5 Hz), 7.44 (d, 1, J=7.3), 7.18 (m, 1), 6.49 (d, 1, J=7.3), 4.78 (d, 1, J=15.6), 4.53 (d, 1, J=15.6), 3.68 (m, 1), 3.55 (m, 2), 3.45 (t, 2, J=5.7), 3.34 (s, 1), 3.17 (m, 1), 2.97 (dd, 1, J=5.2, 15.6), 2.77 (t, 2, J=6.1), 2.61 (m, 3), 2.28 (m, 1), 1.80 (m, 2), 1.58 (m, 1), 1.31 (m, 1), 1.13 (m, 1). MS m/z 424 (M+H). HRMS m/z 424.2343 (M+H, C₂₃H₂₉N₅O₃ calc. 424.2349).

EXAMPLE 34

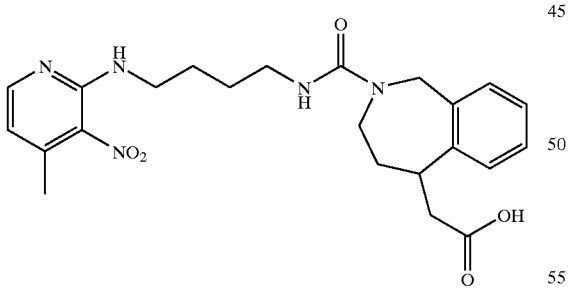

Preparation of 2-(2-(N-(4-(2-pyridylamino-3-nitro-4-methyl)but-1-yl) carbamoyl)-1H,3H,4H,5H-benzo[e]azapin-5-yl)acetic acid Step A: 2-(N-(4-aminoprop-1-yl)amino-3-nitro-4-methyl)pyridine To a stirring solution of 2-chloro-3-nitro-4-methylpyridine in pyridine (0.5 M) was added 1,4-butanediamine (5 eq), and the solution was refluxed for 18 hrs. The solution was then concentrated in vacuo and the residue was partitioned between ethyl acetate and 10% sodium carbonate. The phases were separated, and the organic phase was washed with brine, dried over magnesium sulfate, filtered and concentrated in vacuo. The residue was chromatographed (silica; 10:1:1 EtOH/NH₄OH/H₂O) to afford a viscous pale yellow oil. EI-MS m/z 152 (M+H)⁺

Step B: Methyl 2-(2-(N-(4-(2-pyridylamino-3-nitro-4-methyl)but-1-yl) carbamoyl)-1H,3H,4H-5H-benzo[e]azapin-5-yl)acetate Methyl 2-(1H,2H,3H,4H,5H-benzo[e]azaperhydroepin-5-yl)acetate Hydrochloride was dissolved in methylene chloride and washed with 1N NaOH. The organic layer was separated, dried over sodium sulfate and concentrated by rotary evaporation. The residue was stirred under nitrogen with 20% phosgene in toluene (0.1 M) for 10 mins. After stirring the reaction was concentration by rotary evaporation, the residue was dissolved in THF (0.1 M), followed by addition of diisopropylethylamine (1.5 eq) and 2-(N-(4-aminoprop-1-yl)amino-3-nitro-4-methyl)pyridine (1.2 eq). The reaction was stirred for 18 hr under nitrogen, followed by concentration by rotary evaporation and the product was purified by flash chromatograpy (5% MeOH/CH₂Cl₂). EI-MS m/z 397 (M+H)⁺

Step C: 2-(2-(N-(4-(2-pyridylamino-3-nitro-4-methyl)but-1-yl)carbamoyl)-1H,3H,4H,5H-benzo[e]azapin-5-yl)acetic acid To a stirring solution methyl 2-(2-(N-(4-(2-pyridylamino-3-nitro-4-methyl)but-1-yl) carbamoyl)-1H,3H,4H-5H-benzo[e]azapin-5-yl)acetate in methanol (0.1 M) was added 1N NaOH (3 eq). After 18 hrs, the reaction was neutralized with 10% HCl, concentrated by rotary evaporation and purified by recrystalization from 2% MeOH/CH₂Cl₂. EI-MS m/z 456 (M+H)⁺; ¹H-NMR (400 MHz, CDCl₃): δ11.0 (br s, 1H), 8.12 (d, J=4.9 Hz, 1H), 7.52 (t, J=4.6 Hz, 1H), 7.19 (m, 4H), 6.46 (d, J=4.9 Hz, 1H), 4.77 (m, 1H), 4.48 (q, J=15.2 Hz, 2H), 3.65 (m, 1H), 3.49 (m, 4H), 3.23 (m, 2H), 2.76 (m, 2H), 2.52 (s, 3H), 2.03 (m, 1H), 1.58 (m, 5H).

EXAMPLE 35

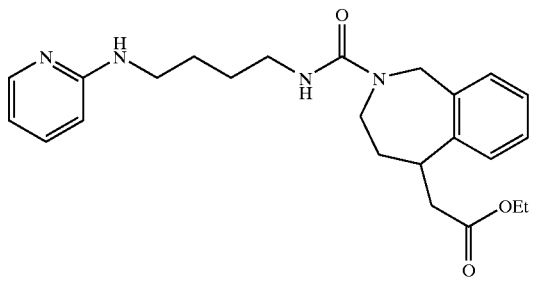

Preparation of ethyl 2-(2-(N-(3-(2-pyridylamino)butyl-1-yl)carbamoyl)-1H,3H,4H-5H-benzo[e]azapin-5-yl)acetate Ethyl 2-(2-(N-(4-(2-pyridylamino)but-1-yl)carbamoyl)-1H,3H,4H,5H-benzo[e]azapin-5-yl)acetate was prepared from 2-(N-(4-aminobut-1-yl)amino)pyridine and ethyl 2-(1H,2H,3H,4H,5H-benzo[e]azaperhydroepin-5-yl)acetate according to the procedure of Example 34. Ethyl 2-(1H,2H,3H,4H,5H-benzo[e]azaperhydroepin-5-yl)acetate was prepared by transesterification of methyl 2-(1H,2H,3H,4H,5H-benzo[e]azaperhydroepin-5-yl)acetate with HCl and ethanol. EI-MS m/z 425 (M+H)⁺; ¹H-NMR (400 MHz, CDCl₃): δ8.08 (d, J=4.7 Hz, 1H), 7.40 (t, J=12.1 Hz, 1H), 7.33–7.12(m, 4H), 6.53 (t, J=6.1 Hz, 1H), 6.33 (d, J=8.3 Hz, 1H), 4.52 (d, J=15.3 Hz, 2H), 4.41(s, 2H), 4.13(q, J=21.4

Hz, 2H), 3.70 (s, 1H), 3.60 (m, 2H), 3.28 (m, 4H), 2.81(m, 1H), 2.70 (m, 1H), 2.05 (m, 1H), 1.64 (m, 1H), 1.25 (t, J=7.10 Hz, 3H).

EXAMPLE 36

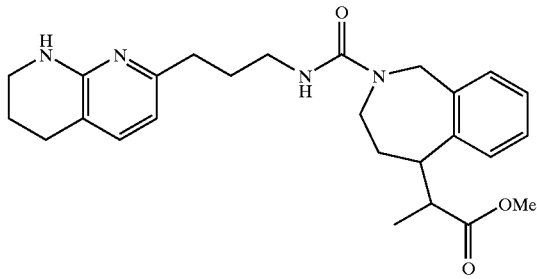

Preparation of methyl 2-(2-(N-(3-(1,2,3,4-tetrahydro pyridino(2,3-b)pyridin-7-yl)propyl)carbamoyl)-1H, 3H,4H,5H-benzo[e]azapin-5-yl)propanoate Step A: Methyl 2-(2-(tert-butoxycarbonyl)-1H,2H,3H,4H, 5H-benzo[e]azaperhydroepin-5-yl)propanoate Methyl 2-(2-(tert-butoxycarbonyl)-1H,3H,4H,5H-benzo [e]azaperhydroepin-5-yl)acetate was dissolved in in tetrahydrofuran (0.2 M). The solution was cooled to −78° C. under nitrogen and the addition of lithium diisopropylamine (1 eq.) was added. After 10 mins, methyl iodide (1 eq) was added and the temperature was warmed to 0° C. and stirred for 30 mins. The reaction was then warmed to room temperature and quenched with water. The solvents were removed in vacuo, followed by dilution with ethyl acetate and extraction with saturated ammonium chloride. The solvents were removed in vacuo to give the product as a colorless oil. EI-MS m/z 334 (M+H)$^+$ Step B: Methyl 2-(1H,2H,3H,4H,5H-benzo[e] azaperhydroepin-5-yl)propanoate Hydrochloride Methyl 2-(2-(tert-butoxycarbonyl)-1H,3H,4H,5H-benzo [e]azaperhydroepin-5-yl)propanoate was dissolved in 4M HCl in dioxane (0.2 M). After 18 hrs, removal of solvent in vacuo, followed by trituration with ether afforded the product. EI-MS m/z 233 (M+H)$^+$ Step C: Methyl 2-(2-(N-(3-(1,2,3,4-tetrahydro pyridino(2,3-b)pyridin-7-yl)propyl)carbamoyl)-1H,3H,4H,5H-benzo[e] azapin-5-yl)propanoate 2-(2-(N-(3-(1,2,3,4-tetrahydropyridino(2,3-b)pyridin-7-yl)propyl)carbamoyl)-1H,3H,4H,5H-benzo[e]azapin-5-yl)propanoate was prepared from 3-(1,2,3,4-tetrahydropyridino[2,3-b]pyridin-7-yl)prop-1-ylamine and methyl 2-(1H,2H,3H,4H,5H-benzo [e]azaperhydroepin-5-yl)propanoate according to the procedure of Example 34. 3-(1,2,3,4-tetrahydropyridino[2,3-b] pyridin-7-yl)prop-1-ylamine was prepared according to Duggan, M. E. WO 98/18460. EI-MS m/z 451 (M+H)$^+$.

EXAMPLE 37

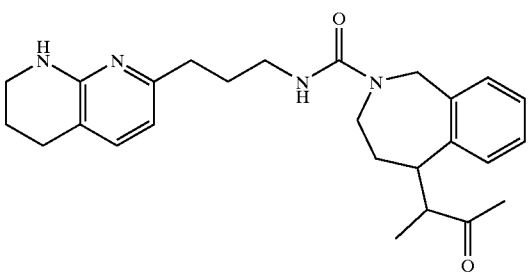

Preparation of 2-(2-(N-(3-(1,2,3,4-tetrahydro pyridino(2,3-b)pyridin-7-yl)propyl)carbamoyl)-1H, 3H,4H,5H-benzo[e]azapin-5-yl)propanoic acid 2-(2-(N-(3-(1,2,3,4-tetrahydropyridino(2,3-b)pyridin-7-yl)propyl)carbamoyl)-1H,3H,4H,5H-benzo[e]azapin-5-yl) propanoic acid was prepared from methyl 2-(2-(N-(3-(1,2, 3,4-tetrahydropyridino(2,3-b)pyridin-7-yl)propyl) carbamoyl)-1H,3H,4H,5H-benzo[e]azapin-5-yl)propanoate according to the procedure of Example 34. EI-MS m/z 437 (M+H)$^+$; $^1$H-NMR (400 MHz, CDCl$_3$): δ10.8 (br s, 1H), 7.25 (m, 6H), 6.37 (m, 1H), 5.04 (d, J=14.2 Hz, 1H), 4.36 (d, J=14.8 Hz, 1H), 3.74 (m, 5H), 3.46 (m, 4H), 3.10 (m, 3H), 2.72 (m, 5H), 2.27 (m, 1H), 1.44 (m, 1H), 1.17 (br s, 3H).

EXAMPLE 38

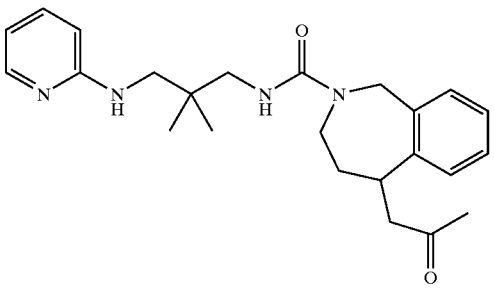

Preparation of 2-(2-{N-[2,2-dimethyl-3-(2-pyridylamino)propyl]carbamoyl}-1H,3H,4H,5H-benzo[e]azepine-5-yl)acetic acid Step A: (3-amino-2,2-dimethylpropyl)-2-pyridylamine A mixture of 2-fluoropyridine and 2,2-dimethyl-1,3-propanediamine (2 eq) in pyridine (0.3M) was refluxed for 18 hrs. and then concentrated by rotary evaporation. The solution was then concentrated in vacuo and the residue was partitioned between ethyl acetate and 10% sodium carbonate. The phases were separated, and the organic phase was washed with brine, dried over magnesium sulfate, filtered and concentrated in vacuo. The product was purified by flash chromatography using 10:1:1 EtOH/NH$_4$OH/H$_2$O as eluent. EI-MS m/z 180 (M+H)$^+$.

Step B: Methyl 2-(2-{N-[2,2-dimethyl-3-(2-pyridylamino) propyl]carbamoyl}-1H,3H,4H,5H-benzo[e]azepine-5-yl) acetate Methyl 2-(2-{N-[2,2-dimethyl-3-(2-pyridylamino) propyl]carbamoyl}-1H,3H,4H,5H-benzo[e]azepine-5-yl) acetate was prepared from (3-amino-2,2-dimethylpropyl)-2-pyridylamine and methyl 2-(1H,2H,3H,4H,5H-benzo[e] azaperhydroepin-5-yl)propanoate according to the procedure of Example 34. EI-MS m/s 425 (M+H)$^+$.

Step C: 2-(2-{N-[2,2-dimethyl-3-(2-pyridylamino)propyl]carbamoyl}-1H,3H,4H,5H-benzo[e]azepine-5-yl)acetic acid 2-(2-{N-[2,2-dimethyl-3-(2-pyridylamino)propyl]carbamoyl}-1H,3H,4H,5H-benzo[e]azepine-5-yl)acetic acid was prepared from methyl 2-(2-{N-[2,2-dimethyl-3-(2-pyridylamino)propyl]carbamoyl}-1H,3H,4H,5H-benzo[e]azepine-5-yl) according to the procedure of Example 34. EI-MS m/z 411 (M+H)⁺; ¹H-NMR (400 MHz, MeOH-d₄): δ7.8 (d, J=5.1, 1H), 7.35 (t, J=7.12, 1H), 7.28 (d, J=7.03, 1H), 7.10 (m, 2H), 7.00 (m, 1H), 6.5–6.4 (m, 2H), 4.5 (q, J=15.37 Hz, 2H), 3.6 (m, 2H), 3.45 (m, 1H), 3.25 (s, 3H), 2.9 (d, J=8.67 Hz, 4H), 2.7–2.06 (m, 2H), 1.95 (m, 1H), 1.55 (m, 1H), 0.7 (s, 6H).

EXAMPLE 39

Preparation of 2-(2-{N-[4-(pyrazin-2-ylamino)butyl]carbamoyl}-1H,3H,4H,5H-benzo[e]azepin-5-yl)acetic acid

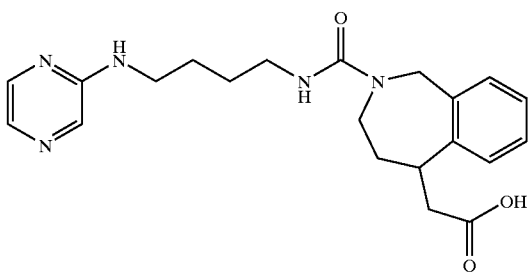

Step A: (4-aminobutyl)pyrazin-2-ylamine (4-aminobutyl)pyrazin-2-ylamine was prepared by refluxing 2-chloropyrazine and 1,4-diaminobutane in pyridine (50 mL) for 18 hrs. The solution was then concentrated in vacuo and the residue was partitioned between ethyl acetate and 10% sodium carbonate. The phases were separated, and the organic phase was washed with brine, dried over magnesium sulfate, filtered and concentrated in vacuo. The desired product was isolated by flash chromatography using 10:1:1 Ethanol/Ammonium Hydroxide/water. EI-MS m/z 167 (M+H)⁺.

Step B: Methyl 2-(2-{N-[2,2-dimethyl-3-(2-pridylamino)propyl]carbamoyl}-1H,3H,4H,5H-benzo[e]azepine-5-yl)acetate Methyl 2-(2-{N-[2,2-dimethyl-3-(2-pyridylamino)propyl]carbamoyl}-1H,3H,4H,5H-benzo[e]azepine-5-yl)acetate was prepared from (4-aminobutyl)pyrazin-2-ylamine and methyl 2-(1H,2H,3H,4H,5H-benzo[e]azaperhydroepin-5-yl)propanoate according to the procedure of Example 34. EI-MS m/z 412 (M+H)⁺.

Step C: 2-(2-{N-[4-(pyrazin-2-ylamino)butyl]carbamovyl-1H,3H,4H,5H-benzo[e]azepin-5-yl)acetic acid 2-(2-{N-[4-(pyrazin-2-ylamino)butyl]carbamoyl}-1H,3H,4H,5H-benzo[e]azepin-5-yl)acetic acid was prepared from methyl 2-(2-{N-[2,2-dimethyl-3-(2-pyridylamino)propyl]carbamoyl}-1H,3H,4H,5H-benzo[e]azepine-5-yl)acetate according to the procedure of Example 34. EI-MS m/z 398 (M+H)⁺. ¹H-NMR (400 MHz, DMSO-d₆): δ7.9 (m, 1H), 7.88 (s, 1H), 7.6 (s, 1H), 7.30 (d, 7.2, 1H), 7.18–7.08 (m, 3H), 6.95 (t, J=5.01, 1H), 6.3 (t, J=5.15, 1H), 4.45 (s, 2H), 3.5 (sb, 2H), 3.15 (m, 3H), 2.95 (m, 2H), 2.20–2.10 (m, 2H), 1.8 (m, 1H), 1.4 (m, 5H).

EXAMPLE 40

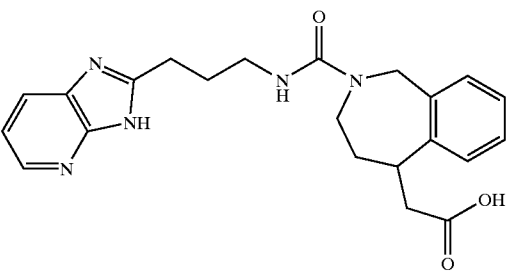

Preparation of 2-[2-[N-(3-imidazolo[5,4-b]pyridin-2-ylpropyl)carbamoyl]-1H,3H,4H,5H-benzo[e]azepin-5-yl}acetic acid Step A: N-(3-amino(2-pyridyl))-4-[(phenylmethoxy)carbonylamino]butanamide 4-[(phenylmethoxy)carbonylamino]butanoic acid (1.1 eq) was dissolved in methylene chloride (0.2M) followed by the addition of 1-[3-(Dimethylamino)propyl]-3-ethylcarbodiimide hydrochloride (EDCA) (1.2 eq) and triethylamine (1.5 eq). The mixture was stirred at room temperature under nitrogen for 30 mins, followed by addition of 2,3-diaminopyridine. The mixture was then stirred at room temperature for 48 hrs., quenched with saturated sodium carbonate and extracted with ether. The organic phase was concentrated in vacuo and chromatographed on silica gel. (10% MeOH/CH₂Cl₂). EI-MS m/z 329 (M+H)⁺.

Step B: N-(3-imidazole[4,5-b]pyridin-2-ylpropyl)(phenylmethoxy)carboxamide

N-(3-amino(2-pyridyl))-4-[(phenylmethoxy)carbonylamino]butanamide was dissolved in acetic acid (0.3M) and refluxed for 18 hrs. The resulting mixture was made basic with saturated sodium carbonate, extracted with methylene chloride, dried over sodium sulfate and concentrated concentrated in vacuo. The resulting residue was purified by flash chromatography (10% MeOH/CH₂Cl₂) EI-MS m/z 311 (M+H)⁺.

Step C: 3-imidazolo[4,5-b]pyridin-2-ylpropylamine

N-(3-imidazole[4,5-b]pyridin-2-ylpropyl)(phenylmethoxy)carboxamide was dissolved in MeOH (60 mL) and 10% Pd/C was added. Hydrogen was bubbled through the mixture and stirred under a balloon atmosphere for 18 hrs. The mixture was filtered through celite and concentrated by high vacuum to afford the desired product. EI-MS m/z 177 (M+H)⁺.

Step D: Methyl 2-{2-[N-(3-imidazolo[5,4-b])yridin-2-ylproyl)carbamoyl]-1H,3H,4H,5H-benzo[e]azelin-5-yl}acetate Methyl 2-{2-[N-(3-imidazolo[5,4-b]pyridin-2-yl-propyl)carbamoyl]-1H,3H,4H,5H-benzo[e]azepin-5-yl}acetate was prepared from 3-imidazolo[4,5-b]pyridin-2-ylpropylamine and methyl 2-(1H,2H,3H,4H,5H-benzo[e]azaperhydroepin-5-yl)propanoate according to the procedure of Example 34. EI-MS m/z 422 (M+H)⁺.

Step E: 2-{2-[N-(3-imidazolo[5,4-b]pyridin-2-ylproyl)carbamoyl]-1H,3H,4H,5H-benzo[e]azepin-5-yl}acetic acid 2-{2-[N-(3-imidazolo[5,4-b]pyridin-2-ylpropyl)carbamoyl]-1H,3H,4H,5H-benzo[e]azepin-5-yl}acetic acid was prepared from methyl 2-{2-[N-(3-imidazolo[5,4-b]pyridin-2-yl-propyl) carbamoyl]-1H,3H,4H,5H-benzo[e]azepin-5-yl}acetate according to the procedure of Example 34. EI-MS m/z 408 (M+H)⁺.

Example 41

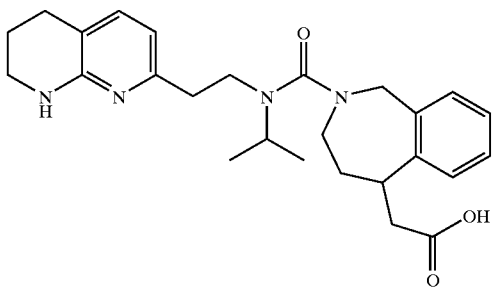

Preparation of 2-{2-[N-(methylethyl)-N-(2-(1,2,3,4-tetrahydroyridino[2,3-b]pyridin-7-yl)ethyl)carbamoyl]-1H,3H,4H,5H-benzo[e]azepin-5-yl]acetic acid Step A: Methyl-2-{2-[N-(methylethyl)-N-(2-(1,2,3,4-tetrahydropyridino[2,3-b]pyridin-7-yl)ethyl) carbamoyl]-1H,3H,4H,5H-benzo[e]azepin-5-yl]acetate Methyl-2-{2-[N-(methylethyl)-N-(2-(1,2,3,4-tetrahydropyridino[2,3-b]pyridin-7-yl)ethyl)carbamoyl]-1H,3H,4H,5H-benzo[e]azepin-5-yl]acetate was prepared from of (methylethyl)(2-(1,2,3,4-tetrahydropyridino [2,3-b]pyridin-7-yl)ethyl)amine and methyl 2-(1H,2H,3H,4H,5H-benzo[e]azaperhydroepin-5-yl)propanoate according to the procedure of Example 34. EI-MS m/z 465 (M+H)+.

Step B: 2-{2-[N-(methylethyl)-N-(2-(1,2,3,4-tetrahydropyridino[2,3-b]pyridin-7-yl)ethyl)carbamoyl]-1H,3H,4H,5H-benzo[e]azepin-5-yl]acetic acid 2-{2-[N-(methylethyl)-N-(2-(1,2,3,4-tetrahydro pyridino[2,3-b]pyridin-7-yl)ethyl)carbamoyl]-1H,3H,4H,5H-benzo[e]azepin-5-yl]acetic acid was prepared from methyl-2-{2-[N-(methylethyl)-N-(2-(1,2,3,4-tetrahydropyridino[2,3-b]pyridin-7-yl)ethyl)carbamoyl]-1H,3H,4H,5H-benzo[e]azepin-5-yl]acetate according to the procedure of Example 34. EI-MS m/z 451 (M+H)+. $^1$H-NMR (400 MHz, CDCl$_3$): δ10.0 (bs, 1H), 7.25–7.10 (m, 6H), 6.25 (d, J=7.27, 1H), 4.5 (q, J=15.30, 2H), 3.7–3.6 (m, 2H), 3.4 (m, 5H), 3.23–3.15 (m, 1H), 2.78–2.65 (m, 5H), 2.65–2.55 (m, 1H), 2.2 (m, 1H), 1.88 (m, 2H), 1.78 (m, 1H), 1.05 (dd, J=6.7, J=10.23, 6H).

EXAMPLE 42

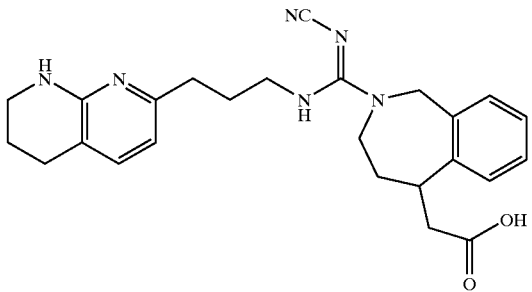

Preparation of 2-(2-aza-2-cyano-1((1,2,3,4-tetrahydropyridino[2,3-b]pyridin-7-yl)propyl)amino)vinyl)-1H,3H,4H,5H-benzo[e]azapin-5-yl) acetic acid Step A: 2-aza-3-phenoxy-3-((3-(1,2,3,4-tetrahydro pyridino [2,3-b]pyridin-7-yl)propyl)amino)prop-2-enenitrile 2-aza-3-phenoxy-3-((3-(1,2,3,4-tetrahydropyridino[2,3-b]pyridin-7-yl)propyl)amino)prop-2-enenitrile was prepared by refluxing 3-(1,2,3,4-tetrahydropyridino [2,3-b]pyridin-7-yl)prop-1-ylamine and 2-aza-3,3 diphenoxyprop-2-enenitrile in acetonitrile for 3 hrs. 3-(1,2,3,4-tetrahydropyridino[2,3-b]pyridin-7-yl)prop-1-ylamine was prepared according to Duggan, M. E. WO 98/18460.

Step B: Methyl 2-(2-aza-2-cyano-1-((3-(1,2,3,4-tetrahydroyridino[2,3-b]pyridin-7-yl)propyl)amino) vinyl)-1H,3H,4H,5H,-benzo[e]azein-5-yl)acetate Methyl 2-(2-aza-2-cyano-1-((3-(1,2,3,4-tetrahydropyridino[2,3-b]pyridin-7-yl)propyl)amino)vinyl)-1H,3H,4H,5H,-benzo[e]azepin-5-yl)acetate was prepared by refluxing 2-aza-3-phenoxy-3-((3-(1,2,3,4-tetrahydropyridino[2,3-b]pyridin-7-yl)propyl)amino)prop-2-enenitrile and and methyl 2-(1H,2H,3H,4H,5H-benzo[e]azaperhydroepin-5-yl)acetate in isopropyl alcohol for 18 hrs. followed by flash chromatography(10% MeOH/CH$_2$Cl$_2$).

Step C: 2-(2-aza-2-cyano-1((1,2,3,4-tetrahydro pyridino[2,3-b]pyridin-7-yl)propyl) amino)vinyl)-1H,3H,4H,5H-benzo[e]azapin-5-yl)acetic acid 2-(2-aza-2-cyano-1((1,2,3,4-tetrahydropyridino[2,3-b]pyridin-7-yl)propyl)amino)vinyl)-1H,3H,4H,5H-benzo[e]azapin-5-yl)acetic acid was prepared from methyl 2-(2-aza-2-cyano-1-((3-(1,2,3,4-tetrahydro pyridino(2,3-b)pyridin-7-yl)propyl)amino)vinyl)-1H,3H,4H,5H,-benzo[e]azapin-5-yl)acetate according to the procedure of Example 34. EI-MS m/z 447 (M+H)+; $^1$H-NMR (400 MHz, d6-DMSO): δ7.50–7.25 (m, 5H), 7.18 (d, J=7.3 Hz, 1H), 6.34 (d, J=7.2 Hz, 1H), 4.81 (q, J=36 Hz, 2H), 3.82 (m, 2H), 3.65–3.48 (m, 5H), 3.40 (t, J=5.3 Hz, 2H), 2.76 (t, J=6.1 Hz, 2H), 2.70 (m, 2H), 2.11 (m, 1H), 1.92 (m, 4H), 1.70 (m, 1H).

EXAMPLE 43

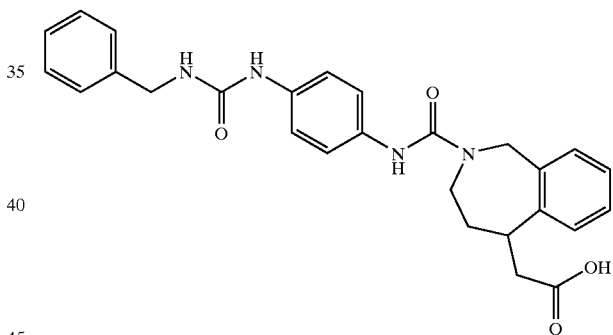

Preparation of 2-(2-(N-((benzylamino)carbonylamino) phenyl)carbamoyl)-1H,3H,4H,5H-benzo[e]azapin-5-yl)acetic acid Step A: Methyl 2-(2-(N-(4-nitrophenyl)carbamoyl)-1H,3H,4H,5H-benzo[e]azapin-5-yl)acetate Methyl 2-(2-(N-(4-nitrophenyl)carbamoyl)-1H,3H,4H,5H-benzo[e]azapin-5-yl)acetate was prepared by reacting 4-nitrophenyl isocyanate and and methyl 2-(1H,2H,3H,4H,5H-benzo[e]azaperhydroepin-5-yl)acetate in dimethyl foramide at 60° C. for 18 hrs followed flash chromatography (10% MeOH/CH$_2$Cl$_2$). EI-MS m/z 384(M+H)+

Step B: Methyl 2-(2-(N-(4-aminolhenyl)carbamoyl)-1H,3H,4H,5H-benzo[e]azapin-5-yl)acetate Methyl 2-(2-(N-(4-aminophenyl)carbamoyl)-1H,3H,4H,5H-benzo[e]azapin-5-yl)acetate was prepared by hydrogenation of methyl 2-(2-(N-(4-nitrophenyl)carbamoyl)-1H,3H,4H,5H-benzo[e]azapin-5-yl)acetate with Pd/C in methanol. EI-MS m/z 354 (M+H)+

Step C: Methyl 2-(2-(N-((benzylamino)carbonylamino) phenyl)carbamoyl)-1H,3H,4H,5H-benzo[e]azapin-5-yl) acetate Methyl 2-(2-(N-((benzylamino)carbonylamino)phenyl) carbamoyl)-1H,3H,4H,5H-benzo[e]azapin-5-yl)acetate was prepared by heating methyl 2-(2-(N-(4-aminophenyl) carbamoyl)-1H,3H,4H,5H-benzo[e]azapin-5-yl)acetate and benzyl isocyanate in dimethyl foramide at 60° C. for 18 hrs followed dy flash chromotography (10% MeOH/CH$_2$Cl$_2$). EI-MS m/z 487 (M+H)$^+$ Step D: 2-(2-(N-((benzylamino)carbonylamino)p henyl) carbamoyl)-1H,3H,4H,5H-benzo[e]azapin-5-yl)acetic acid 2-(2-(N-((benzylamino)carbonylamino)phenyl) carbamoyl)-1H,3H,4H,5H-benzo[e]azapin-5-yl)acetic acid was prepared from methyl 2-(2-(N-((benzylamino) carbonylamino)phenyl)carbamoyl)-1H,3H,4H,5H-benzo[e] azapin-5-yl)acetate according to the procedure of Example 34. EI-MS m/z 473 (M+H)$^+$; $^1$H-NMR (400 MHz, d6-DMSO): δ8.22 (s, 1H), 8.09 (s, 1H), 7.25–6.95 (m, 13H), 6.39 (t, J=6.0 Hz, 1H), 4.52 (q, J=35 Hz, 2H), 4.12 (d, J=5.3 Hz, 2H), 3.55 (m, 2H), 3.38 (m, 1H), 2.61 (m, 2H), 1.81 (m, 1H), 1.47 (m, 1H).

EXAMPLE 44

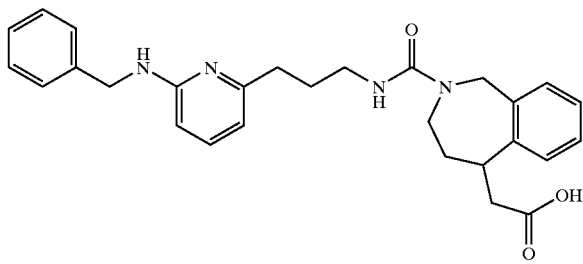

Preparation of 2-(2-(N-(3-(2-pyridylamino)propyl) carbamoyl)-1H,3H,4H,5H-benzo[e]azapin-5-yl) acetic acid Step A: (tert-butoxy)-N-(6-methyl(2-pyridyl))carboxamide To a stirring solution of 2-amino-6-methylpyridine in methylene chloride (1.0 M) was added di-tert-butyl dicarbonate (1 eq), and the solution was stirred for 4 hrs. The solution was then concentrated in vacuo and the residue was purified by flash chromatography (50% EtOAc/Hexane). EI-MS m/z 209 (M+H)$^+$ Step B: (tert-butoxy)-N-(6-but-3-enyl(2-pyridyl)) carboxamide To a stirring solution of (tert-butoxy)-N-(6-methyl(2-pyridyl))carboxamide in tetrahydrofuran (0.1 M) was added n-butyl lithium (2.1 eq) at −78° C. and the solution was warmed to 25° C. and stirred for 1 hr. The solution was then cooled back down to −78° C. followed by addition of allyl bromide (1.5 eq) and continued strirring for 1 hr. The reaction was quenched with saturated ammonium chloride, diluted with ethyl acetate and separated. The organic layer was washed with brine and dried with magnesium sulfate, filtered and concentrated in vacuo. The residue was purified by flash chromatography (5% EtOAc/Hexane). EI-MS m/z 249(M+H)$^+$ Step C: N-[6-(3,4-dihydroxybutyl)(2-pyridyl)](tert-butoxy) carboxamide To a stirring solution of 4-methylmorpholine N-oxide(2.1 eq) and osmium tetraoxide (2.5 eq) in tetrahydrofuran/water (5 eq/1 eq) was added (tert-butoxy)-N-(6-but-3-enyl(2-pyridyl))carboxamide (1.0 eq) at 25° C. and stirred for 18 hr. The reaction was quenched with solution of sodium bisulfate (0.5M) and sodium sulfite (1M) and stirred for 30 mins. The reaction was poured into a brine and extracted with ethyl acetate. The organic layer was dried with sodium sulfate, filtered and concentrated in vacuo. The residue was purified by flash chromatography (50% EtOAc/Hexane). EI-MS m/z 283(M+H)$^+$ Step D: (tert-butoxy)-N-[6-(3-oxopropyl)(2-pyridyl)] carboxamide To a stirring solution of N-[6-(3,4-dihydroxybutyl)(2-pyridyl)](tert-butoxy)carboxamide in tetrahydrofuran/water (1 eq/1 eq, 0.1M) was added sodium metaperiodate (1.3 eq) at 0° C. and stirred for 1 hr. The reaction was warmed to room temperature and diluted with ethyl acetate. The reaction was extracted with saturated sodium bicarbonate, dried with sodium sulfate, filtered and concentrated in vacuo to yield the product. EI-MS m/z 251(M+H)$^+$ Step E: (tert-butoxy)-N-[6-(3-(hydroxyimino)proyl)(2-pyridyl)]carboxamide To a stirring solution of (tert-butoxy)-N-[6-(3-oxopropyl)(2-pyridyl)]carboxamide_in methanol (0.1M) was added sodium acetate (2.0 eq) and hydroxyamine hydrochloride. The reaction was then heated to 60° C. and stirred for 18 hr. The reaction was cooled to room temperature and diluted with water. The reaction was extracted with diethyl ether. The organic layer was washed with saturated sodium bicarbonate, brine and dried with sodium sulfate, filtered and concentrated in vacuo to yield the product. EI-MS m/z 266(M+H)$^+$ Step F: N-[6-(3-aminopropyl)(2-pyridyl)](tert-butoxy) carboxamide To a solution of (tert-butoxy)-N-[6-(3-(hydroxyimino) propyl)(2-pyridyl)]carboxamide in ethanol/acetic acid (4 eq/1 eq, 0.1M) under nitrogen was added 5% palladium on carbon. The reaction was stirred under hydrogen at 60 psi for 18 hr. The reaction was filtered thru celite and concentrated in vacuo to yield the product. EI-MS m/z 252(M+H)$^+$ Step G: Methyl 2-{2-[N-(3-{6-[(tert-butoxy) carbonylaminol-2-pyridyl}proyl)carbamoyl]-1H,3H,4H, 5H-benzo[e]azetin-5-yl}acetate Methyl 2-(1H,2H,3H,4H,5H-benzo[e]azaperhydroepin-5-yl)acetate Hydrochloride was dissolved in methylene chloride and washed with 1N NaOH. The organic layer was separated, dried over sodium sulfate and concentrated by rotary evaporation. The residue was stirred under nitrogen with 20% phosgene in toluene (0.1 M) for 10 mins. After concentration by rotary evaporation, the residue was dissolved in THF (0.1 M), followed by addition of diisopropylethylamine (1.5 eq) and N-[6-(3-aminopropyl)(2-pyridyl)](tert-butoxy) carboxamide (1.2 eq). The reaction was stirred for 18 hr under nitrogen, followed by concentration by rotary evaporation and the product was purified by flash chromatography (5% MeOH/CH$_2$Cl$_2$). EI-MS m/z 497 (M+H)$^+$ Step H: Methyl 2-(2-{N-[3-(6-amino-2-pyridyl)propyl] carbamoyl}-1H,3H,4H,5H-benzo[e]azepin-5-yl)acetate Methyl 2-{2-[N-(3-{6-[(tert-butoxy)carbonylamino]-2-pyridyl}propyl)carbamoyl]-1H,3H,4H,5H-benzo[e]azepin-5-yl}acetate_was dissolved in 4M HCl/dioxane and stirred for 3 hrs. at room temperature. The reaction was concentration by rotary evaporation and the product was purified by trituation with diethyl ether. EI-MS m/z 397 (M+H)$^+$ Step I: Methyl 2-{2-rN-(3-{6-[benzylaminol-2-pyridyl}propyl)carbamoyl]-1H,3H,4H,5H-benzo[e]azepin-5-yl}acetate To a stirring solution of Methyl 2-(2-{N-[3-(6-amino-2-pyridyl)propyl]carbamoyl}-1H,3H,4H,5H-benzo[e]azepin-5-yl)acetate in dichloroethane (0.4 M) at RT under nitrogen was added benzaldehyde (1.2 eq), sodium triacetoxyborohydride (2 eq), and acetic acid (4 eq). After 5 hr the reaction was carefully quenched with 2M sodium carbonate and extracted with methylene chloride. The organic phase was dried over magnesium sulfate, filtered and concentrated in vacuo. The residue was purified by flash chromatography (10% MeOH/CH$_2$Cl$_2$) to afford the product. EI-MS m/z 487(M+H)$^+$ Step J: 2-{2-[N-(3-{6-[benzylaminol-2-pyridyl}propyl)carbamoyl]-1H,3H,4H,5H-benzore]azepin-5-yl}acetic acid To a stirring solution methyl 2-{2-[N-(3-{6-[benzyl amino]-2-pyridyl}propyl)carbamoyl]-1H,3H,4H,5H-benzo[e]azepin-5-yl}acetate in methanol (0.1 M) was added 1N NaOH (3 eq). After 18 hrs, the reaction was neutralized with 10% HCl, concentrated concentrated in vacuo and purified by recrystalization from 2% MeOH/CH$_2$Cl$_2$. EI-MS m/z 473 (M+H)$^+$; $^1$H-NMR (400 MHz, d2-D$_2$O): δ7.32–7.08 (m, 10H), 6.48 (m, 2H), 4.37 (s, 2H), 4.51 (m, 2H), 4.36 (m, 3H), 3.99 (t, J=3.7 Hz, 2H), 2.61≧2.34 (m, 5H), 1.75 (m, 1H), 1.63 (t, J=3.4 Hz, 2H).

EXAMPLE 45

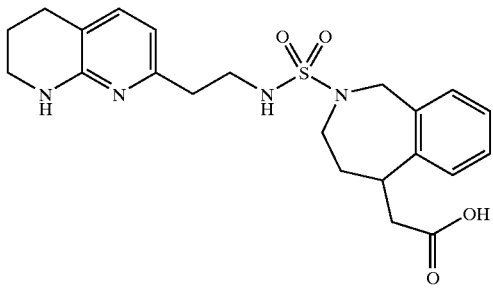

Preparation of 2-(2-(((2-(1,2,3,4-tetrahydro pyridino (2,3-b)pyridin-7-yl)ethyl)amino)sulfonyl)-1H,3H, 4H,5H-benzo[e]azain-5-yl)acetic acid 2-(2-(N-(2-(1,2,3,4-tetrahydropyridino(2,3-b)pyridin-7-yl)ethyl)amino)sulfonyl)-1H,3H,4H,5H-benzo[e]azapin-5-yl)acetic acid was prepared from 3-(1,2,3,4-tetrahydropyridino[2,3-b]pyridin-7-yl)ethylamine and methyl 2-(1H,2H,3H,4H,5H-benzo[e]azaperhydroepin-5-yl)acetate according to the procedure of Example 14. 2-(1,2,3,4-tetrahydropyridino[2,3-b]pyridin-7-yl)ethylamine was prepared according to Duggan, M. E. WO 98/18460. EI-MS m/z 445 (M+H)$^+$; $^1$H-NMR (400 MHz, d6-DMSO): δ7.11–687 (m, 5H), 6.10 (m, 1H), 4.21 (q, J=48.6 Hz, 2H), 3.50–3.29 (m, 3H), 3.11 (m, 2H), 2.80 (m, 2H), 2.55–2.44 (m, 4H), 2.19 (m, 2H), 1.80 (m, 1H), 1.68 (m, 2H), 1.45 (m, 1H).

EXAMPLE 46

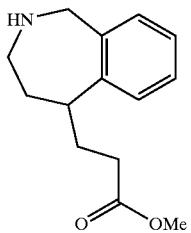

Preparation of methyl 3-(1H,2H,3H,4H,5H-benzo[e] azaperhydroepin-5-yl)propanoate Hydrochloride Step A: Tert-butyl 5-(2-hydroxyethyl)-1H,3H,4H,5H-benzo[e]azaperhydroepine-2-carboxylate Tert-butyl 5-(2-hydroxyethyl)-1H,3H,4H,5H-benzo[e]azaperhydroepine-2-carboxylate was prepared by reacting methyl 2-(2-(tert-butoxycarbonyl)-1H,3H,4H,5H-benzo[e]azaperhydroepin-5-yl)acetate with diisobutylaluminiumhydride(3 eq.) in toluene(0.1M) at 0° C. for 1.5 hrs. The reaction was quenched with 1N HCl at 0° C. and extracted with ethyl acetate. The organic layer was washed with additional 1N HCl, saturated sodium bicarbonate and water. Dried with sodium sulfate, filtered and concentrated in vacuo to afford the product. EI-MS m/z 292 (M+H)$^+$ Step B: Tert-butyl 5-(2(4-methylphenyl)sulfonyloxy)-1H, 3H,4H,5H-benzore]azaperhydroepine-2-carboxylate Tert-butyl 5-(2((4-methylphenyl)sulfonyloxy)-1H,3H, 4H,5H-benzo[e]azaperhydroepine-2-carboxylate was prepared by stirring tert-butyl 5-(2-hydroxyethyl)-1H,3H,4H, 5H-benzo[e]azaperhydroepine-2-carboxylate with tosyl chloride(1.1 eq) and triethyl amine(1.5 eq) in methylene chloride at 25° C. for 18 hrs. Dilute with methylene chloride and extract with water. Dried with sodium sulfate, filtered and concentrated in vacuo. Flash chromatography (25% ETOAc/Hex) afforded the product. EI-MS m/z 446 (M+H)$^+$ Step C: Tert-butyl 5-(2-cyanoethyl)-1H,3H,4H,5H-benzo[e] azaperhydroepine-2-carboxylate Tert-butyl 5-(2-cyanoethyl)-1H,3H,4H,5H-benzo[e]azaperhydroepine-2-carboxylate was prepared by stirring tert-butyl 5-(2((4-methylphenyl)sulfonyloxy)-1H,3H,4H,5H-benzo[e] azaperhydroepine-2-carboxylate in dimethyl sulfoxide (0.1M) with sodium cyanide (5 eq at 25° C. for 18 hrs. Dilute with ethyl acetate and extract with water. Dried with sodium sulfate, filtered and concentrated in vacuo to afford the product. EI-MS m/z 323 (M+Na)$^+$ Step D: Methyl 3-(1H,2H,3H,4H,5H-benzo[e] azaperhydroepin-5-yl)propanotate Hydrochloride Methyl 3-(1H,2H,3H,4H,5H-benzo[e]azaperhydroepin-5-yl)propanoate Hydrochloride was prepared by stirring tert-butyl 5-(2-cyanoethyl)-1H,3H,4H,5H-benzo[e] azaperhydroepine-2-carboxylate in methanol with the addition of excess 4M HCl/dioxane for 24 hrs. Concentrated in vacuo to afford the product. EI-MS m/z 234 (M+H)$^+$

EXAMPLE 47

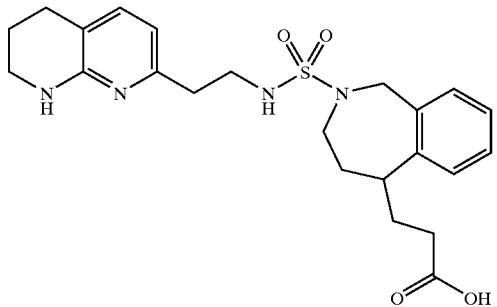

Preparation of 3-(2-(N-(2-(1,2,3,4-tetrahydropyridino (2,3-b)pyridin-7-yl)ethyl)amino) sulfonyl)-1H,3H,4H,5H-benzo[e]azapin-5-yl) oropanoic acid 3-(2-(N-(2-(1,2,3,4-tetrahydropyridino(2,3-b)pyridin-7-yl)ethyl)amino)sulfonyl)-1H,3H,4H,5H-benzo[e]azapin-5-yl)propanoic acid was prepared from 3-(1,2,3,4-tetrahydropyridino[2,3-b]pyridin-7-yl)ethylamine and methyl 3-(1H,2H,3H,4H,5H-benzo[e]azaperhydroepin-5-yl)propanoate according to the procedure of Example 14. 2-(1,2,3,4-tetrahydropyridino[2,3-b]pyridin-7-yl)

ethylylamine was prepared according to Duggan, M. E. WO 98/18460. EI-MS m/z 459 (M+H)+; $^1$H-NMR (400 MHz, d6-DMSO): δ7.39(m, 1H), 7.30 (m, 3H), 7.18 (d, J=7.2 Hz, 1H), 6.35 (d, J=7.3 Hz, 1H), 4.50 (m, 2H), 3.58 (m, 2H), 3.38 (t, J=5.4 Hz, 2H), 3.08 (m, 3H), 2.69 (m, 4H), 2.40(m, 2H), 2.21 (m, 1H), 2.10 (m, 2H), 1.92 (m, 2H), 1.80 (m, 1H).

EXAMPLE 48

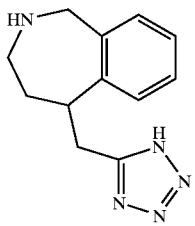

Preparation of 5-(1H-1,2,3,4-tetraazol-5-ylmethyl)-1H,2H,3H,4H,5H-benzo[e]azaperhydroepine-2-carboxylate Step A: 3-(((2-bromophenyl)methyl)amino)propan-1-ol To a stirring solution of 2-bromobenzaldehyde in dichloroethane (0.4 M) at RT under nitrogen was added 3-aminopropanol (1.5 eq), sodium triacetoxyborohydride (2 eq), and acetic acid (4 eq). After 5 hr the reaction was carefully quenched with 2M sodium carbonate and extracted with methylene chloride. The organic phase was extracted with 1N hydrochloric acid. The aqueous phase was neutralized with 1N sodium hydroxide and extracted with methylene chloride. The organic phase was dried over sodium sulfate, filtered and concentrated in vacuo to afford the product. EI-MS m/z 245 (M+H)+

Step B: (Tert-butoxy)-N-((2-bromophenyl)methyl)-N-(3-hydroxypropyl)carboxamide

To a stirring solution of 3-(((2-bromophenyl)methyl)amino)propan-1-ol in methylene chloride (0.1 M) was added di-tert-butyl dicarbonate (1.1 eq). After 1 hr. the solvent was removed by rotary evaporation, and the residue partitioned between ether and 1N HCl. The ethereal portion was dried over sodium sulfate filtered and concentrated in vacuo to afford the product. EI-MS m/z 344 (M+H)+

Step C: N-((3E)-4-cyanbut-3-enyl(tert-butoxy)-N-((2-bromophenyl)methyl)carboxamide To a stirring solution of dimethyl sulfoxide (3.8 eq) in methylene chloride (0.1 M) at –78° C. was added oxalyl chloride (1.8 eq). After 10 min., (tert-butoxy)-N-((2-bromophenyl)methyl)-N-(3-hydroxypropyl) carboxamide (1 eq) was added. After stirring for 30 min., diisopropylethylamine (4 eq) was added, and the reaction was allowed to warm to RT. After 30 min, (triphenylphosphoranyidene)-acetonitrile(1.2 eq) was added, and stirring was continued for 18 hr. The mixture was poured into water and extracted with ethyl acetate. The organic phase was washed with water and brine, dried over sodium sulfate, filtered and concentrated in vacuo to afford the product. EI-MS m/z 365 (M+H)+

Step D: Tert-butyl-5-(cyanomethylene)-1H,3H,4H-benzo[e]azaperhydroepine-2-carboxlate To a stirring solution of N-((3E)-4-cyanbut-3-enyl (tert-butoxy)-N-((2-bromophenyl)methyl) carboxamide in acetonitrile(0.1 M) was added triethylamine (1.2 eq) and palladium acetate (0.05 eq) and tri-o-tolylphosphine(0.01 eq). The reaction was refluxed for 18 hr under nitrogen cooled to RT. The solvent was removed by rotary evaporation and the product was purified by flash chromatograpy (25% EtOAc/Hexane). EI-MS m/z 283 (M–H)−

Step E: Tert-butyl-5-(cyanomethyl)-1H,3H,4H-benzo[e]azaperhydroepine-2-carboxlate To a stirring solution of tert-butyl-5-(cyanomethylene)-1H,3H,4H-benzo[e]azaperhydroepine-2-carboxlate in methanol (0.1 M) was added magnesium turnings (10 eq) and the mixture was refluxed for 18 hr. The mixture was filtered through celite and concentrated by rotary evaporation. The product was purified by flash chromatography (25% EtOAc/Hexane). EI-MS m/z 287 (M+H)+

Step F: Tert-butyl-5-(1H-1,2,3,4-tetraazol-5-ylmethyl)-1H,3H,4H-benzo[e]azaerhydroepine-2-carboxlate Tert-butyl-5-(1H-1,2,3,4-tetraazol-5-ylmethyl)-1H,3H,4H-benzo[e]azaperhydroepine-2-carboxlate was prepared by reacting tert-butyl-5-(cyanomethyl)-1H,3H,4H-benzo[e]azaperhydroepine-2-carboxlate with sodium azide (1.8 eq) and trimethyl tin chloride in toluene at reflux for 48 hrs. Solvent was evaporated to dryness, diluted with methylene chloride(100 ml) and extracted with 1N HCl. Solvent was evaporated and the product was purified by flash chromatography (10% MeOH/CH$_2$Cl$_2$).EI-MS m/z 328 (M–H)−

Step G: 5-(1H-1,2,3,4-tetraazol-5-ylmethyl)-1H,2H,3H,4H-benzo[e]azaperhydroepine-2-carboxlate Hydrochloride Tert-butyl-5-(1H-1,2,3,4-tetraazol-5-ylmethyl)-1H,3H,4H-benzo[e]azaperhydroepine-2-carboxlate was dissolved in 4M HCl in dioxane (0.2 M). After 18 hrs, removal of solvent in vacuo, followed by trituration with ether afforded the product. EI-MS m/z 230 (M+H)+

EXAMPLE 49

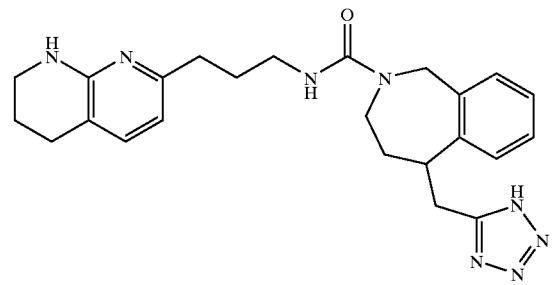

Preparation of [5-(1H-1,2,3,4-tetraazol-5-ylmethyl))1H,3H,4H,5H-benzo[e]azeoin-2-yl)]—N-(3-(1,2,3,4-tetrahydrolyridino[2,3-b]pyridin-7-yl)propyl) carboxamide

[5-(1H-1,2,3,4-tetraazol-5-ylmethyl))1H,3H,4H,5H-benzo[e]azepin-2-yl)]—N-(3-(1,2,3,4-tetrahydropyridino[2,3-b]pyridin-7-yl)propyl)carboxamide was prepared from 3-(1,2,3,4-tetrahydropyridino[2,3-b]pyridin-7-yl)prop-1-ylamine and 5-(1H-1,2,3,4-tetraazol-5-ylmethyl)-1H,2H,3H,4H,5H-benzo[e]azaperhydroepine-2-carboxylate according to the procedure of Example 34. 3-(1,2,3,4-tetrahydropyridino[2,3-b]pyridin-7-yl)prop-1-ylamine was prepared according to Duggan, M. E. WO 98/18460. EI-MS m/z 447 (M+H)+.

EXAMPLE 50

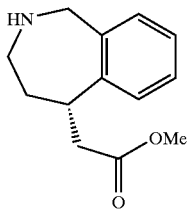

Preparation of-Methyl 2-((5S)-1H,2H,3H,4H,5H-benzo[e]azaperhydroein-5-yl)acetate Hydrochloride Step A: Methyl 2-((5S)-2-(tert-butoxycarbonyl)-1H,3H,4H,5H-benzo[e]azaperhydroepin-5-yl)acetate Methyl 2-(1H,2H,3H,4H,5H-benzo[e]azaperhydroepin-5-yl)acetate was prepared according to the procedure of Example 34. The product was separated and purified by reverse phase high pressure liquid chromatography (2% EtOH/Hexane) on a Chiralpak AD (250×4.6 mm i.d.) column at room temperature at a flow rate of 1.0 ml/min. EI-MS m/z 318 (M+H)+

Step B: Methyl 2-((5S)-1H,2H,3H.4H,5H-benzo[e]azaperhydroepin-5-yl)acetate Hydrochloride (+)-Methyl 2-((5S)-2-(tert-butoxycarbonyl)-1H,3H,4H,5H-benzo[e]azaperhydroepin-5-yl)acetate was dissolved in 4M HCl in dioxane (0.2 M). After 18 hrs, removal of solvent in vacuo, followed by trituration with ether afforded the product. EI-MS m/z 220 (M+H)+, Optical Rotation: +0.104 degree.

EXAMPLE 51

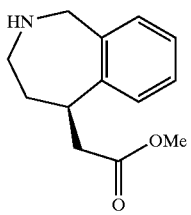

Preparation of Methyl 2-((5R)-1H,2H,3H,4H.5H-benzo[e]azaperhydroeoin-5-yl)acetate Hydrochloride Step A: Methyl 2-((5R)-2-(tert-butoxycarbonyl)-1H,3H,4H,5H-benzo[e]azaoerhydroepin-5-yl)acetate Methyl 2-(1H,2H,3H,4H,5H-benzo[e]azaperhydroepin-5-yl)acetate was prepared according to the procedure of Example 34. The product was separated and purified by reverse phase high pressure liquid chromatography (2% EtOH/Hexane) on a Chiralpak AD (250×4.6 mm i.d.) column at room temperature at a flow rate of 1.0 ml/min. EI-MS m/z 318 (M+H)+

Step F: Methyl 2-((5R)-1H,2H,3H,4H,5H-benzo[e]azaperhydroepin-5-yl) acetate Hyvdrochloride (−)-Methyl 2-((5R) -2-(tert-butoxycarbonyl) -1H, 3H, 4H, 5H-benzo[e]azaperhydroepin-5-yl) acetate was dissolved in 4M HCl in dioxane (0.2 M). After 18 hrs, removal of solvent in vacuo, followed by trituration with ether afforded the product. EI-MS m/z 220 (M+H)+, Optical Rotation: −0.113 degree.

EXAMPLE 52

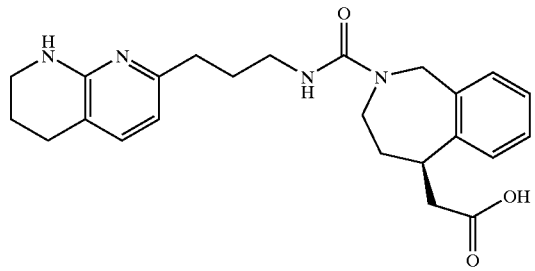

Preparation of 2-((5R)-2-(N-(3-(1,2,3,4-tetrahydro pyridino(2,3-b)pyridin-7-yl)prop-1-yl)carbamoyl)-1H,3H,4H,5H-benzo[e]azapin-5-yl)acetic acid 2-((5R)-2-(N-(3-(1,2,3,4-tetrahydropyridino(2,3-b) pyridin-7-yl)prop-1-yl)carbamoyl)-1H,3H,4H,5H-benzo[e] azapin-5-yl)acetic acid was prepared from 3-(1,2,3,4-tetrahydropyridino[2,3-b]pyridin-7-yl)prop-1-ylamine and methyl 2-((5R)-1H,2H,3H,4H,5H-benzo[e]azaperhydroepin-5-yl)acetate according to the procedure of Example 34. 3-(1,2,3,4-tetrahydro pyridino[2,3-b]pyridin-7-yl)prop-1-ylamine was prepared according to Duggan, M. E. WO 98/18460. EI-MS m/z 423 (M+H)+; 1H-NMR (400 MHz, d6-DMSO): δ7.30–6.85 (m, 5H), 6.25 (m, 1H), 6.18 (d, J=7.3 Hz, 1H), 4.41 (q, J=37.5 Hz, 2H), 3.59 (m, 1H), 3.40 (m, 2H), 3.28 m, 2H), 2.95 (m, 2H), 2.60 (t, J=6.0 Hz, 2H), 2.31 (m, 4H), 1.77 (m, 3H), 1.61 (t, J=7.4 Hz, 2H), 1.40 (m, 1H).

EXAMPLE 53

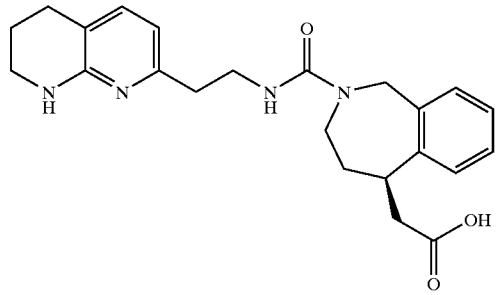

Preparation of 2-((5R)-2-(N-(3-(1,2,3,4-tetrahydro pyridino(2,3-b)pyridin-7-yl)ethyl)carbamoyl)-1H,3H,4H,5H-benzo[e]azapin-5-yl)acetic acid 2-((5r)-2-(N-(3-(1,2,3,4-tetrahydropyridino(2,3-b) pyridin-7-yl)ethylyl)carbamoyl)-1H,3H,4H,5H-benzo[e] azapin-5-yl)acetic acid was prepared from 3-(1,2,3,4-tetrahydropyridino[2,3-b]pyridin-7-yl)ethylamine and -methyl 2-((5r)-1H,2H,3H,4H,5H-benzo[e]azaperhydroepin-5-yl)acetate according to the procedure of Example 34. 3-(1,2,3,4-tetrahydro pyridino[2,3-b]pyridin-7-yl)ethylamine was prepared according to Duggan, M. E. WO 98/18460. EI-MS m/z 409 (M+H)+; 1H-NMR (400 MHz, d6-DMSO): δ7.30–6.94 (m, 5H) 6.41 (bs, 1H), 6.30 (s, 1H), 6.20 (d, J=7.2 Hz, 1H), 4.47 (q, J=38 Hz, 2H), 3.60 (m, 1H), 3.45 (m, 2H), 3.23–3.20 (m, 5H), 2.60 (m, 2H), 2.30 (m, 2H), 1.74 (m, 3H), 1.40 (m, 2H).

EXAMPLE 54

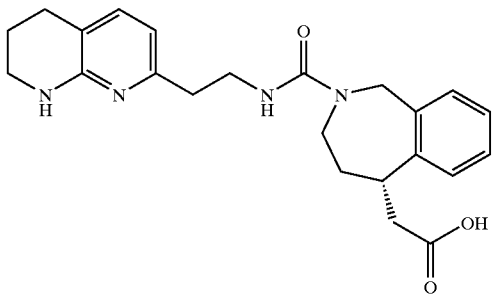

Preparation of 2-((5S)-2-(N-(3-(1,2,3,4-tetrahydro pyridino(2.3-b)pyridin-7-yl)ethyl)carbamoyl)-1H, 3H,4H,5H-benzo[e]azapin-5-yl)acetic acid 2-((5S)-2-(N-(3-(1,2,3,4-tetrahydropyridino(2,3-b) pyridin-7-yl)eth-yl)carbamoyl)-1H,3H,4H,5H-benzo[e] azapin-5-yl)acetic acid was prepared from 3-(1,2,3,4-tetrahydropyridino[2,3-b]pyridin-7-yl)ethyl amine and methyl 2-((5s)-1H,2H,3H,4H,5H-benzo[e]azaperhydroepin-5-yl)acetate according to the procedure of example 34. 3-(1,2,3,4-tetrahydropyridino[2,3-b]pyridin-7-yl)ethyl amine was prepared according to Duggan, M. E. WO 98/18460. EI-MS m/z 409 (M+H)$^+$; $^1$H-NMR (400 MHz, d6-DMSO): δ7.30–6.95 (m, 5H), 6.38 (bs, 1H), 6.29 (s, 1H), 6.20 (d, J=6.8 Hz, 1H), 4.48 (q, J=38.6 Hz, 2H), 3.60 (m, 1H), 3.45 (m, 2H), 3.28–3.22 (m, 5H), 2.61 (m, 2H), 2.34 (m, 2H), 1.80 (m, 3H), 1.46 (m, 2H).

EXAMPLE 55

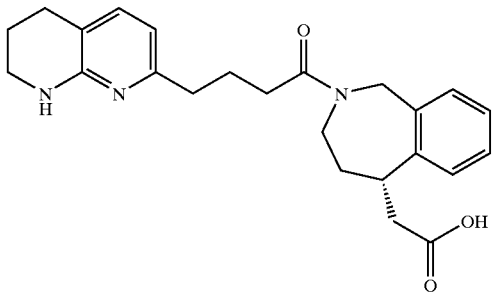

Preparation of 2-((5S)-2-(4-(1,2,3,4-tetrahydro pyridino(2,3-b)pyridin-7-yl)butanoyl)carbamoyl)-1H,3H,4H,5H-benzo[e]azapin-5-yl)acetic acid 2-Methyl-((5S)-2-(4-(1,2,3,4-tetrahydropyridino(2,3-b) pyridin-7-yl)butanoyl)carbamoyl)-1H,3H,4H,5H-benzo[e] azapin-5-yl)acetic acid was prepared from 3-(1,2,3,4-tetrahydropyridino[2,3-b]pyridin-7-yl)butyic acid and methyl 2-((5s)-1H,2H,3H,4H,5H-benzo[e]azaperhydroepin-5-yl)acetate by stirring the two compounds in acetonitrile (0.1M) with triethylamine (1.1 eq) and 1-(3-dimethylaminopropyl)-3-ethyl carbodiimide hydrochloride (1.1 eq) for 18 hrs at room temperture. The reaction was concentrated concentrated in vacuo and purified by flash chromatography to gave 2-methyl-((5S)-2-(N-(3-(1,2,3,4-tetrahydropyridino(2,3-b)pyridin-7-yl)prop-1-yl) carbamoyl)-1H,3H,4H,5H-benzo[e]azapin-5-yl)acetate. 2-((5s)-2-(4-(1,2,3,4-tetrahydropyridino(2,3-b)pyridin-7-yl) butanoyl)carbamoyl)-1H,3H,4H,5H-benzo[e]azapin-5-yl) acetic acid was prepared according to example 34. 3-(1,2, 3,4-tetrahydropyridino[2,3-b]pyridin-7-yl)butyic acid was prepared according to Duggan, M. E. WO 98/18460. EI-MS m/z 406 (M-H); $^1$H-NMR (400 MHz, d6-DMSO): δ7.27–6.97 (m, 5H), 6.21 (bs, 1H), 6.17 (m, 1H), 4.52 (q, J=33.6Hz, 2H), 3.80 (m, 1H), 3.56–3.45(m, 2H), 3.30 (s, 2H), 2.94 (m, 2H), 2.60 (m, 4H), 2.36 (m, 2H), 2.25( m, 3H), 1.65 (m, 4H), 1.50 (m, 2H).

EXAMPLE 56

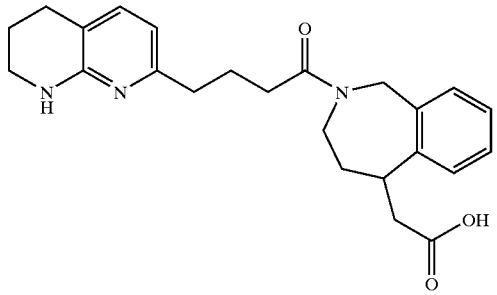

Preparation of 2-[2-(4-(1,2,3,4-tetrahydro pyridino [2,3-b]pyridin-7-yl)butanoyl)-1H,3H,4H,5H-benzo [e]azepin-5-yl]acetic acid Step A: Methyl-2-[2-(4-{1-[(tert-butyl)oxycarbonyl]-1,2,3, 4-tetrahydropyridino[2,3-b]pyridin-7-yl}butanoyl)-1H,3H, 4H,5H-benzo[e]azepin-5-yl]acetate Methyl-2-[2-(4-{1-[(tert-butyl)oxycarbonyl]-1,2,3,4-tetrahydropyridino[2,3-b]pyridin-7-yl}butanoyl)-1H,3H, 4H,5H-benzo[e]azepin-5-yl]acetate according to the procedure of Example 55. EI-MS m/z 422 (M+H)$^+$.

Step B: 2-[2-(4-(1,2,3,4-tetrahydropyridino[2,3-b]pyridin-7-yl)butanoyl)-1H,3H,4H,5H-benzo[e]azepin-5-yl]acetic acid To methyl-2-[2-(4-{1-[(tert-butyl)oxycarbonyl]-1,2,3,4-tetrahydropyridino[2,3-b]pyridin-7-yl}butanoyl)-1H,3H, 4H,5H-benzo[e]azepin-5-yl]acetate was added 4.0M HCl/ dioxane (4 mL) and the resulting mixture was stirred for 18 hrs at room temperature, concentrated by rotary evaporation, diluted in MeOH followed by the addition of 1N NaOH (5 eq). The mixture was stirred at room temperature for 48 hrs., acidified with 1N HCl, concentrated by rotary evaporation and extracted with dichloromethane. The organic solvent was concentrated concentrated in vacuo to afford the desired product. EI-MS m/z 408 (M+H)$^+$. $^1$H-NMR (400MHz, CDCl$_3$): δ7.3–7.1 (m, 4H), 6.35 (m, 2H), 4.75 (d, J=15.1, 1H), 4.55 (m, 2H), 3.8 (m, 1H), 3.5 (m, 5H), 2.4 (m, 3H), 2.15 (m,2H), 2.0 (m,3H), 1.9 (m, 3H), 1.7 (m, 1H).

EXAMPLE 57

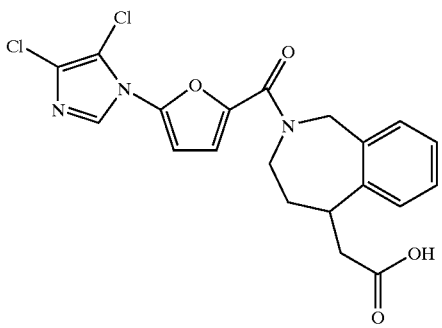

Preparation of 2-(2-((5-((4,5-dichloroimidazolyl)methyl-2-furyl)carbonyl)-1H,3H,4H,5H-benzo[e]azapin-5-yl)acetic acid 2-(2-((5-((4,5-Dichloroimidazolyl)methyl-2-furyl)carbonyl)-1H,3H,4H,5H-benzo[e]azapin-5-yl)acetic acid was prepared from 5-((4,5-dichloroimidazolyl) methyl-2-furyl)carboxylic acid and methyl 2-1H,2H,3H,4H,5H-benzo[e]azaperhydroepin-5-yl)acetate by stirring the two compounds in acetonitrile (0.1M) with triethylamine(1.1 eq) and 1-(3-dimethylaminopropyl)-3-ethylcarbodiimide hydrochloride (1.1 eq) for 18 hrs at room temperature. The reaction was concentrated concentrated in vacuo and purified by flash chromatography to gave methyl-2-(2-((5-((4,5-dichloroimidazolyl)methyl-2-furyl)carbonyl)-1H,3H,4H,5H-benzo[e]azapin-5-yl)acetate. 2-(2-((5-((4,5-dichloroimidazolyl)methyl-2-furyl)carbonyl)-1H,3H,4H,5H-benzo[e]azapin-5-yl)acetic acid was prepared according to example 34. EI-MS m/z 449 (M+H)$^+$; $^1$H-NMR (500 MHz, CDCl$_3$) δ10.8 (br s, 1H), 7.56 (m, 1H), 7.23 (m, 4H), 6.93 (m, 1H), 6.43 (m, 1H), 5.07 (m, 2H), 4.64 (m, 2H), 3.82 (m, 1H), 3.58 (m, 1H), 2.72 (m, 1H), 2.18 (m, 1H), 1.58 (m, 1H).

EXAMPLE 58

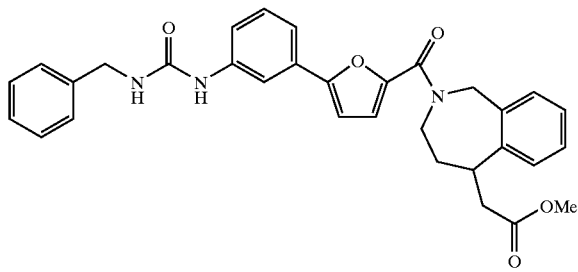

Preparation of Methyl 2-(2-((5-((benzylamino)carbonyl amino)phenyl)-2-furyl)carbonyl)-1H,3H,4H,5H-benzo[e]azapin-5-yl)acetate Methyl 2-(2-((5-((benzylamino)carbonylamino)phenyl)-2-furyl)carbonyl)-1H,3H,4H,5H-benzo[e]azapin-5-yl) acetate as prepared from 5-((benzylamino)carbonyl amino)phenyl)-2-furyl)carboxylic acid and methyl 2-1H,2H,3H,4H,5H-benzo[e]azaperhydroepin-5-yl)acetate by stirring the two compounds in acetonitrile (0.1M) with triethylamine (1.1 eq) and 1-(3-dimethylaminopropyl)-3-ethylcarbodiimide hydrochloride (1.1 eq) for 18 hrs at room temperature. The reaction was concentrated concentrated in vacuo and purified by flash chromatography to gave methyl 2-(2-((5-((benzylamino)carbonylamino)phenyl)-2-furyl)carbonyl)-1H,3H,4H,5H-benzo[e]azapin-5-yl)acetate. EI-MS m/z 538 (M+H)$^+$.

EXAMPLE 59

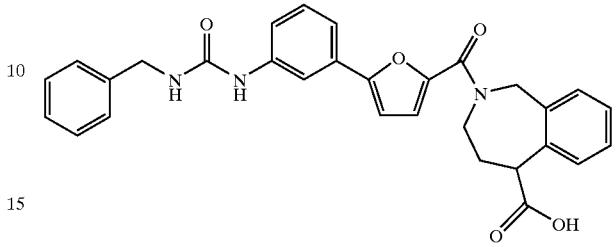

Preparation of 2-(2-((5-((benzylamino)carbonylamino)phenyl)-2-furyl)carbonyl)-1H,3H,4H,5H-benzo[e]azapin-5-yl)acetic acid 2-(2-((5-((benzylamino)carbonylamino)phenyl)-2-furyl)carbonyl)-1H,3H,4H,5H-benzo[e]azapin-5-yl)acetic acid was prepared according to example 34. EI-MS m/z 524 (M+H)$^+$; $^1$H-NMR (400 MHz, CDCl$_3$): δ11.2 (br s, 1H), 8.00 (br s, 1H), 7.49 (m, 1H), 7.24 (m, 12H), 6.48 (d, J=3.3 Hz, 1H), 5.86 (m, 1H), 4.77 (m, 2H), 4.42 (m, 2H), 3.73 (m, 1H), 3.65 (m, 1H), 3.32 (m, 1H), 2.97 (m, 1H), 2.75 (m, 1H), 2.59 (m, 1H), 1.50 (m, 1H).

EXAMPLE 60

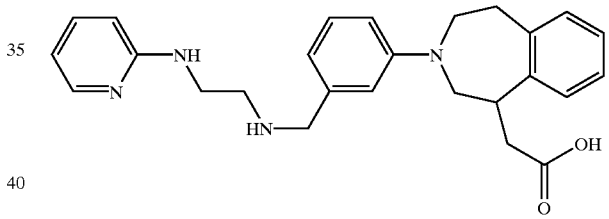

Preparation of 2-[3-(3-{N-[2-(2-pyridylamino)ethyl]carbamoyl}phenyl)-1H,2H,4H,5H-benzo[d]azaperhydroepinyl]acetic acid Step A: 2-(2-bromophenyl)-N-[3-(hydroxymethyl)phenyl]acetamide To a stirring solution of 2-(2-bromophenyl)acetic acid in dichloromethane (0.2 M) was added (3-aminophenyl)methan-1-ol (1.2 eq), triethylamine (1.5 eq), and EDAC (1.5 eq). After 2 hrs, the solution was washed with water, 10% HCl, 10% sodium carbonate, and water, dried over magnesium sulfate, filtered and concentrated in vacuo to afford a colorless solid. EI-MS m/z 320/322 (M+H)$^+$ Step B: (3-{[2-(2-bromophenyl)ethyl]amino}phenyl)methan-1-ol 2-(2-bromophenyl)-N-[3-(hydroxymethyl)phenyl]acetamide was dissolved THF (0.2 M), followed by addition of BH$_3$·DMS (3 eq), and the reaction was heated to reflux with stirring. After 2 hrs, the mixture was cooled to room temperature, and quenched with excess 10% HCl. The mixture was heated to reflux for 1 hr, and then cooled to room temperature. After washing with EtOAc, the aqueous phase was made alkaline with 10% sodium carbonate, and extracted with EtOAc. The organic phase was washed with brine, dried over magnesium sulfate, filtered and concentrated in vacuo. The residue was triturated with EtOAc to afford a colorless solid. EI-MS m/z 307/309 (M+H)+

Step C: Methyl (2E)-4-{[2-(2-bromophenyl)ethyl[]3-(hydroxymethyl)phenyl]amino}but-2-enoate (3-{[2-(2-bromophenyl)ethyl]amino}phenyl)methan-1-ol was dissolved in acetonitrile (0.2 M), followed by addition of methyl 4-bromocrotonate (1.2 eq) and triethylamine (1.5 eq), and the reaction was refluxed for 18 hrs. After cooling to room temperature, the reaction was diluted with EtOAc, washed with 10% sodium carbonate, water, and brine, dried over magnesium sulfate, filtered and concentrated in vacuo. Flash chromatography (silica; 50% EtOAc/Hex) afforded a colorless oil. EI-MS m/z 403/405 (M+H)+

Step D: Methyl 2-{3-[3-(hydroxymethyl)phenyl]-2H,4H,5H-benzo[d]azaperhydroepinylidene}acetate Methyl (2E)-4-{[2-(2-bromophenyl)ethyl][3-(hydroxymethyl)phenyl]amino}but-2-enoate was dissolved in toluene (0.1M) followed by addition of triethylamine (1 eq), tetrakis(triphenylphosphine) palladium (0.05 eq), and 2M sodium carbonate (15%/v). The mixture was heated to reflux ofor 18 hrs. with vigorous stirring. After cooling to room temperature, the phases were separated, and the organic phase was washed with water and brine, dried over magnesium sulfate, filtered and concentrated in vacuo. The residue was dissolved in EtOAc and extracted 5× with 6N HCl. The combined extracts were neutralized with 10% sodium carbonate, and extracted with EtOAc. The organic phase was washed with brine, dried over magnesium sulfate, filtered and concentrated to afford a yellow oil. EI-MS m/z 323 (M+H)+

Step E: Methyl 2-{3-[3-(hydroxymethyl)phenyl]-1H,2H,4H,5H-benzo[d]azaperhydroepinyl}acetate Methyl 2-{3-[3-(hydroxymethyl)phenyl]-2H,4H,5H-benzo[d]azaperhydroepinylidene}acetate was dissolved in MeOH (0.1M) followed by addition of magnesium turnings (10 eq) and the mixture was refluxed for 18 hr. The mixture was filtered through celite and concentrated by rotary evaporation. The product was purified by flash chromatography (25% EtOAc/Hexane). EI-MS m/z 325 (M+H)+

Step F: Methyl 2-[3-(3-formylphenyl)-1H,2H,4H,5H-benzo[benzo[d]azaperhydroepinyl}acetate Methyl 2-{3-[3-(hydroxymethyl)phenyl]-1H,2H,4H,5H-benzo[d]azaperhydroepinyl}acetate was dissolved in methylene chloride (0.1M) followed by addition of triethylamine (1 eq), dimethyl sulfoxide (2 eq) and sulfur trioxide-pyridine (1 eq) and stirred for 5 hrs. The mixture was filtered through celite and concentrated by rotary evaporation. The product was purified by flash chromatography (20% EtOAc/Hexane). EI-MS m/z 323 (M+H)+

Step G: Methyl 2-[3-(3-{N-[2-(2-pyridylamino)ethyl]carbamoyl}phenyl)-1H,2H,4H,5H-benzo[d]azaperhydroepinyl]acetate Methyl 2-[3-(3-formylphenyl)-1H,2H,4H,5H-benzo[d]azaperhydroepinyl]acetate was dissolved in methylene chloride (0.4M) at RT under nitrogen followed by addition of and 2-(N-(2-aminoethyl)amino) pyridine (1.5 eq), sodium triacetoxyborohydride (2 eq), and acetic acid (4 eq). After 5 hrs., the reaction was carefully quenched with 2M sodium carbonate and extracted with methylene chloride. The organic phase was extracted with 1N hydrochloric acid. The aqueous phase was neutralized with 1N sodium hydroxide and extracted with methylene chloride. The organic phase was dried over sodium sulfate, filtered and concentrated in vacuo to afford the product. EI-MS m/z 445 (M+H)+

Step H: 2-[3-(3-{N-[2-(2-pyridylamino)ethyl]carbamoyl}phenyl)-1H,2H,4H,5H-benzo[d]azaperhydroepinyl]acetic acid To a stirring solution of methyl 2-[3-(3-{N-[2-(2-pyridylamino)ethyl]carbamoyl}phenyl)-1H,2H,4H,5H-benzo[d]azaperhydroepinyl]acetate in methanol (0.1 M) was added 1N NaOH (3 eq). After 18 hrs, the reaction was neutralized with 10% HCl, concentrated by rotary evaporation and purified by recrystalization from 2% MeOH/CH$_2$Cl$_2$. EI-MS m/z 431 (M+H)+; $^1$H-NMR (400 MHz, d6-DMSO): δ7.908(d, J=4.8Hz, 1H), 7.33 (m, 2H), 7.21–7.04 (m, 3H), 6.83 (m, 1H), 6.61 (d, J=7.3 Hz, 1H), 6.49 (m, 2H), 3.86 (m, 2H), 3.75 (m, 2H), 3.35 (t, J=3.5Hz), 3.05 (m, 1H), 2.93 (m, 3H), 2.40 (m, 2H), 2.25 (m, 1H), 2.09 (t, J=3.5Hz, 1H).

EXAMPLE 61

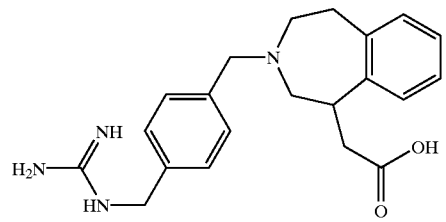

Preparation of 2-[3-({4-[(amidinoamino)methyl]phenyl}methyl)-1H,2H,4H,5H-benzo[d]azepinyl]acetic acid Step A: Tert-butyl (2Z)-2-aza-3-[(tert-butoxy)carbonylamino]-3-methylthioprop-2-enoate To a stirring solution of methylthiocarboxamidine in methylene chloride (0.2 M) was added di-tert-butyl dicarbonate (4 eq), followed by saturated sodium carbonate. After stirring for 18 hr the reaction was diluted with methylene chloride and separated, dried over magnesium sulfate, filtered and concentrated in vacuo. Flash chromatography (silica; 10% CHCl$_3$) afforded a colorless solid. EI-MS m/z 291(M+H)+

Step B: Tert-butyl (2E)-3-amino-2-aza-3-[(tert-butoxy)carbonylamino]prop-2-enoate Tert-butyl (2Z)-2-aza-3-[(tert-butoxy)carbonylamino]-3-methylthioprop-2-enoate was dissolved in MeOH (0.1M) followed by addition of 1N NH$_4$OH (5 eq). After stirring overnight the solution was concentrated in vacuo to afford a colorless solid. EI-MS m/z 411 (M+H)+.

Step C: (Tert-butoxy)-N-{(tert-butoxy)carbonylamino]iminomethyl}-N-{[4-(bromomethyl)phenyl]methyl}carboxamide Tert-butyl (2E)-3-amino-2-aza-3-[(tert-butoxy)carbonyl amino]prop-2-enoate was dissolved in dimethyl foramide (0.1M) followed by addition of NaH (1 eq). After stirring for 5 mins. the addition of α,α'-dibromo-p-xylene in dimethyl foramide was added. The solution was stirred for 18 hrs. and then quenched with saturated ammonium chloride. Diluted with ethyl acetate and washed with water, brine and dried with magnesium sulfate. The solution was concentrated in vacuo to afford a colorless foam. EI-MS m/z 444 (M+H)+.

Step D: Methyl 2-[3-({4-[((tert-butoxy)-N-{[(tert-butoxy)carbonylamino]iminomethyl}carbonylamino) methyl]phenyl}methyl)-1H,2H,4H,5H-benzo[d]azepinyl]acetate Methyl 2-(3-(phenylmethyl)-2H,4H,5H-benzo[d]azaperhydroepin-1-ylidene)acetate and (tert-butoxy)-N-{[(tert-butoxy)carbonylamino]iminomethyl}-N-{[4-(bromomethyl)phenyl]methyl}carboxamide were dissolved in acetonitrile (0.1M) followed by addition of triethylamine (1 eq). After stirring for 18 hrs. at 60° C. the reaction was cooled to room temperature and diluted with ethyl acetate The solution was extracted with 10% sodium bicarbonate, water and brine. The organic layer was dried with magnesium sulfate and concentrated in vacuo to afford a colorless foam. Flash chromatography (silica; 100% EtOAc) afforded a colorless solid. EI-MS m/z 444 (M+H)+.

Step E: 2-[3-({4-[((tert-butoxy)-N-{[carbonylamino] iminomethyl}carbonylamino) methyl]phenyl}methyl)-1H,2H,4H,5H-benzo[d]azepinyl]acetic acid To a stirring solution Methyl 2-[3-({4-[((tert-butoxy)-N-{[(tert-butoxy)carbonylamino] iminomethyl}carbonylamino)methyl]phenyl}methyl)-1H,2H,4H,5H-benzo[d]azepinyl]acetate in methanol (0.1 M) was added 1N NaOH (3 eq). After 18 hrs, the reaction was neutralized with 10% HCl, concentrated by rotary evaporation and purified by recrystalization from 2% MeOH/CH$_2$Cl$_2$. EI-MS m/z 466.

Step F: 2-[3-({4-[(amidinoamino)methyl]phenyl}methyl)-1H,2H,4H,5H-benzo[d]azepinyl]acetic acid 2-[3-({4-[((tert-butoxy)-N-{[carbonylamino] iminomethyl}carbonylamino) methyl]phenyl}methyl)-1H,2H,4H,5H-benzo[d]azepinyl]acetic acid was dissolved in 4M HCl/dioxane and stirred for 3 hrs. at room temperature. The reaction was concentration by rotary evaporation and the product was purified by trituation with diethyl ether. EI-MS m/z 366 (M+H)+; (M+H)+; $^1$H-NMR (400 MHz, d2-D$_2$O): δ7.40 (d, J=8.0Hz, 1H), 7.3 (d, J=8.0Hz, 2H), 7.24–7.09 (m, 4H), 4.39(s, 2H), 4.22 (q, J=6.5Hz, 2H), 3.70–3.60 (m, 2H), 3.48 (m, 1H), 3.24 (m, 2H), 3.01–2.78 (m, 2H), 2.71 (m, 1H).

EXAMPLE 62

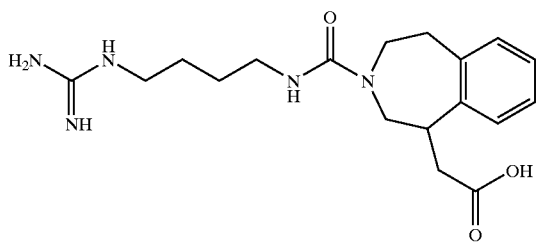

Preparation of 2-(3-{N-[4-(amidinoamino)butyl]carbamoyl}-1H,2H,4H,5H-benzo[d]azepinyl)acetic acid Step A: tert-butyl (2E)-3-[(4-aminobutyl)amino]-2-aza-3-[(tert-butoxy)carbonylamino]prop-2-enoate Tert-butyl (2Z)-2-aza-3-[(tert-butoxy)carbonylamino)-3-methylthioprop-2-enoate was dissolved in MeOH (0.1M) followed by the addition of 1,4-diaminobutane (5 eq). After stirring for 18 hrs., the solution was concentrated in vacuo. The residue was partitioned between ethyl acetate and water. The organic layer was separated and extracted with 10% HCl. The aqueous layer was neutralized with sodium bicarbonate and extracted with ethyl acetate. The organic layers were combined, dried over magnesium sulfate and concentrated in vacuo. Flash chromatography (10% MeOH/CH$_2$Cl$_2$) afforded the product. EI-MS 331(M+H)+.

Step B: tert-butyl(2E)-2-aza-3-[(tert-butoxy)carbonylamino]-3-{[4-({1-[(methoxycarbonyl)methyl[(1H,2H,4H,5H-benzo[d]azepin-3-yl)}carbonylamino)butyl]amino}prop-2-enoate Methyl-2-(1H,2H,3H,4H,5H-benzo[d]azaperhydroepinyl)acetate Hydrocloride was dissolved in methylene chloride and washed with 1N NaOH. The organic layer was separated, dried over sodium sulfate and concentrated by rotary evaporation. Excess of phosgene (20% in toluene) was added and stirred for 5 min. The excess of phosgene was evaporated and the residue was diluted with DMF (2.5 mL) ander nitrogen. Tert-butyl (2E)-3-[(4-aminobutyl)amino]-2-aza-3-[(tert-butoxy)carbonylamino] prop-2-enoate and triethylamine, previously dissolved in DMF (2 mL), were added to the mixture. The resulting mixture was stirred for 18 hrs. at room temperature, concentrated in high vacuum and chromatographed on silica gel using 10% MeOH/CH$_2$Cl$_2$ as eluent. EI-MS m/z 576 (M+H)+.

Step C: 2-(3-{N-[4-(amidinoamino)butyl]carbamoyl}-1H,2H,4H,5H-benzo[d]azepinyl)acetic acid Tert-butyl(2E)-2-aza-3-[(tert-butoxy)carbonylamino]-3-{[4-({1-[(methoxycarbonyl)methyl](1H,2H,4H,5H-benzo[d]azepin-3-yl)}carbonylamino)butyl]amino}prop-2-enoate was dissolved in ethanol (40 mL) followed by the addition of 1N NaOH (7 mL). The mixture was stirred overnight at room temperature, acidified with 1N HCl and extracted with dichloromethane. The organic layer was washed with water, dried over sodium sulfate, concentrated by high vacuum and chromatographed on silica gel using 5% MeOH/CH$_2$Cl$_2$ as eluent. The resulting product was dissolved in 4.0M HCl/dioxane, stirred for 18 hrs., concentrated by rotary evaporation and the residue obtained was re-dissolved in acetonitrile to remove excess of HCl and afforded the desired product. EI-MS m/z 396 (M−H)−. $^1$H-NMR (400 MHz, MeOH-d$_4$): δ7.80 (s, 1H), 7.00 (m, 4H), 3.82–3.6 (m, 2H), 3.5 (s, 1H), 3.45–3.31 (m, 2H), 3.10 (m, 5H), 2.80–2.5 (m, 3H), 1.5–1.35 (m, 5H).

EXAMPLE 63

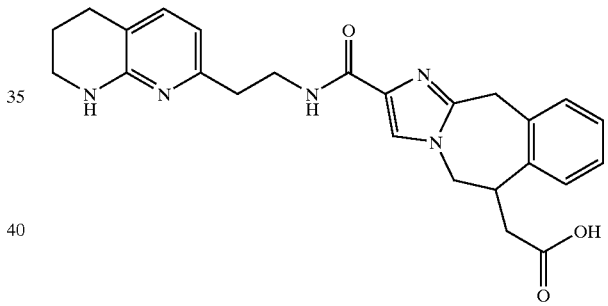

Preparation 2-{2-[N-(2-(1,2,3,4-tetrahydropyridino [2,3-b]pyridin-7-yl)ethyl)carbamoyl]-4H,5H,10H-benzo[d]imidazolo[1,2-a]azepin-5-yl}acetic acid Step A: 2-(4-bromophenyl)ethanenitrile To a stirring solution of 2-bromo benzylbromide in dimethyl sulfoxide (1.0 M) was added sodium cyanide (2 eq), and the solution was stirred for 18 hrs. The reaction was then diluted with water and extracted with ethyl acetate. The organic phase was washed with 10% HCl, brine and dried with magnesium sulfate. The solution was concentrated in vacuo to afford the product. EI-MS m/z 196, 198 (M+H)+

Step B: 2-(4-bromophenyl)-1-(hydroxyimino)ethylamine

To a stirring solution of 2-(4-bromophenyl) ethanenitrile in methanol/water (1 eq/1 eq, 0.1 M) was added hydroxyamine hydrochloride (2.1 eq) and sodium carbonate (2.0 eq). The reaction was stirred at 60° C. for 5 hrs. The reaction was diluted with ethyl acetate and separated. The organic layer was washed with 10% hydochloric acid and separated. The aqueous layer was neutrized with 10% sodium carbonate and extracted with ethyl acetate. The organic layer was dried with magnesium sulfate, filtered and concentrated in vacuo to afford the product. EI-MS m/z 229, 231(M+H)+

Step C: Phenylmethyl (3E)-4-[(1Z)-2-amino-1-aza-3-(4-bromophenyl)prop-1-enyloxy]but-3-enoate To a stirring solution of 2-(4-bromophenyl)-1-(hydroxyimino)ethylamine (1.0 eq) in ethanol (0.1M) was added phenylmethyl prop-2-ynoate (2.0 eq) at 25° C. and stirred for 36 hrs. The reaction concentrated in vacuo, and the residue was purified by flash chromatography (40% EtOAc/Hexane). EI-MS m/z 389, 391(M+H)$^+$ Step D: Phenylmethyl 2-[(2-bromophenyl)methyl] imidazole-4-carboxylate Phenylmethyl (3E)-4-[(1Z)-2-amino-1-aza-3-(4-bromophenyl)prop-1-enyloxy]but-3-enoate in diphenyl ether at 200° C. for 2 hrs. The reaction was cooled to room temperature and diluted with ethyl acetate. The reaction was extracted with 10% hydrochloric acid. The aqueous layer was neutralized with saturated sodium bicarbonate and extracted with ethyl acetate. The organic layer was extracted with brine, and the organic layer was dried with magnesium sulfate, filtered and concentrated in vacuo. The residue was purified by flash chromatography (20% EtOAc/Hexane). EI-MS m/z 369/371(M+H)$^+$ Step E: Methyl (2E)-4-{2-[(2-bromophenyl)methyl]-4-[benzyloxycarbonyl]imidazolyl}but-2-enoate To a stirring solution of phenylmethyl 2-[(2-bromophenyl)methyl]imidazole-4-carboxylate in dimethyl foramide (0.1M) was added sodium hydride (1.2 eq) The reaction was allowed to stir for 10 mins. followed by addition of methyl 4-bromocrotonate continued stirring for 18 hr. The reaction was diluted with water and extracted with ethyl acetate. The organic layer was extracted with 10% hydrochloric acid and the aqueous layer was neutralized with saturated sodium carbonate. The aqueous layer eas extracted with ethyl acetate and dried with magnesium sulfate, filtered and concentrated in vacuo. The residue was purified by flash chromatography (50% EtOAc/Hexane). EI-MS m/z 406/408 (M+H)$^+$ Step F: Methyl 2-{2-benzyloxycarbonyl]-4H,5H,10H-benzo[d]imidazolo[1,2-a]azepin-5-yl}acetate To a solution of methyl (2E)-4-{2-[(2-bromophenyl)methyl]-4-[benzyloxycarbonyl]imidazolyl}but-2-enoate in benzene was added tributyl tin hydride (2 eq) and 2,2"-azobisisobutyronitrile (20%/ wt) under nitrogen. The reaction was stirred under nitrogen at reflux for 2 hrs. The reaction was cooled to room temperature and concentrated in vacuo. The residue was purified by flash chromatography (50% EtOAc/Hexane). EI-MS m/z 391(M+H)$^+$ Step G: 5-[(methoxycarbonyl)methyl]-4H,5H,10H-benzo[d]imidazolo]1,2-a]azepine-2-carboxylic acid Methyl 2-{2-[benzyloxycarbonyl]-4H,5H,10H-benzo[d]imidazolo[1,2-a]azepin-5-yl}acetate was dissolved in ethanol followed by addition of 10% palladium on carbon (10%/wt), and subjected to hydrogenation at ballon pressure. After 3 hrs, the mixture was filtered through celite and concentrated in vacuo to afford a viscous oil.

Step H: Methyl 2-{2-[N-(2-(1,2,3,4-tetrahydropyridino [2,3-b]pyridin-7-yl)ethyl)carbamoyl]-4H,5H,10H-benzo[d]imidazolo[1,2-a]azepin-5-yl}acetate 5-[(Methoxycarbonyl)methyl]-4H,5H,10H-benzo[d]imidazolo[1,2-a]azepine-2-carboxylic acid and 2-(1,2,3,4-tetrahydropyridino[2,3-b]pyridin-7-yl)ethylamine were dissolved in methylene chloride (0.1M) with triethylamine (1.1 eq) and 1-(3-dimethylaminopropyl)-3-ethylcarbodiimide hydrochloride (1.1 eq) and stirred for 18 hrs at room temperature. The reaction was diluted with methylene chloride and washed with water, dried with magnesium sulfate and concentrated under vacuum. The residue was purified by flash chromatography (10% MeOH/ CH$_2$Cl$_2$). EI-MS m/z 459(M+H)$^+$ Step I: 2-{2-[N-(2-(1,2,3,4-tetrahydropyridino[2,3-b]pyridin-7-yl)ethyl)carbamoyl]-4H,5H,10H-benzo[d]imidazolo[1,2-a]azepin-5-yl}acetic acid To a stirring solution of methyl 2-{2-[N-(2-(1,2,3,4-tetrahydropyridino[2,3-b]pyridin-7-yl)ethyl) carbamoyl]-4H,5H,10H-benzo[d]imidazolo[1,2-a]azepin-5-yl}acetate in methanol (0.1 M) was added 1N NaOH (3 eq). After 18 hrs, the reaction was neutralized with 10% HCl, concentrated by rotary evaporation and purified by recrystalization from 2% MeOH/CH$_2$Cl$_2$. EI-MS m/z 431 (M+H)$^+$.

EXAMPLE 64

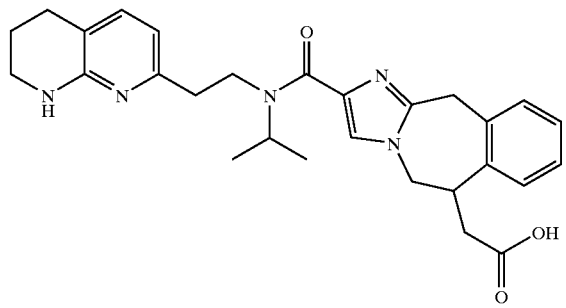

Preparation 2-{2-[N-(methylethyl)-N-(2-(1,2,3,4-tetrahydropyridino[2,3-b]pyridin-7-yl)ethyl) carbamoyl]-4H,5H,10H-benzo[d]imidazolo[1,2-a] azepin-5-yl}acetic acid Step A: Methyl 2-{2-[N-(methylethyl)-N-(2-(1,2,3,4-tetrahydropyridino[2.3-b]pyridin-7-yl)ethyl) carbamoyl]-4H,5H,10H-benzo[d]imidazolo[1,2-a]azepin-5-yl}acetate 5-[(methoxycarbonyl)methyl]-4H,5H,10H-benzo[d]imidazolo[1,2-a]azepine-2-carboxylic acid and 2-N-methylethyl-(1,2,3,4-tetrahydropyridino[2,3-b]pyridin-7-yl) ethylamine were dissolved in methylene chloride (0.1M) with triethylamine(1.1 eq) and 1-(3-dimethylaminopropyl)-3-ethylcarbodiimide hydrochloride (1.1 eq) and stirred for 18 hrs at room temperature. The reaction was diluted with methylene chloride and washed with water, dried over magnesium sulfate and concentrated concentrated in vacuo. The residue was purified by flash chromatography (10% MeOH/ CH$_2$Cl$_2$). EI-MS m/z 501(M+H)$^+$ Step B: 2-{2-[N-(methylethyl)-N-(2-(1,2,3,4-tetrahydro pyridino[2,3-b]pyridin-7-yl)ethyl)carbamoyl]-4H,5H, 10H-benzo[d]imidazolo[1,2-a]azepin-5-yl}acetic acid To a stirring solution of methyl 2-{2-[N-(methyethyl)-N-(2-(1,2,3,4-tetrahydropyridino[2,3-b]pyridin-7-yl)ethyl) carbamoyl]-4H,5H,10H-benzo[d]imidazolo[1,2-a]azepin-5-yl}acetate in methanol (0.1 M) was added 1N NaOH (3 eq). After 18 hrs, the reaction was neutralized with 10% HCl, concentrated by rotary evaporation and purified by recrystalization from 2% MeOH/CH$_2$Cl$_2$. EI-MS m/z 487 (M+H)$^+$; $^1$H-NMR (400 MHz, d-CDCl$_3$): δ7.50 (s, 1H), 7.34–7.09 (m, 4H), 6.20 (d, J=6.3Hz, 1H), 5.50 (m, 1H), 4.37–4.00 (m, 2H), 3.46–3.17 (m, 3H), 2.88 (m, 1H), 2.69 (m, 4H), 2.25 (d, J=13.0 Hz, 2H), 1.86 (m, 3H), 1.60 (m, 7H).

EXAMPLE 65

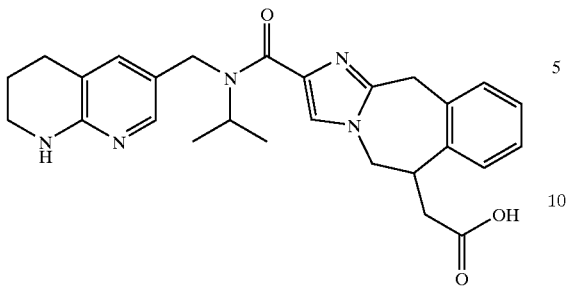

Preparation of 2-{2-[N-(methylethyl)-N-(1,2,3,4tetrahydropyridino[2,3-b]pyridine-6-ylmethyl)carbamoyl]-4H,5H,10H-benzo[d]imidazolo[1,2-a]azepin-5-yl}acetic acid Step A: (methylethyl)(1,2,3,4-tetrahydropyridino[2,3-b]pyridin-7-ylmethyl)amine To a solution of 1,2,3,4-tetrahydropyridino[2,3-b]pyridine-7-carbaldehyde in dry dichloromethane (32 mL) were added 4° A seives, sodium sulfate and isopropyl amine. The mixture was cooled to 0° C. followed by the addition of acetic acid (300 μL). The resulting mixture was stirred at room temperature under nitrogen for 18 hrs. The mixture was filtered through celite, diluted with ethyl acetate, washed with saturated sodium bicarbonate and brine, dried over sodium sulfate, evaporated concentrated in vacuo and purified by flash chromatography(10% MeOH/CH$_2$Cl$_2$ ). EI-MS m/z 206 (M+H)$^+$.

Step B: Methyl-2-{2-[N-(methylethyl)-N-(1,2,3,4-tetrahydropyridino[2,3-b]pyridine-6-ylmethyl)carbamoyl]-4H,5H,10H-benzo[d]imidazolo[1,2-a]azepin-5-yl}acetate

[(Methoxycarbonyl)methyl]-4H,5H,10H-benzo[d]imidazole [3,2-f]azepine-2-carboxylic acid was dissolved in methylene chloride (1 mL) followed by the addition of diisopropyl ethylamine (1.2 eq) and EDC (1.2 eq). Methylethyl(1,2,3,4-tetrahydropyridino[2,3-b]pyridin-7-ylmethyl)amine was dissolved in methylene chloride (1 mL), and added to the resulting mixture. The reaction was stirred at room temperature for 18 hrs., concentrated by rotary evaporation and purified by flash chromatography (5% MeOH/CH$_2$Cl$_2$ ). EI-MS m/z 488 (M+H)$^+$.

Step C: 2-{2-[N-(methylethyl)-N-(1,2,3,4tetrahydropyridino[2,3-b]pyridine-6-ylmethyl)carbamoyl]-4H,5H,10H-benzo[d]imidazolo1,2-a]azepin-5-yl}acetic acid Methyl-2-{2-[N-(methylethyl)-N-(1,2,3,4-tetrahydropyridino[2,3-b]pyridine-6-ylmethyl) carbamoyl]-4H,5H,10H-benzo[d]imidazolo[1,2-a]azepin-5-yl}acetate was dissolved in methanol (0.2M) followed by the addition of 1N NaOH (5 eq). The mixture was stirred at room temperature for 18 hrs., acidified with 1N NaOH, concentrated by rotary evaporation and the product was purified by flash chromatography (5% MeOH/CH$_2$Cl$_2$) EI-MS m/z 474 (M+H)$^+$; $^1$H-NMR (400 MHz, MeOH-d,): δ7.43–7.10 (m, 6H), 6.5 (s, 1H), 5.45 (s, 2H), 4.53–4.40 (m.3H), 4.12–3.83 (m,3H), 3.40 (m,2H), 2.70 (m,3H), 2.55 (m,1H), 1.85(m, 2H), 1.15(d, J=6.33 Hz, 6H).

EXAMPLE 66

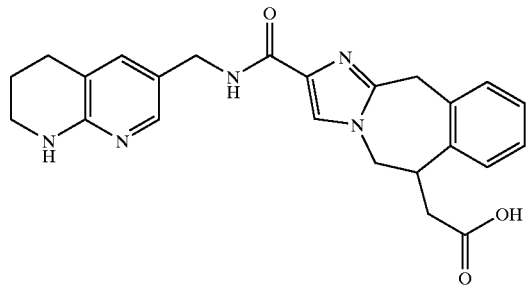

Preparation of 2-{2-[N-(1,2,3,4-tetrahydropyridino[2,3-b]pyridin-6-ylmethyl)carbamoyl]-4H,5H,10H-benzo[d]imidazolo[1,2-a]azepin-5-yl}acetic acid Step A: Dimethoxypyridino[3,2-e]pyridin-2-ylmethane A mixture of 2-aminopyridine-3-carbaldehyde, prepared according to Duggan, M. E. WO 98/18460, pyruvic aldehyde dimethylacetal (4 eq) and L-proline (0.3 eq) in MeOH (0.2M) were refluxed under nitrogen for 20 hr. The mixture cooled to room temperature, concentrated by rotary evaporation and the residue was diluted with methylene chloride (32 mL) and washed with water and brine, dried over sodium sulfate, filtered, concentrated concentrated in vacuo . The residue was purified by flash chromatography (10% MeOH/CH$_2$Cl$_2$ ). $^1$H-NMR (400 MHz, CDCl$_3$): 9.15 (dd, J=1.95, J=4.20, 1H), 8.25 (d, J=8.42, 1H), 8.20 (dd, J=1.95, 8.14, 1H), 7.8 (d, J=8.36, 1H), 7.52 (q, J=4.24, 1H), 5.5 (s, 1H), 3.5 (s, 6H).

Step B: Dimethoxy-1,2,3,4-tetrahydropyridino[2,3-b]pyridin-7-ylmethane

Dimethoxypyridino[3,2-e]pyridin-2-ylmethane was dissolved in methanol (0.5M) followed by addition of 10% Pd/C), and subjected to hydrogenation at ballon pressure. The mixture was filtered through celite and concentrated by rotary evaporation. EI-MS m/z 209 (M+H)$^+$.

Step C: 1,2,3,4-tetrahydropyridino[2,3-b]pyridin-7-carbaldehyde

Dimethoxy-1,2,3,4-tetrahydropyridino[2,3-b]pyridin-7-ylmethane was dissolved in trifluoroacetic acid (14 mL) and stirred under nitrogen for 16 hrs. The mixture was quenched with saturated sodium bicarbonate, extracted with methylene chloride, dried over sodium sulfate, filtered, in vacuo and purified by flash chromatography (5% MeOH/CH$_2$Cl$_2$ ). EI-MS m/z 163 (M+H)$^+$.

Step D: 1,2,3,4-tetrahydropyridino[2,3-b]pyridin-7-ylmethylamine

Hydroxyamine hydrochloride (2 eq), sodium acetatetrihydrate (2 eq) and water (0.4M) were heated at 60° C. 1,2,3,4-tetrahydropyridino[2,3-b]pyridine-7-carbaldehyde was dissolved in methanol (2.5 mL) and added to the resulting solution. Additional methanol was added until the solution became clear, the reaction was stirred at 60° C. for 18 hrs. The mixture was cooled to room temperature, diluted with water (25 mL) and extracted with ether. The organic layer was extracted with saturated sodium bicarbonate and brine, dried over sodium sulfate, filtered and concentrated by in vacuo. To a solution of the oxime in trifluoroacetic acid (5 mL) was added zinc dust (5.6 eq) in several portions, while keeping the temperature between 15–25° C. After stirring for 15 mins., the mixture was added to a solution of an aqueous 2N NaOH (39 mL) solution and methylene chloride (21 mL) at 0° C. and stirred for an additional 15 mins. The reaction was filtered and the organic layer was separated, washed with water and brine, dried over sodium sulfate and concentrated in vacuo to yield the product. EI-MS m/z 163(M+H)+.

Step E: Methyl-2-{2-[N-(1,2,3,4-tetrahydropyridino [2,3-b]pyridin-6-ylmethyl)carbamoyl]-4H,5H,10H-benzo[d]imidazolo[1,2-a]azepin-5-yl}acetate 5-[(methoxycarbonyl)methyl]-4H,5H,10H-benzo[d]imidazole[3,2-f]azepine-2-carboxylic acid was dissolved in methylene chloride (0.5 mL), followed by addition of diisopropyl ethylamine (1.2 eq) and EDC (1.2 eq). 1,2,3,4-tetrahydropyridino[2,3-b]pyridin-7-ylmethylamine was dissolved methylene chloride (0.5 mL) and added to the resulting solution. The reaction was stirred at room temperature for 48 hrs., concentrated in vacuo and purified by flash chromatography (5% MeOH/CH$_2$Cl$_2$). EI-MS m/z 446 (M+H)+.

Step F: 2-{2-[N-(1,2,3,4-tetrahydropyridino[2,3-b]pyridin-6-ylmethyl)carbamoyl]-4H,5H,10H-benzo[d]imidazolo[1,2-a]azepin-5-yl}acetic acid Methyl-2-2-[N-(1,2,3,4-tetrahydropyridino[2,3-b]pyridin-6-ylmethyl)carbamoyl]-4H,5H,10H-benzo[d]imidazolo[1,2-a]azepin-5-yl)acetate was dissolved in MeOH (6 mL) and 1N NaOH (5 eq) was added. The mixture was stirred at room temperature for 18 hrs., acidified with 1N HCl, concentrated in vacuo and the product was purified by flash chromatography (5% MeOH/CH$_2$Cl$_2$). EI-MS m/z 432 (M+H)+. $^1$H-NMR (400 MHz, MeOH-d$_4$): δ7.55 (s, 1H), 7.38–7.10 (m, 6H), 6.5 (d, J=5.77, 1H), 4.54–4.46 (m, 2H), 4.37 (s, 2H), 4.10 (d, J=15.6, 2H), 3.95 (t, J=11.79, 2H), 3.30 (m, 2H), 2.7 (m, 2H), 2.5 (m, 1H), 1.85 (m, 2H).

EXAMPLE 67

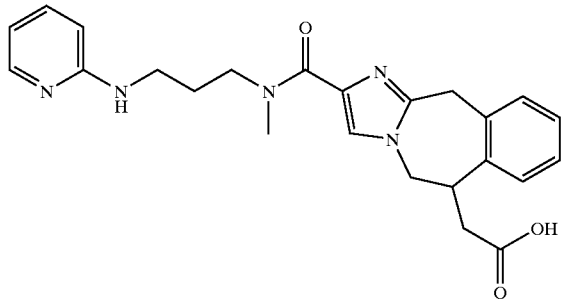

Preparation of 2-(2-{N-methyl-N-[3-(2-pyridylamino)propyl]carbamoyl}-4H,5H,10H-benzo[d]imidazolo[1,2-a]azepin-5-yl)acetic acid Step A: Methyl-2-(2-{N-methyl-N-[3-(2-pyridylamino)propyl]carbamoyl}-4H,5H,10H-benzo[d]imidazolo[1,2-a]azepin-5-yl)acetate

[(Methoxycarbonyl)methyl]-4H,5H,10H-benzo[d]imidazole[3,2-f]azepine-2-carboxylic acid was dissolved in methylene chloride (0.5 mL), followed by addition of diisopropyl ethylamine (1.2 eq) and EDC (1.2 eq). 1,2,3,4-tetrahydropyridino[2,3-b]pyridin-7-ylmethylamine was dissolved methylene chloride (0.5 mL) and added to the resulting solution. The reaction was stirred at room temperature for 48 hrs., concentrated in vacuo and purified by flash chromatography (5% MeOH/CH$_2$Cl$_2$). EI-MS m/z 448 (M+H)+.

Step B: 2-(2-{N-methyl-N-[3-(2-pyridylamino)propyl]carbamoyl}-4H,5H,10H-benzo[d]imidazolo[1,2-a]azepin-5-yl)acetic acid Methyl-2-(2-{N-methyl-N-[3-(2-pyridylamino)propyl]carbamoyl}-4H,5H,10H-benzo[d]imidazolo[1,2-a]azepin-5-yl)acetate was dissolved in MeOH (6 mL) and 1N NaOH (5 eq) was added. The mixture was stirred at room temperature for 18 hrs., acidified with 1N HCl, concentrated in vacuo and the product was purified by flash chromatography (5% MeOH/CH$_2$Cl$_2$). EI-MS m/z 434 (M+H)+. $^1$H-NMR (400 MHz, CDCl$_3$): δ8.0 (d, J=5.4, 1H), 7.4 (m, 2H), 7.3 (m, 4H), 6.55 (m, 3H), 4.20–4.05 (m, 4H), 3.9 (m, 1H), 3.3 (t, J=6.8, 2H), 3.15 (s, 3H), 2.7 (dd, J=16.5, J=6.3, 2H), 1.9 (m, 2H).

EXAMPLE 68

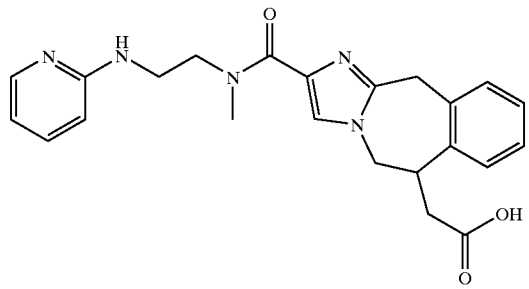

Preparation of 2-(2-{N-methyl-N-[2-(2-pyridylamino)ethyl]carbamoyl}-4H,5H,10H-benzo[d]imidazolo[1,2-a]azepin-5-yl)acetic acid Step A: Methyl-2-(2-{N-methyl-N-[2-(2-pyridylamino)ethyl]carbamoyl}-4H,5H,10H-benzo[d]imidazolo[1,2-a]azepin-5-yl)acetate

[(Methoxycarbonyl)methyl]-4H,5H,10H-benzo[d]imidazole[3,2-f]azepine-2-carboxylic acid was dissolved in methylene chloride (0.5 mL), followed by addition of diisopropyl ethylamine (1.2 eq) and EDC (1.2 eq). 1,2,3,4-tetrahydropyridino[2,3-b]pyridin-7-ylmethylamine was dissolved methylene chloride (0.5 mL) and added to the resulting solution. The reaction was stirred at room temperature for 48 hrs., concentrated in vacuo and purified by flash chromatography (5% MeOH/CH$_2$Cl$_2$). EI-MS m/z 434 (M+H)+.

Step B: 2-(2-{N-methyl-N-[2-(2-pyridylamino)ethyl]carbamoyl}-4H,5H,10H-benzo[d]imidazolo[1,2-a]azepin-5-yl)acetic acid Methyl-2-(2-{N-methyl-N-[2-(2-pyridylamino)ethyl]carbamoyl}-4H,5H,10H-benzo[d]imidazolo[1,2-a]azepin-5-yl)acetate was dissolved in MeOH (6 mL) and 1N NaOH (5 eq) was added. The mixture was stirred at room temperature for 18 hrs., acidified with 1N HCl, concentrated in vacuo and the product was purified by flash chromatography (5% MeOH/CH$_2$Cl$_2$). EI-MS m/z 420 (M+H)+. $^1$H-NMR (400 MHz, d$_6$-DMSO): δ12.35 (s, 1H), 7.5 (s, 1H), 7.33–7.16 (m, 8H), 6.5 (bs, 1H), 4.4 (m, 1H), 4.10–3.8 (m, 4H), 3.15 (s, 3H), 2.9 (m, 2H), 2.8–2.6 (m, 2H), 1.75 (s, 2H).

EXAMPLE 69

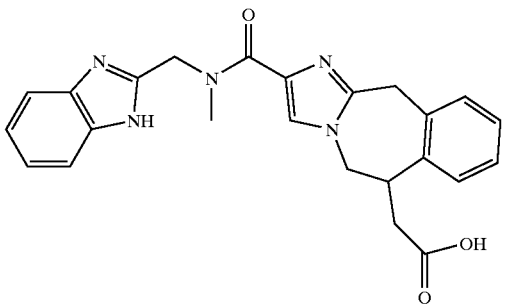

Preparation of 2-{2-[N-(benzimidazol-2-ylmethyl)-N-methylcarbamoyl]-4H,5H,10H-benzo[d]imidazolo[1,2-a]azepin-5-yl}acetic acid Step A: Methyl-2-{2-[N-(benzimidazol-2-ylmethyl)-N-methylcarbamoyl]-4H,5H,10H-benzo[d]imidazolo[1,2-a]azepin-5-yl}acetate

[(Methoxycarbonyl)methyl]-4H,5H,10H-benzo[d]imidazole[3,2-f]azepine-2-carboxylic acid was dissolved in methylene chloride (0.5 mL), followed by addition of diisopropyl ethylamine (1.2 eq) and EDC (1.2 eq). 1,2,3,4-tetrahydropyridino[2,3-b]pyridin-7-ylmethylamine was dissolved methylene chloride (0.5 mL) and added to the resulting solution. The reaction was stirred at room temperature for 48 hrs., concentrated in vacuo and purified by flash chromatography (5% MeOH/CH$_2$Cl$_2$). EI-MS m/z 444 (M+H)$^+$.

Step B: 2-{2-[N-(benzimidazol-2-ylmethyl)-N-methylcarbamoyl]-4H,5H,10H-benzo[d]imidazolo[1,2-a]azepin-5-yl}acetic acid Methyl-2-{2-[N-(benzimidazol-2-ylmethyl)-N-methylcarbamoyl]-4H,5H,10H-benzo[d]imidazolo[1,2-a]azepin-5-yl}acetate was dissolved in MeOH (6 mL) and 1N NaOH (5 eq) was added. The mixture was stirred at room temperature for 18 hrs., acidified with 1N HCl concentrated in vacuo and the product was purified by flash chromatography (5% MeOH/CH$_2$Cl$_2$). EI-MS m/z 430 (M+H)$^+$.
$^1$H-NMR (400 MHz, MeOH-d$_4$) δ7.42 (s, 1H), 7.17 (m, 8H), 4.4 (m, 2H), 4.10–3.90 (m, 4H), 3.3 (m, 2H), 3.0 (m, 2H), 2.10 (m, 2H).

EXAMPLE 70

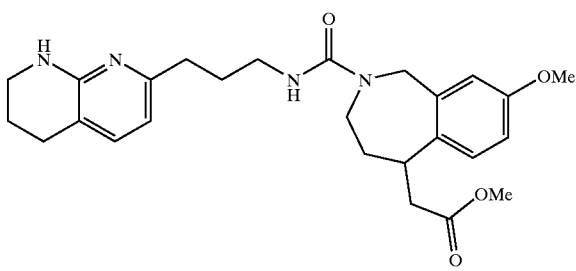

Preparation of Methyl 2-(8-methoxy-2-(N-(3-(1,2,3,4-tetrahydropyridino[2,3,b]pyridin-7-yl)propyl)carbamoyl)-1H,3H,4H,5H-benzo[e]azaperhydroepin-5-yl) acetate Methyl 2-(8-methoxy-1H,2H,3H,4H,5H-benzo[e]azaperhydroepin-5-yl)acetate (1 eq, prepared according to Example 56) was stirred under nitrogen with 20% phosgene (1.1 eq) in toluene for 10 min. The excess phosgene was removed by rotary evaporation and the crude product was dissolved in 1:1 THF/DMF (0.25 M), followed by addition of diisopropylethylamine (1.1 eq) and 3-(1,2,3,4-tetrahydropyridino[2,3,b]pyridin-7-yl) propylamine (1.1 eq, prepared according to Duggan, M. E. WO 98/18460). The reaction was stirred for 12 h at RT under nitrogen, concentrated in vacuo and the product was purified by flash chromatograpy (2–5% MeOH/CH$_3$Cl) to give methyl 2-(8-methoxy-2-(N-(3-(1,2,3,4-tetrahydropyridino[2,3,b]pyridin-7-yl)propyl) carbamoyl)-1H,3H,4H,5H-benzo[e]azaperhydroepin-5-yl) acetate as a clear oil. EI-MS m/z 467 (M+H)$^+$.

EXAMPLE 71

Preparation of 2-(8-methoxy-2-(N-(3-(1,2,3,4-tetrahydropyridino[2,3,b]pyridin-7-yl)propyl)carbamoyl)-1H,3H,4H,5H-benzo[e]azaperhydroepin-5-yl) acetic acid

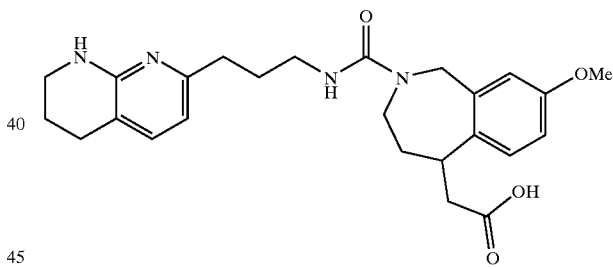

1 N NaOH solution (3 eq) was added to a solution of methyl 2-(8-methoxy-2-(N-(3-(1,2,3,4-tetrahydro pyridino[2,3,b]pyridin-7-yl)propyl)carbamoyl)-1H,3H,4H,5H-benzo[e]azaperhydroepin-5-yl)acetate (1 eq) in methanol (0.10 M) and the resulting mixture stirred under nitrogen for 12 h. The mixture was neutralized to pH=7 with 1N HCl solution and concentrated in vacuo. Purification by flash chromatography on silica gel (4–6% MeOH/CH$_2$Cl$_2$) gave 2-(8-methoxy-2-(N-(3-(1,2,3,4-tetrahydropyridino[2,3,b]pyridin-7-yl)propyl)carbamoyl)-1H,3H,4H,5H-benzo[e]azaperhydroepin-5-yl)acetic acid as a white solid. EI-MS m/z 453 (M+H)$^+$; $^1$H-NMR (400 MHz, CDCl$_3$): .11.0 (br s, 1H), 7.22 (d, J=7.3 Hz, 1H), 7.08 (d, J=8.5 Hz, 1H), 6.84 (d, J=2.5 Hz, 1H), 6.70 (dd, J=8.4, 2.5 Hz, 1H), 6.27 (d, J=7.3 Hz, 1H), 5.74 (m, 1H), 4.65 (d, J=15.1 Hz, 1H), 4.41 (d, J=15.1 Hz, 1H), 3.72 (s, 3H), 3.66 (m, 1H), 3.45 (m, 4H), 3.30 (m, 1H), 3.16 (m, 1H), 2.69 (m, 6H), 2.12 (m, 1H), 1.87 (m, 2H), 1.80 (m, 2H), 1.52 (m, 1H)

EXAMPLE 72

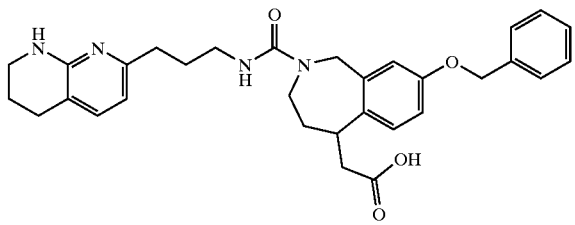

Preparation of 2-(8-benzyloxy-2-(N-(3-(1,2,3,4-tetrahydropyridino[2,3,b])pyridin-7-yl)propyl) carbamoyl)-1H,3H,4H,5H-benzo[e] azaperhydroepin-5-yl) acetic acid Step A: Methyl 2-(8-hydroxy-1H,2H,3H,4H,5H-benzo[e]azaperhydroepin-5-yl)acetic acid Boron tribromide (2 eq) was added to a solution of methyl 2-(8-methoxy-1H,2H,3H,4H,5H-benzo[e]azaperhydroepin-5-yl)acetate (1 eq, prepared according to Example 56) in methylene chloride (0.1 M) at −78° C. and the resulting mixture allowed to warm to RT with stirring under nitrogen. Quenched with 10% HCl solution and washed with 1N HCl solution followed by brine. Collected aqueous layer and concentrated in vacuo to give 2-(8-hydroxy-1H,2H,3H,4H, 5H-benzo[e]azaperhydroepin-5-yl)acetic acid as a white solid. EI-MS m/z 222 (M+H)$^+$.

Step B: Methyl 2-(8-hydroxy-1H,2H,3H,4H,5H-benzo[e]azaperhydroepin-5-yl)acetate

Thionyl chloride (1.2 eq) was added to a solution of 2-(8-hydroxy-1H,2H,3H,4H,5H-benzo[e]azaperhydroepin-5-yl)acetic acid (1 eq) in methanol (0.1 M) at 0° C. and the resulting mixture was allowed to warm to RT with stirring under nitrogen. Concentrated in vacuo, dissolved residue in methylene chloride, and washed with saturated NaHCO$_3$ solution. Dried organics over sodium sulfate and concentrated in vacuo to give methyl 2-(8-hydroxy-1H,2H,3H,4H, 5H-benzo[e]azaperhydroepin-5-yl)acetate as a white solid. EI-MS m/z 236 (M+H)$^+$.

Step C: Methyl 2-(2-(tert-butoxycarbonyl)-8-hydroxy-1H, 2H,3H,4H,5H-benzo[e]azaperhydroepin-5-yl)acetate Di-tert-butyl dicarbonate (1.1 eq) was added to a solution of methyl 2-(8-hydroxy-1H,2H,3H,4H,5H-benzo[e] azaperhydroepin-5-yl)acetate in methylene chloride (0.50 M) at RT and the resulting mixture stirred under nitrogen 5 hrs. Concentrated in vacuo and purified by flash chromatography on silica gel (10–20% EtOAc/Hexane) to give methyl 2-(2-(tert-butoxycarbonyl)-8-hydroxy-1H,2H,3H, 4H,5H-benzo[e]azaperhydroepin-5-yl)acetate as a clear oil. EI-MS m/z 336 (M+H)$^+$.

Step D: Methyl 2-(2-(tert-butoxycarbonyl)-8-benzyloxy-1H,2H,3H,4H,5H-benzo[e]azaperhydroepin-5-yl)acetate NaH (1.2 eq) was added to a solution of methyl 2-(2-(tert-butoxycarbonyl)-8-hydroxy-1H,2H,3H,4H,5H-benzo[e]azaperhydroepin-5-yl)acetate (1 eq) in THF (0.10M) at 0° C. under nitrogen. After 10 min, benzyl bromide (1.2 eq) was added and the resulting mixture allowed to warm to RT with stirring. The reaction was quenched with saturated NaHCO$_3$ solution and concentrated in vacuo. The residue was dissolved in ethyl acetate and washed with water. The organics were dried over Na$_2$SO$_4$, concentrated in vacuo, and purified by flash chromatography on silica gel (10–20% EtOAc/Hexane) to give methyl 2-(2-(tert-butoxycarbonyl)-8-benzyloxy-1H,2H,3H,4H,5H-benzo[e]azaperhydroepin-5-yl)acetate as a clear oil. EI-MS m/z 426 (M+H)$^+$.

Step E: Methyl 2-(8-benzyloxy-1H,2H,3H,4H,5H-benzo[e]azaperhydroepin-5-yl)acetate Methyl 2-(2-(tert-butoxycarbonyl)-8-benzyloxy-1H,2H, 3H,4H,5H-benzo[e]azaperhydroepin-5-yl)acetate (1 eq) and 4.0 M HCl/dioxane (5 eq) were stirred at RT under nitrogen for 3 h. The solvents were removed by rotary evaporation and the residue dissolved in methylene chloride and washed with 1N NaOH. The organics were dried over sodium sulfate and concentrated in vacuo to give methyl 2-(8-benzyloxy-1H,2H,3H,4H,5H-benzo[e]azaperhydroepin-5-yl)acetate as a white solid. EI-MS m/z 326 (M+H)$^+$.

Step F: 2-(8-benzyloxy-2-(N-(3-(1,2,3,4-tetrahydropyridino [2,3,b]pyridin-7-yl)propyl) carbamoyl)-1H,3H,4H,5H-benzo[e]azaperhydroepin-5-yl)acetate Methyl 2-(8-benzyloxy-1H,2H,3H,4H,5H-benzo[e] azaperhydroepin-5-yl)acetate (1 eq) was stirred under nitrogen with 20% phosgene (1.1 eq) in toluene for 10 min. The excess phosgene was removed by rotary evaporation and the crude product was dissolved in 1:1 THF/DMF (0.25 M), followed by addition of diisopropylethylamine (1.1 eq) and 3-(1,2,3,4-tetrahydropyridino[2,3,b]pyridin-7-yl) propylamine (1.1 eq, prepared according to Duggan, M. E. WO 98/18460). The reaction was stirred for 12 h at RT under nitrogen, concentrated in vacuo and the product was purified by flash chromatograpy (2–5% MeOH/CH$_3$Cl) to give methyl 2-(8-benzyloxy-2-(N-(3-(1,2,3,4-tetrahydropyridino [2,3,b]pyridin-7-yl)propyl) carbamoyl)-1H,3H,4H,5H-benzo[e]azaperhydroepin-5-yl) acetate as a clear oil. EI-MS m/z 543 (M+H)$^+$.

Step G: Preparation of 2-(8-benzyloxy-2-(N-(3-(1,2,3,4-tetrahydropyridino[2,3,b]pyridin-7-yl) propyl)carbamoyl)-1H,3H,4H,5H-benzo[e]azaperhydroepin-5-yl)acetic acid 1 N NaOH solution (3 eq) was added to a solution of methyl 2-(8-benzyloxy-2-(N-(3-(1,2,3,4-tetrahydro pyridino [2,3,b]pyridin-7-yl)propyl)carbamoyl)-1H,3H,4H,5H-benzo[e]azaperhydroepin-5-yl)acetate (1 eq) in methanol (0.10 M) and the resulting mixture stirred under nitrogen for 12 h. The mixture was neutralized to pH=7 with 1N HCl solution and concentrated in vacuo. Purification by flash chromatography on silica gel (4–6% MeOH/CH$_2$Cl$_2$) gave 2-(8-benzyloxy-2-(N-(3-(1,2,3,4-tetrahydropyridino [2,3,b] pyridin-7-yl)propyl)carbamoyl)-1H,3H,4H,5H-benzo[e] azaperhydroepin-5-yl)acetic acid as a white solid. EI-MS m/z 529 (M+H)$^+$; $^1$H-NMR (400 MHz, CDCl$_3$) δ10.7 (br s, 1H), 7.39 (m, 6H), 7.04 (d, J=8.4 Hz, 1H), 6.91 (m, 1H), 6.83 (m, 1H), 6.31 (d, J=7.2 Hz, 1H), 5.30 (s, 2H), 5.03 (br s, 2H), 4.32 (m, 1H), 4.21 (m, 1H), 3.67 (m, 1H), 3.47 (m, 4H), 3.22 (m, 1H), 3.11 (m, 1H), 2.70 (m, 6H), 1.90 (m, 3H), 1.74 (m, 2H), 1.63 (m, 1H).

EXAMPLE 73

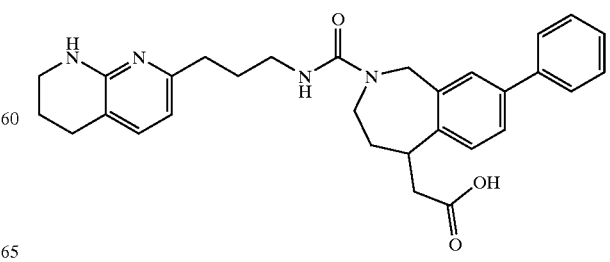

Preparation of 2-(8-phenyl-2-(N-(3-(1,2,3,4-tetrahydropyridino[2,3,b]pyridin-7-yl)propyl)carbamoyl)-1H,3H,4H,5H-benzo[e]azaperhydroepin-5-yl) acetic acid Step A: Methyl 2-(2-(tert-butoxycarbonyl)-8-trifluoromethanesulfonyl-1H,2H,3H,4H,5H-benzo[e]azaperhydroepin-5-yl)acetate Triflic anhydride (1.1 eq) was added to a solution of methyl 2-(2-(tert-butoxycarbonyl)-8-hydroxy-1H,2H,3H,4H,5H-benzo[e]azaperhydroepin-5-yl)acetate (1 eq, prepared according to Example 72, Step C) and 2,6-lutidine (1.3. eq) in methylene chloride (0.1 M) at 0° C. and the resulting mixture stirred under nitrogen for 1 h. Water was added, the organic layer collected, washed with 1N HCl solution, and dried over magnesium sulfate. Concentration in vacuo gave methyl 2-(2-(tert-butoxycarbonyl)-8-trifluoromethanesulfonyl-1H,2H,3H,4H,5H-benzo[e]azaperhydroepin-5-yl)acetate as a clear oil. EI-MS m/z 468 (M+H)$^+$.

Step B: Methyl 2-(2-((tert-butyl)oxycarbonyl)-8-phenyl-1H,3H,4H,5H-benzo[e]azaperhydroepin-5-yl)acetate Toluene (0.1 M) was added to a degassed mixture of methyl 2-(2-((tert-butyl)oxycarbonyl)-8-trifluoromethanesulfonyl-1H,3H,4H,5H-benzo[e]azaperhydroepin-5-yl)acetate (1 eq) phenylboronic acid (2 eq), tetrakis (triphenylphosphine)palladium(0) (0.1 eq), and potassium carbonate (2 eq) and the resulting mixture heated at 90° C. for 12 h. Concentrated in vacuo and purified by flash chromatography on silica gel (20% EtOAc/Hexane) to give methyl 2-(2-((tert-butyl)oxycarbonyl)-8-phenyl-1H,3H,4H,5H-benzo[e]azaperhydroepin-5-yl)acetate as a clear oil. EI-MS m/z 396 (M+H)$^+$.

Step C: Methyl 2-(8-phenyl-1H,2H,3H,4H,5H-benzo[e]azaperhydroepin-5-yl)acetate

Methyl 2-(2-(tert-butoxycarbonyl)-8-phenyl-1H,2H,3H,4H,5H-benzo[e]azaperhydroepin-5-yl)acetate (1 eq) and 4.0 M HCl/dioxane (5 eq) were stirred at RT under nitrogen for 3 h. The solvents were removed by rotary evaporation and the residue dissolved in methylene chloride and washed with 1N NaOH. The organics were dried over sodium sulfate and concentrated in vacuo to give methyl 2-(8-phenyl-1H,2H,3H,4H,5H-benzo[e]azaperhydroepin-5-yl)acetate as a clear oil. EI-MS m/z 296 (M+H)$^+$.

Step D: 2-(8-phenyl-2-(N-(3-(1,2,3,4-tetrahydro pyridino[2,3,b]pyridin-7-yl)propyl)carbamoyl)-1H,3H,4H,5H-benzo[e]azaperhydroepin-5-yl) acetate Methyl 2-(8-phenyl-1H,2H,3H,4H,5H-benzo[e]azaperhydroepin-5-yl)acetate (1 eq) was stirred under nitrogen with 20% phosgene (1.1 eq) in toluene for 10 min. The excess phosgene was removed by rotary evaporation and the crude product was dissolved in 1:1 THF/DMF (0.25 M), followed by addition of diisopropylethylamine (1.1 eq) and 3-(1,2,3,4-tetrahydropyridino[2,3,b]pyridin-7-yl)propylamine (1.1 eq, prepared according to Duggan, M. E. WO 98/18460). The reaction was stirred for 12 h at RT under nitrogen, concentrated in vacuo and the product was purified by flash chromatograpy (2–5% MeOH/CH$_3$Cl) to give methyl 2-(8-phenyl-2-(N-(3-(1,2,3,4-tetrahydropyridino[2,3,b]pyridin-7-yl)propyl) carbamoyl)-1H,3H,4H,5H-benzo[e]azaperhydroepin-5-yl) acetate as a clear oil. EI-MS m/z 513 (M+H)$^+$.

Step E: Preparation of 2-(8-phenyl-2-(N-(3-(1,2,3,4-tetrahydropyridino[2,3,b]pyridin-7-yl)propyl) carbamoyl)-1H,3H,4H,5H-benzo[e]azaperhydroepin-5-yl)acetic acid 1 N NaOH solution (3 eq) was added to a solution of methyl 2-(8-phenyl-2-(N-(3-(1,2,3,4-tetrahydropyridino[2,3,b]pyridin-7-yl)propyl)carbamoyl)-1H,3H,4H,5H-benzo[e]azaperhydroepin-5-yl)acetate (1 eq) in methanol (0.10 M) and the resulting mixture stirred under nitrogen for 12 h. The mixture was neutralized to pH=7 with 1N HCl solution and concentrated in vacuo. Purification by flash chromatography on silica gel (4–6% MeOH/CH$_2$Cl$_2$) gave 2-(8-phenyl-2-(N-(3-1,2,3,4-tetrahydropyridino[2,3,b]pyridin-7-yl)propyl) carbamoyl)-1H,3H,4H,5H-benzo[e]azaperhydroepin-5-yl) acetic acid as a white solid. EI-MS m/z 499 (M+H)$^+$; $^1$H-NMR (400 MHz, CDCl$_3$): δ10.9 (br s, 1H), 7.41 (m, 6H), 7.09 (d, J=8.4 Hz, 1H), 6.93 (m, 1H), 6.85 (m, 1H), 6.29 (d, J=7.2 Hz, 1H), 5.57 (br s, 1H), 4.91 (br s, 1H), 4.32 (m, 2H), 3.50 (m, 4H), 3.27 (m, 1H), 3.11 (m, 1H), 2.68 (m, 6H), 2.34 (m, 1H), 1.90 (m, 4H), 1.74 (m, 1H), 1.42 (m, 1H).

EXAMPLE 74

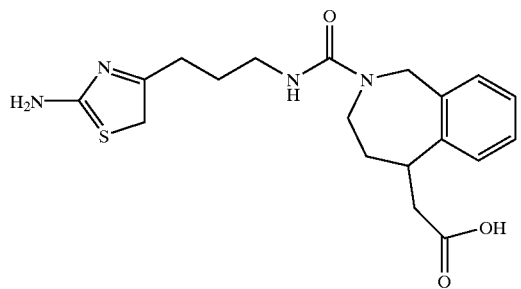

Preparation of 2-(2-{N-[3-(2-amino-5H-1,3-thiazol-4-yl)propyl]carbamoyl}-1H,3H,4H,5H-benzo[e]azepin-5-yl)acetic acid Step A: Preparation of methyl 6-bromo-5-oxohexanoate Ethyl 4-acetylbutyrate was dissolved in MeOH (0.5M) and cooled to 0° C. Bromine (1.0 eq) was added dropwise and the mixture was stirred at room temperature for 18 hrs. The solvent was removed in vacuo and the residue was dissolved in ether, washed with water, saturated sodium bicarbonate, brine, dried over sodium sulfate. The solvent was removed in vacuo and the residue was purified by flash chromatograpy (7% EtOAc/Hexanes). EI-MS m/z 224 (M+H)$^+$.

Step B: Preparation of Methyl 4-(2-amino-3H-1,3-thiazol-4-yl)butanoate

Methyl 6-bromo-5-oxohexanoate and thiourea (1.2 eq) in ethanol (0.2M solution) were refluxed for 18 hrs. The reaction was cooled to room temperature, diluted with ethyl acetate, washed with water and brine. The organic layer was dried over sodium sulfate, concentrated in vacuo and the residue was purified by flash chromatography (100% ethyl acetate). EI-MS m/z 201 (M+H)$^+$.

Step C: Preparation of 4-((2-tert-butoxy)carbonylamino)-1,3-thiazol-4-yl)butanoic acid Methyl 4-(2-amino-3H-1,3-thiazol-4-yl)butanoate was dissolved in methylene chloride followed by the addition of di-ter-butyl dicarbonate (1.1 eq) and a catalytic amount of 4-(dimethylamino)pyridine (DMAP). The resulting mixture was refluxed until the starting material was consumed, concentrated in vacuo and the residue was purified by flash chromatography (60% Hexanes/EtOAc). EI-MS m/z 401 (M+H)$^+$. The ester was dissolved in ethanol and 1N NaOH was added. The reaction was stirred for 18 hrs. Followed by addition of 1N HCl. The mixture was concentrated in vacuo. EI-MS m/z 285 (M–H)$^-$.

Step D: Methyl 2-(2-(N-(3-(2-pyridylamino)prop-1-yl) carbamoyl)-1H,3H,4H-5H-benzo[e]azapin-5-yl)acetate Methyl 2-(1H,2H,3H,4H,5H-benzo[e]azaperhydroepin-5-yl)acetate Hydrochloride was dissolved in methylene chloride and washed with 1N NaOH. The organic layer was separated, dried over sodium sulfate and concentrated by rotary evaporation. A solution of 4-((2-tert-butoxy) carbonylamino)-1,3-thiazol-4-yl) butanoic acid, triethylamine (2 eq) in toluene (0.2M solution) and DPPA (1.5 eq) was refluxed for 2 h, then methyl 2-(1H,2H,3H,4H,5H-benzo[e]azaperhydroepin-5-yl)acetate was added. The reaction mixture was refluxed overnight, brought to room temperature, concentrated and extracted with dichloromethane and water (1:1). The organic layers were combined, dried over magnesium sulfate and concentrated by high vacuum. The resulting residue was purified by flash chromatography (10% MeOH/CH$_2$Cl$_2$). EI-MS m/z 503 (M+H)$^+$.

Step E: 2-(2-{N-[3-(2-amino-5H-1,3-thiazol-4yl)propyl]carbamoyl}-1H,3H,4H,5H-benzo[e]azepin-5-yl)acetic acid 2-(2-{N-[3-(2-amino-5H-1,3-thiazol-4-yl)propyl]carbamoyl}-1H,3H,4H,5H-benzo[e]azepin-5-yl)acetic acid was prepared from the saponification of methyl 2-(2-(N-(3-(2-pyridylamino)prop-1-yl) carbamoyl)-1H,3H,4H-5H-benzo[e]azapin-5-yl)acetate in ethanol (60 mL) and 1N NaOH (20 mL). The mixture was stirred overnight at room temperature, acidified with 1N HCl, concentrated and the residue was extracted with dichloromethane (CH$_2$Cl$_2$). The organic solvent was concentrated and the residue was dissolved in 4.0M HCl/dioxane and stirred at room temperature overnight. The mixture was concentrated by high vacuum and the residue was redissolved in acetonitrile to afford the desired product. EI-MS m/z 389 (M+H)$^+$.

EXAMPLE 75

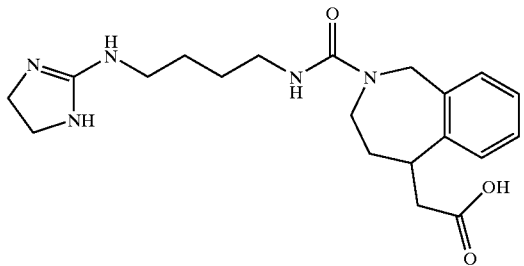

Preparation of 2-(2-(N-(4-(4,5-dihydroimidazo-2-yl)aminobut-1-yl)carbamoyl)-1H,3H,4H-5H-benzo[e]azapin-5-yl)acetic acid Step A: Methyl 2-(2-(N-(4-tertbutoxycarbonylaminobut-1-yl)carbamoyl)-1H,3H,4H-5H-benzo[e]azapin-5-yl)acetate Methyl 2-(1H,2H,3H,4H,5H-benzo[e]azaperhydroepin-5-yl)acetate Hydrochloride was dissolved in methylene chloride and washed with 1N sodium hydroxide. The organic layer was separated, dried over sodium sulfate and concentrated by rotary evaporation. The residue stirred under nitrogen with 20% phosgene in toluene (0.1M) for 10 mins. After stirring, the reaction was concentrated in vacuo and the residue was dissolved in tetrahydrofuran (0.1M), followed by addition of diisopropylethylamine (1.5 eq) and 4-tertbutoxycarbamoyl but-1-yl amine(1.2 eq). The reaction was stirred at 60° C. for 1 h under nitrogen, cooled to room temperature and diluted with ethyl acetate. The mixture was washed with saturated sodium bicarbonate and the organic phase was dried over sodium sulfate and concentrated in vacuo. The product was purified by flash chromatograpy (EtOAc/Hexane 1:1 to 1:0). EI-MS m/z 434 (M+H)$^+$ Step B: Methyl 2-(2-(N-(4-aminobut-1-yl)carbamoyl)-1H,3H,4H-5H-benzo[e]azapin-5-yl)acetate Methyl 2-(2-(N-(4-tertbutoxycarbonylaminobut-1-yl)carbamoyl)-1H,3H,4H-5H-benzo[e]azapin-5-yl)acetate was stirred in HCl in ethyl acetate (1.17M, 20 mL) at room temperature for 12 h. The solvent was removed under vacuum and the residue was trituated with ether. The product was diluted with methylene chloride and extracted with sodium hydroxide (0.5M). The organic phase was concentrated in vacuo and azeotroped with toluene to yield the product as a white solid. EI-MS m/z 334 (M+H)$^+$ Step C: 2-(2-(N-(4-(4,5-dihydroimidazo-2-yl)aminobut-1-yl)carbamoyl)-1H,3H,4H-5H-benzo[e]azapin-5-yl) acetic acid A solution of methyl 2-(2-(N-(4-aminobut-1-yl)carbamoyl)-1H,3H,4H-5H-benzo[e]azapin-5-yl)acetate, 4,5-dihydroimidazo-2-yl methyl sulfide hydrogen iodide (2 eq), and sodium bicarbonate (200 mg) in dioxane/water (3ml/2ml) was heated at 100° C. for 24 h. The mixture was cooled to room temperature and the product was purified by preparative HPLC (18 mg). EI-MS m/z 388 (M+H)$^+$; $^1$H-NMR (400 MHz, MeOH-d4): δ7.34 (d, J=7.0 Hz, 1H), 7.28–7.20 (m, 3H), 4.60 (q, J=15.0 Hz, 2H), 3.7–3.55 (m, 6H), 3.36 (m, 1H), 3.22–3.17 (m, 4H), 3.02 (t, J=Hz, 1H), 2.89–2.74 (m, 2H), 2.10–2.04 (m, 1H), 1.68–1.66 (m, 1H), 1.55–1.52 (m, 4H).

EXAMPLE 76

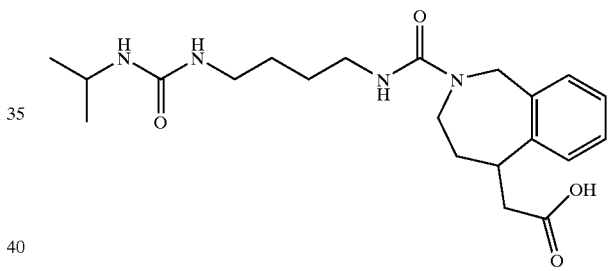

Preparation of 2-(2-(N-(4-(2-propylcarbamoyl)aminobut-1-yl)carbamoyl)-1H,3H,4H-5H-benzo[e]azapin-5-yl) acetic acid Step A: Methyl 2-(2-(N-(4-aminobut-1-yl)carbamoyl)-1H,3H,4H-5H-benzo[e]azapin-5-yl)acetate Methyl 2-(2-(N-(4-aminobut-1-yl)carbamoyl)-1H,3H,4H-5H-benzo[e]azapin-5-yl)acetate was prepared according to the procedure of example 75.

Step B: 2-(2-(N-(4-(2-propylcarbamoyl)aminobut-1-yl)carbamoyl)-1H,3H,4H-5H-benzo[e]azapin-5-yl)acetic acid A solution of methyl 2-(2-(N-(4-aminobut-1-yl)carbamoyl)-1H,3H,4H-5H-benzo[e]azapin-5-yl)acetate and 2-propyl isocyanate (1 eq) in ethyl acetate (2 mL) was heated at 60° C. for 48 hrs. The solvent was removed in vacuo and the residue was dissolved in methanol (0.1M) and 1N sodium hydroxide (3 eq). The mixture was heated at 60° C. for 24 hrs. The product was purified by preparative HPLC as a white solid (TFA salt, 55.5 mg, 59%): EI-MS m/z 405 (M+H); $^1$H-NMR (400 MHz, MeOH-d4): 7.29–7.14 (m, 4H), 4.54 (q, J=15.0 Hz, 2H), 3.79 (m,1H), 3.66 (m, 1H), 3.54 (m, 2H), 3.15–3.06 (m, 4H), 2.84–2.79 (m, 1H), 2.74–2.68 (m, 1H), 2.05–2.00 (m, 1H), 1.62–1.58 (m, 1H), 1.40–1.38 (m, 4H), 1.1 (d, J=6.8 Hz, 6H).

EXAMPLE 77

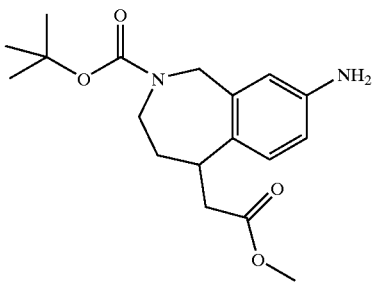

Preparation of Methyl 2-{8-amino-2-[(tert-butyl) oxycarbonyl-1H,3H,4H,5H-benzo[e]azepin-5-yl}acetate Step A: (2-Bromo-5-nitrophenyl)methan-1-ol To a stirring solution of 2-bromo-5-nitrobenzoic acid (1 eq) in tetrahydrofuran (0.4 M) at 0° C. under nitrogen was added BH$_3$/THF (1 M) (1.5 eq). The reaction mixture was stirred at 70° C. for 1 hr and quenched with methanol. The reaction mixture was concentrated in vacuo to afford the product. EI-MS m/z 232 (M+H)$^+$.

Step B: 2-Bromo-5-nitrobenzaldehyde

To a stirring solution of (2-bromo-5-nitrophenyl) methan-1-ol (1 eq) in methylene chloride (0.1 M) at room temperature was added pyridinium chlorochromate (2 eq). After 2 hr the reaction mixture was filtered through celite and the product was purified by flash chromatography (15% EtOAc/Hexane). EI-MS m/z 230 (M+H)$^+$.

Step C: 3-{[(2-bromo-5-nitrophenyl)methyl]amino}propan-1-ol

To a stirring solution of 2-bromo-5-nitrobenzaldehyde (1 eq) in methylene chloride (0.1 M) at room temperature was added 3-amino-1-propanol (2 eq). After stirring for 4 hr, sodium triacetoxyborohydride (2 eq) and acetic acid (5 eq) was added. The reaction mixture was stirred for 3 hr and carefully quenched with methanol. The organic phase was washed with saturated sodium bicarbonate and brine. The organic phase was dried over anhydrous sodium sulfate, filtered, concentrated in vacuo and purified by flash chromatography (10% EtOAc/Hexane). EI-MS m/z 289 (M+H)$^+$.

Step D: (tert-Butoxy)-N-[(2-bromo-5-nitrophenyl)methyl]-N-(3-hydroxypropyl)carboxamide To a stirring solution of 3-{[(2-bromo-5-nitrophenyl) methyl]amino}propan-1-ol (1 eq) in tetrahydrofuran (0.07 M) and saturated sodium bicarbonate (20 eq) at room temperature was added di-tert-butyl dicarbonate (2 eq). After stirring for 4 hr, the solvent was removed by rotary evaporation and the residue was extracted with ethyl acetate. The organic phase was separated, washed with brine, dried over anhydrous sodium sulfate, filtered and concentrated in vacuo. The residue was purified by flash chromatography (10% EtOAc/Hexane). EI-MS m/z 389 (M+H)$^+$.

Step E: (tert-Butoxy)-N-[(2-bromo-5-nitrophenyl)methyl]-N-(3-oxopropyl)carboxamide To a stirring solution of (tert-butoxy)-N-[(2-bromo-5-nitrophenyl)methyl]-N-(3-hydroxypropyl)carboxamide (1 eq) in methylene chloride (0.1 M) at room temperature was added Dess-Martin reagent (1.2 eq). After stirring for 1.5 hr, the reaction mixture was quenched with ether, saturated sodium bicarbonate, and followed by the addition of solid sodium thiosulfate. The organic phase was separated, washed with brine, dried over anhydrous sodium sulfate, filtered and concentrated in vacuo to afford product. EI-MS m/z 387 (M+H)$^+$.

Step F: Methyl (2E)-5-{(tert-butoxy)-N-[(2-bromo-5-nitrophenyl)methyl]carbonylamino}pent-2-enoate To a stirring solution of (tert-butoxy)-N-[(2-bromo-5-nitrophenyl)methyl]-N-(3-oxopropyl)carboxamide (1 eq) in 200 ml of tetrahydrofuran (0.06 M) at room temperature was added methyl (triphenylphosphoranylidene) acetate (1.5 eq). The reaction mixture was stirred at 80° C. for 2 hr and the reaction solvent was removed by rotary evaporation. The residue was partitioned between ethyl acetate and saturated sodium bicarbonate. The organic phase was separated, washed with brine, dried over anhydrous sodium sulfate, filtered and concentrated in vacuo. The residue was purified by flash chromatography (20% EtOAc/Hexane). EI-MS m/z: 443 (M+H)$^+$.

Step G: Methyl (2E)-5-{N-[(3-amino-6-bromophenyl)methyl](tert-butoxy)carbonylamino}pent-2-enoate To a stirring solution of methyl (2E)-5-{(tert-butoxy)-N-[(2-bromo-5-nitrophenyl)methyl]carbonyl amino}pent-2-enoate (1 eq) in 20 ml of N,N-dimethylformamide (0.1 M) at room temperature was added tin (II) chloride dihydrate (10 eq). After stirring for 3 hr, the solvent was removed by rotary evaporation. The residue was partitioned between ethyl acetate and saturated sodium bicarbonate. The mixture was filtered through celite. The organic phase was separated, washed with brine, dried over anhydrous sodium sulfate, filtered and concentrated in vacuo. The residue was purified by flash chromatography (20% EtOAc/Hexane). EI-MS m/z 413 (M+H)$^+$.

Step H: Methyl 2-{8-amino-2-[(tert-butyl)oxycarbonyl]-1H,3H,4H-benzo[e]azepin-5-ylidene}acetate To a stirring solution of methyl (2E)-5-{N-[(3-amino-6-bromophenyl)methyl](tert-butoxy)carbonylamino}pent-2-enoate (1 eq) in toluene (0.08 M) at room temperature was added tetrakis(triphenylphosphine) palladium(0.03 eq) and triethylamine (3 eq). The reaction mixture was stirred at 100° C. for 18 hr and filtered through celite. The reaction solvent was removed by rotary evaporation. The residue was partitioned between ethyl acetate and saturated sodium bicarbonate. The organic phase was separated, washed with brine, dried over anhydrous sodium sulfate, filtered and concentrated in vacuo. The residue was purified by flash chromatography (30% EtOAc/Hexane). EI-MS m/z 333 (M+H)$^+$.

Step I: Methyl 2-{8-amino-2-[(tert-butyl)oxycarbonyl]-1H,3H,4H,5H-benzo[e]azepin-5-yl}acetate To a stirring solution of methyl 2-[8-amino-2-[(tert-butyl)oxycarbonyl]-1H,3H,4H-benzo[e]azepin-5-ylidene}acetate in 25 ml of ethanol at room temperature was added 10% Pd/C(0.01M). The reaction was stirred under hydrogenation conditions at ballon pressure. After stirring for 4 hr, the reaction mixture was filtered through celite. The reaction solvent was removed by rotary evaporation. The residue was purified by flash chromatography (50% EtOAc/Hexane). EI-MS m/z 335 (M+H)$^+$.

EXAMPLE 78

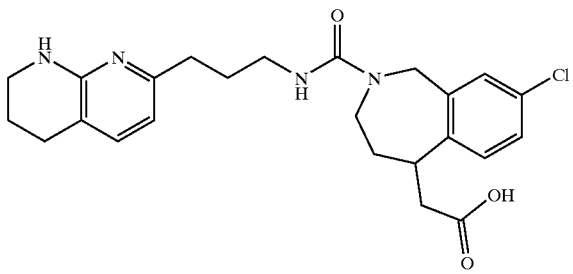

Preparation of 2-{8-Chloro-2-[N-(3-(1,2,3,4-tetrahydropyridino[2,3-b]pyridin-7-yl)propyl)carbamoyl]-1H,3H,4H,5H-benzo[e]azepin-5-yl}acetic acid Step A: Methyl 2-{2-[(tert-butyl)oxycarbonyl-8-chloro-1H,3H,4H,5H-benzo[e]azepin-5-yl}acetate To a stirring solution of copper (II) chloride (1.2 eq) in dry acetonitrile (0.3 M) was added tert-butyl nitrite (1.5 eq) through syringe at room temperature under nitrogen. The resulting dark green suspension was then heated at 65° C. for 15 min. Methyl 2-{8-amino-2-[(tert-butyl)oxycarbonyl]-1H,3H,4H,5H-benzo[e]azepin-5-yl}acetate (1 eq) in acetonitrile (0.13 M) was added slowly for 5 min. The resulting black solution was heated at 65° C. for 1 hr. The reaction mixture was diluted with methylene chloride and aqueous ammonium hydroxide. The organic phase was separated, washed with brine, dried over anhydrous sodium sulfate, filtered and concentrated in vacuo. The residue was purified by flash chromatography (30% EtOAc/Hexane). EI-MS m/z 353 (M+H)$^+$.

Step B: Methyl 2-{8-chloro-2-[N-(3-(1,2,3,4-tetrahydropyridino[2,3-b]pyridin-7-yl)propyl) carbamoyl]-1H,3H,4H,5H-benzo[e]azepin-5-yl}acetate A solution of methyl 2-{2-[(tert-butyl)oxycarbonyl-8-chloro-1H,3H,4H,5H-benzo[e]azepin-5-yl}acetate (1 eq) in 1.17 M of HCl/ethyl acetate (30 eq) was stirred at room temperature for 18 hr. The reaction mixture was concentrated and dried under vacuum oven. The resulting residue was dissolved in methylene chloride (0.15 M) and followed by the addition of phosgene/toluene (20%) (10 eq) under nitrogen. After stirring for 1 hr, the solvent was removed by rotary evaporation. The residue was dissolved in 1 ml of N,N-dimethylformamide (0.07 M), followed by the addition of 3-(1,2,3,4-tetrahydropyridino[2,3-b]pyridin-7-yl)propylamine (2 eq) and N,N-diisopropylethylamine (10 eq). The reaction mixture was heated at 50° C. for 2 hr. The reaction solvent was removed by rotary evaporation and the residue was purified by flash chromatography (5% methanol/methylene chloride. EI-MS m/z 471 (M+H)$^+$.

Step C: 2-{8-Chloro-2-[N-(3-(1,2,3,4-tetrahydro pyridino[2,3-b]pyridin-7-yl)propyl)carbamoyl1-1H,3H,4H,5H-benzo[e]azepin-5-yl}acetic acid To a stirring solution of methyl 2-{8-chloro-2-[N-(3-(1,2,3,4-tetrahydropyridino[2,3-b]pyridin-7-yl)propyl)carbamoyl]-1H,3H,4H,5H-benzo[e]azepin-5-yl}acetate (1 eq) in tetrahydrofuran (0.05 M) and water (0.05 M) was added lithium hydroxide monohydrate (1.5 eq). The reaction mixture was stirred at room temperature for 10 h. 1 M of hydrogen chloride (1.5 eq) was added and the reaction solvent was evaporated in vacuo. The residue was diluted with (5% MeOH/CH$_2$Cl$_2$ and the precipitate was filtered. The filtrate was concentrated and dried under vacuum oven for 24 h to afford product. EI-MS m/z 457 (M+H)$^+$; $^1$H NMR (CD$_3$OD; 400 MHz): δ7.53 (d, J=7.3 Hz, 1H), 7.39 (s, 1H), 7.18 (s, 2H), 6.51 (d, 7.3 Hz, 1H), 4.56 (s, 2H), 3.80–3.45 (m, 5H), 3.21 (m, 2H), 2.80 (m, 4H), 2.75 (m, 2H), 2.00–1.50 (m, 6H).

EXAMPLE 79

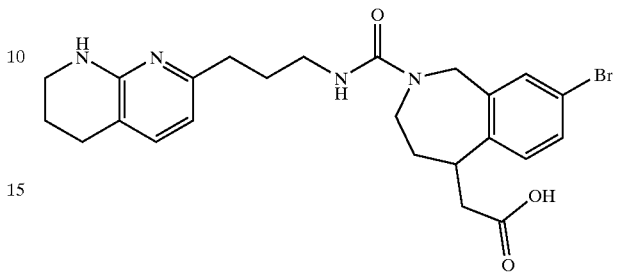

Preparation of 2-{8-Bromo-2-[N-(3-(1,2,3,4-tetrahydro pyridino[2,3-b]pyridin-7-yl)propyl)carbamoyl]-1H,3H,4H,5H-benzo[e]azepin-5-yl}acetic acid Step A: Methyl 2-{2-[(tert-butyl)oxycarbonyl]-8-bromo-1H,3H,4H,5H-benzo[e]azepin-5-yl}acetate To a stirring solution of copper (II) bromide (1.3) in dry acetonitrile (0.22 M) was added tert-butyl nitrite (1.8 eq) through syringe at room temperature under nitrogen. The resulting dark green suspension was then heated at 65° C. for 15 min. Methyl 2-{8-amino-2-[(tert-butyl)oxycarbonyl]-1H,3H,4H,5H-benzo[e]azepin-5-yl}acetate (1 eq) in acetonitrile (0.1 M) was added slowly for 5 min. The resulting black solution was heated at 65° C. for 2 hr. The reaction mixture was diluted with methylene chloride and aqueous ammonium hydroxide. The organic phase was separated, washed with brine, dried over anhydrous sodium sulfate, filtered and concentrated in vacuo. The residue was purified by flash chromatography (30% EtOAc/Hexane). EI-MS m/z 398 (M+H)$^+$.

Step B: Methyl 2-{8-bromo-2-[N-(3-(1,2,3,4-tetrahydro pyridino[2,3-b]pyridin-7-yl)propyl)carbamoyl]-1H,3H,4H,5H-benzo[e]azepin-5-yl}acetate Methyl 2-{8-bromo-2-[N-(3-(1,2,3,4-tetrahydropyridino[2,3-b]pyridin-7-yl)propyl)carbamoyl]-1H,3H,4H,5H-benzo[e]azepin-5-yl}acetate was prepared from methyl 2-{2-[(tert-butyl)oxycarbonyl]-8-bromo-1H,3H,4H,5H-benzo[e]azepin-5-yl}acetate according to the procedure of Example 34. EI-MS m/z 515 (M+H)$^+$.

Step C: 2-{8-Bromo-2-[N-(3-(1,2,3,4-tetrahydropyridino[2,3-b]pyridin-7-yl)propyl)carbamoyl]-1H,3H,4H,5H-benzo[e]azepin-5-yl}acetic acid 2-{8-Bromo-2-[N-(3-(1,2,3,4-tetrahydropyridino[2,3-b]pyridin-7-yl)propyl)carbamoyl]-1H,3H,4H,5H-benzo[e]azepin-5-yl}acetic acid was prepared from methyl 2-{8-bromo-2-[N-(3-(1,2,3,4-tetrahydropyridino [2,3-b]pyridin-7-yl)propyl)carbamoyl]-1H,3H,4H,5H-benzo[e]azepin-5-yl}acetate according to the precedure of Example 34. EI-MS m/z 501 (M+H)$^+$; $^1$H NMR (CD$_3$OD; 400 MHz): δ7.55 (m, 2H), 7.34 (d, 1H), 7.14 (d, J=8.3 Hz, 1H), 6.51 (d, J=7.3 Hz 1H), 4.57 (s, 2H), 3.80–3.45 (m, 5H), 3.21 (m, 2H), 2.76 (m, 4H), 2.52 (m, 2H), 2.00–1.50 (m, 6H).

EXAMPLE 80

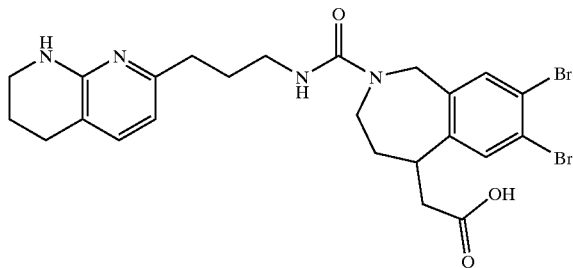

Preparation of 2-{7,8-Dibromo-2-[N-(3-(1,2,3,4-tetrahydropyridino[2,3-b]pyridin-7-yl)propyl) carbamoyl]-1H,3H,4H,5 H-benzo[e]azepin-5-yl}acetic acid Step A: Methyl 2-{7,8-dibromo-2-[N-(3-(1,2,3,4-tetrahydropyridino[2,3-b]pyridin-7-yl)propyl) carbamoyl]-1H,3H,4H,5H-benzo[e]azepin-5-yl}acetate During the column chromatography of methyl 2-{8-bromo-2-[N-(3-(1,2,3,4-tetrahydropyridino[2,3-b]pyridin-7-yl)propyl)carbamoyl]-1H,3H,4H,5H-benzo[e]azepin-5-yl}acetate, methyl 2-{7,8-dibromo-2-[N-(3-(1,2,3,4-tetrahydropyridino[2,3-b]pyridin-7-yl)propyl)carbamoyl]-1H,3H,4H,5H-benzo[e]azepin-5-yl}acetate was obtained. EI-MS m/z 594 (M+H)$^+$.

Step B: 2-{7,8-Dibromo-2-[N-(3-(1,2,3,4-tetrahydropyridino[2,3-b]pyridin-7-yl)propyl)carbamoyl]-1H,3H,4H,5H-benzo[e]azepin-5-yl}acetic acid 2-{7,8-Dibromo-2-[N-(3-(1,2,3,4-tetrahydropyridino[2,3-b]pyridin-7-yl)propyl)carbamoyl]-1H,3H,4H,5H-benzo[e]azepin-5-yl}acetic acid was prepared from methyl 2-{7,8-dibromo-2-[N-(3-(1,2,3,4-tetrahydro pyridino[2,3-b]pyridin-7-yl)propyl)carbamoyl]-1H,3H,4H,5H-benzo[e]azepin-5-yl}acetate according to the procedure of Example 34. EI-MS m/z 580 (M+H)$^+$; $^1$H NMR (CD$_3$OD; 400 MHz): δ7.67(s, 1H), 7.53(d, J=7.4 Hz, 7.49(s, 1H), 6.50 (d, J=7.4 Hz, 1H), 4.88 (s, 2H), 3.45–3.80 (m, 5H), 3.21 (m, 2H), 2.76 (m, 4H), 2.50 (m, 2H), 2.00–1.50 (m, 6H).

EXAMPLE 81

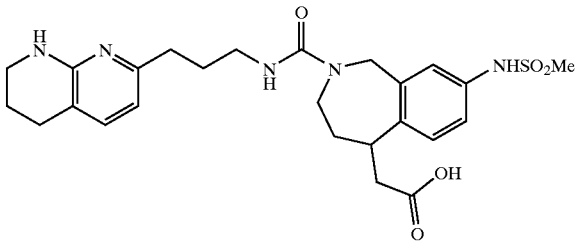

Preparation of 2-{8-[(Methylsulfonyl)amino]-2-[N-(3-(1,2,3,4-tetrahydropyridino[2,3-b]pyridin-7-yl) Propyl)carbamoyl]-1H,3H,4H,5H-benzo[e]azepin-5-yl}acetic acid Step A: Methyl 2-{2-[(tert-butyl)oxycarbonyl-8-[(methylsulfonyl)amino]-1H,3H,4H,5H-benzo[e]azepin-5-yl}acetate To a stirring solution of methyl 2-{8-amino-2-[(tert-butyl)oxycarbonyl]-1H,3H,4H,5H-benzo[e]azepin-5-yl}acetate (1 eq) in methylene chloride (0.1 M) was added methanesulfonyl chloride (1.1 eq) and triethylamine (5 eq) at room temperature. After stirring for 5 hr, the reaction mixture was diluted with methylene chloride. The organic phase was washed with saturated sodium bicarbonate, brine, dried over anhydrous sodium sulfate, filtered and concentrated in vacuo. The residue was purified by flash chromatography (20% EtOAc/Hexane). EI-MS m/z 413 (M+H)$^+$.

Step B: Methyl 2-{8-[(methylsulfonyl)amino]-2-[N-(3-(1,2,3,4-tetrahydropyridino[2,3-b]pyridin-7-yl)propyl)carbamoyl]-1H,3H,4H,5H-benzo[e]azepin-5-yl}acetate Methyl 2-{8-[(methylsulfonyl)amino]-2-[N-(3-(1,2,3,4-tetrahydropyridino[2,3-b]pyridin-7-yl)propyl) carbamoyl]-1H,3H,4H,5H-benzo[e]azepin-5-yl}acetate was prepared from methyl 2-{2-[(tert-butyl)oxycarbonyl]-8-[(methylsulfonyl)amino]-1H,3H,4H,5H-benzo[e]azepin-5-yl}acetate according to the procedure of Example 34. EI-MS m/z 530 (M+H)$^+$.

Step C: 2-{8-[(Methylsulfonyl)amino]-2-[N-(3-(1,2,3,4-tetrahydropyridino[2,3-b]pyridin-7-yl)propyl) carbamoyl]-1H,3H,4H,5H-benzo[e]azepin-5-yl}acetic acid 2-{8-[(Methylsulfonyl)amino]-2-[N-(3-(1,2,3,4-tetrahydropyridino[2,3-b]pyridin-7-yl)propyl) carbamoyl]-1H,3H,4H,5H-benzo[e]azepin-5-yl}acetic acid was prepared from methyl 2-{8-[(methylsulfonyl)amino]-2-[N-(3-(1,2,3,4-tetrahydropyridino[2,3-b]pyridin-7-yl)propyl) carbamoyl]-1H,3H,4H,5H-benzo[e]azepin-5-yl}acetate according to the procedure of Example 34. EI-MS m/z 516 (M+H)$^+$; $^1$H NMR (CD$_3$OD; 400 MHz): δ7.52 (d, J=7.3 Hz, 1H), 7.28 (s, 1H), 7.19 (d, J=8.2 Hz, 1H), 7.05 (d, J=6.6 Hz, 1H), 6.51 (d, J=14.7 Hz, 1H), 4.55 (s, 2H), 3.70–3.50 (m, 5H), 3.21 (m, 2H), 2.92 (s, 3H), 2.75 (m, 4H), 2.55 (m, 2H), 2.00–1.60 (m, 6H).

EXAMPLE 82

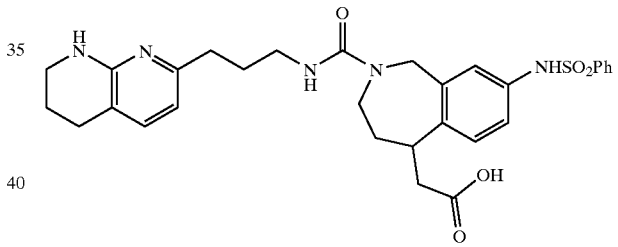

Preparation of 2-{8-[(Phenylsulfonyl)amino]-2-[N-(3-(1,2,3,4-tetrahydropyridino[2,3-b]pyridin-7-yl) propyl) carbamoyl]-1H,3H,4H,5H-benzo[e]azepin-5-yl}acetic acid Step A: Methyl 2-{2-[(tert-butyl)oxycarbonyl-8-[(phenylsulfonyl)amino]-1H,3H,4H,5H-benzo[e]azepin-5-yl}acetate To a stirring solution of methyl 2-{8-amino-2-[(tert-butyl)oxycarbonyl]-1H,3H,4H,5H-benzo[e]azepin-5-yl}acetate (1 eq) in methylene chloride (0.1 M) was added benzenesulfonyl chloride (1.1 eq) and triethylamine (5 eq) at room temperature. After stirring for 5 hr, the reaction mixture was diluted with methylene chloride. The organic phase was washed with saturated sodium bicarbonate, brine, dried over anhydrous sodium sulfate, filtered and concentrated in vacuo. The residue was purified by flash chromatography (20% EtOAc/Hexane). EI-MS m/z 475 (M+H)$^+$.

Step B: Methyl 2-{8-[(phenylsulfonyl)amino]-2-[N-(3-(1,2,3,4-tetrahydropyridino[2,3-b]pyridin-7-yl)propyl) carbamoyl]-1H,3H,4H,5H-benzo[e]azepin-5-yl}acetate Methyl 2-{8-[(phenylsulfonyl)amino]-2-[N-(3-(1,2,3,4-tetrahydropyridino[2,3-b]pyridin-7-yl)propyl) carbamoyl]-1H,3H,4H,5H-benzo[e]azepin-5-yl}acetate was prepared from methyl 2-{2-[(tert-butyl)oxycarbonyl]-8-[(phenylsulfonyl)amino]-1H,3H,4H,5H-benzo[e]azepin-5-yl}acetate according to the procedure of Example 34. EI-MS m/z 592 (M+H)+.

Step C: 2-{8-[(Phenylsulfonyl)amino]-2-[N-(3-(1,2,3,4-tetrahydropyridino[2,3-b]pyridin-7-yl)propyl) carbamoyl]-1H,3H,4H,5H-benzo[e]azepin-5-yl}acetic acid 2-{8-[(Phenylsulfonyl)amino]-2-[N-(3-(1,2,3,4-tetrahydropyridino[2,3-b]pyridin-7-yl)propyl) carbamoyl]-1H,3H,4H,5H-benzo[e]azepin-5-yl}acetic acid was prepared from methyl 2-{8-[(phenylsulfonyl)amino]-2-[N-(3-(1,2,3,4-tetrahydropyridino[2,3-b]pyridin-7-yl)propyl) carbamoyl]-1H,3H,4H,5H-benzo[e]azepin-5-yl}acetate according to the procedure of Example 34. EI-MS m/z 578 (M+H)+; $^1$H NMR (CD$_3$OD; 400 MHz): 7.71 (d, J=7.2 Hz, 2H), 7.51 (m, 2H), 7.44(d, 2H), 7.22 (s, 1H), 7.03 (d, J=8.1 Hz, 1H), 6.82 (d, J=6.4 Hz, 1H), 6.51 (d, J=7.2 Hz, 1H), 4.51 (s, 2H), 3.50–3.65 (m, 5H), 3.21 (m, 2H), 2.80–2.60 (m, 4H), 2.52 (m, 2H), 2.00–1.50 (m, 6H)

EXAMPLE 83

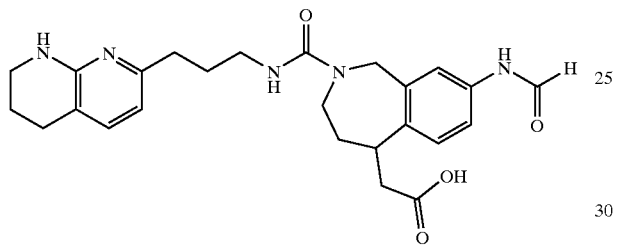

Preparation of 2-{8-Carbonylamino-2-[N-(3-(1,2,3,4-tetrahydropyridino[2,3-b]pyridin-7-yl)propyl) carbamoyl]-1H,3H,4H,5H-benzo[e]azepin-5-yl}acetic acid Step A: Methyl 2-(2-[(tert-butyl)oxycarbonyl]-8-{[(4-nitrophenyl)methoxy]carbonylamino}-1H,3H,4H,5H-benzo[e]azepin-5-yl)acetate To a stirring solution of methyl 2-{8-amino-2-[(tert-butyl)oxycarbonyl]-1H,3H,4H,5H-benzo[e]azepin-5-yl}acetate (1 eq) in methylene chloride (0.1 M) was added 4-nitrobenzyl chloroformate (1.1 eq) and triethylamine (5 eq) at room temperature. After stirring for 5 hr, the reaction mixture was diluted with methylene chloride. The organic phase was washed with saturated sodium bicarbonate, brine, dried over anhydrous sodium sulfate, filtered and concentrated in vacuo. The residue was purified by flash chromatography (20% EtOAc/Hexane). EI-MS m/z 514 (M+H)+.

Step B: Methyl 2-(8-{[(4-nitrophenyl)methoxycarbonyl amino}-2-[N-(3-(1,2,3,4-tetrahydropyridino[2,3-b]pyridin-7-yl)propyl)carbamoyl]-1H,3H,4H,5H-benzo[e]azepin-5-yl)acetate Methyl 2-(8-{[(4-nitrophenyl)methoxy]carbonylamino}-2-[N-(3-(1,2,3,4-tetrahydropyridino[2,3-b]pyridin-7-yl)propyl)carbamoyl]-1H,3H,4H,5H-benzo[e]azepin-5-yl)acetate was prepared from methyl 2-(2-[(tert-butyl)oxycarbonyl]-8-{[(4-nitrophenyl)methoxy]carbonylamino}-1H,3H,4H,5H-benzo[e]azepin-5-yl)acetate according to the procedure of Example 34. EI-MS m/z 631 (M+H)+.

Step C: Methyl 2-{8-carbonylamino-2-[N-(3-(1,2,3,4-tetrahydropyridino[2,3-b]pyridin-7-yl)propyl) carbamoyl]-1H,3H,4H,5H-benzo[e]azepin-5-yl}acetate To a stirring solution of methyl 2-(8-{[(4-nitro phenyl)methoxy]carbonylamino}-2-[N-(3-(1,2,3,4-tetrahydropyridino[2,3-b]pyridin-7-yl)propyl) carbamoyl]-1H,3H,4H,5H-benzo[e]azepin-5-yl)acetate in ethanol (0.05 M) at room temperature was added 10% Pd/C (0.10M). After stirring 4 hr, under hydrogen, at balloon pressure, the reaction mixture was filtered through celite. The reaction solvent was removed by rotary evaporation. The residue was purified by flash chromatography (50% EtOAc/Hexane). EI-MS m/z 480 (M+H)+.

Step D: 2-{8-Carbonylamino-2-[N-(3-(1,2,3,4-tetrahydropyridino[2,3-b]pyridin-7-yl)propyl) carbamoyl]-1H,3H,4H,5H-benzo[e]azepin-5-yl}acetic acid 2-{8-Carbonylamino-2-[N-(3-(1,2,3,4-tetrahydropyridino[2,3-b]pyridin-7-yl)propyl)carbamoyl]-1H,3H,4H,5H-benzo[e]azepin-5-yl}acetic acid was prepared from methyl 2-{8-carbonylamino-2-[N-(3-(1,2,3,4-tetrahydropyridino[2,3-b]pyridin-7-yl)propyl) carbamoyl]-1H,3H,4H,5H-benzo[e]azepin-5-yl}acetate according to the procedure of Example 34. EI-MS m/z 466 (M+H)+; $^1$H NMR (CD$_3$OD; 400 MHz): δ7.98 (s, 1H), 7.60–7.20 (m, 4H), 6.56 (d, J=7.3 Hz, 1H), 4.60 (s, 2H), 3.70–3.40 (m, 2H), 3.30 (m, 2H), 2.80–2.70 (m, 4H), 2.63 (m, 2H), 2.00–1.50 (m, 6H).

EXAMPLE 84

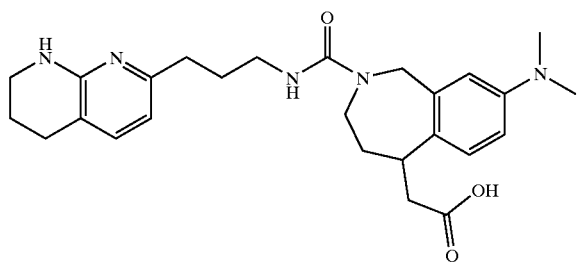

Preparation of 2-{8-(Dimethylamino)-2-[N-(3-(1,2,3,4-tetrahydropyridino[2,3-b]pyridin-7-yl)propyl) carbamoyl]-1H,3H,4H,5H-benzo[e]azepin-5-yl}acetic acid Step A: Methyl 2-{8-(dimethylamino)-2-[(tert-butyl)oxycarbonyl-1H,3H,4H,5H-benzo[e]azepin-5-yl}acetate To a stirring solution of methyl 2-{8-amino-2-[(tert-butyl)oxycarbonyl]-1H,3H,4H,5H-benzo[e]azepin-5-yl}acetate (1 eq) in benzene (0.02 M) at room temperature was added Pd/C (10%) (20% weight) and HCHO (37%) (20 eq). After stirring for 4 hr under hydrogen, at balloon pressure, the reaction mixture was filtered through celite. The reaction solvent was removed by rotary evaporation. The residue was purified by flash chromatography (50% EtOAc/Hexane). EI-MS m/z 363 (M+H)+.

Step B: Methyl 2-{8-(dimethylamino)-2-[N-(3-(1,2,3,4-tetrahydropyridino[2,3-b]pyridin-7-yl)propyl) carbamoyl]-1H,3H,4H,5H-benzo[e]azepin-5-yl}acetate Methyl 2-{8-(dimethylamino)-2-[N-(3-(1,2,3,4-tetrahydropyridino[2,3-b]pyridin-7-yl)propyl) carbamoyl]-1H,3H,4H,5H-benzo[e]azepin-5-yl}acetate was prepared from methyl 2-{8-(dimethylamino)-2-[(tert-butyl)oxycarbonyl]-1H,3H,4H,5H-benzo[e]azepin-5-yl}acetate according to the procedure of Example 34. EI-MS m/z 480 (M+H)+.

Step C: 2-{8-(Dimethylamino)-2-[N-(3-(1,2,3,4-tetrahydropyridino[2,3-b]pyridin-7-yl)propyl) carbamoyl]-1H,3H,4H,5H-benzo[e]azepin-5-yl}acetic acid 2-{8-(Dimethylamino)-2-[N-(3-(1,2,3,4-tetrahydro pyridino[2,3-b]pyridin-7-yl)propyl)carbamoyl]-1H,3H,4H,5H-benzo[e]azepin-5-yl}acetic acid was prepared from methyl 2-{8-(dimethylamino)-2-[N-(3-(1,2,3,4-tetrahydropyridino[2,3-b]pyridin-7-yl)propyl)carbamoyl]-1H,3H,4H,5H-benzo[e]azepin-5-yl}acetate according to the procedure of Example 34. EI-MS m/z 466 (M+H)+; 1H NMR (CD3OD; 400 MHz): δ7.51 (d, J=7.4 Hz, 1H), 7.08 (d, J=4.8 Hz, 1H), 6.91 (s, 1H), 6.71 (m, 1H), 6.46 (d, J=7.4 Hz, 1H), 4.51 (m, 2H), 3.70–3.40 (m, 5H), 3.21 (m, 2H), 2.92 (s, 6H), 2.80–2.70 (m, 4H), 2.69 (m, 2H), 2.00–1.50 (m, 6H).

EXAMPLE 85

Using the procedures of the above general description and the above examples, the following compounds were prepared.

| Name | Mass. Spec. (M + H) |
|---|---|
| 2-(2-(N-(3-(6-(methylamino)-2-pyridyl)propyl)carbamoyl)-1H, 3H, 4H, 5H-benzo[e]azapin-5-yl)acetic acid | 397 |
| 2-(2-(N-(2-(1,2,3,4-tetrahydropyridino(2,3-b)pyridin-7-yl)ethyl)carbamoyl)-1H, 3H, 4H, 5H-benzo[e]azapin-5-yl)acetic acid | 409 |
| 2-(3-(N-(2-(1,2,3,4-tetrahydropyridino(2,3-b)pyridin-7-yl)propyl)amino)sulfonyl)-1H, 3H, 4H, 5H-benzo[e]azapin-5-yl)acetic acid | 459 |
| 3-(2-(N-(2-(1,2,3,4-tetrahydropyridino(2,3-b)pyridin-7-yl)ethyl)carbamoyl)-1H, 3H, 4H, 5H-benzo[e]azapin-5-yl)propanoic acid | 423 |
| 3-(2-(N-(3-(1,2,3,4-tetrahyrdropyridino(2,3-b)pyridin-7-yl)propyl)carbamoyl-1H, 3H, 4H, 5H-benzo[e]azapin-5-yl)propanoic acid | 437 |
| 3-(2-(N-(3-(1,2,3,4-tetrahydropyridino(2,3-b)pyridin-7-yl)propyl)amino)sulfonyl)-1H, 3H, 4H, 5H-benzo[e]azapin-5-yl)propanoic acid | 473 |
| 3-{3-[N-(3-(1,2,3,4-tetrahydropyridino[2,3-b]pyridin-7-yl)propyl)carbamoyl]-1H, 2H, 4H, 5H-benzo[d]azepinyl}propanoic acid | 437 |
| 2-[3-({N-[5-(2-pyridylamino)pentyl]carbamoyl}methyl)-1H, 2H, 4H, 5H-benzo[d]azepinyl]acetic acid | 425 |
| 2-[3-({3-[(amidinoamino)methyl]phenyl}methyl)-1H, 2H, 4H, 5H-benzo[d]azepinyl]acetic acid | −401 |
| 2-[3-({[5-(2-pyridylamino)pentyl]amino}sulfonyl)-1H, 2H, 4H, 5H-benzo[d]azepinyl]acetic acid | 447 |
| 2-[3-(2-{[4-(2-pyridylamino)butyl]amino}acetyl)-1H, 2H, 4H, 5H-benzo[d]azepinyl]acetic acid | 411 |
| 2-(2-{N-[3-(5-methyl-1,2,3,4-tetrahydropyridino[2,3-b]pyridin-7-yl)propyl]carbamoyl}-1H, 3H, 4H, 5H-benzo[e]azapin-5-yl)acetic acid | 437 |
| 2-(3-oxo-2-{3-[2-(2-pyridylamino)ethoxy]phenyl}-1H, 4H, 5H-benzo[e]azepin-5-yl)acetic acid | 432 |
| 2-[2-({N-[2-(2-pyridylamino)ethyl]carbamoyl}methyl)-1H, 3H, 4H, 5H-benzo[e]azepin-5-yl]acetic acid | 383 |
| 2-[3-oxo-2-(3-{N-[2-(2-pyridylamino)ethyl]carbamoyl}propyl)-1H, 4H, 5H-benzo[e]azepin-5-yl]acetic acid | 411 |
| 2-{3-[(4-{2-[(2-pyridylamino)methyl]phenyl}phenyl)methyl]-1H, 2H, 4H, 5H-benzo[d]azepinyl}acetic acid | 478 |
| 2-(3-{N-(2-(2-pyridylamino)ethyl)carbamoyl}-1H, 2H, 4H, 5H-benzo[d]azepinyl)acetic acid | 369 |
| 2-(3-(N-(2-(1,2,3,4-tetrahydropyridino[2,3-b]pyridin-7-yl)ethyl)carbamoyl)-1H, 2H, 4H, 5H-benzo[d]azepin-1-yl)acetic acid | 409 |
| 2-(8-fluoro-2-(N-(2-(1,2,3,4-tetrahydropyridino(2,3-b)pyridin-7-yl)ethyl)carbamoyl)-1H, 3H, 4H, 5H-benzo[e]azapin-5-yl)acetic acid | 427 |
| 2-{8-fluoro-2-[N-(2-pyridino[3,2-e]pyridin-2-ylethyl)carbamoyl]-1H, 3H, 4H, 5H-benzo[e]azaperhydroepin-5-yl}acetic acid | 423 |
| 2-{8-fluoro-2-[N-(3-(1,2,3,4-tetrahydropyridino[3,2-e]pyridin-2-yl)propyl)carbamoyl]-1H, 3H, 4H, 5H-benzo[e]azaperhydroepin-5-yl}acetic acid | 441 |
| 2-(2-(N-(5-(6-amino-5-methyl-2-pyridyl)pent-1-yl)carbamoyl)-1H, 3H, 4H, 5H-benzo[e]azapin-5-y)acetic acid | 426 |
| 2-(8-hydroxy-2-(N-(4-(2-pyridylamino)but-1-yl)carbamoyl)-1H, 3H, 4H, 5H-benzo[e]azapin-5-yl)acetic acid | 413 |
| 2-(2-(N-(2-(2-pyridylamino)ethyl)carbamoyl)-1H, 3H, 4H, 5H-benzo[e]azapin-5-yl)acetic acid | 369 |
| 2-{3-[N-(3-pyridino[3,2-e]pyridin-2-ylpropyl)carbamoyl]-1H, 2H, 4H, 5H-benzo[d]azepinyl}acetic acid | 419 |
| 2-{2-[N-(1,2,3,4-tetrahydropyridino[2,3-b]pyridin-7-ylmethyl)carbamoyl]-1H, 3H, 4H, 5H-benzo[e]azepin-5-yl}acetic acid | 395 |
| 2-[2-(N-{4-[(4-methyl-2-pyridyl)amino]butyl}carbamoyl)-1H, 3H, 4H, 5H-benzo[e]azepin-5-yl]acetic acid | 411 |
| 2-{2-[N-(4-{[5-(trifluoromethyl)-2-pyridyl]amino}butyl)carbamoyl]-1H, 3H, 4H, 5H-benzo[e]azepin-5-yl}acetic acid | 465 |
| 2-[2-(N-{4-[(5-chloro-2-pyridyl)amino]butyl}carbamoyl)-1H, 3H, 4H, 5H-benzo[e]azepin-5-yl]acetic acid | 432 |
| 2-{2-[N-(4-{[benzylamino]carbonylamino}butyl)carbamoyl]-1H, 3H, 4H, 5H-benzo[e]azepin-5-yl}acetic acid | 558 |
| 2-[2-(N-{4-[(phenylamino)carbonylamino]butyl}carbamoyl)-1H, 3H, 4H, 5H-benzo[e]azepin-5-yl]acetic acid | 553 |
| 2-{8-[(butylsulfonyl)amino]-2-[N-(3-(1,2,3,4-tetrahydropyridino[2,3-b]pyridin-7-yl)propyl)carbamoyl]-1H, 3H, 4H, 5H-benzo[e]azepin-5-yl}acetic acid | 559 |

EXAMPLE 86

Using the procedures of the above general description and the above examples, the compounds of Tables 1–4 (wherein OBn represents benzyloxy) can be prepared.

TABLE 1

E—B—(Alk)$_p$—Q—(Alk)$_q$—A

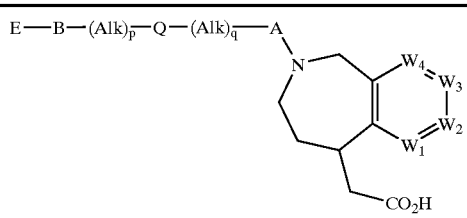

| E-B-(Alk)$_p$-Q-(Alk)$_q$-A- | W$_1$ | W$_2$ | W$_3$ | W$_4$ |
|---|---|---|---|---|
| (4-(benzimidazol-2-yl amino)butyl)carbamyl | C—H | C—H | C—H | C—H |
| (4-(benzimidazol-2-yl amino)ethyl)carbamyl | C—H | C—H | C—H | C—H |
| (4-(benzoxazol-2-yl amino)butyl)carbamyl | C—H | C—H | C—H | C—H |
| (4-(benzoxazol-2-yl amino)ethyl)carbamyl | C—H | C—H | C—H | C—H |
| (4-(imidazolo[5,4-b] | C—H | C—H | C—H | C—H |

TABLE 1-continued

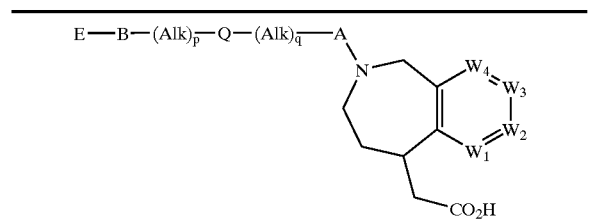

| E-B-(Alk)$_p$-Q-(Alk)$_q$-A- | $W_1$ | $W_2$ | $W_3$ | $W_4$ |
|---|---|---|---|---|
| (4-(imidazolo[5,4-b]pyridin-2-ylamino)butyl)carbamyl | C—H | C—H | C—H | C—H |
| (4-(imidazolo[5,4-b]pyridin-2-ylamino)ethyl)carbamyl | C—H | C—H | C—H | C—H |
| (4-(1,3-oxazolo[4,5-b]pyridin-2-ylamino)butyl)carbamyl | C—H | C—H | C—H | C—H |
| (4-(1,3-oxazolo[4,5-b]pyridin-2-ylamino)ethyl)carbamyl | C—H | C—H | C—H | C—H |
| (3-benzimidazol-2-yl propyl)carbamyl | C—H | C—H | C—H | C—H |
| (3-benzoxazol-2-yl propyl)carbamyl | C—H | C—H | C—H | C—H |
| (3-imidazolo[4,5-b]pyridin-2-ylpropyl)carbamyl | C—H | C—H | C—H | C—H |
| (3-(1,3-oxazolo[4,5-b]pyridin-2-yl)propyl)carbamyl | C—H | C—H | C—H | C—H |
| (benzimidazol-5-yl methyl)carbamyl | C—H | C—H | C—H | C—H |
| (benzoxazol-5-yl methyl)carbamyl | C—H | C—H | C—H | C—H |
| (2-aminobebenzimidazol-5-ylmethyl)carbamyl | C—H | C—H | C—H | C—H |
| (2-aminobenzoxazol-5-yl methyl)carbamyl | C—H | C—H | C—H | C—H |
| (3-imidazolo[4,5-e]pyridin-5-ylpropyl)carbamyl | C—H | C—H | C—H | C—H |
| (3-(1,3-oxazolo[4,5-e]pyridin-5-yl)propyl)carbamyl | C—H | C—H | C—H | C—H |
| (5-(2-piperidyl)pentyl)carbamyl | C—H | C—H | C—H | C—H |
| 3-2-piperidyl)propyl | C—H | C—H | C—H | C—H |
| (4-imidazol-2-ylamino)butyl)carbamyl | C—H | C—H | C—H | C—H |
| (4-(1,3-oxazol-2-yl)amino)butyl)carbamyl | C—H | C—H | C—H | C—H |
| (3-5-amino-1,3-oxazol-2-yl)propyl)carbamyl | C—H | C—H | C—H | C—H |
| (3-(5-amino-imidazol-2-yl)propyl)carbamyl | C—H | C—H | C—H | C—H |
| (4-(3,4,5,6-tetrahydro pyrimidin-2-ylamino)butyl)carbamyl | C—H | C—H | C—H | C—H |
| (4-(2-imidazolin-2-yl amino)butyl)carbamyl | C—H | C—H | C—H | C—H |
| 4-(2-pyridylaminobutyl)carbamyl | C—H | C—H | C—H | C—H |
| 3-(1,2,3,4-tetrahydro pyridino(2,3-b)pyridin-7-yl)-propyl)carbamoyl | C—H | C—H | C—H | C—H |
| (4-(4-methyl)-2-pyridyl)amino)butyl)carbamyl | C—H | C—H | C—H | C—H |
| (4-(benzimidazol-2-yl amino)butyl)carbamyl | N | C—H | C—H | C—H |
| (4-(benzimidazol-2-yl amino)ethyl)carbamyl | N | C—H | C—H | C—H |
| (4-(benzoxazol-2-yl amino)butyl)carbamyl | N | C—H | C—H | C—H |
| (4-(benzoxazol-2-yl amino)ethyl)carbamyl | N | C—H | C—H | C—H |
| (4-imidazolo[5,4-b]pyridin-2-ylamino)butyl)carbamyl | N | C—H | C—H | C—H |

TABLE 1-continued

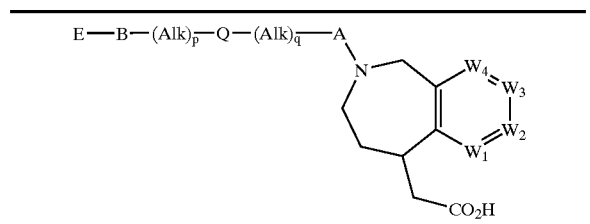

| E-B-(Alk)$_p$-Q-(Alk)$_q$-A- | $W_1$ | $W_2$ | $W_3$ | $W_4$ |
|---|---|---|---|---|
| (4-(imidazolo[5,4-b]pyridin-2-ylamino)ethyl)carbamyl | N | C—H | C—H | C—H |
| (4-(1,3-oxazolo[4,5-b]pyridin-2-ylamino)butyl)carbamyl | N | C—H | C—H | C—H |
| (4-(1,3-oxazolo[4,5-b]pyridin-2-ylamino)ethyl)carbamyl | N | C—H | C—H | C—H |
| (3-benzimidazol-2-yl propyl)carbamyl | N | C—H | C—H | C—H |
| (3-benzoxazol-2-yl propyl)carbamyl | N | C—H | C—H | C—H |
| (3-imidazolo[4,5-b]pyridin-2-ylpropyl)carbamyl | N | C—H | C—H | C—H |
| (3-(1,3-oxazolo[4,5-b]pyridin-2-yl)propyl)carbamyl | N | C—H | C—H | C—H |
| (benzimidazol-5-yl methyl)carbamyl | N | C—H | C—H | C— |
| (benzoxazol-5-yl methyl(carbamyl) | N | C—H | C—H | C—H |
| (2-aminobenzimidazol-5-ylmethyl)carbamyl | N | C—H | C—H | C—H |
| (2-aminobenzoxazol-5-yl methyl)carbamyl | N | C—H | C—H | C—H |
| (3-imidazolo[4,5-e]pyridin-5-ylpropyl)carbamyl | N | C—H | C—H | C—H |
| (3-(1,3-oxazolo[4,5-e]pyridin-5-yl)propyl)carbamyl | N | C—H | C—H | C—H |
| (5-(2-piperidyl)pentyl)carbamyl | N | C—H | C—H | C—H |
| 3-2-piperidyl)propyl | N | C—H | C—H | C—H |
| (4-imidazol-2-ylamino)butyl)carbamyl | N | C—H | C—H | C—H |
| (4-(1,3-oxazol-2-yl)amino)butyl)carbamyl | N. | C—H | C—H | C—H |
| (3-(5-amino-1,3-oxazol-2 yl)propyl)carbamyl | N | C—H | C—H | C—H |
| (3-(5-amino-imidazol-2-yl)propyl)carbamyl | N | C—H | C—H | C—H |
| (4-(3-4,5,6-tetrahydro pyrimidin-2-ylamino)butyl)carbamyl | N | C—H | C—H | C—H |
| (4-(2-imidazolin-2-yl amino)butyl)carbamyl | N | C—H | C—H | C—H |
| 4-(2-pyridylaminobutyl)carbamoyl | N | C—H | C—H | C—H |
| 3-(1,2,3,4-tetrahydro pyridino(2,3-b)pyridin-7-yl)-propyl)carbamoyl | N | C—H | C—H | C—H |
| (4-(4-methyl)-2-pyridyl)amino)butyl)carbamyl | N | C—H | C—H | C—H |
| (4-(benzimidazol-2-yl amino)butyl)carbamyl | C—H | N | C—H | C—H |
| (4-(benzimidazol-2-yl amino)ethyl)carbamyl | C—H | N | C—H | C—H |
| (4-(benzoxazol-2-yl amino)butyl)carbamyl | C—H | N | C—H | C—H |
| (4-(benzoxazol-2-yl amino)ethyl)carbamyl | C—H | N | C—H | C—H |
| (4-(imidazolo[5,4-b]pyridin-2-ylamino)butyl)carbamyl | C—H | N | C—H | C—H |

TABLE 1-continued

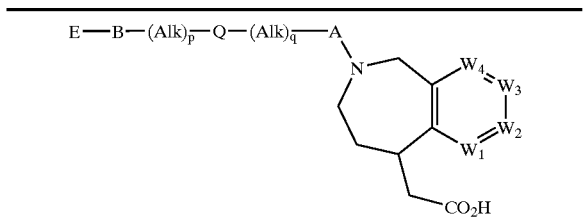

| E-B-(Alk)$_p$-Q-(Alk)$_q$-A- | W$_1$ | W$_2$ | W$_3$ | W$_4$ |
|---|---|---|---|---|
| (4-(imidazolo[5,4-b]pyridin-2-ylamino)ethyl)carbamyl | C—H | N | C—H | C—H |
| (4-(1,3-oxazolo[4,5-b]pyridin-2-ylamino)butyl)carbamyl | C—H | N | C—H | C—H |
| (4-(1,3-oxazolo[4,5-b]pyridin-2-ylamino)ethyl)carbamyl | C—H | N | C—H | C—H |
| (3-benzimidazol-2-yl propyl)carbamyl | C—H | N | C—H | C—H |
| (3-benzoxazol-2-yl propyl)carbamyl | C—H | N | C—H | C—H |
| (3-imidazolo[4,5-b]pyridin-2-ylpropyl)carbamyl | C—H | N | C—H | C—H |
| (3-(1,3-oxazolo[4,5-b]pyridin-2-yl)propyl)carbamyl | C—H | N | C—H | C—H |
| (benzimidazol-5-yl methyl)carbamyl | C—H | N | C—H | C—H |
| (benzoxazol-5-yl methyl)carbamyl | C—H | N | C—H | C—H |
| (2-aminobebenzimidazol-5-ylmethyl)carbamyl | C—H | N | C—H | C—H |
| (2-aminobenzoxazol-5-yl methyl)carbamyl | C—H | N | C—H | C—H |
| (3-imidazolo[4,5-e]pyridin-5-ylpropyl)carbamyl | C—H | N | C—H | C—H |
| (3-(1,3-oxazolo[4,5-e]pyridin-5-yl)propyl)carbamyl | C—H | N | C—H | C—H |
| (5-(2-piperidyl)pentyl)carbamyl | C—H | N | C—H | C—H |
| 3-(2-piperidyl)propyl | C—H | N | C—H | C—H |
| (4-imidazol-2-ylamino)butyl)carbamyl | C—H | N | C—H | C—H |
| (4-(1,3-oxazol-2-yl)amino)butyl)carbamyl | C—H | N | C—H | C—H |
| (3-(5-amino-1,3-oxazol-2-yl)propyl)carbamyl | C—H | N | C—H | C—H |
| (3-(5-amino-imidazol-2-yl)propyl)carbamyl | C—H | N | C—H | C—H |
| (4-(3,4,5,6-tetrahydro pyrimidin-2-ylamino)butyl)carbamyl | C—H | N | C—H | C—H |
| (4-(2-imidazolin-2-yl amino)butyl)carbamyl | C—H | N | C—H | C—H |
| 4-(2-pyridylaminobutyl)carbamoyl | C—H | N | C—H | C—H |
| 3-(1,2,3,4-tetrahydro pyridino(2,3-b)pyridin-7-yl)-propyl)carbamoyl | C—H | N | C—H | C—H |
| (4-(4-methyl)-2-pyridyl)amino)butyl)carbamyl | C—H | N | C—H | C—H |
| (4-(benzimidazol-2-yl amino)butyl)carbamyl | C—H | C—H | N | C—H |
| (4-(benzimidazol-2-yl amino)ethyl)carbamyl | C—H | C—H | N | C—H |
| (4-(benzoxazol-2-yl amino)butyl)carbamyl | C—H | C—H | N | C—H |
| (4-(benzoxazol-2-yl amino)ethyl)carbamyl | C—H | C—H | N | C—H |
| (4-(imidazolo[5,4-b]pyridin-2-ylamino)butyl)carbamyl | C—H | C—H | N | C—H |
| (4-(imidazolo[5,4-b]pyridin-2-ylamino)ethyl)carbamyl | C—H | C—H | N | C—H |

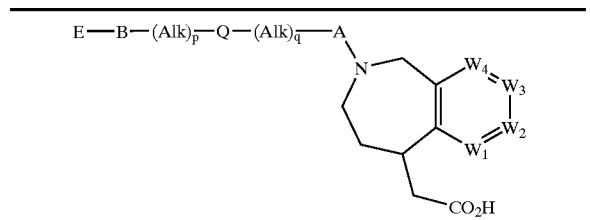

| E-B-(Alk)$_p$-Q-(Alk)$_q$-A- | W$_1$ | W$_2$ | W$_3$ | W$_4$ |
|---|---|---|---|---|
| (4-(1,3-oxazolo[4,5-b]pyridin-2-ylamino)butyl)carbamyl | C—H | C—H | N | C—H |
| (4-(1,3-oxazolo[4,5-b]pyridin-2-ylamino)ethyl)carbamyl | C—H | C—H | N | C—H |
| (3-benzimidazol-2-yl propyl)carbamyl | C—H | C—H | N | C—H |
| (3-benzoxazol-2-yl propyl)carbamyl | C—H | C—H | N | C—H |
| (3-imidazolo[4,5-b]pyridin-2-ylpropyl)carbamyl | C—H | C—H | N | C—H |
| (3-(1,3-oxazolo[4,5-b]pyridin-2-yl)propyl)carbamyl | C—H | C—H | N | C—H |
| (benzimidazol-5-yl methyl)carbamyl | C—H | C—H | N | C—H |
| (benzoxazol-5-yl methyl)carbamyl | C—H | C—H | N | C—H |
| (2-aminobenzimidazol-5-ylmethyl)carbamyl | C—H | C—H | N | C—H |
| (2-aminobenzoxazol-5-yl methyl)carbamyl | C—H | C—H | N | C—H |
| (3-imidazolo[4,5-e]pyridin-5-ylpropyl)carbamyl | C—H | C—H | N | C—H |
| (3-(1,3-oxazolo[4,5-e]pyridin-5-yl)propyl)carbamyl | C—H | C—H | N | C—H |
| (5-(2-piperidyl)pentyl)carbamyl | C—H | C—H | N | C—H |
| 3-(2-piperidyl)propyl | C—H | C—H | N | C—H |
| (4-imidazol-2-ylamino)butyl)carbamyl | C—H | C—H | N | C—H |
| (4-(1,3-oxazol-2-yl)amino)butyl)carbamyl | C—H | C—H | N | C—H |
| (3-(5-amino-1,3-oxazol-2-yl)propyl)carbamyl | C—H | C—H | N | C—H |
| (3-(5-amino-imidazol-2-yl)propyl)carbamyl | C—H | C—H | N | C—H |
| (4-(3,4,5,6-tetrahydro pyrimidin-2-ylamino)butyl)carbamyl | C—H | C—H | N | C—H |
| (4-(2-imidazolin-2-yl amino)butyl)carbamyl | C—H | C—H | N | C—H |
| 4-(2-pyridylaminobutyl)carbamoyl | C—H | C—H | N | C—H |
| 3-(1,2,3,4-tetrahydro pyridino(2,3-b)pyridin-7-yl)-propyl)carbamoyl | C—H | C—H | N | C—H |
| (4-(4-methyl)-2-pyridyl)amino)butyl)carbamyl | C—H | C—H | N | C—H |
| (4-(benzimidazol-2-yl amino)butyl)carbamyl | C—H | C—H | C—H | N |
| (4-(benzimidazol-2-yl amino)ethyl)carbamyl | C—H | C—H | C—H | N |
| (4-(benzoxazol-2-yl amino)butyl)carbamyl | C—H | C—H | C—H | N |
| (4-(benzoxazol-2-yl amino)ethyl)carbamyl | C—H | C—H | C—H | N |
| (4-(imidazolo[5,4-b]pyridin-2-ylamino)butyl)carbamyl | C—H | C—H | C—H | |
| (4-(imidazolo[5,4-b]pyridin-2-ylamino)ethyl)carbamyl | C—H | C—H | C—H | N |

TABLE 1-continued

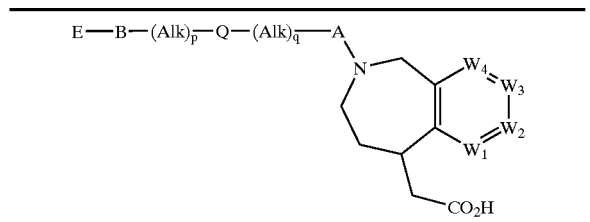

| E-B-(Alk)$_p$-Q-(Alk)$_q$-A- | W$_1$ | W$_2$ | W$_3$ | W$_4$ |
|---|---|---|---|---|
| carbamyl (4-(1,3-oxazolo[4,5-b]pyridin-2-ylamino)butyl) carbamyl | C—H | C—H | C—H | N |
| (4-(1,3-oxazolo[4,5-b]pyridin-2-ylamino)ethyl) carbamyl | C—H | C—H | C—H | N |
| (3-benzimidazol-2-yl propyl)carbamyl | C—H | C—H | C—H | N |
| (3-benzoxazol-2-yl propyl)carbamyl | C—H | C—H | C—H | N |
| (3-imidazolo[4,5-b]pyridin-2-ylpropyl)carbamyl | C—H | C—H | C—H | N |
| (3-(1,3-oxazolo[4,5-b]pyridin-2-yl)propyl) carbamyl | C—H | C—H | C—H | N |
| (benzimidazol-5-yl methyl)carbamyl | C—H | C—H | C—H | N |
| (benzoxazol-5-yl methyl)carbamyl | C—H | C—H | C—H | N |
| (2-aminobebenzimidazol-5-ylmethyl)carbamyl | C—H | C—H | C—H | N |
| (2-aminobenzoxazol-5-yl methyl)carbamyl | C—H | C—H | C—H | N |
| (3-imidazolo[4,5-e]pyridin-5-ylpropyl)carbamyl | C—H | C—H | C—H | N |
| (3-(1,3-oxazolo[4,5-e]pyridin-5-yl)propyl) carbamyl | C—H | C—H | C—H | N |
| (5-(2-piperidyl)pentyl) carbamyl | C—H | C—H | C—H | N |
| 3-(2-piperidyl)propyl | C—H | C—H | C—H | N |
| (4-imidazol-2-ylamino) butyl)carbamyl | C—H | C—H | C—H | N |
| (4-(1,3-oxazol-2-yl) amino)butyl)carbamyl | C—H | C—H | C—H | N |
| (3-(5-amino-1,3-oxazol-2-yl)propyl)carbamyl | C—H | C—H | C—H | N |
| (3-(5-amino-imidazol-2-yl)propyl)carbamyl | C—H | C—H | C—H | N |
| (4-(3,4,5,6-tetrahydro pyrimidin-2-ylamino)butyl) carbamyl | C—H | C—H | C—H | N |
| (4-(2-imidazolin-2-yl amino)butyl)carbamyl | C—H | C—H | C—H | N |
| 4-(2-pyridylaminobutyl) carbamoyl | C—H | C—H | C—H | N |
| 3-(1,2,3,4-tetrahydro pyridino(2,3-b)pyridin-7-yl)-propyl)carbamoyl | C—H | C—H | C—H | N |
| (4-(4-methyl)-2-pyridyl) amino)butyl)carbamyl | C—H | C—H | C—H | N |
| (4-(benzimidazol-2-yl amino)butyl)carbamyl | C—H | C—H | C—CH$_3$ | C—H |
| (4-(benzimidazol-2-yl amino)ethyl)carbamyl | C—H | C—H | C—CH$_3$ | C—H |
| (4-(benzoxazol-2-yl amino)butyl)carbamyl | C—H | C—H | C—CH$_3$ | C—H |
| (4-(benzoxazol-2-yl amino)ethyl)carbamyl | C—H | C—H | C—CH$_3$ | C—H |
| (4-(imidazolo[5,4-b]pyridin-2-ylamino)butyl) carbamyl | C—H | C—H | C—CH$_3$ | C—H |
| (4-(imidazolo[5,4-b]pyridin-2-ylamino)ethyl) carbamyl | C—H | C—H | C—CH$_3$ | C—H |
| (4-(1,3-oxazolo[4,5-b]pyridin-2-ylamino)butyl) carbamyl | C—H | C—H | C—CH$_3$ | C—H |
| (4-(1,3-oxazolo[4,5-b]pyridin-2-ylamino)ethyl) carbamyl | C—H | C—H | C—CH$_3$ | C—H |
| (3-benzimidazol-2-yl propyl)carbamyl | C—H | C—H | C—CH$_3$ | C—H |
| (3-benzoxazol-2-yl propyl)carbamyl | C—H | C—H | C—CH$_3$ | C— |
| (3-imidazolo[4,5-b]pyridin-2-ylpropyl)carbamyl | C—H | C—H | C—CH$_3$ | C—H |
| (3-(1,3-oxazolo[4,5-b]pyridin-2-yl)propyl) carbamyl | C—H | C—H | C—CH$_3$ | C—H |
| (benzimidazol-5-yl methyl)carbamyl | C—H | C—H | C—CH$_3$ | C—H |
| (benzoxazol-5-yl methyl)carbamyl | C—H | C—H | C—CH$_3$ | C—H |
| (2-aminobebenzimidazol-5-ylmethyl)carbamyl | C—H | C—H | C—CH$_3$ | C—H |
| (2-aminobenzoxazol-5-yl methyl)carbamyl | C—H | C—H | C—CH$_3$ | C—H |
| (3-imidazolo[4,5-e]pyridin-5-ylpropyl)carbamyl | C—H | C—H | C—CH$_3$ | C—H |
| (3-(1,3-oxazolo[4,5-e]pyridin-5-yl)propyl) carbamyl | C—H | C—H | C—CH$_3$ | C—H |
| (5-(2-piperidyl)pentyl) carbamyl | C—H | C—H | C—CH$_3$ | C—H |
| 3-(2-piperidyl)propyl | C—H | C—H | C—CH$_3$ | C—H |
| (4-imidazol-2-ylamino) butyl)carbamyl | C—H | C—H | C—CH$_3$ | C—H |
| (4-(1,3-oxazol-2-yl) amino)butyl)carbamyl | C—H | C—H | C—CH$_3$ | C—H |
| (3-(5-amino-1,3-oxazol-2-yl)propyl)carbamyl | C—H | C—H | C—CH$_3$ | C—H |
| (3-(5-amino-imidazol-2-yl)propyl)carbamyl | C—H | C—H | C—CH$_3$ | C—H |
| (4-(3,4,5,6-tetrahydro pyrimidin-2-ylamino)butyl) carbamyl | C—H | C—H | C—CH$_3$ | C—H |
| (4-(2-imidazolin-2-yl amino)butyl)carbamyl | C—H | C—H | C—CH$_3$ | C—H |
| 4-(2-pyridylaminobutyl) carbamoyl | C—H | C—H | C—CH$_3$ | C—H |
| 3-(1,2,3,4-tetrahydro pyridino(2,3-b)pyridin-7-yl)-propyl)carbamoyl | C—H | C—H | C—CH$_3$ | C—H |
| (4-(4-methyl)-2-pyridyl) amino)butyl)carbamyl | C—H | C—H | C—CH$_3$ | C—H |
| (4-(benzimidazol-2-yl amino)butyl)carbamyl | C—H | C—H | C—OBn | C—H |
| (4-(benzimidazol-2-yl amino)ethyl)carbamyl | C—H | C—H | C—OBn | C—H |
| (4-(benzoxazol-2-yl amino)butyl)carbamyl | C—H | C—H | C—OBn | C—H |
| (4-(benzoxazol-2-yl amino)ethyl)carbamyl | C—H | C—H | C—OBn | C—H |
| (4-(imidazolo[5,4-b]pyridin-2-ylamino)butyl) carbamyl | C—H | C—H | C—OBn | C—H |
| (4-(imidazolo[5,4-b]pyridin-2-ylamino)ethyl) carbamyl | C—H | C—H | C—OBn | C—H |
| (4-(1,3-oxazolo[4,5-b] | C—H | C—H | C—OBn | C—H |

TABLE 1-continued

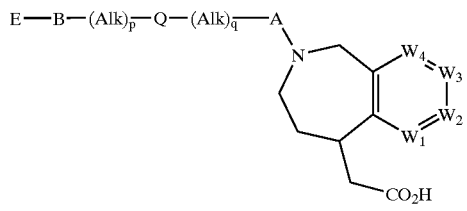

| E-B-(Alk)p-Q-(Alk)q-A- | W1 | W2 | W3 | W4 |
|---|---|---|---|---|
| pyridin-2-ylamino)butyl) carbamyl | | | | |
| (4-(1,3-oxazolo[4,5-b] pyridin-2-ylamino)ethyl) carbamyl | C—H | C—H | C—OBn | C—H |
| (3-benzimidazol-2-yl propyl)carbamyl | C—H | C—H | C—OBn | C—H |
| (3-benzoxazol-2-yl propyl)carbamyl | C—H | C—H | C—OBn | C—H |
| (3-imidazolo[4,5-b]pyridin-2-ylpropyl)carbamyl | C—H | C—H | C—OBn | C—H |
| (3-(1,3-oxazolo[4,5-b] pyridin-2-yl)propyl) carbamyl | C—H | C—H | C—OBn | C—H |
| (benzimidazol-5-yl methyl)carbamyl | C—H | C—H | C—OBn | C—H |
| (benzoxazol-5-yl methyl)carbamyl | C—H | C—H | C—OBn | C—H |
| (2-aminobebenzimidazol-5-ylmethyl)carbamyl | C—H | C—H | C—OBn | C—H |
| (2-aminobenzoxazol-5-yl methyl)-carbamyl | C—H | C—H | C—OBn | C—H |
| (3-imidazolo[4,5-e]pyridin-5-ylpropyl)carbamyl | C—H | C—H | C—OBn | C—H |
| (3-(1,3-oxazolo[4,5-e] pyridin-5-yl)propyl) carbamyl | C—H | C—H | C—OBn | C—H |
| (5-(2-piperidyl)pentyl) carbamyl | C—H | C—H | C—OBn | C—H |
| 3-(2-piperidyl)propyl | C—H | C—H | C—OBn | C—H |
| (4-imidazol-2-ylamino) butyl)carbamyl | C—H | C—H | C—OBn | C—H |
| (4-(1,3-oxazol-2-yl) amino)butyl)carbamyl | C—H | C—H | C—OBn | C—H |
| (3-(5-amino-1,3-oxazol-2-yl)propyl)carbamyl | C—H | C—H | C—OBn | C—H |
| (3-(5-amino-imidazol-2-yl)propyl)carbamyl | C—H | CLH | C—OBn | C—H |
| (4-(3,4,5,6-tetrahydro pyrimidin-2-ylamino)butyl) carbamyl | C—H | C—H | C—OBn | C—H |
| (4-(2-imidazolin-2-yl amino)butyl)carbamyl | C—H | C—H | C—OBn | C—H |
| 4-(2-pyridylaminobutyl) carbamoyl | C—H | C—H | C—OBn | C—H |
| 3-(1,2,3,4-tetrahydro pyridino(2,3-b)pyridin-7-yl)-propyl)carbamoyl | C—H | C—H | C—OBn | C—H |
| (4-(4-methyl)-2-pyridyl) amino)butyl)-carbamyl | C—H | C—H | C—OBn | C—H |
| (4-(benzimidazol-2-yl amino)butyl)carbamyl | C—H | C—H | C—Cl | C—H |
| (4-(benzimidazol-2-yl amino)ethyl)carbamyl | C—H | C—H | C—Cl | C—H |
| (4-(benzoxazol-2-yl amino)butyl)carbamyl | C—H | C—H | C—Cl | C—H |
| (4-(benzoxazol-2-yl amino)ethyl)carbamyl | C—H | C—H | C—Cl | C—H |
| (4-(imidazolo[5,4-b] pyridin-2-ylamino)butyl) carbamyl | C—H | C—H | C—Cl | C—H |
| (4-(imidazolo[5,4-b] pyridin-2-ylamino)ethyl) carbamyl | C—H | C—H | C—Cl | C—H |
| (4-(1,3-oxazolo[4,5-b] pyridin-2-ylamino)butyl) | C—H | C—H | C—Cl | C—H |

TABLE 1-continued

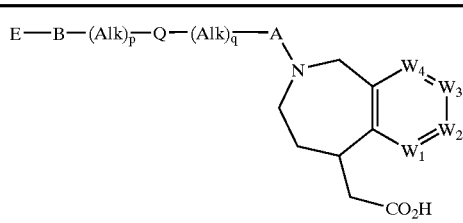

| E-B-(Alk)p-Q-(Alk)q-A- | W1 | W2 | W3 | W4 |
|---|---|---|---|---|
| carbamyl | | | | |
| (4-(1,3-oxazolo[4,5-b] pyridin-2-ylamino)ethyl) carbamyl | C—H | C—H | C—Cl | C—H |
| (3-benzimidazol-2-yl propyl)carbamyl | C—H | C—H | C—Cl | C—H |
| (3-benzoxazol-2-yl propyl)carbamyl | C—H | C—H | C—Cl | C—H |
| (3-imidazolo[4,5-b]pyridin-2-ylpropyl)carbamyl | C—H | C—H | C—Cl | C—H |
| (3-(1,3-oxazolo[4,5-b] pyridin-2-yl)propyl) carbamyl | C—H | C—H | C—Cl | C—H |
| (benzimidazol-5-yl methyl)carbamyl | C—H | C—H | C—Cl | C—H |
| (benzoxazol-5-yl methyl)carbamyl | C—H | C—H | C—Cl | C—H |
| (2-aminobebenzimidazol-5-ylmethyl)carbamyl | C—H | C—H | C—Cl | C—H |
| (2-aminobenzoxazol-5-yl methyl)carbamyl | C—H | C—H | C—Cl | C—H |
| (3-imidazolo[4,5-e]pyridin-5-ylpropyl)carbamyl | C—H | C—H | C—Cl | C—H |
| (3-(1,3-oxazolo[4,5-e] pyridin-5-yl)propyl) carbamyl | C—H | C—H | C—Cl | C—H |
| (5-(2-piperidyl)pentyl) carbamyl | C—H | C—H | C—Cl | C—H |
| 3-2-piperidyl)propyl | C—H | C—H | C—Cl | C—H |
| (4-imidazol-2-ylamino) butyl)carbamyl | C—H | C—H | C—Cl | C—H |
| (4-(1,3-oxazol-2-yl) amino)butyl)carbamyl | C—H | C—H | C—Cl | C—H |
| (3-(5-amino-1,3-oxazol-2-yl)propyl)carbamyl | C—H | C—H | C—Cl | C—H |
| (3-(5-amino-imidazol-2-yl)propyl)carbamyl | C—H | C—H | C—Cl | C—H |
| (4-(3,4,5,6-tetrahydro pyrimidin-2-ylamino)butyl) carbamyl | C—H | C—H | C—Cl | C—H |
| (4-(2-imidazolin-2-yl amino)butyl)carbamyl | C—H | C—H | C—Cl | C—H |
| 4-(2-pyridylaminobutyl) carbamoyl | C—H | C—H | C—Cl | C—H |
| 3-(1,2,3,4-tetrahydro pyridino(2,3-b)pyridin-7-yl)-propyl)carbamoyl | C—H | C—H | C—Cl | C—H |
| (4-(4-methyl)-2-pyridyl) amino)butyl)carbamyl | C—H | C—H | C—Cl | C—H |

TABLE 2

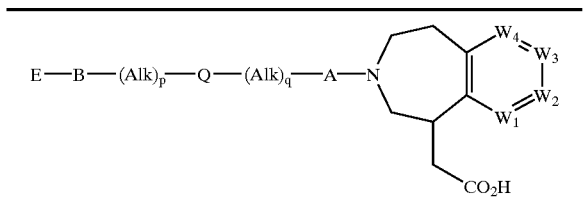

| E—B—(Alk)p—Q—(Alk)q—A— | $W_1$ | $W_2$ | $W_3$ | $W_4$ |
|---|---|---|---|---|
| (4-(benzimidazol-2-yl amino)butyl)carbamyl | C—H | C—H | C—H | C—H |
| (4-(benzimidazol-2-yl amino)ethyl)carbamyl | C—H | C—H | C—H | C—H |
| (4-(benzoxazol-2-yl amino)butyl)carbamyl | C—H | C—H | C—H | C—H |
| (4-(benzoxazol-2-yl amino)ethyl)carbamyl | C—H | C—H | C—H | C—H |
| (4-(imidazolo[5,4-b] pyridin-2-ylamino)butyl) carbamyl | C—H | C—H | C—H | C—H |
| (4-(imidazolo[5,4-b] pyridin-2-ylamino)ethyl) carbamyl | C—H | C—H | C—H | C—H |
| (4-(1,3-oxazolo[4,5-b] pyridin-2-ylamino)butyl) carbamyl | C—H | C—H | C—H | C—H |
| (4-(1,3-oxazolo[4,5-b] pyridin-2-ylamino)ethyl) carbamyl | C—H | C—H | C—H | C—H |
| (3-benzimidazol-2-yl propyl)carbamyl | C—H | C—H | C—H | C—H |
| (3-benzoxazol-2-yl propyl)carbamyl | C—H | C—H | C—H | C—H |
| (3-imidazolo[4,5-b]pyridin-2-ylpropyl)carbamyl | C—H | C—H | C—H | C—H |
| (3-(1,3-oxazolo[4,5-b] pyridin-2-yl)propyl) carbamyl | C—H | C—H | C—H | C—H |
| (benzimidazol-5-yl methyl)carbamyl | C—H | C—H | C—H | C—H |
| (benzoxazol-5-yl methyl)carbamyl | C—H | C—H | C—H | C—H |
| (2-aminobebenzimidazol-5-ylmethyl)carbamyl | C—H | C—H | C—H | C—H |
| (2-aminobenzoxazol-5-yl methyl)carbamyl | C—H | C—H | C—H | C—H |
| (3-imidazolo[4,5-e]pyridin-5-ylpropyl))carbamyl | C—H | C—H | C—H | C—H |
| (3-(1,3-oxazolo[4,5-e] pyridin-5-yl)propyl) carbamyl | C—H | C—H | C—H | C—H |
| (5-(2-piperidyl)pentyl) carbamyl | C—H | C—H | C—H | C—H |
| 3-(2-piperidyl)propyl | C—H | C—H | C—H | C—H |
| (4-imidazol-2-ylamino) butyl)carbamyl | C—H | C—H | C—H | C—H |
| (4-(1,3-oxazol-2-yl) amino)butyl)carbamyl | C—H | C—H | C—H | C—H |
| (3-(5-amino-1,3-oxazol-2-yl)propyl)carbamyl | C—H | C—H | C—H | C—H |
| (3-(5-amino-imidazol-2-yl)propyl)carbamyl | C—H | C—H | C—H | C—H |
| (4-(3,4,5,6-tetrahydro pyrimidin-2-ylamino)butyl) carbamyl | C—H | C—H | C—H | C—H |
| (4-(2-imidazolin-2-yl amino)butyl)carbamyl | C—H | C—H | C—H | C—H |
| 4-(2-pyridylaminobutyl) carbamoyl | C—H | C—H | C—H | C—H |
| 3-(1,2,3,4-tetrahydro pyridino(2,3-b)pyridin-7-yl)-propyl)carbamoyl | C—H | C—H | C—H | C—H |
| (4-(4-methyl)-2-pyridyl) amino)butyl)carbamyl | C—H | C—H | C—H | C—H |
| (4-(benzimidazol-2-yl amino)butyl)carbamyl | N | C—H | C—H | C—H |
| (4-(benzimidazol-2-yl amino)ethyl)carbamyl | N | C—H | C—H | C—H |
| (4-(benzoxazol-2-yl amino)butyl)carbamyl | N | C—H | C—H | C—H |
| (4-(benzoxazol-2-yl amino)ethyl)carbamyl | N | C—H | C—H | C—H |
| (4-(imidazolo[5,4-b] pyridin-2-ylamino)butyl) carbamyl | N | C—H | C—H | C—H |
| (4-(imidazolo[5,4-b] pyridin-2-ylamino)ethyl) carbamyl | N | C—H | C—H | C—H |
| (4-(1,3-oxazolo[4,5-b] pyridin-2-ylamino)butyl) carbamyl | N | C—H | C—H | C—H |
| (4-(1,3-oxazolo[4,5-b] pyridin-2-ylamino)ethyl) carbamyl | N | C—H | C—H | C—H |
| (3-benzimidazol-2-yl propyl)carbamyl | N | C—H | C—H | C—H |
| (3-benzoxazol-2-yl propyl)carbamyl | N | C—H | C—H | C—H |
| (3-imidazolo[4,5-b]pyridin-2-ylpropyl)carbamyl | N | C—H | C—H | C—H |
| (3-(1,3-oxazolo[4,5-b] pyridin-2-yl)propyl) carbamyl | N | C—H | C—H | C—H |
| (benzimidazol-5-yl methyl)carbamyl | N | C—H | C—H | C—H |
| (benzoxazol-5-yl methyl)carbamyl | N | C—H | C—H | C—H |
| (2-aminobenzimidazol-5-ylmethyl)carbamyl | N | C—H | C—H | C—H |
| (2-aminobenzoxazol-5-yl methyl)carbamyl | N | C—H | C—H | C—H |
| (3-imidazolo[4,5-e]pyridin-5-ylpropyl))carbamyl | N | C—H | C—H | C—H |
| (3-(1,3-oxazolo[4,5-e] pyridin-5-yl)propyl) carbamyl | N | C—H | C—H | C—H |
| (5-(2-piperidyl)pentyl) carbamyl | N | C—H | C—H | C—H |
| 3-(2-piperidyl)propyl | N | C—H | C—H | C—H |
| (4-imidazol-2-ylamino) butyl)carbamyl | N | C—H | C—H | C—H |
| (4-(1,3-oxazol-2-yl) amino)butyl)carbamyl | N | C—H | C—H | C—H |
| (3-(5-amino-1,3-oxazol-2-yl)propyl)carbamyl | N | C—H | C—H | C—H |
| (3-(5-amino-imidazol-2-yl)propyl)carbamyl | N | C—H | C—H | C—H |
| (4-(3,4,5,6-tetrahydro pyrimidin-2-ylamino)butyl) carbamyl | N | C—H | C—H | C—H |
| (4-(2-imidazolin-2-yl amino)butyl)carbamyl | N | C—H | C—H | C—H |
| 4-(2-pyridylaminobutyl) carbamoyl | N | C—H | C—H | C—H |
| 3-(1,2,3,4-tetrahydro pyridino(2,3-b)pyridin-7-yl)-propyl)carbamoyl | N | C—H | C—H | C—H |
| (4-(4-methyl)-2-pyridyl) amino)butyl)carbamyl | N | C—H | C—H | C—H |
| (4-(benzimidazol-2-yl amino)butyl)carbamyl | C—H | N | C—H | C—H |
| (4-(benzimidazol-2-yl amino)ethyl)carbamyl | C—H | N | C—H | C—H |

TABLE 2-continued

E—B—(Alk)$_p$—Q—(Alk)$_q$—A—N-[7-membered ring fused with W$_1$W$_2$W$_3$W$_4$ ring, with CH$_2$CO$_2$H substituent]

| E—B—(Alk)$_p$—Q—(Alk)$_q$—A— | W$_1$ | W$_2$ | W$_3$ | W$_4$ |
|---|---|---|---|---|
| (4-(benzoxazol-2-yl amino)butyl)carbamyl | C—H | N | C—H | C—H |
| (4-(benzoxazol-2-yl amino)ethyl)carbamyl | C—H | N | C—H | C—H |
| (4-(imidazolo[5,4-b]pyridin-2-ylamino)butyl)carbamyl | C—H | N | C—H | C—H |
| (4-(imidazolo[5,4-b]pyridin-2-ylamino)ethyl)carbamyl | C—H | N | C—H | C—H |
| (4-(1,3-oxazolo[4,5-b]pyridin-2-ylamino)butyl)carbamyl | C—H | N | C—H | C—H |
| (4-(1,3-oxazolo[4,5-b]pyridin-2-ylamino)ethyl)carbamyl | C—H | N | C—H | C—H |
| (3-benzimidazol-2-yl propyl)carbamyl | C—H | N | C—H | C—H |
| (3-benzoxazol-2-yl propyl)carbamyl | C—H | N | C—H | C—H |
| (3-imidazolo[4,5-b]pyridin-2-ylpropyl)carbamyl | C—H | N | C—H | C—H |
| (3-(1,3-oxazolo[4,5-b]pyridin-2-yl)propyl)carbamyl | C—H | N | C—H | C—H |
| (benzimidazol-5-yl methyl)carbamyl | C—H | N | C—H | C—H |
| (benzoxazol-5-yl methyl)carbamyl | C—H | N | C—H | C—H |
| (2-aminobebenzimidazol-5-ylmethyl)carbamyl | C—H | N | C—H | C—H |
| (2-aminobenzoxazol-5-yl methyl)carbamyl | C—H | N | C—H | C—H |
| (3-imidazolo[4,5-e]pyridin-5-ylpropyl))carbamyl | C—H | N | C—H | C—H |
| (3-(1,3-oxazolo[4,5-e]pyridin-5-yl)propyl)carbamyl | C—H | N | C—H | C—H |
| (5-(2-piperidyl)pentyl)carbamyl | C—H | N | C—H | C—H |
| 3-(2-piperidyl)propyl | C—H | N | C—H | C—H |
| (4-imidazol-2-ylamino)butyl)carbamyl | C—H | N | C—H | C—H |
| (4-(1,3-oxazol-2-yl)amino)butyl)carbamyl | C—H | N | C—H | C—H |
| (3-(5-amino-1,3-oxazol-2-yl)propyl)carbamyl | C—H | N | C—H | C—H |
| (3-(5-amino-imidazol-2-yl)propyl)carbamyl | C—H | N | C—H | C—H |
| (4-(3,4,5,6-tetrahydro pyrimidin-2-ylamino)butyl)carbamyl | C—H | N | C—H | C—H |
| (4-(2-imidazolin-2-yl amino)butyl)carbamyl | C—H | N | C—H | C—H |
| 4-(2-pyridylaminobutyl)carbamoyl | C—H | N | C—H | C—H |
| 3-(1,2,3,4-tetrahydro pyridino(2,3-b)pyridin-7-yl)-propyl)carbamoyl | C—H | N | C—H | C—H |
| (4-(4-methyl)-2-pyridyl)amino)butyl)carbamyl | C—H | N | C—H | C—H |
| (4-(benzimidazol-2-yl amino)butyl)carbamyl | C—H | C—H | N | C—H |
| (4-(benzimidazol-2-yl amino)ethyl)carbamyl | C—H | C—H | N | C—H |
| (4-(benzoxazol-2-yl amino)butyl)carbamyl | C—H | C—H | N | C—H |
| (4-(benzoxazol-2-yl amino)ethyl)carbamyl | C—H | C—H | N | C—H |
| (4-(imidazolo[5,4-b]pyridin-2-ylamino)butyl)carbamyl | C—H | C—H | N | C—H |
| (4-(imidazolo[5,4-b]pyridin-2-ylamino)ethyl)carbamyl | C—H | C—H | N | C—H |
| (4-(1,3-oxazolo[4,5-b]pyridin-2-ylamino)butyl)carbamyl | C—H | C—H | N | C—H |
| (4-(1,3-oxazolo[4,5-b]pyridin-2-ylamino)ethyl)carbamyl | C—H | C—H | N | C—H |
| (3-benzimidazol-2-yl propyl)carbamyl | C—H | C—H | N | C—H |
| (3-benzoxazol-2-yl propyl)carbamyl | C—H | C—H | N | C—H |
| (3-imidazolo[4,5-b]pyridin-2-ylpropyl)carbamyl | C—H | C—H | N | C—H |
| (3-(1,3-oxazolo[4,5-b]pyridin-2-yl)propyl)carbamyl | C—H | C—H | N | C—H |
| (benzimidazol-5-yl methyl)carbamyl | C—H | C—H | N | C—H |
| (benzoxazol-5-yl methyl)carbamyl | C—H | C—H | N | C—H |
| (2-aminobenzimidazol-5-ylmethyl)carbamyl | C—H | C—H | N | C—H |
| (2-aminobenzoxazol-5-yl methyl)carbamyl | C—H | C—H | N | C—H |
| (3-imidazolo[4,5-e]pyridin-5-ylpropyl))carbamyl | C—H | C—H | N | C—H |
| (3-(1,3-oxazolo[4,5-e]pyridin-5-yl)propyl)carbamyl | C—H | C—H | N | C—H |
| (5-(2-piperidyl)pentyl)carbamyl | C—H | C—H | N | C—H |
| 3-(2-piperidyl)propyl | C—H | C—H | N | C—H |
| (4-imidazol-2-ylamino)butyl)carbamyl | C—H | C—H | N | C—H |
| (4-(1,3-oxazol-2-yl)amino)butyl)carbamyl | C—H | C—H | N | C—H |
| (3-(5-amino-1,3-oxazol-2-yl)propyl)carbamyl | C—H | C—H | N | C—H |
| (3-(5-amino-imidazol-2-yl)propyl)carbamyl | C—H | C—H | N | C—H |
| (4-(3,4,5,6-tetrahydro pyrimidin-2-ylamino)butyl)carbamyl | C—H | C—H | N | C—H |
| (4-(2-imidazolin-2-yl amino)butyl)carbamyl | C—H | C—H | N | C—H |
| 4-(2-pyridylaminobutyl)carbamoyl | C—H | C—H | N | C—H |
| 3-(1,2,3,4-tetrahydro pyridino(2,3-b)pyridin-7-yl)-propyl)carbamoyl | C—H | C—H | N | C—H |
| (4-(4-methyl)-2-pyridyl)amino)butyl)carbamyl | C—H | C—H | N | C—H |
| (4-(benzimidazol-2-yl amino)butyl)carbamyl | C—H | C—H | C—H | N |
| (4-(benzimidazol-2-yl amino)ethyl)carbamyl | C—H | C—H | C—H | N |
| (4-(benzoxazol-2-yl amino)butyl)carbamyl | C—H | C—H | C—H | N |
| (4-(benzoxazol-2-yl amino)ethyl)carbamyl | C—H | C—H | C—H | N |

TABLE 2-continued

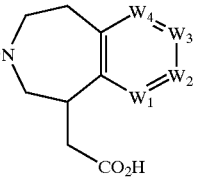

| E—B—(Alk)$_p$—Q—(Alk)$_q$—A— | W$_1$ | W$_2$ | W$_3$ | W$_4$ |
|---|---|---|---|---|
| (4-(imidazolo[5,4-b]pyridin-2-ylamino)butyl)carbamyl | C—H | C—H | C—H | N |
| (4-(imidazolo[5,4-b]pyridin-2-ylamino)ethyl)carbamyl | C—H | C—H | C—H | N |
| (4-(1,3-oxazolo[4,5-b]pyridin-2-ylamino)butyl)carbamyl | C—H | C—H | C—H | N |
| (4-(1,3-oxazolo[4,5-b]pyridin-2-ylamino)ethyl)carbamyl | C—H | C—H | C—H | N |
| (3-benzimidazol-2-yl propyl)carbamyl | C—H | C—H | C—H | N |
| (3-benzoxazol-2-yl propyl)carbamyl | C—H | C—H | C—H | N |
| (3-imidazolo[4,5-b]pyridin-2-ylpropyl)carbamyl | C—H | C—H | C—H | N |
| (3-(1,3-oxazolo[4,5-b]pyridin-2-yl)propyl)carbamyl | C—H | C—H | C—H | N |
| (benzimidazol-5-yl methyl)carbamyl | C—H | C—H | C—H | N |
| (benzoxazol-5-yl methyl)carbamyl | C—H | C—H | C—H | N |
| (2-aminobebenzimidazol-5-ylmethyl)carbamyl | C—H | C—H | C—H | N |
| (2-aminobenzoxazol-5-yl methyl)carbamyl | C—H | C—H | C—H | N |
| (3-imidazolo[4,5-e]pyridin-5-ylpropyl))carbamyl | C—H | C—H | C—H | N |
| (3-(1,3-oxazolo[4,5-e]N pyridin-5-yl)propyl)carbamyl | C—H | C—H | C—H | N |
| (5-(2-piperidyl)pentyl)carbamyl | C—H | C—H | C—H | N |
| 3-(2-piperidyl)propyl | C—H | C—H | C—H | N |
| (4-imidazol-2-ylamino)butyl)carbamyl | C—H | C—H | C—H | N |
| (4-(1,3-oxazol-2-yl)amino)butyl)carbamyl | C—H | C—H | C—H | N |
| (3-(5-amino-1,3-oxazol-2-yl)propyl)carbamyl | C—H | C—H | C—H | N |
| (3-(5-amino-imidazol-2-yl)propyl)carbamyl | C—H | C—H | C—H | N |
| (4-(3,4,5,6-tetrahydro pyrimidin-2-ylamino)butyl)carbamyl | C—H | C—H | C—H | N |
| (4-(2-imidazolin-2-yl amino)butyl)carbamyl | C—H | C—H | C—H | N |
| 4-(2-pyridylaminobutyl)carbamoyl | C—H | C—H | C—H | N |
| 3-(1,2,3,4-tetrahydro pyridino(2,3-b)pyridin-7-yl)-propyl)carbamoyl | C—H | C—H | C—H | N |
| (4-(4-methyl)-2-pyridyl)amino)butyl)carbamyl | C—H | C—H | C—H | N |
| (4-(benzimidazol-2-yl amino)butyl)carbamyl | C—H | C—H | C—CH$_3$ | C—H |
| (4-(benzimidazol-2-yl amino)ethyl)carbamyl | C—H | C—H | C—CH$_3$ | C—H |
| (4-(benzoxazol-2-yl amino)butyl)carbamyl | C—H | C—H | C—CH$_3$ | C—H |
| (4-(benzoxazol-2-yl amino)ethyl)carbamyl | C—H | C—H | C—CH$_3$ | C—H |
| (4-(imidazolo[5,4-b]pyridin-2-ylamino)butyl)carbamyl | C—H | C—H | C—CH$_3$ | C—H |

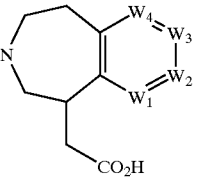

| E—B—(Alk)$_p$—Q—(Alk)$_q$—A— | W$_1$ | W$_2$ | W$_3$ | W$_4$ |
|---|---|---|---|---|
| (4-(imidazolo[5,4-b]pyridin-2-ylamino)ethyl)carbamyl | C—H | C—H | C—CH$_3$ | C—H |
| (4-(1,3-oxazolo[4,5-b]pyridin-2-ylamino)butyl)carbamyl | C—H | C—H | C—CH$_3$ | C—H |
| (4-(1,3-oxazolo[4,5-b]pyridin-2-ylamino)ethyl)carbamyl | C—H | C—H | C—CH$_3$ | C—H |
| (3-benzimidazol-2-yl propyl)carbamyl | C—H | C—H | C—CH$_3$ | C—H |
| (3-benzoxazol-2-yl propyl)carbamyl | C—H | C—H | C—CH$_3$ | C—H |
| (3-imidazolo[4,5-b]pyridin-2-ylpropyl)carbamyl | C—H | C—H | C—CH$_3$ | C—H |
| (3-(1,3-oxazolo[4,5-b]pyridin-2-yl)propyl)carbamyl | C—H | C—H | C—CH$_3$ | C—H |
| (benzimidazol-5-yl methyl)carbamyl | C—H | C—H | C—CH$_3$ | C—H |
| (benzoxazol-5-yl methyl)carbamyl | C—H | C—H | C—CH$_3$ | C—H |
| (2-aminobenzimidazol-5-ylmethyl)carbamyl | C—H | C—H | C—CH$_3$ | C—H |
| (2-aminobenzoxazol-5-yl methyl)carbamyl | C—H | C—H | C—CH$_3$ | C—H |
| (3-imidazolo[4,5-e]pyridin-5-ylpropyl))carbamyl | C—H | C—H | C—CH$_3$ | C—H |
| (3-(1,3-oxazolo[4,5-e]pyridin-5-yl)propyl)carbamyl | C—H | C—H | C—CH$_3$ | C—H |
| (5-(2-piperidyl)pentyl)carbamyl | C—H | C—H | C—CH$_3$ | C—H |
| 3-(2-piperidyl)propyl | C—H | C—H | C—CH$_3$ | C—H |
| (4-imidazol-2-ylamino)butyl)carbamyl | C—H | C—H | C—CH$_3$ | C—H |
| (4-(1,3-oxazol-2-yl)amino)butyl)carbamyl | C—H | C—H | C—CH$_3$ | C—H |
| (3-(5-amino-1,3-oxazol-2-yl)propyl)carbamyl | C—H | C—H | C—CH$_3$ | C—H |
| (3-(5-amino-imidazol-2-yl)propyl)carbamyl | C—H | C—H | C—CH$_3$ | C—H |
| (4-(3,4,5,6-tetrahydro pyrimidin-2-ylamino)butyl)carbamyl | C—H | C—H | C—CH$_3$ | C—H |
| (4-(2-imidazolin-2-yl amino)butyl)carbamyl | C—H | C—H | C—CH$_3$ | C—H |
| 4-(2-pyridylaminobutyl)carbamoyl | C—H | C—H | C—CH$_3$ | C—H |
| 3-(1,2,3,4-tetrahydro pyridino(2,3-b)pyridin-7-yl)-propyl)carbamoyl | C—H | C—H | C—CH$_3$ | C—H |
| (4-(4-methyl)-2-pyridyl)amino)butyl)carbamyl | C—H | C—H | C—CH$_3$ | C—H |
| (4-(benzimidazol-2-yl amino)butyl)carbamyl | C—H | C—H | C—OBn | C—H |
| (4-(benzimidazol-2-yl amino)ethyl)carbamyl | C—H | C—H | C—OBn | C—H |
| (4-(benzoxazol-2-yl amino)butyl)carbamyl | C—H | C—H | C—OBn | C—H |
| (4-(benzoxazol-2-yl amino)ethyl)carbamyl | C—H | C—H | C—OBn | C—H |
| (4-(imidazolo[5,4-b]pyridin-2-ylamino)butyl)carbamyl | C—H | C—H | C—OBn | C—H |
| (4-(imidazolo[5,4-b] | C—H | C—H | C—OBn | C—H |

TABLE 2-continued

E—B—(Alk)p—Q—(Alk)q—A—N[7-membered ring with W1,W2,W3,W4]—CH2—CO2H

| E—B—(Alk)p—Q—(Alk)q—A— | W1 | W2 | W3 | W4 |
|---|---|---|---|---|
| (4-(1,3-oxazolo[4,5-b]pyridin-2-ylamino)ethyl)carbamyl | C—H | C—H | C—OBn | C—H |
| (4-(1,3-oxazolo[4,5-b]pyridin-2-ylamino)butyl)carbamyl | C—H | C—H | C—OBn | C—H |
| (4-(1,3-oxazolo[4,5-b]pyridin-2-ylamino)ethyl)carbamyl | C—H | C—H | C—OBn | C—H |
| (3-benzimidazol-2-yl propyl)carbamyl | C—H | C—H | C—OBn | C—H |
| (3-benzoxazol-2-yl propyl)carbamyl | C—H | C—H | C—OBn | C—H |
| (3-imidazolo[4,5-b]pyridin-2-ylpropyl)carbamyl | C—H | C—H | C—OBn | C—H |
| (3-(1,3-oxazolo[4,5-b]pyridin-2-yl)propyl)carbamyl | C—H | C—H | C—OBn | C—H |
| (benzimidazol-5-yl methyl)carbamyl | C—H | C—H | C—OBn | C—H |
| (benzoxazol-5-yl methyl)carbamyl | C—H | C—H | C—OBn | C—H |
| (2-aminobebenzimidazol-5-ylmethyl)carbamyl | C—H | C—H | C—OBn | C—H |
| (2-aminobenzoxazol-5-yl methyl)carbamyl | C—H | C—H | C—OBn | C—H |
| (3-imidazolo[4,5-e]pyridin-5-ylpropyl))carbamyl | C—H | C—H | C—OBn | C—H |
| (3-(1,3-oxazolo[4,5-e]pyridin-5-yl)propyl)carbamyl | C—H | C—H | C—OBn | C—H |
| (5-(2-piperidyl)pentyl)carbamyl | C—H | C—H | C—OBn | C—H |
| 3-(2-piperidyl)propyl | C—H | C—H | C—OBn | C—H |
| (4-imidazol-2-ylamino)butyl)carbamyl | C—H | C—H | C—OBn | C—H |
| (4-(1,3-oxazol-2-yl)amino)butyl)carbamyl | C—H | C—H | C—OBn | C—H |
| (3-(5-amino-1,3-oxazol-2-yl)propyl)carbamyl | C—H | C—H | C—OBn | C—H |
| (3-(5-amino-imidazol-2-yl)propyl)carbamyl | C—H | C—H | C—OBn | C—H |
| (4-(3,4,5,6-tetrahydro pyrimidin-2-ylamino)butyl)carbamyl | C—H | C—H | C—OBn | C—H |
| (4-(2-imidazolin-2-yl amino)butyl)carbamyl | C—H | C—H | C—OBn | C—H |
| 4-(2-pyridylaminobutyl)carbamoyl | C—H | C—H | C—OBn | C—H |
| 3-(1,2,3,4-tetrahydro pyridino(2,3-b)pyridin-7-yl)-propyl)carbamoyl | C—H | C—H | C—OBn | C—H |
| (4-(4-methyl)-2-pyridyl)amino)butyl)carbamyl | C—H | C—H | C—OBn | C—H |
| (4-(benzimidazol-2-yl amino)butyl)carbamyl | C—H | C—H | C—Cl | C—H |
| (benzimidazol-2-yl amino)ethyl)carbamyl | C—H | C—H | C—Cl | C—H |
| (4-(benzoxazol-2-yl amino)butyl)carbamyl | C—H | C—H | C—Cl | C—H |
| (4-(benzoxazol-2-yl amino)ethyl)carbamyl | C—H | C—H | C—Cl | C—H |
| (4-(imidazolo[5,4-b]pyridin-2-ylamino)butyl)carbamyl | C—H | C—H | C—Cl | C—H |
| (4-(imidazolo[5,4-b]pyridin-2-ylamino)ethyl)carbamyl | C—H | C—H | C—Cl | C—H |
| (4-(1,3-oxazolo[4,5-b]pyridin-2-ylamino)butyl)carbamyl | C—H | C—H | C—Cl | C—H |
| (4-(1,3-oxazolo[4,5-b]pyridin-2-ylamino)ethyl)carbamyl | C—H | C—H | C—Cl | C—H |
| (3-benzimidazol-2-yl propyl)carbamyl | C—H | C—H | C—Cl | C—H |
| (3-benzoxazol-2-yl propyl)carbamyl | C—H | C—H | C—Cl | C—H |
| (3-imidazolo[4,5-b]pyridin-2-ylpropyl)carbamyl | C—H | C—H | C—Cl | C—H |
| (3-(1,3-oxazolo[4,5-b]pyridin-2-yl)propyl)carbamyl | C—H | C—H | C—Cl | C—H |
| (benzimidazol-5-yl methyl)carbamyl | C—H | C—H | C—Cl | C—H |
| (benzoxazol-5-yl methyl)carbamyl | C—H | C—H | C—Cl | C—H |
| (2-aminobebenzimidazol-5-ylmethyl)carbamyl | C—H | C—H | C—Cl | C—H |
| (2-aminobenzoxazol-5-yl methyl)carbamyl | C—H | C—H | C—Cl | C—H |
| (3-imidazolo[4,5-e]pyridin-5-ylpropyl))carbamyl | C—H | C—H | C—Cl | C—H |
| (3-(1,3-oxazolo[4,5-e]pyridin-5-yl)propyl)carbamyl | C—H | C—H | C—Cl | C—H |
| (5-(2-piperidyl)pentyl)carbamyl | C—H | C—H | C—Cl | C—H |
| 3-(2-piperidyl)propyl | C—H | C—H | C—Cl | C—H |
| (4-imidazol-2-ylamino)butyl)carbamyl | C—H | C—H | C—Cl | C—H |
| (4-(1,3-oxazol-2-yl)amino)butyl)carbamyl | C—H | C—H | C—Cl | C—H |
| (3-(5-amino-1,3-oxazol-2-yl)propyl)carbamyl | C—H | C—H | C—Cl | C—H |
| (3-(5-amino-imidazol-2-yl)propyl)carbamyl | C—H | C—H | C—Cl | C—H |
| (4-(3,4,5,6-tetrahydro pyrimidin-2-ylamino)butyl)carbamyl | C—H | C—H | C—Cl | C—H |
| (4-(2-imidazolin-2-yl amino)butyl)carbamyl | C—H | C—H | C—Cl | C—H |
| 4-(2-pyridylaminobutyl)carbamoyl | C—H | C—H | C—Cl | C—H |
| 3-(1,2,3,4-tetrahydro pyridino(2,3-b)pyridin-7-yl)-propyl)carbamoyl | C—H | C—H | C—Cl | C—H |
| (4-(4-methyl)-2-pyridyl)amino)butyl)carbamyl | C—H | C—H | C—Cl | C—H |

TABLE 3

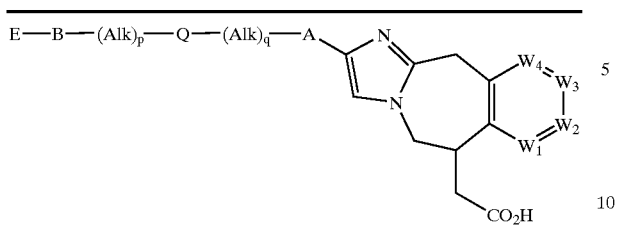

| E—B—(Alk)p—Q—(Alk)q—A— | W1 | W2 | W3 | W4 |
|---|---|---|---|---|
| (4-(benzimidazol-2-yl amino)butyl)carbamyl | C—H | C—H | C—H | C—H |
| (4-(benzimidazol-2-yl amino)ethyl)carbamyl | C—H | C—H | C—H | C—H |
| (4-(benzoxazol-2-yl amino)butyl)carbamyl | C—H | C—H | C—H | C—H |
| (4-(benzoxazol-2-yl amino)ethyl)carbamyl | C—H | C—H | C—H | C—H |
| (4-(imidazolo[5,4-b]pyridin-2-ylamino)butyl)carbamyl | C—H | C—H | C—H | C—H |
| (4-(imidazolo[5,4-b]pyridin-2-ylamino)ethyl)carbamyl | C—H | C—H | C—H | C—H |
| (4-(1,3-oxazolo[4,5-b]pyridin-2-ylamino)butyl)carbamyl | C—H | C—H | C—H | C—H |
| (4-(1,3-oxazolo[4,5-b]pyridin-2-ylamino)ethyl)carbamyl | C—H | C—H | C—H | C—H |
| (3-benzimidazol-2-yl propyl)carbamyl | C—H | C—H | C—H | C—H |
| (3-benzoxazol-2-yl propyl)carbamyl | C—H | C—H | C—H | C—H |
| (3-imidazolo[4,5-b]pyridin-2-ylpropyl)carbamyl | C—H | C—H | C—H | C—H |
| (3-(1,3-oxazolo[4,5-b]pyridin-2-yl)propyl)carbamyl | C—H | C—H | C—H | C—H |
| (benzimidazol-5-yl methyl)carbamyl | C—H | C—H | C—H | C—H |
| (benzoxazol-5-yl methyl)carbamyl | C—H | C—H | C—H | C—H |
| (2-aminobebenzimidazol-5-ylmethyl)carbamyl | C—H | C—H | C—H | C—H |
| (2-aminobenzoxazol-5-yl methyl)carbamyl | C—H | C—H | C—H | C—H |
| (3-imidazolo[4,5-e]pyridin-5-ylpropyl)carbamyl | C—H | C—H | C—H | C—H |
| (3-(1,3-oxazolo[4,5-e]pyridin-5-yl)propyl)carbamyl | C—H | C—H | C—H | C—H |
| (5-(2-piperidyl)pentyl)carbamyl | C—H | C—H | C—H | C—H |
| 3-(2-piperidyl)propyl | C—H | C—H | C—H | C—H |
| (4-imidazol-2-ylamino)butyl)carbamyl | C—H | C—H | C—H | C—H |
| (4-(1,3-oxazol-2-yl)amino)butyl)carbamyl | C—H | C—H | C—H | C—H |
| (3-(5-amino-1,3-oxazol-2-yl)propyl)carbamyl | C—H | C—H | C—H | C—H |
| (3-(5-amino-imidazol-2-yl)propyl)carbamyl | C—H | C—H | C—H | C—H |
| (4-(3,4,5,6-tetrahydro pyrimidin-2-ylamino)butyl)carbamyl | C—H | C—H | C—H | C—H |
| (4-(2-imidazolin-2-yl amino)butyl)carbamyl | C—H | C—H | C—H | C—H |
| 4-(2-pyridylaminobutyl) carbamoyl | C—H | C—H | C—H | C—H |
| 3-(1,2,3,4-tetrahydro pyridino(2,3-b)pyridin-7-yl)-propyl)carbamoyl | C—H | C—H | C—H | C—H |
| (4-(4-methyl-2-pyridyl) amino)butyl)carbamyl | C—H | C—H | C—H | C—H |
| (4-(benzimidazol-2-yl amino)butyl)carbamyl | N | C—H | C—H | C—H |
| (4-(benzimidazol-2-yl amino)ethyl)carbamyl | N | C—H | C—H | C—H |
| (4-(benzoxazol-2-yl amino)butyl)carbamyl | N | C—H | C—H | C—H |
| (4-(benzoxazol-2-yl amino)ethyl)carbamyl | N | C—H | C—H | C—H |
| (4-(imidazolo[5,4-b]pyridin-2-ylamino)butyl)carbamyl | N | C—H | C—H | C—H |
| (4-(imidazolo[5,4-b]pyridin-2-ylamino)ethyl)carbamyl | N | C—H | C—H | C—H |
| (4-(1,3-oxazolo[4,5-b]pyridin-2-ylamino)butyl)carbamyl | N | C—H | C—H | C—H |
| (4-(1,3-oxazolo[4,5-b]pyridin-2-ylamino)ethyl)carbamyl | N | C—H | C—H | C—H |
| (3-benzimidazol-2-yl propyl)carbamyl | N | C—H | C—H | C—H |
| (3-benzoxazol-2-yl propyl)carbamyl | N | C—H | C—H | C—H |
| (3-imidazolo[4,5-b]pyridin-2-ylpropyl)carbamyl | N | C—H | C—H | C—H |
| (3-(1,3-oxazolo[4,5-b]pyridin-2-yl)propyl)carbamyl | N | C—H | C—H | C—H |
| (benzimidazol-5-yl methyl)carbamyl | N | C—H | C—H | C—H |
| (benzoxazol-5-yl methyl)carbamyl | N | C—H | C—H | C—H |
| (2-aminobenzimidazol-5-ylmethyl)carbamyl | N | C—H | C—H | C—H |
| (2-aminobenzoxazol-5-yl methyl)carbamyl | N | C—H | C—H | C—H |
| (3-imidazolo[4,5-e]pyridin-5-ylpropyl)carbamyl | N | C—H | C—H | C—H |
| (3-(1,3-oxazolo[4,5-e]pyridin-5-yl)propyl)carbamyl | N | C—H | C—H | C—H |
| (5-(2-piperidyl)pentyl)carbamyl | N | C—H | C—H | C—H |
| 3-(2-piperidyl)propyl | N | C—H | C—H | C—H |
| (4-imidazol-2-ylamino)butyl)carbamyl | N | C—H | C—H | C—H |
| (4-(1,3-oxazol-2-yl)amino)butyl)carbamyl | N | C—H | C—H | C—H |
| (3-(5-amino-1,3-oxazol-2-yl)propyl)carbamyl | N | C—H | C—H | C—H |
| (3-(5-amino-imidazol-2-yl)propyl)carbamyl | N | C—H | C—H | C—H |
| (4-(3,4,5,6-tetrahydro pyrimidin-2-ylamino)butyl)carbamyl | N | C—H | C—H | C—H |
| (4-(2-imidazolin-2-yl amino)butyl)carbamyl | N | C—H | C—H | C—H |
| 4-(2-pyridylaminobutyl) carbamoyl | N | C—H | C—H | C—H |
| 3-(1,2,3,4-tetrahydro pyridino(2,3-b)pyridin-7-yl)-propyl)carbamyl | N | C—H | C—H | C—H |
| (4-(4-methyl-2-pyridyl) amino)butyl)carbamyl | N | C—H | C—H | C—H |
| (4-(benzimidazol-2-yl amino)butyl)carbamyl | C—H | N | C—H | C—H |

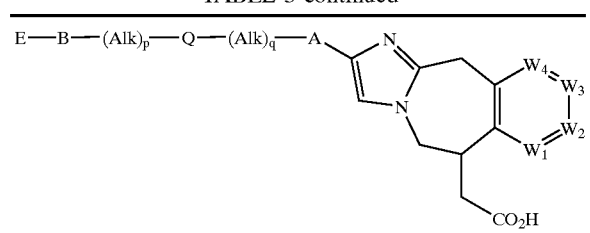

TABLE 3-continued

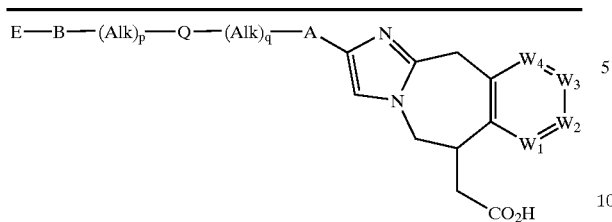

| E—B—(Alk)p—Q—(Alk)q—A— | W1 | W2 | W3 | W4 |
|---|---|---|---|---|
| (4-(benzimidazol-2-yl amino)ethyl)carbamyl | C—H | N | C—H | C—H |
| (4-(benzoxazol-2-yl amino)butyl)carbamyl | C—H | N | C—H | C—H |
| (4-(benzoxazol-2-yl amino)ethyl)carbamyl | C—H | N | C—H | C—H |
| (4-(imidazolo[5,4-b]pyridin-2-ylamino)butyl)carbamyl | C—H | N | C—H | C—H |
| (4-(imidazolo[5,4-b]pyridin-2-ylamino)ethyl)carbamyl | C—H | N | C—H | C—H |
| (4-(1,3-oxazolo[4,5-b]pyridin-2-ylamino)butyl)carbamyl | C—H | N | C—H | C—H |
| (4-(1,3-oxazolo[4,5-b]pyridin-2-ylamino)ethyl)carbamyl | C—H | N | C—H | C—H |
| (3-benzimidazol-2-yl propyl)carbamyl | C—H | N | C—H | C—H |
| (3-benzoxazol-2-yl propyl)carbamyl | C—H | N | C—H | C—H |
| (3-imidazolo[4,5-b]pyridin-2-ylpropyl)carbamyl | C—H | N | C—H | C—H |
| (3-(1,3-oxazolo[4,5-b]pyridin-2-yl)propyl)carbamyl | C—H | N | C—H | C—H |
| (benzimidazol-5-yl methyl)carbamyl | C—H | N | C—H | C—H |
| (benzoxazol-5-yl methyl)carbamyl | C—H | N | C—H | C—H |
| (2-aminobebenzimidazol-5-ylmethyl)carbamyl | C—H | N | C—H | C—H |
| (2-aminobenzoxazol-5-yl methyl)carbamyl | C—H | N | C—H | C—H |
| (3-imidazolo[4,5-e]pyridin-5-ylpropyl)carbamyl | C—H | N | C—H | C—H |
| (3-(1,3-oxazolo[4,5-e]pyridin-5-yl)propyl)carbamyl | C—H | N | C—H | C—H |
| (5-(2-piperidyl)pentyl)carbamyl | C—H | N | C—H | C—H |
| 3-(2-piperidyl)propyl | C—H | N | C—H | C—H |
| (4-imidazol-2-ylamino)butyl)carbamyl | C—H | N | C—H | C—H |
| (4-(1,3-oxazol-2-yl)amino)butyl)carbamyl | C—H | N | C—H | C—H |
| (3-(5-amino-1,3-oxazol-2-yl)propyl)carbamyl | C—H | N | C—H | C—H |
| (3-(5-amino-imidazol-2-yl)propyl)carbamyl | C—H | N | C—H | C—H |
| (4-(3,4,5,6-tetrahydro pyrimidin-2-ylamino)butyl)carbamyl | C—H | N | C—H | C—H |
| (4-(2-imidazolin-2-yl amino)butyl)carbamyl | C—H | N | C—H | C—H |
| 4-(2-pyridylaminobutyl) carbamoyl | C—H | N | C—H | C—H |
| 3-(1,2,3,4-tetrahydro pyridino(2,3-b)pyridin-7-yl)-propyl)carbamyol | C—H | N | C—H | C—H |
| (4-(4-methyl)-2-pyridyl) amino)butyl)carbamyl | C—H | N | C—H | C—H |
| (4-(benzimidazol-2-yl amino)butyl)carbamyl | C—H | C—H | N | C—H |
| (4-(benzimidazol-2-yl amino)ethyl)carbamyl | C—H | C—H | N | C—H |
| (4-(benzoxazol-2-yl amino)butyl)carbamyl | C—H | C—H | N | C—H |
| (4-(benzoxazol-2-yl amino)ethyl)carbamyl | C—H | C—H | N | C—H |
| (4-(imidazolo[5,4-b]pyridin-2-ylamino)butyl)carbamyl | C—H | C—H | N | C—H |
| (4-(imidazolo[5,4-b]pyridin-2-ylamino)ethyl)carbamyl | C—H | C—H | N | C—H |
| (4-(1,3-oxazolo[4,5-b]pyridin-2-ylamino)butyl)carbamyl | C—H | C—H | N | C—H |
| (4-(1,3-oxazolo[4,5-b]pyridin-2-ylamino)ethyl)carbamyl | C—H | C—H | N | C—H |
| (3-benzimidazol-2-yl propyl)carbamyl | C—H | C—H | N | C—H |
| (3-benzoxazol-2-yl propyl)carbamyl | C—H | C—H | N | C—H |
| (3-imidazolo[4,5-b]pyridin-2-ylpropyl)carbamyl | C—H | C—H | N | C—H |
| (3-(1,3-oxazolo[4,5-b]pyridin-2-yl)propyl)carbamyl | C—H | C—H | N | C—H |
| (benzimidazol-5-yl methyl)carbamyl | C—H | C—H | N | C—H |
| (benzoxazol-5-yl methyl)carbamyl | C—H | C—H | N | C—H |
| (2-aminobenzimidazol-5-ylmethyl)carbamyl | C—H | C—H | N | C—H |
| (2-aminobenzoxazol-5-yl methyl)carbamyl | C—H | C—H | N | C—H |
| (3-imidazolo[4,5-e]pyridin-5-ylpropyl)carbamyl | C—H | C—H | N | C—H |
| (3-(1,3-oxazolo[4,5-e]pyridin-5-yl)propyl)carbamyl | C—H | C—H | N | C—H |
| (5-(2-piperidyl)pentyl)carbamyl | C—H | C—H | N | C—H |
| 3-(2-piperidyl)propyl | C—H | C—H | N | C—H |
| (4-imidazol-2-ylamino)butyl)carbamyl | C—H | C—H | N | C—H |
| (4-(1,3-oxazol-2-yl)amino)butyl)carbamyl | C—H | C—H | N | C—H |
| (3-(5-amino-1,3-oxazol-2-yl)propyl)carbamyl | C—H | C—H | N | C—H |
| (3-(5-amino-imidazol-2-yl)propyl)carbamyl | C—H | C—H | N | C—H |
| (4-(3,4,5,6-tetrahydro pyrimidin-2-ylamino)butyl)carbamyl | C—H | C—H | N | C—H |
| (4-(2-imidazolin-2-yl amino)butyl)carbamyl | C—H | C—H | N | C—H |
| 4-(2-pyridylaminobutyl) carbamoyl | C—H | C—H | N | C—H |
| 3-(1,2,3,4-tetrahydro pyridino(2,3-b)pyridin-7-yl)-propyl)carbamoyl | C—H | C—H | N | C—H |
| (4-(4-methyl)-2-pyridyl) amino)butyl)carbamyl | C—H | C—H | N | C—H |
| (4-(benzimidazol-2-yl amino)butyl)carbamyl | C—H | C—H | C—H | N |
| (4-(benzimidazol-2-yl amino)ethyl)carbamyl | C—H | C—H | C—H | N |

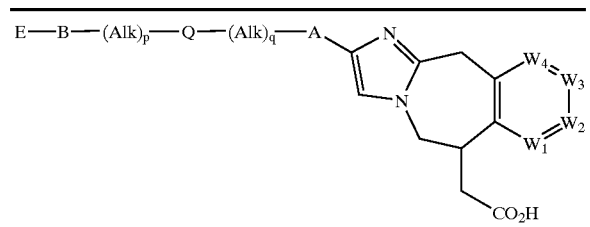

TABLE 3-continued

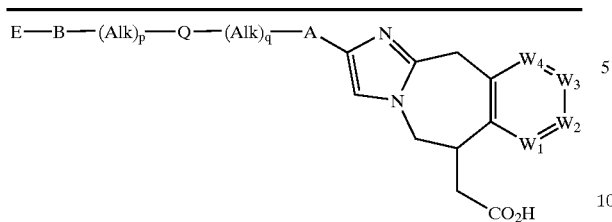

| E—B—(Alk)$_p$—Q—(Alk)$_q$—A— | W$_1$ | W$_2$ | W$_3$ | W$_4$ |
|---|---|---|---|---|
| (4-(benzoxazol-2-yl amino)butyl)carbamyl | C—H | C—H | C—H | N |
| (4-(benzoxazol-2-yl amino)ethyl)carbamyl | C—H | C—H | C—H | N |
| (4-(imidazolo[5,4-b]pyridin-2-ylamino)butyl)carbamyl | C—H | C—H | C—H | N |
| (4-(imidazolo[5,4-b]pyridin-2-ylamino)ethyl)carbamyl | C—H | C—H | C—H | N |
| (4-(1,3-oxazolo[4,5-b]pyridin-2-ylamino)butyl)carbamyl | C—H | C—H | C—H | N |
| (4-(1,3-oxazolo[4,5-b]pyridin-2-ylamino)ethyl)carbamyl | C—H | C—H | C—H | N |
| (3-benzimidazol-2-yl propyl)carbamyl | C—H | C—H | C—H | N |
| (3-benzoxazol-2-yl propyl)carbamyl | C—H | C—H | C—H | N |
| (3-imidazolo[4,5-b]pyridin-2-ylpropyl)carbamyl | C—H | C—H | C—H | N |
| (3-(1,3-oxazolo[4,5-b]pyridin-2-yl)propyl)carbamyl | C—H | C—H | C—H | N |
| (benzimidazol-5-yl methyl)carbamyl | C—H | C—H | C—H | N |
| (benzoxazol-5-yl methyl)carbamyl | C—H | C—H | C—H | N |
| (2-aminobebenzimidazol-5-ylmethyl)carbamyl | C—H | C—H | C—H | N |
| (2-aminobenzoxazol-5-yl methyl)carbamyl | C—H | C—H | C—H | N |
| (3-imidazo[4,5-e]pyridin-5-ylpropyl)carbamyl | C—H | C—H | C—H | N |
| (3-(1,3-oxazolo[4,5-e]pyridin-5-yl)propyl)carbamyl | C—H | C—H | C—H | N |
| (5-(2-piperidyl)pentyl)carbamyl | C—H | C—H | C—H | N |
| 3-(2-piperidyl)propyl | C—H | C—H | C—H | N |
| (4-imidazol-2-ylamino)butyl)carbamyl | C—H | C—H | C—H | N |
| (4-(1,3-oxazol-2-yl)amino)butyl)carbamyl | C—H | C—H | C—H | N |
| (3-(5-amino-1,3-oxazol-2-yl)propyl)carbamyl | C—H | C—H | C—H | N |
| (3-(5-amino-imidazol-2-yl)propyl)carbamyl | C—H | C—H | C—H | N |
| (4-(3,4,5,6-tetrahydro pyrimidin-2-ylamino)butyl)carbamyl | C—H | C—H | C—H | N |
| (4-(2-imidazolin-2-yl amino)butyl)carbamyl | C—H | C—H | C—H | N |
| 4-(2-pyridylaminobutyl)carbamoyl | C—H | C—H | C—H | N |
| 3-(1,2,3,4-tetrahydro pyridino(2,3-b)pyridin-7-yl)-propyl)carbamoyl | C—H | C—H | C—H | N |
| (4-(4-methyl)-2-pyridyl)amino)butyl)carbamyl | C—H | C—H | C—H | N |
| (4-(benzimidazol-2-yl amino)butyl)carbamyl | C—H | C—H | C—CH$_3$ | C—H |
| (4-(benzimidazol-2-yl amino)ethyl)carbamyl | C—H | C—H | C—CH$_3$ | C—H |
| (4-(benzoxazol-2-yl amino)butyl)carbamyl | C—H | C—H | C—CH$_3$ | C—H |

TABLE 3-continued

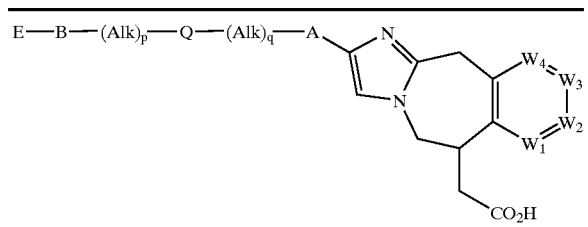

| E—B—(Alk)$_p$—Q—(Alk)$_q$—A— | W$_1$ | W$_2$ | W$_3$ | W$_4$ |
|---|---|---|---|---|
| (4-(benzoxazol-2-yl amino)ethyl)carbamyl | C—H | C—H | C—CH$_3$ | C—H |
| (4-(imidazolo[5,4-b]pyridin-2-ylamino)butyl)carbamyl | C—H | C—H | C—CH$_3$ | C—H |
| (4-(imidazolo[5,4-b]pyridin-2-ylamino)ethyl)carbamyl | C—H | C—H | C—CH$_3$ | C—H |
| (4-(1,3-oxazolo[4,5-b]pyridin-2-ylamino)butyl)carbamyl | C—H | C—H | C—CH$_3$ | C—H |
| (4-(1,3-oxazolo[4,5-b]pyridin-2-ylamino)ethyl)carbamyl | C—H | C—H | C—CH$_3$ | C—H |
| (3-benzimidazol-2-yl propyl)carbamyl | C—H | C—H | C—CH$_3$ | C—H |
| (3-benzoxazol-2-yl propyl)carbamyl | C—H | C—H | C—CH$_3$ | C—H |
| (3-imidazolo[4,5-b]pyridin-2-ylpropyl)carbamyl | C—H | C—H | C—CH$_3$ | C—H |
| (3-(1,3-oxazolo[4,5-b]pyridin-2-yl)propyl)carbamyl | C—H | C—H | C—CH$_3$ | C—H |
| (benzimidazol-5-yl methyl)carbamyl | C—H | C—H | C—CH$_3$ | C—H |
| (benzoxazol-5-yl methyl)carbamyl | C—H | C—H | C—CH$_3$ | C—H |
| (2-aminobenzimidazol-5-ylmethyl)carbamyl | C—H | C—H | C—CH$_3$ | C—H |
| (2-aminobenzoxazol-5-yl methyl)carbamyl | C—H | C—H | C—CH$_3$ | C—H |
| (3-imidazolo[4,5-e]pyridin-5-ylpropyl)carbamyl | C—H | C—H | C—CH$_3$ | C—H |
| (3-(1,3-oxazolo[4,5-e]pyridin-5-yl)propyl)carbamyl | C—H | C—H | C—CH$_3$ | C—H |
| (5-(2-piperidyl)pentyl)carbamyl | C—H | C—H | C—CH$_3$ | C—H |
| 3-(2-piperidyl)propyl | C—H | C—H | C—CH$_3$ | C—H |
| (4-imidazol-2-ylamino)butyl)carbamyl | C—H | C—H | C—CH$_3$ | C—H |
| (4-(1,3-oxazol-2-yl)amino)butyl)carbamyl | C—H | C—H | C—CH$_3$ | C—H |
| (3-(5-amino-1,3-oxazol-2-yl)propyl)carbamyl | C—H | C—H | C—CH$_3$ | C—H |
| (3-(5-amino-imidazol-2-yl)propyl)carbamyl | C—H | C—H | C—CH$_3$ | C—H |
| (4-(3,4,5,6-tetrahydro pyrimidin-2-ylamino)butyl)carbamyl | C—H | C—H | C—CH$_3$ | C—H |
| (4-(2-imidazolin-2-yl amino)butyl)carbamyl | C—H | C—H | C—CH$_3$ | C—H |
| 4-(2-pyridylaminobutyl)carbamoyl | C—H | C—H | C—CH$_3$ | C—H |
| 3-(1,2,3,4-tetrahydro pyridino(2,3-b)pyridin-7-yl)-propyl)carbamoyl | C—H | C—H | C—CH$_3$ | C—H |
| (4-(4-methyl-2-pyridyl)amino)butyl)carbamyl | C—H | C—H | C—CH$_3$ | C—H |
| (4-(benzimidazol-2-yl amino)butyl)carbamyl | C—H | C—H | C—OBn | C—H |
| (4-(benzimidazol-2-yl amino)ethyl)carbamyl | C—H | C—H | C—OBn | C—H |
| (4-(benzoxazol-2-yl amino)butyl)carbamyl | C—H | C—H | C—OBn | C—H |

TABLE 3-continued

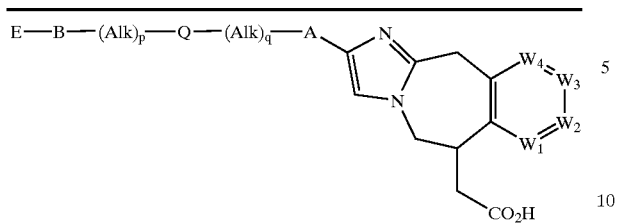

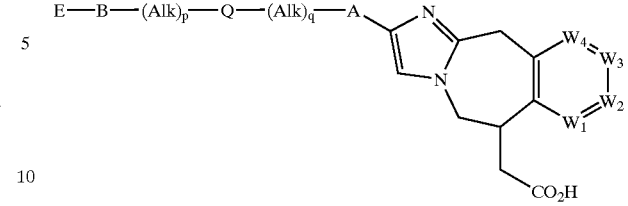

| E—B—(Alk)p—Q—(Alk)q—A— | W1 | W2 | W3 | W4 |
|---|---|---|---|---|
| (4-(benzoxazol-2-yl amino)ethyl)carbamyl | C—H | C—H | C—OBn | C—H |
| (4-(imidazolo[5,4-b]pyridin-2-ylamino)butyl)carbamyl | C—H | C—H | C—OBn | C—H |
| (4-(imidazolo[5,4-b]pyridin-2-ylamino)ethyl)carbamyl | C—H | C—H | C—OBn | C—H |
| (4-(1,3-oxazolo[4,5-b]pyridin-2-ylamino)butyl)carbamyl | C—H | C—H | C—OBn | C—H |
| (4-(1,3-oxazolo[4,5-b]pyridin-2-ylamino)ethyl)carbamyl | C—H | C—H | C—OBn | C—H |
| (3-benzimidazol-2-yl propyl)carbamyl | C—H | C—H | C—OBn | C—H |
| (3-benzoxazol-2-yl propyl)carbamyl | C—H | C—H | C—OBn | C—H |
| (3-imidazolo[4,5-b]pyridin-2-ylpropyl)carbamyl | C—H | C—H | C—OBn | C—H |
| (3-(1,3-oxazolo[4,5-b]pyridin-2-yl)propyl)carbamyl | C—H | C—H | C—OBn | C—H |
| (benzimidazol-5-yl methyl)carbamyl | C—H | C—H | C—OBn | C—H |
| (benzoxazol-5-yl methyl)carbamyl | C—H | C—H | C—OBn | C—H |
| (2-aminobebenzimidazol-5-ylmethyl)carbamyl | C—H | C—H | C—OBn | C—H |
| (2-aminobenzoxazol-5-yl methyl)carbamyl | C—H | C—H | C—OBn | C—H |
| (3-imidazolo[4,5-e]pyridin-5-ylpropyl)carbamyl | C—H | C—H | C—OBn | C—H |
| (3-(1,3-oxazolo[4,5-e]pyridin-5-yl)propyl)carbamyl | C—H | C—H | C—OBn | C—H |
| (5-(2-piperidyl)pentyl)carbamyl | C—H | C—H | C—OBn | C—H |
| 3-(2-piperidyl)propyl | C—H | C—H | C—OBn | C—H |
| (4-imidazol-2-ylamino)butyl)carbamyl | C—H | C—H | C—OBn | C—H |
| (4-(1,3-oxazol-2-yl)amino)butyl)carbamyl | C—H | C—H | C—OBn | C—H |
| (3-(5-amino-1,3-oxazol-2-yl)propyl)carbamyl | C—H | C—H | C—OBn | C—H |
| (3-(5-amino-imidazol-2-yl)propyl)carbamyl | C—H | C—H | C—OBn | C—H |
| (4-(3,4,5,6-tetrahydro pyrimidin-2-ylamino)butyl)carbamyl | C—H | C—H | C—OBn | C—H |
| (4-(2-imidazolin-2-yl amino)butyl)carbamyl | C—H | C—H | C—OBn | C—H |
| 4-(2-pyridylaminobutyl)carbamoyl | C—H | C—H | C—OBn | C—H |
| 3-(1,2,3,4-tetrahydro pyridino(2,3-b)pyridin-7-yl)-propyl)carbamoyl | C—H | C—H | C—OBn | C—H |
| (4-(4-methyl)-2-pyridyl)amino)butyl)carbamyl | C—H | C—H | C—OBn | C—H |
| (4-(benzimidazol-2-yl amino)butyl)carbamyl | C—H | C—H | C—Cl | C—H |
| (4-(benzimidazol-2-yl amino)ethyl)carbamyl | C—H | C—H | C—Cl | C—H |
| (4-(benzoxazol-2-yl amino)butyl)carbamyl | C—H | C—H | C—Cl | C—H |
| (4-(benzoxazol-2-yl amino)ethyl)carbamyl | C—H | C—H | C—Cl | C—H |
| (4-(imidazolo[5,4-b]pyridin-2-ylamino)butyl)carbamyl | C—H | C—H | C—Cl | C—H |
| (4-(imidazolo[5,4-b]pyridin-2-ylamino)ethyl)carbamyl | C—H | C—H | C—Cl | C—H |
| (4-(1,3-oxazolo[4,5-b]pyridin-2-ylamino)butyl)carbamyl | C—H | C—H | C—Cl | C—H |
| (4-(1,3-oxazolo[4,5-b]pyridin-2-ylamino)ethyl)carbamyl | C—H | C—H | C—Cl | C—H |
| (3-benzimidazol-2-yl propyl)carbamyl | C—H | C—H | C—Cl | C—H |
| (3-benzoxazol-2-yl propyl)carbamyl | C—H | C—H | C—Cl | C—H |
| (3-imidazolo[4,5-b]pyridin-2-ylpropyl)carbamyl | C—H | C—H | C—Cl | C—H |
| (3-(1,3-oxazolo[4,5-b]pyridin-2-yl)propyl)carbamyl | C—H | C—H | C—Cl | C—H |
| (benzimidazol-5-yl methyl)carbamyl | C—H | C—H | C—Cl | C—H |
| (benzoxazol-5-yl methyl)carbamyl | C—H | C—H | C—Cl | C—H |
| (2-aminobebenzimidazol-5-ylmethyl)carbamyl | C—H | C—H | C—Cl | C—H |
| (2-aminobenzoxazol-5-yl methyl)carbamyl | C—H | C—H | C—Cl | C—H |
| (3-imidazolo[4,5-e]pyridin-5-ylpropyl)carbamyl | C—H | C—H | C—Cl | C—H |
| (3-(1,3-oxazolo[4,5-e]pyridin-5-yl)propyl)carbamyl | C—H | C—H | C—Cl | C—H |
| (5-(2-piperidyl)pentyl)carbamyl | C—H | C—H | C—Cl | C—H |
| 3-(2-piperidyl)propyl | C—H | C—H | C—Cl | C—H |
| (4-imidazol-2-ylamino)butyl)carbamyl | C—H | C—H | C—Cl | C—H |
| (4-(1,3-oxazol-2-yl)amino)butyl)carbamyl | C—H | C—H | C—Cl | C—H |
| (3-(5-amino-1,3-oxazol-2-yl)propyl)carbamyl | C—H | C—H | C—Cl | C—H |
| (3-(5-amino-imidazol-2-yl)propyl)carbamyl | C—H | C—H | C—Cl | C—H |
| (4-(3,4,5,6-tetrahydro pyrimidin-2-ylamino)butyl)carbamyl | C—H | C—H | C—Cl | C—H |
| (4-(2-imidazolin-2-yl amino)butyl)carbamyl | C—H | C—H | C—Cl | C—H |
| 4-(2-pyridylaminobutyl)carbamoyl | C—H | C—H | C—Cl | C—H |
| 3-(1,2,3,4-tetrahydro pyridino(2,3-b)pyridin-7-yl)-propyl)carbamoyl | C—H | C—H | C—Cl | C—H |
| (4-(4-methyl)-2-pyridyl)amino)butyl)carbamyl | C—H | C—H | C—Cl | C—H |

TABLE 4

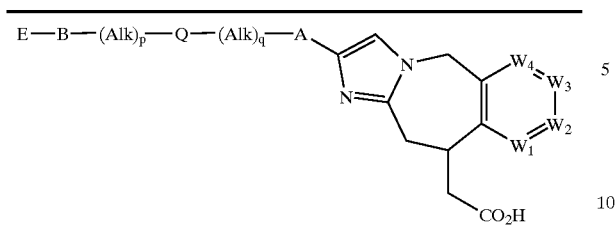

| E—B—(Alk)p—Q—(Alk)q—A— | W1 | W2 | W3 | W4 |
|---|---|---|---|---|
| (4-(benzimidazol-2-yl amino)butyl)carbamyl | C—H | C—H | C—H | C—H |
| (4-(benzimidazol-2-yl amino)ethyl)carbamyl | C—H | C—H | C—H | C—H |
| (4-(benzoxazol-2-yl amino)butyl)carbamyl | C—H | C—H | C—H | C—H |
| (4-(benzoxazol-2-yl amino)ethyl)carbamyl | C—H | C—H | C—H | C—H |
| (4-(imidazolo[5,4-b]pyridin-2-ylamino)butyl)carbamyl | C—H | C—H | C—H | C—H |
| (4-(imidazolo[5,4-b]pyridin-2-ylamino)ethyl)carbamyl | C—H | C—H | C—H | C—H |
| (4-(1,3-oxazolo[4,5-b]pyridin-2-ylamino)butyl)carbamyl | C—H | C—H | C—H | C—H |
| (4-(1,3-oxazolo[4,5-b]pyridin-2-ylamino)ethyl)carbamyl | C—H | C—H | C—H | C—H |
| (3-benzimidazol-2-yl propyl)carbamyl | C—H | C—H | C—H | C—H |
| (3-benzoxazol-2-yl propyl)carbamyl | C—H | C—H | C—H | C—H |
| (3-imidazolo[4,5-b]pyridin-2-ylpropyl)carbamyl | C—H | C—H | C—H | C—H |
| (3-(1,3-oxazolo[4,5-b]pyridin-2-yl)propyl)carbamyl | C—H | C—H | C—H | C—H |
| (benzimidazol-5-yl methyl)carbamyl | C—H | C—H | C—H | C—H |
| (benzoxazol-5-yl methyl)carbamyl | C—H | C—H | C—H | C—H |
| (2-aminobebenzimidazol-5-ylmethyl)carbamyl | C—H | C—H | C—H | C—H |
| (2-aminobenzoxazol-5-yl methyl)carbamyl | C—H | C—H | C—H | C—H |
| (3-imidazolo[4,5-e]pyridin-5-ylpropyl)carbamyl | C—H | C—H | C—H | C—H |
| (3-(1,3-oxazolo[4,5-e]pyridin-5-yl)propyl)carbamyl | C—H | C—H | C—H | C—H |
| (5-(2-piperidyl)pentyl)carbamyl | C—H | C—H | C—H | C—H |
| 3-2-piperidyl)propyl | C—H | C—H | C—H | C—H |
| (4-imidazol-2-ylamino)butyl)carbamyl | C—H | C—H | C—H | C—H |
| (4-(1,3-oxazol-2-yl)amino)butyl)carbamyl | C—H | C—H | C—H | C—H |
| (3-(5-amino-1,3-oxazol-2-yl)propyl)carbamyl | C—H | C—H | C—H | C—H |
| (3-(5-amino-imidazol-2-yl)propyl)carbamyl | C—H | C—H | C—H | C—H |
| (4-(3,4,5,6-tetrahydro pyrimidin-2-ylamino)butyl)carbamyl | C—H | C—H | C—H | C—H |
| (4-(2-imidazolin-2-yl amino)butyl)carbamyl | C—H | C—H | C—H | C—H |
| 4-(2-pyridylaminobutyl)carbamoyl | C—H | C—H | C—H | C—H |
| 3-(1,2,3,4-tetrahydro pyridino(2,3-b)pyridin-7-yl)-propyl)carbamoyl | C—H | C—H | C—H | C—H |
| (4-(4-methyl-2-pyridyl)amino)butyl)carbamyl | C—H | C—H | C—H | C—H |
| (4-(benzimidazol-2-yl | N | C—H | C—H | C—H |

TABLE 4-continued

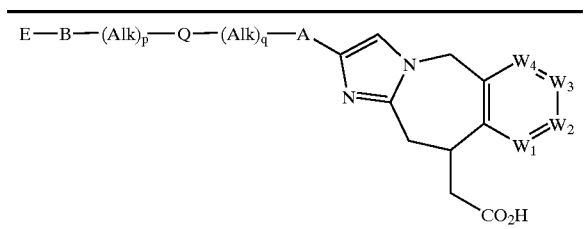

| E—B—(Alk)p—Q—(Alk)q—A— | W1 | W2 | W3 | W4 |
|---|---|---|---|---|
| amino)butyl)carbamyl | | | | |
| (4-(benzimidazol-2-yl amino)ethyl)carbamyl | N | C—H | C—H | C—H |
| (4-(benzoxazol-2-yl amino)butyl)carbamyl | N | C—H | C—H | C—H |
| (4-(benzoxazol-2-yl amino)ethyl)carbamyl | N | C—H | C—H | C—H |
| (4-(imidazolo[5,4-b]pyridin-2-ylamino)butyl)carbamyl | N | C—H | C—H | C—H |
| (4-(imidazolo[5,4-b]pyridin-2-ylamino)ethyl)carbamyl | N | C—H | C—H | C—H |
| (4-(1,3-oxazolo[4,5-b]pyridin-2-ylamino)butyl)carbamyl | N | C—H | C—H | C—H |
| (4-(1,3-oxazolo[4,5-b]pyridin-2-ylamino)ethyl)carbamyl | N | C—H | C—H | C—H |
| (3-benzimidazol-2-yl propyl)carbamyl | N | C—H | C—H | C—H |
| (3-benzoxazol-2-yl propyl)carbamyl | N | C—H | C—H | C—H |
| (3-imidazolo[4,5-b]pyridin-2-ylpropyl)carbamyl | N | C—H | C—H | C—H |
| (3-(1,3-oxazolo[4,5-b]pyridin-2-yl)propyl)carbamyl | N | C—H | C—H | C—H |
| (benzimidazol-5-yl methyl)carbamyl | N | C—H | C—H | C—H |
| (benzoxazol-5-yl methyl)carbamyl | N | C—H | C—H | C—H |
| (2-aminobenzimidazol-5-ylmethyl)carbamyl | N | C—H | C—H | C—H |
| (2-aminobenzoxazol-5-yl methyl)carbamyl | N | C—H | C—H | C—H |
| (3-imidazolo[4,5-e]pyridin-5-ylpropyl)carbamyl | N | C—H | C—H | C—H |
| (3-(1,3-oxazolo[4,5-e]pyridin-5-yl)propyl)carbamyl | N | C—H | C—H | C—H |
| (5-(2-piperidyl)pentyl)carbamyl | N | C—H | C—H | C—H |
| 3-2-piperidyl)propyl | N | C—H | C—H | C—H |
| (4-imidazol-2-ylamino)butyl)carbamyl | N | C—H | C—H | C—H |
| (4-(1,3-oxazol-2-yl)amino)butyl)carbamyl | N | C—H | C—H | C—H |
| (3-(5-amino-1,3-oxazol-2-yl)propyl)carbamyl | N | C—H | C—H | C—H |
| (3-(5-amino-imidazol-2-yl)propyl)carbamyl | N | C—H | C—H | C—H |
| (4-(3,4,5,6-tetrahydro pyrimidin-2-ylamino)butyl)carbamyl | N | C—H | C—H | C—H |
| (4-(2-imidazolin-2-yl amino)butyl)carbamyl | N | C—H | C—H | C—H |
| 4-(2-pyridylaminobutyl) carbamoyl | N | C—H | C—H | C—H |
| 3-(1,2,3,4-tetrahydro pyridino(2,3-b)pyridin-7-yl)-propyl)carbamoyl | N | C—H | C—H | C—H |
| (4-(4-methyl-2-pyridyl)amino)butyl)carbamyl | N | C—H | C—H | C—H |
| (4-(benzimidazol-2-yl amino)butyl)carbamyl | C—H | N | C—H | C—H |

TABLE 4-continued

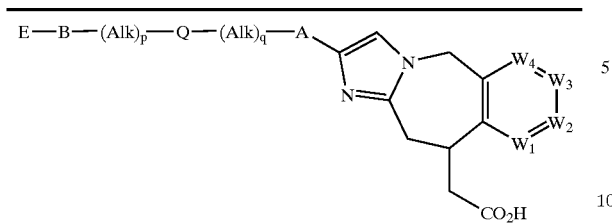

| E—B—(Alk)p—Q—(Alk)q—A— | $W_1$ | $W_2$ | $W_3$ | $W_4$ |
|---|---|---|---|---|
| (4-(benzimidazol-2-yl amino)ethyl)carbamyl | C—H | N | C—H | C—H |
| (4-(benzoxazol-2-yl amino)butyl)carbamyl | C—H | N | C—H | C—H |
| (4-(benzoxazol-2-yl amino)ethyl)carbamyl | C—H | N | C—H | C—H |
| (4-(imidazolo[5,4-b] pyridin-2-ylamino)butyl) carbamyl | C—H | N | C—H | C—H |
| (4-(imidazolo[5,4-b] pyridin-2-ylamino)ethyl) carbamyl | C—H | N | C—H | C—H |
| (4-(1,3-oxazolo[4,5-b] pyridin-2-ylamino)butyl) carbamyl | C—H | N | C—H | C—H |
| (4-(1,3-oxazolo[4,5-b] pyridin-2-ylamino)ethyl) carbamyl | C—H | N | C—H | C—H |
| (3-benzimidazol-2-yl propyl)carbamyl | C—H | N | C—H | C—H |
| (3-benzoxazol-2-yl propyl)carbamyl | C—H | N | C—H | C—H |
| (3-imidazolo[4,5-b]pyridin-2-ylpropyl)carbamyl | C—H | N | C—H | C—H |
| (3-(1,3-oxazolo[4,5-b] pyridin-2-yl)propyl) carbamyl | C—H | N | C—H | C—H |
| (benzimidazol-5-yl methyl)carbamyl | C—H | N | C—H | C—H |
| (benzoxazol-5-yl methyl)carbamyl | C—H | N | C—H | C—H |
| (2-aminobebenzimidazol-5-ylmethyl)carbamyl | C—H | N | C—H | C—H |
| (2-aminobenzoxazol-5-yl methyl)carbamyl | C—H | N | C—H | C—H |
| (3-imidazolo[4,5-e]pyridin-5-ylpropyl)carbamyl | C—H | N | C—H | C—H |
| (3-(1,3-oxazolo[4,5-e] pyridin-5-yl)propyl) carbamyl | C—H | N | C—H | C—H |
| (5-(2-piperidyl)pentyl) carbamyl | C—H | N | C—H | C—H |
| 3-(2-piperidyl)propyl | C—H | N | C—H | C—H |
| (4-imidazol-2-ylamino) butyl)carbamyl | C—H | N | C—H | C—H |
| (4-(1,3-oxazol-2-yl) amino)butyl)carbamyl | C—H | N | C—H | C—H |
| (3-(5-amino-1,3-oxazol-2-yl)propyl)carbamyl | C—H | N | C—H | C—H |
| (3-(5-amino-imidazol-2-yl)propyl)carbamyl | C—H | N | C—H | C—H |
| (4-(3,4,5,6-tetrahydro pyrimidin-2-ylamino)butyl) carbamyl | C—H | N | C—H | C—H |
| (4-(2-imidazolin-2-yl amino)butyl)carbamyl | C—H | N | C—H | C—H |
| 4-(2-pyridylaminobutyl) carbamoyl | C—H | N | C—H | C—H |
| 3-(1,2,3,4-tetrahydro pyridino(2,3-b)pyridin-7-yl)-propyl)carbamoyl | C—H | N | C—H | C—H |
| (4-(4-methyl)-2-pyridyl) amino)butyl)carbamyl | C—H | N | C—H | C—H |
| (4-(benzimidazol-2-yl amino)butyl)carbamyl | C—H | C—H | N | C—H |
| (4-(benzimidazol-2-yl amino)ethyl)carbamyl | C—H | C—H | N | C—H |

TABLE 4-continued

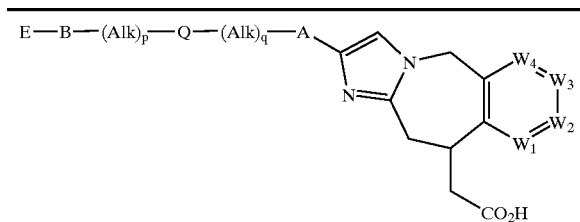

| E—B—(Alk)p—Q—(Alk)q—A— | $W_1$ | $W_2$ | $W_3$ | $W_4$ |
|---|---|---|---|---|
| (4-(benzoxazol-2-yl amino)butyl)carbamyl | C—H | C—H | N | C—H |
| (4-(benzoxazol-2-yl amino)ethyl)carbamyl | C—H | C—H | N | C—H |
| (4-(imidazolo[5,4-b] pyridin-2-ylamino)butyl) carbamyl | C—H | C—H | N | C—H |
| (4-(imidazolo[5,4-b] pyridin-2-ylamino)ethyl) carbamyl | C—H | C—H | N | C—H |
| (4-(1,3-oxazolo[4,5-b] pyridin-2-ylamino)butyl) carbamyl | C—H | C—H | N | C—H |
| (4-(1,3-oxazolo[4,5-b] pyridin-2-ylamino)ethyl) carbamyl | C—H | C—H | N | C—H |
| (3-benzimidazol-2-yl propyl)carbamyl | C—H | C—H | N | C—H |
| (3-benzoxazol-2-yl propyl)carbamyl | C—H | C—H | N | C—H |
| (3-imidazolo[4,5-b]pyridin-2-ylpropyl)carbamyl | C—H | C—H | N | C—H |
| (3-(1,3-oxazolo[4,5-b] pyridin-2-yl)propyl) carbamyl | C—H | C—H | N | C—H |
| (benzimidazol-5-yl methyl)carbamyl | C—H | C—H | N | C—H |
| (benzoxazol-5-yl methyl)carbamyl | C—H | C—H | N | C—H |
| (2-aminobenzimidazol-5-ylmethyl)carbamyl | C—H | C—H | N | C—H |
| (2-aminobenzoxazol-5-yl methyl)carbamyl | C—H | C—H | N | C—H |
| (3-imidazolo[4,5-e]pyridin-5-ylpropyl)carbamyl | C—H | C—H | N | C—H |
| (3-(1,3-oxazolo[4,5-e] pyridin-5-yl)propyl) carbamyl | C—H | C—H | N | C—H |
| (5-(2-piperidyl)pentyl) carbamyl | C—H | C—H | N | C—H |
| 3-(2-piperidyl)propyl | C—H | C—H | N | C—H |
| (4-imidazol-2-ylamino) butyl)carbamyl | C—H | C—H | N | C—H |
| (4-(1,3-oxazol-2-yl) amino)butyl)carbamyl | C—H | C—H | N | C—H |
| (3-(5-amino-1,3-oxazol-2-yl)propyl)carbamyl | C—H | C—H | N | C—H |
| (3-(5-amino-imidazol-2-yl)propyl)carbamyl | C—H | C—H | N | C—H |
| (4-(3,4,5,6-tetrahydro pyrimidin-2-ylamino)butyl) carbamyl | C—H | C—H | N | C—H |
| (4-(2-imidazolin-2-yl amino)butyl)carbamyl | C—H | C—H | N | C—H |
| 4-(2-pyridylaminobutyl) carbamoyl | C—H | C—H | N | C—H |
| 3-(1,2,3,4-tetrahydro pyridino(2,3-b)pyridin-7-yl)-propyl)carbamoyl | C—H | C—H | N | C—H |
| (4-(4-methyl)-2-pyridyl) amino)butyl)carbamyl | C—H | C—H | N | C—H |
| (4-(benzimidazol-2-yl amino)butyl)carbamyl | C—H | C—H | C—H | N |
| (4-(benzimidazol-2-yl amino)ethyl)carbamyl | C—H | C—H | C—H | N |

TABLE 4-continued

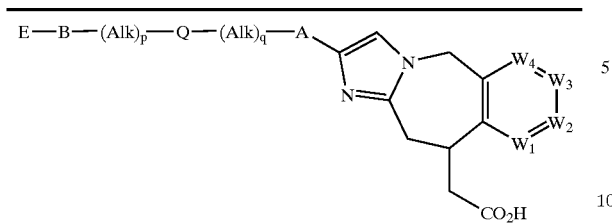

| E—B—(Alk)p—Q—(Alk)q—A— | W1 | W2 | W3 | W4 |
|---|---|---|---|---|
| (4-(benzoxazol-2-yl amino)butyl)carbamyl | C—H | C—H | C—H | N |
| (4-(benzoxazol-2-yl amino)ethyl)carbamyl | C—H | C—H | C—H | N |
| (4-(imidazolo[5,4-b]pyridin-2-ylamino)butyl)carbamyl | C—H | C—H | C—H | N |
| (4-(imidazolo[5,4-b]pyridin-2-ylamino)ethyl)carbamyl | C—H | C—H | C—H | N |
| (4-(1,3-oxazolo[4,5-b]pyridin-2-ylamino)butyl)carbamyl | C—H | C—H | C—H | N |
| (4-(1,3-oxazolo[4,5-b]pyridin-2-ylamino)ethyl)carbamyl | C—H | C—H | C—H | N |
| (3-benzimidazol-2-yl propyl)carbamyl | C—H | C—H | C—H | N |
| (3-benzoxazol-2-yl propyl)carbamyl | C—H | C—H | C—H | N |
| (3-imidazolo[4,5-b]pyridin-2-ylpropyl)carbamyl | C—H | C—H | C—H | N |
| (3-(1,3-oxazolo[4,5-b]pyridin-2-yl)propyl)carbamyl | C—H | C—H | C—H | N |
| (benzimidazol-5-yl methyl)carbamyl | C—H | C—H | C—H | N |
| (benzoxazol-5-yl methyl)carbamyl | C—H | C—H | C—H | N |
| (2-aminobebenzimidazol-5-ylmethyl)carbamyl | C—H | C—H | C—H | N |
| (2-aminobenzoxazol-5-yl methyl)carbamyl | C—H | C—H | C—H | N |
| (3-imidazolo[4,5-e]pyridin-5-ylpropyl)carbamyl | C—H | C—H | C—H | N |
| (3-(1,3-oxazolo[4,5-e]pyridin-5-yl)propyl)carbamyl | C—H | C—H | C—H | N |
| (5-(2-piperidyl)pentyl)carbamyl | C—H | C—H | C—H | N |
| 3-(2-piperidyl)propyl | C—H | C—H | C—H | N |
| (4-imidazol-2-ylamino)butyl)carbamyl | C—H | C—H | C—H | N |
| (4-(1,3-oxazol-2-yl)amino)butyl)carbamyl | C—H | C—H | C—H | N |
| (3-(5-amino-1,3-oxazol-2-yl)propyl)carbamyl | C—H | C—H | C—H | N |
| (3-(5-amino-imidazol-2-yl)propyl)carbamyl | C—H | C—H | C—H | N |
| (4-(3,4,5,6-tetrahydro pyrimidin-2-ylamino)butyl)carbamyl | C—H | C—H | C—H | N |
| (4-(2-imidazolin-2-yl amino)butyl)carbamyl | C—H | C—H | C—H | N |
| 4-(2-pyridylaminobutyl)carbamoyl | C—H | C—H | C—H | N |
| 3-(1,2,3,4-tetrahydro pyridino(2,3-b)pyridin-7-yl)-propyl)carbamoyl | C—H | C—H | C—H | N |
| (4-(4-methyl)-2-pyridyl)amino)butyl)carbamyl | C—H | C—H | C—H | N |
| (4-(benzimidazol-2-yl amino)butyl)carbamyl | C—H | C—H | C—CH3 | C—H |
| (4-(benzimidazol-2-yl amino)ethyl)carbamyl | C—H | C—H | C—CH3 | C—H |
| (4-(benzoxazol-2-yl amino)butyl)carbamyl | C—H | C—H | C—CH3 | C—H |

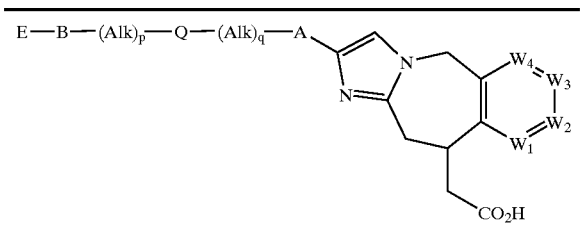

| E—B—(Alk)p—Q—(Alk)q—A— | W1 | W2 | W3 | W4 |
|---|---|---|---|---|
| (4-(benzoxazol-2-yl amino)ethyl)carbamyl | C—H | C—H | C—CH3 | C—H |
| (4-(imidazolo[5,4-b]pyridin-2-ylamino)butyl)carbamyl | C—H | C—H | C—CH3 | C—H |
| (4-(imidazolo[5,4-b]pyridin-2-ylamino)ethyl)carbamyl | C—H | C—H | C—CH3 | C—H |
| (4-(1,3-oxazolo[4,5-b]pyridin-2-ylamino)butyl)carbamyl | C—H | C—H | C—CH3 | C—H |
| (4-(1,3-oxazolo[4,5-b]pyridin-2-ylamino)ethyl)carbamyl | C—H | C—H | C—CH3 | C—H |
| (3-benzimidazol-2-yl propyl)carbamyl | C—H | C—H | C—CH3 | C—H |
| (3-benzoxazol-2-yl propyl)carbamyl | C—H | C—H | C—CH3 | C—H |
| (3-imidazolo[4,5-b]pyridin-2-ylpropyl)carbamyl | C—H | C—H | C—CH3 | C—H |
| (3-(1,3-oxazolo[4,5-b]pyridin-2-yl)propyl)carbamyl | C—H | C—H | C—CH3 | C—H |
| (benzimidazol-5-yl methyl)carbamyl | C—H | C—H | C—CH3 | C—H |
| (benzoxazol-5-yl methyl)carbamyl | C—H | C—H | C—CH3 | C—H |
| (2-aminobenzimidazol-5-ylmethyl)carbamyl | C—H | C—H | C—CH3 | C—H |
| (2-aminobenzoxazol-5-yl methyl)carbamyl | C—H | C—H | C—CH3 | C—H |
| (3-imidazolo[4,5-e]pyridin-5-ylpropyl)carbamyl | C—H | C—H | C—CH3 | C—H |
| (3-(1,3-oxazolo[4,5-e]pyridin-5-yl)propyl)carbamyl | C—H | C—H | C—CH3 | C—H |
| (5-(2-piperidyl)pentyl)carbamyl | C—H | C—H | C—CH3 | C—H |
| 3-(2-piperidyl)propyl | C—H | C—H | C—CH3 | C—H |
| (4-imidazol-2-ylamino)butyl)carbamyl | C—H | C—H | C—CH3 | C—H |
| (4-(1,3-oxazol-2-yl)amino)butyl)carbamyl | C—H | C—H | C—CH3 | C—H |
| (3-(5-amino-1,3-oxazol-2-yl)propyl)carbamyl | C—H | C—H | C—CH3 | C—H |
| (3-(5-amino-imidazol-2-yl)propyl)carbamyl | C—H | C—H | C—CH3 | C—H |
| (4-(3,4,5,6-tetrahydro pyrimidin-2-ylamino)butyl)carbamyl | C—H | C—H | C—CH3 | C—H |
| (4-(2-imidazolin-2-yl amino)butyl)carbamyl | C—H | C—H | C—CH3 | C—H |
| 4-(2-pyridylaminobutyl)carbamoyl | C—H | C—H | C—CH3 | C—H |
| 3-(1,2,3,4-tetrahydro pyridino(2,3-b)pyridin-7-yl)-propyl)carbamoyl | C—H | C—H | C—CH3 | C—H |
| (4-(4-methyl)-2-pyridyl)amino)butyl)carbamyl | C—H | C—H | C—CH3 | C—H |
| (4-(benzimidazol-2-yl amino)butyl)carbamyl | C—H | C—H | C—OBn | C—H |
| (4-(benzimidazol-2-yl amino)ethyl)carbamyl | C—H | C—H | C—OBn | C—H |
| (4-(benzoxazol-2-yl amino)butyl)carbamyl | C—H | C—H | C—OBn | C—H |

TABLE 4-continued

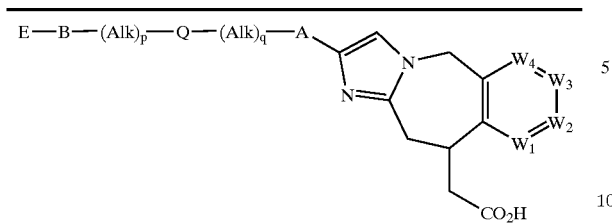

| E—B—(Alk)$_p$—Q—(Alk)$_q$—A— | W$_1$ | W$_2$ | W$_3$ | W$_4$ |
|---|---|---|---|---|
| (4-(benzoxazol-2-yl amino)ethyl)carbamyl | C—H | C—H | C—OBn | C—H |
| (4-(imidazolo[5,4-b]pyridin-2-ylamino)butyl)carbamyl | C—H | C—H | C—OBn | C—H |
| (4-(imidazolo[5,4-b]pyridin-2-ylamino)ethyl)carbamyl | C—H | C—H | C—OBn | C—H |
| (4-(1,3-oxazolo[4,5-b]pyridin-2-ylamino)butyl)carbamyl | C—H | C—H | C—OBn | C—H |
| (4-(1,3-oxazolo[4,5-b]pyridin-2-ylamino)ethyl)carbamyl | C—H | C—H | C—OBn | C—H |
| (3-benzimidazol-2-yl propyl)carbamyl | C—H | C—H | C—OBn | C—H |
| (3-benzoxazol-2-yl propyl)carbamyl | C—H | C—H | C—OBn | C—H |
| (3-imidazolo[4,5-b]pyridin-2-ylpropyl)carbamyl | C—H | C—H | C—OBn | C—H |
| (3-(1,3-oxazolo[4,5-b]pyridin-2-yl)propyl)carbamyl | C—H | C—H | C—OBn | C—H |
| (benzimidazol-5-yl methyl)carbamyl | C—H | C—H | C—OBn | C—H |
| (benzoxazol-5-yl methyl)carbamyl | C—H | C—H | C—OBn | C—H |
| (2-aminobebenzimidazol-5-ylmethyl)carbamyl | C—H | C—H | C—OBn | C—H |
| (2-aminobenzoxazol-5-yl methyl)carbamyl | C—H | C—H | C—OBn | C—H |
| (3-imidazolo[4,5-e]pyridin-5-ylpropyl)carbamyl | C—H | C—H | C—OBn | C—H |
| (3-(1,3-oxazolo[4,5-e]pyridin-5-yl)propyl)carbamyl | C—H | C—H | C—OBn | C—H |
| (5-(2-piperidyl)pentyl)carbamyl | C—H | C—H | C—OBn | C—H |
| 3-(2-piperidyl)propyl | C—H | C—H | C—OBn | C—H |
| (4-imidazol-2-ylamino)butyl)carbamyl | C—H | C—H | C—OBn | C—H |
| (4-(1,3-oxazol-2-yl)amino)butyl)carbamyl | C—H | C—H | C—OBn | C—H |
| (3-(5-amino-1,3-oxazol-2-yl)propyl)carbamyl | C—H | C—H | C—OBn | C—H |
| (3-(5-amino-imidazol-2-yl)propyl)carbamyl | C—H | C—H | C—OBn | C—H |
| (4-(3,4,5,6-tetrahydro pyrimidin-2-ylamino)butyl)carbamyl | C—H | C—H | C—OBn | C—H |
| (4-(2-imidazolin-2-yl amino)butyl)carbamyl | C—H | C—H | C—OBn | C—H |
| 4-(2-pyridylaminobutyl)carbamoyl | C—H | C—H | C—OBn | C—H |
| 3-(1,2,3,4-tetrahydro pyridino(2,3-b)pyridin-7-yl)-propyl)carbamoyl | C—H | C—H | C—OBn | C—H |
| (4-(4-methyl)-2-pyridyl)amino)butyl)carbamyl | C—H | C—H | C—OBn | C—H |
| (4-(benzimidazol-2-yl amino)butyl)carbamyl | C—H | C—H | C—Cl | C—H |
| (4-(benzimidazol-2-yl amino)ethyl)carbamyl | C—H | C—H | C—Cl | C—H |
| (4-(benzoxazol-2-yl amino)butyl)carbamyl | C—H | C—H | C—Cl | C—H |
| (4-(benzoxazol-2-yl amino)ethyl)carbamyl | C—H | C—H | C—Cl | C—H |
| (4-(imidazolo[5,4-b]pyridin-2-ylamino)butyl)carbamyl | C—H | C—H | C—Cl | C—H |
| (4-(imidazolo[5,4-b]pyridin-2-ylamino)ethyl)carbamyl | C—H | C—H | C—Cl | C—H |
| (4-(1,3-oxazolo[4,5-b]pyridin-2-ylamino)butyl)carbamyl | C—H | C—H | C—Cl | C—H |
| (4-(1,3-oxazolo[4,5-b]pyridin-2-ylamino)ethyl)carbamyl | C—H | C—H | C—Cl | C—H |
| (3-benzimidazol-2-yl propyl)carbamyl | C—H | C—H | C—Cl | C—H |
| (3-benzoxazol-2-yl propyl)carbamyl | C—H | C—H | C—Cl | C—H |
| (3-imidazolo[4,5-b]pyridin-2-ylpropyl)carbamyl | C—H | C—H | C—Cl | C—H |
| (3-(1,3-oxazolo[4,5-b]pyridin-2-yl)propyl)carbamyl | C—H | C—H | C—Cl | C—H |
| (benzimidazol-5-yl methyl)carbamyl | C—H | C—H | C—Cl | C—H |
| (benzoxazol-5-yl methyl)carbamyl | C—H | C—H | C—Cl | C—H |
| (2-aminobebenzimidazol-5-ylmethyl)carbamyl | C—H | C—H | C—Cl | C—H |
| (2-aminobenzoxazol-5-yl methyl)carbamyl | C—H | C—H | C—Cl | C—H |
| (3-imidazolo[4,5-e]pyridin-5-ylpropyl)carbamyl | C—H | C—H | C—Cl | C—H |
| (3-(1,3-oxazolo[4,5-e]pyridin-5-yl)propyl)carbamyl | C—H | C—H | C—Cl | C—H |
| (5-(2-piperidyl)pentyl)carbamyl | C—H | C—H | C—Cl | C—H |
| 3-(2-piperidyl)propyl | C—H | C—H | C—Cl | C—H |
| (4-imidazol-2-ylamino)butyl)carbamyl | C—H | C—H | C—Cl | C—H |
| (4-(1,3-oxazol-2-yl)amino)butyl)carbamyl | C—H | C—H | C—Cl | C—H |
| (3-(5-amino-1,3-oxazol-2-yl)propyl)carbamyl | C—H | C—H | C—Cl | C—H |
| (3-(5-amino-imidazol-2-yl)propyl)carbamyl | C—H | C—H | C—Cl | C—H |
| (4-(3,4,5,6-tetrahydro pyrimidin-2-ylamino)butyl)carbamyl | C—H | C—H | C—Cl | C—H |
| (4-(2-imidazolin-2-yl amino)butyl)carbamyl | C—H | C—H | C—Cl | C—H |
| 4-(2-pyridylaminobutyl)carbamoyl | C—H | C—H | C—Cl | C—H |
| 3-(1,2,3,4-tetrahydro pyridino(2,3-b)pyridin-7-yl)-propyl)carbamoyl | C—H | C—H | C—Cl | C—H |
| (4-(4-methyl)-2-pyridyl)amino)butyl)carbamyl | C—H | C—H | C—Cl | C—H |

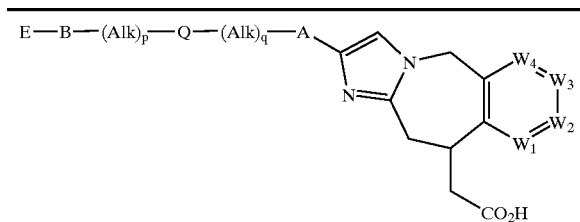

EXAMPLE 87

Using the procedures of the above general description and the above examples, the following compounds of Table 5 can be prepared. The groups B[2]A, B[3]A, IBA(I), IBA(II), TBA(I) and TBA(III) represent the ring systems as defined above.

TABLE 5

| E-B- | -(Alk)$_p$-Q-(Alk)$_q$-A-G |
|---|---|
| benzimidazol-2-yl | 4-(7,8-methylenedioxy-5-(carboxypropyl)-B[2]A-2-yl methyl)phenylmethyl |
| 5-chlorobenzoxazol-2-yl | 3-(5-(carboxymethyl)-9-methoxy-8-aza-B[2]A-2-yl) cyclopentylaminocarbonyl-methyl |
| oxazol-2-yl | 3-(5-(N-(2-carboxypropyl carbonyl)aminocarbonyl methyl)-8-methyl-9-aza-3-oxy-B[2]A-2-yl)propyl |
| 3,4,5,6-tetrahydropyrimid-2-ylmethylcarbonyl | 2-(1-hydroxy-5-(carboxy methyl)-9-aza-B[3]A-3-ylcarbonyl)pyrrolid-1-yl |
| 4,5-dihydroimidazol-2-yl | 3-(4-(6-methoxy-5-(3-carboxyprop-1-yl)-1-oxy-B[2]A-2-ylmethyl)phenyl)prop-1-yl |
| piperid-2-ylcarbonyl | 2-(5-((α-aspartylamino)carbonylmethyl)-B[2]A-2-yl)ethylamino |
| pyrid-2-yl | 4-(5-(carboxymethyl)-7,9-diaza-B[2]A-2-ylsulfonyl amino)pyrid-2-ylmethyl |
| 7-azaindolin-6-yl | 3-(3-(2,4-dioxy-5-(tetrazolylmethyl)-B[3]A-3-yl)but-1-ylamino)propyl |
| 7-azabenzimidazol-2-yl | 2-(4-(5-(carboxymethyl)-6-aza-B[3]A-3-ylcarbonyl)piperid-1-yl)ethyl |
| 7-azabenzoxazol-2-ylcarbonyl | 4-(6-(carboxymethyl)-8,10-difluoro-TBA(I)-2-ylthio)but-2-n-1-yl |
| 4-azabenzimidazol-2-yl | 5-(10-(carboxymethyl)-6-methoxy-7-aza-TBA(III)-2-ylsulfonylamino)pent-1-yl |
| 5-fluoro-4-azabenzoxazol-2-yl | 2-(10-(4-carboxybut-1-yl)-8-aza-IBA(II)-2-yl carbonylamino)ethyl |
| 1,2,3,4-tetrahydro-1,8-naphthyrid-7-yl | 2-(4-(7,8-dichloro-5-(carboxymethyl)-6-aza-B[3]A-3-ylcarbonyl)piperid-1-yl)ethyl |
| 5,6,7,8-tetrahydropyrido[2,3-b]azepin-8-yl | 3-(6-(carboxymethyl)-9-aza-IBA(I)-2-ylamino)prop-1-ylamino |
| 3,4-dihydropyrido[3,2-b]-1,4-oxazin-6-ylamino | 2-(10-(carboxymethyl)-7,9-dimethoxy-TBA(III)-2-yl oxy)ethyl |
| 3,4-dihydropyrido[3,2-b]-1,4-thiazin-6-yl | 3-(6-(carboxymethyl)-IBA(I)-2-yloxy)ethylamino |
| amidino | 2-(4-(5-(carboxymethyl)-8-aza-B[3]A-3-ylcarbonyl)piperid-1-yl)ethyl |
| N-methylamidino | 4-(10-(carboxymethyl)-8-carboxy-9-aza-TBA(III)-2-ylcarbonylaminomethyl)phenyl |
| N,N'-dimethylamidino | 3-(3-(2-oxy-5-(tetrazolyl methyl)-B[3]A-3-yl)but-1-ylamino)propyl |
| N-cyclopropylamidino | 1-(6-(2-carboxyethyl)-11-oxy-IBA(I)-2-yl)pent-4-yl |
| 5,6-dimethylbenzimidazol-2-ylamino | 4-(2-(5-(2-hydroxy-1-carboxyethyl)-7-aza-B[3]A-3-ylcarbonyl)ethenyl)phenylmethyl |
| 4-CF$_3$-benzoxazol-2-ylamino | 3-(3-(4-oxy-5-(tetrazolyl methyl)-B[3]A-3-yl)but-1-ylamino)propyl |
| 4-methylimidazol-2-ylamino | 2-(N-methyl-N-(6-(carboxy methyl)-IBA(I)-2-ylmethyl)aminocarbonyl)ethyl |

TABLE 5-continued

| E-B- | -(Alk)$_p$-Q-(Alk)$_q$-A-G |
|---|---|
| oxazol-2-ylamino | 3,3-dimethyl-5-(5-(1-carboxypropyl)-6,8-diaza-B[3]A-3-yl)pent-1-yl |
| 4,5-dihydroimidazol-2-ylamino | 2-(6-(2-carboxyethyl)-11-oxy-10-aza-IBA(I)-2-yl)ethyl |
| 6-methylpyrid-2-ylamino | 2-(6-(5-carboxy-3-hydroxy pentyl)-IBA(I)-2-ylamino sulfonyl)phenylmethyl |
| 7-azabenzoxazol-2-ylamino | 2-(6-((2-carboxyethyl carbonylamino)carbonyl methyl)-TBA(I)-2-ylthio)ethyl |
| 4-azabenzimidazol-2-ylamino | 3-(10-(carboxymethyl)-IBA(II)-2-ylamino)prop-1-yl |
| 4,7-diazabenzimidazol-2-ylamino | 2-(6-(carboxymethyl)-8-methyl-9-aza-IBA(I)-2-yl methoxy)ethyl |
| 4,7-diazabenzoxazol-2-ylamino | 2-(6-(2-carboxyethyl)-11-oxy-IBA(I)-2-yl)ethyl |
| 1,2,3,4-tetrahydro-1,8-naphthyrid-7-ylamino | 3-hydroxy-5-(5-(1-carboxy propyl)-7-aza-B[3]A-3-yl)pent-1-yl |
| 5,6,7,8-tetrahydropyrido[2,3-b]azepin-8-ylamino | 2-(10-(carboxymethyl)-IBA(II)-2-ylmethylcarbonyl)amino)ethyl |
| (4-amidinophenyl)sulfonyl amino | 2-(6-(carboxymethyl)-8-methoxy-7-aza-IBA(I)-2-yl methoxy)ethyl |
| 3-amidinophenylthio | 2-(6-(3-carboxyprop-1-yl)-IBA(I)-2-ylaminosulfonyl)phenylmethyl |
| 2-((3-guanidino cyclohexyl)aminocarbonyl) ethylaminocarbonyl | 4-(1-hydroxy-5-(1-carboxypropyl)-B[3]A-3-yl sulfonyl)piperazin-1-yl |
| 4-amidinopiperazin-1-yl | 2-hydroxy-3-(5-(2-carboxy ethyl)-7-methylthio-6,8-diaza-B[3]A-3-ylcarbonyl)prop-1-ylcarbonyl |
| N-methylamidinoamino | 2-(6-(carboxymethyl)-8-aza-TBA(I)-2-yloxy)ethyl |
| 3,4-dihydropyrido[3,2-b]-1,4-oxazin-6-ylamino | 3-(5-(2-carboxyethyl)-7-aza-B[3]A-3-ylthio)prop-1-yl |
| 3,4-dihydropyrido[3,2-b]-1,4-thiazin-6-ylamino | 2-(6-(carboxymethyl)-7-aza-IBA(I)-2-ylmethoxy)ethyl |
| 1,2,3,4-tetrahydro-1,8-naphthyrid-4-ylamino | (5-(carboxymethyl)-7-aza-B[2]A-2-ylamino)methyl carbonyl |
| 2-aminobenzoxazol-5-yl | 2-(3-methyl-6-(carboxy methyl)-IBA(I)-2-yl carbonylamino)cyclohexyl |
| 5-aminoimidazol-2-yl aminosulfonylamino | 3-(5-(2-carboxyethyl)-7-aza-B[3]A-3-ylthio)prop-1-yl |
| 5-aminooxazol-2-ylmethyl | 2-hydroxy-3-(5-(2-carboxy ethyl)-7-methylthio-6,8-diaza-B[3]A-3-ylcarbonyl)prop-1-ylcarbonyl |
| 2-aminoindol-5-yl | 3-(6-(carboxymethyl)-IBA(I)-2-yloxy)ethyloxy |
| 4-methyl-2-aminopyrid-6-yl | (5-(2-carboxyethyl)-B[3]A-3-ylmethylcarbonylamino)methyl |
| 2-amino-6-fluoro-7-azabenzimidazol-4-yl sulfonylamino | 2-(N'-methyl-N'-(N-methyl-N-(10-(carboxymethyl)-8-methoxy-7,9-diaza-IBA(II)-2-ylmethyl)aminocarbonyl)amino)ethyl |
| 2-amino-7-azabenzoxazol-5-ylcarbonylamino | 2-(6-(carboxymethyl)-IBA(I)-2-ylmethyl)carbonyl amino)ethyl |
| (1-methyl-2-amino-4-azabenzimidazol-5-ylamino)methylcarbonylamino | 4-(6-(carboxymethyl)-IBA(I)-2-ylcarbonylamino)thien-2-ylmethyl |
| 2-amino-4-azabenzoxazol-7- | 4-(10-(carboxymethyl)-6- |

TABLE 5-continued

| E-B- | -(Alk)$_p$-Q-(Alk)$_q$-A-G |
|---|---|
| yloxy | methyl-IBA(II)-2-yl carbonyl)pent-1-yl |
| 2-amino-4,7-diazabenzimidazol-5-yl | 2-(6-(carboxymethyl)-9-aza-IBA(I)-2-ylamino)ethyl |
| 2-amino-4,7-diazabenzimidazol-6-yl aminosulfonyl | 3-(10-(carboxymethyl)-7-aminosulfonyl-IBA(II)-3-yl carbonylaminomethyl)pyrrol-1-yl |
| 2-(4,7-diazabenzoxazol-5-ylamino)ethylsulfonylamino | 4-(6-(carboxymethyl)-IBA(I)-2-ylaminomethyl) pyrimid-2-yl |
| 2-amino-5-methyl-4,7-diazabenzoxazol-6-yl | 3-(3-(6-(carboxymethyl)-10-aza-IBA(I)-2-ylamino) prop-1-yloxy)prop-1-yl |
| (7-amino-1,2,3,4-tetrahydro-1,8-naphthyrid-1-ylmethyl)carbonylamino | 2-(5-(carboxymethyl)-8-hydroxy-B[3]A-3-yl)ethyl carbonylamino)ethyl |
| 1,2,3,4-tetrahydro-1,8-naphthyrid-5-ylmethylamino | 3-(3-(2-oxy-5-(2-tetrazolylethyl)-B[3]A-3-yl)prop-1-ylsulfonyl |
| (3,4-methylenedioxy phenyl)iminomethyl-amino | 3-(11-hydroxy-10-(carboxy methyl)-5-oxy-6,8-diaza-IBA(II)-2-yl)prop-1-yl |
| N-cyclohexylguanidino | 3-(10-(carboxymethyl)-5-oxy-IBA(II)-2-yl)prop-1-yl |
| (4-hydroxypiperid-1-yl) iminomethyl-amino | 4-(3-methoxy-10-(carboxy methyl)-5-methyl-IBA(II)-2-ylcarbonyl)phenylmethyl |
| 3,4-dihydropyrido[3,2-b]-1,4-oxazin-7-ylamino | 2-(10-(carboxymethyl)-7,8-methylenedioxy-IBA(II)-2-yl)ethyl |
| 1,1-dioxy-3,4-dihydro pyrido[3,2-b]-1,4-thiazin-7-ylamino | 2-(10-(carboxymethyl)-8-methoxy-7,9-diaza-IBA(II)-2-ylaminocarbonyl)ethyl |
| 3,4-dihydropyrido[3,2-b]-1,4-oxazin-3-ylcarbonyl amino | 2-(10-(carboxymethyl)-IBA(II)-3-ylcarbonylamino) ethyl |
| 3,4-dihydro-pyrido[3,2-b]-1,4-thiazin-4-ylmethyl carbonylamino | 2-(N-methyl-N-(10-(carboxy methyl)-IBA(II)-2-ylthio methylcarbonyl)amino)ethyl |
| 2-(2-guanidinofur-5-yl) prop-2-ylaminosulfonyl | 2-(5-((histidylamino) carbonylmethyl)-8-chloro-B[2]A-2-yl)ethylamino |
| 2-(1,2,3,4-tetrahydro-1,8-naphthyrid-6-yl)ethoxy | 3-(5-(2-carboxyethyl)-9-CF$_3$-8-aza-B[2]A-2-yl sulfonyl)propyl |
| 1,2,3,4-tetrahydro-1,8-naphthyrid-2-yl carbonylamino | 4-(3-(4-(7-methyl-5-(carboxymethyl)-1-oxy-B[2]A-2-yl)prop-1-yloxy) but-1-yl |
| 3-methyl-1,2,3,4-tetrahydropyrido[2,3-b] pyrazin-1-yl | 3-(5-(carboxymethyl)-8,9-dimethoxy-B[2]A-2-yl carbonylaminomethyl carbonyl)but-1-yl |

EXAMPLE 88

Biological Studies

The following assays can be used to characterize the biological activity properties of compounds of the invention. Purified integrin $\alpha_v\beta_3$ may be obtained using the methods of Marcinkiewicz et al. (Protein Expression Purif. 8:68–74, 1996) and Pytela et al. (Meth. Enzymol. 144:475–489, 1987). Purified integrin $\alpha_v\beta_5$ may be obtained using the methods of Smith et al. (J. Biol. Chem. 265:11008–13, 1990). Purified integrin $\alpha_v\beta_6$ may be obtained using the methods of Busk et al. (J. Biol. Chem. 267:5790–6, 1992).

Primary human umbilical cord endothelial cells (HUVEC) can be used to show that the compounds of the invention inhibit cellular proliferation and/or cellular adhesion.

HUVEC Proliferation Assay

1. Coat 3 NUNC polystyrene 96 well plate (VWR, 62409–120; lids 62409–118) with vitronectin (purified internally), fibronectin (Collaborative Biomed 40008A) or fibrinogen (Calbiochem 341578) 50 ng/well in 50 µl PBS, 1 hr @ RT.
2. Trypsinize HUVEC's:
   a. rinse with 5 mls PBS (no Ca, Mg)
   b. 2 ml trypsin, remove
   c. 10 ml growth medium
3. Rinse vitronectin plates 1× in 200 µl PBS –/– and add 3000 cells per well in 100 ul growth medium (EBM2 (Clonetics, CC-3156)+EGM2 bullet kit (CC-4176)).
4. Incubate 24 hours at 37° C. to allow attachment.
5. Remove growth medium and add 100 µl growth medium+drugs (25 µM and down by five fold steps in DMSO-0.25% final DMSO concentration).
6. Incubate for 3 days changing media (+drugs).
7. Remove non-adherent cells on Friday with Raindance 12 well plate washer.
8. Wash twice with 200 µl PBS (+Mg & Ca).
9. Tap out excess liquid.
10. Freeze @ –70° C. for 30 minutes.
11. Thaw plate and add 150 µl CyQuant fluorescent dye (Molecular Probes C-7026).
12. Read after 4 minutes @ 485λ (excitation), 530λ (emission).

HUVEC Adhesion Assay

1. Coat 2 NUNC polystyrene 96 well plates (VWR, 62409–120; lids 62409–118) with 50 µl vitronectin (purified internally) at 50 ng/well in PBS (–Mg & Ca), for 1 hour @ 37° C.
2. Rinse with PBS & block with 150 µl PBS/1% BSA (Sigma A8918), 1 hour at @ 37° C.
3. Prepare drug dilutions:
   a. 400 fold concentrate in 100% DMSO
   b. 0.25% DMSO [assay]$_{final}$
   c. 10 mM & down (25 µM$_{final}$ & down)
   d. dilute 1 µl of 400 fold conc into 200 µl adhesion media
   e. use 50 µl/well
4. Trypsinize HUVEC's:
   a. rinse with 5 ml PBS (no Ca, Mg)
   b. 2 ml trypsin, remove
   c. 10 ml growth medium
5. Spin @ 1200 rpm for 10 minutes.
6. Rinse blocking buffer from assay plate and add 50 µl of drug dilutions.
7. Resuspend cells in adhesion media, count and add 2e4 cells/well in 50 µl (4e5/ml).
8. Incubate 60 minutes @ 37° C.
9. Remove non-adherent cells with Raindance 12 well plate washer.
10. Wash twice with 200 µl PBS (+Mg & Ca)
11. Tap out excess liquid.
12. Freeze @ –70° C. for 30 minutes to overnite.
13. Thaw plate and add 150 µl CyQuant fluorescent dye (Molecular Probes C-7026).
14. Read after 2–5 minutes @ 485λ (excitation), 530λ (emission).

Adhesion medium: Media 199 (which contains 36 mM CaCl$_2$ and 0.8 mM MgSO$_4$), 0.5% BSA, 10 mM HEPES, 1 mM MgCl$_2$, and 1 mM MnCl$_2$

Integrin Binding Assay

Purification of Vitronectin

Vitronectin was prepared from out-dated human plasma as described by Yatohgo et al. (Cell Struct. Funct. 13:281–292, 1988) with modifications. Normal human blood collected in citrate tubes was centrifuged and clotted overnight with the addition of $CaCl_2$. The clot was centrifuged, filtered at 0.45 µm, and applied to a Heparin Sepharose column that was equilibrated with 10 mM $NaPO_4$, 5 mM EDTA, 0.13 M NaCl pH 7.7. The column flow through was collected as a single pool, urea was added to a final concentration of 8M, and mixed overnight. The sample was then incubated with Heparin Sepharose which had been equilibrated with 10 mM $NaPO_4$, 5 mM EDTA, 8 M urea pH 7.7 (buffer A) overnight. The Heparin Sepharose was separated from the liquid by centrifugation and washed once with buffer A, buffer A+0.13 M NaCl, and buffer A+0.13 NaCl and 10 mM BME. The vitronectin was eluted from the column with buffer A+0.5 M NaCl. The fractions containing Vitronectin were buffer exchanged into PBS and stored at −70° C.

Ruthenylation of Vitronectin and Fibrinogen

Purified human vitronectin or purified human fibrinogen (Calbiochem) was dialyzed into 50 mM borate, 100 mM NaCl pH 8.0. A stock solution of ruthenium (II) tris bipyridine N-hydroxysuccinimide ester (Origen TAG® Ester, Igen Inc. Gaithersburg, Md.) was freshly prepared by adding 50 µL DMSO to 150 µg of the Origen TAG-NHS ester. Fifty microliters of the Origen TAG-NHS ester was added to one fifth molar ratio of the matrix protein. After one hour incubation at 25° C., the reaction was quench by the addition of 50 µL of 2 M glycine. Unincorporated ruthenium and excess glycine were removed by dialysis into PBS, 0.05% $NaN_3$. Protein concentrations were determined using Micro-BCA (Pierce, Rockford, Ill.). Origen TAG incorporation was assessed at 455 nm ($e=13,700$ $M^{-1}cm^{-1}$). Vitronectin-Ru and Fibrinogen-Ru were stored at −70° C. until needed.

Purification of Platelet Fibrinogen Receptor αIIbβ3

Twelve units of outdated platelets were washed with PBS and centrifuged at low speed to remove RBCs. The washed platelets were lysed in, 20 mM Tris-HCl pH 7.4, 140 mM NaCl, 2 mM $CaCl_2$, 1 mM pefabloc, 3% octylglucoside with gentle stirring for two hours at 4° C. The lysate was centrifuged at 100,000xg for 1 hour to pellet insoluble cellular debris. The resulting supernatant was applied to a lentil lectin (EY labs) column and washed with lysis buffer containing 1% octylglucoside (binding buffer) until a stable UV baseline was reached. Purified αIIbβ3 was eluted from the column with binding buffer containing 10% dextrose. Purified αIIbβ3 was stored at −70° C. until needed.

Purification of αvβ3 and αvβ5

Frozen placentas were thawed overnight at 4° C., cut into 1 cm sections, and washed with 50 mM Tris-HCl, 100 mM NaCl, 1 mM PMSF pH 7.5 (buffer A). The placentas were then incubated overnight in buffer A with the addition of 3% (w/v) octyglucoside. Extracted protein was separated from whole tissue by centrifugation. The extract was then 0.45 µm filtered and $NaN_3$ was added to a final concentration of 0.02%. The sample was then loaded on to an anti-αvβ3 or anti-αvβ5 affinity column, washed with buffer A plus 1% (w/v) octylglucoside, and eluted with Gentle Elution Buffer® (Pierce). The fractions containing αvβ3 or αvβ5 were exchanged into buffer A plus 1% octylglucoside and stored at −70° C. Purified αvβ3 and αvβ5 were also purchased from Chemicon International Inc.

Incorporation of αvβ3, αvβ5, or αIIbβ3 on paramagnetic beads

αvβ3, αvβ5, or αIIbβ3 paramagnetic beads were prepared from 4.5µ uncoated Dynabeads® (Dynal®, Lake Success, N.Y.). Uncoated Dynabeads® were washed three times in phosphate buffered saline pH 7.4 (PBS) and resuspended in 50 mM Tris-HCl, 100 mM NaCl, 1 mM $MgCl_2$, 1 mM $CaCl_2$, and 1 mM $MnCl_2$ pH 7.5 (Buffer A). Purified receptor αvβ3, αvβ5 (Chemicon), or αIIbβ3 were quickly diluted in buffer A and added to the uncoated Dynabeads® at a ratio of 50 µg protein to $10^7$ beads. The bead suspension was incubated with agitation overnight at 4° C. The beads were washed three times in buffer A, 0.1% bovine serum albumin (BSA) and resuspended buffer A+3% BSA. After three hours at 4° C. the beads were wash three times in Buffer A, 1% BSA, 0.05% azide and stored at −70° C. until needed.

Solid Phase Bindinq Assay

All compounds were dissolved and serially diluted in 100% DMSO prior to a final dilution in assay buffer (50 mM Tris-HCl pH 7.5, 100 mM NaCl, 1 mM $CaCl_2$, 1 mM $MgCl_2$, 1 mM $MnCl_2$, 1% BSA, 0.05% Tween-20) containing Vitronectin-Ru or Fibrinogen-Ru and appropriate integrin coated paramagnetic beads. The assay mixture was incubated at 25° C. for two hours with agitation and subsequently read on an Origen Analyzer® (Igen Inc. Gaithersburg, Md.) Non-specific binding was determined using 1 µM Vitronectin, 1 µM Fibrinogen or 5 mM EDTA. The data was prepared using a four-parameter fit by the Levenburg Marquardt algorithm (XLfit® ID Business Solutions.) Ki values were calculated using the equation of Cheng and Prusoff (Biochem. Pharmacology 22:3099–3108, 1973).

The following compounds exhibit activities in the HUVEC proliferation assay and/or HUVEC adhesion assay with $IC_{50}$ values of 30 µM or less:

2-(2-(N-(3-(2-pyridylamino)propyl)carbamoyl)-1H,3H,4H,5H-benzo[e]azapin-5-yl)acetic acid;

2-(2-(N-(4-(2-pyridylamino)butyl)carbamoyl)-1H,3H,4H,5H-benzo[e]azapin-5-yl)acetic acid;

2-(2-(N-(5-(2-pyridylamino)pent-1-yl)carbamoyl)-1H,3H,4H,5H-benzo[e]azapin-5-yl)acetic acid;

2-(2-(N-methyl-N-(4-(2-pyridylamino)but-1-yl)carbamoyl)-1H,3H,4H,5H-benzo[e]azapin-5-yl)acetic acid;

2-(2-(N-(4-(2-pyridylamino)-trans-cyclohexyl) carbamoyl)-1H,3H,4H,5H-benzo[e]azapin-5-yl)acetic acid;

2-(2-(((4-(2-pyridylamino)methyl)piperid-1-yl) carbonyl)-1H,3H,4H,5H-benzo[e]azapin-5-yl)acetic acid;

2-(2-(N-(3-(2-pyridylamino)methylphenyl)carbamoyl)-1H,3H,4H,5H-benzo[e]azapin-5-yl)acetic acid;

2-(2-(N-(4-((6-methyl-2-pyridyl)amino)but-1-yl)carbamoyl)-1H,3H,4H,5H-benzo[e]azapin-5-yl)acetic acid;

2-(2-(N-(4-(pyrimidin-2-ylamino)but-1-yl)carbamoyl)-1H,3H,4H,5H-benzo[e]azapin-5-yl)acetic acid;

2-(2-(N-(3-(6-amino-2-pyridyl))prop-1-yl)carbamoyl)-1H,3H,4H,5H-benzo[e]azapin-5-yl)acetic acid;

2-(2-(N-(3-(6-(tert-butoxycarbonylamino)-2-pyridyl)propyl)carbamoyl)-1H,3H,4H,5H-benzo[e]azapin-5-yl)acetic acid;

2-(2-(N-(3-(1,2,3,4-tetrahydropyridino(2,3-b)pyridin-7-yl)prop-1-yl)carbamoyl)-1H,3H,4H,5H-benzo[e]azapin-5-yl)acetic acid;

2-(2-(((4-(2-pyridylamino)but-1-yl)amino)sulfonyl)-1H,3H,4H,5H-benzo[e]azapin-5-yl)acetic acid;

2-(2-(((3-(2-pyridylamino)prop-1-yl)amino)sulfonyl)-1H,3H,4H,5H-benzo[e]azapin-5-yl)acetic acid;

2-(2-(2-((2-(2-pyridylamino)ethyl)amino)acetyl)-1H,3H,4H,5H-benzo[e]azapin-5-yl)acetic acid;

2-(2-(2-((3-(2-pyridylamino)prop-1-yl)amino)acetyl-1H, 3H,4H,5H-benzo[e]azapin-5-yl)acetic acid;

2-(2-(2-((4-(2-pyridylamino)but-1-yl)amino)acetyl-1H,3H, 4H,5H-benzo[e]azapin-5-yl-acetic acid;

2-(2-((N-(3-(2-pyridylamino)prop-1-yl)carbamoyl) methyl)-1H,3H,4H,5H-benzo[e]azapin-5-yl)acetic acid;

2-(2-(4-(2-pyridylamino)but-1-oxy carbonyl)-1H,3H,4H, 5H-benzo[e]azapin-5-yl)acetic acid;

2-(8-methoxy-2-(N-(4-(2-pyridylamino)but-1-yl) carbamoyl)-1H,3H,4H,5H-benzo[e]azaperhydroepin-5-yl)acetic acid;

2-(8-fluoro-2-(N-(3-(1,2,3,4-tetrahydropyridino[2,3,b] pyridin-7-yl)propyl)carbamoyl)-1H,3H,4H,5H-benzo[e] azaperhydroepin-5-yl)acetic acid;

2-(2-([N-(4-(2-pyridylamino)prop-1-yl)carbamoyl) methyl)-3-oxo-1H,4H,5H-benzo(e)azepin-5-yl)acetic acid;

2-(3-({N-(4-(2-pyridylamino)but-1-yl)carbamoyl}methyl)-1H,2H,4H,5H-benzo[d]azepin-1-yl)acetic acid;

2-(3-{[N-(3-(1,2,3,4-tetrahydropyridino[2,3-b]pyridin-7-yl) propyl)carbamoyl]methyl}-1H,2H,4H,5H-benzo[d] azepinyl)acetic acid;

2-(3-[N-(5-(2-pyridylamino)pent-1-yl)carbamoyl)-1H,2H, 4H,5H-benzo[d]azepinyl)acetic acid;

2-{3-(N-(3-(1,2,3,4-tetrahydropyridino[2,3-b]pyridin-7-yl) propyl)carbamoyl)-1H,2H,4H,5H-benzo[d]azepin-1-yl}acetic acid;

2-{3-(7-(2-pyridylamino)heptanoyl)-1H,2H,4H,5H-benzo[d]azepin-1-yl}acetic acid;

2-(2-(N-(3-(1,2,3,4-tetrahydropyridino(2,3-b)pyridin-7-yl) propyl)carbamoyl)-1H,3H,4H,5H-benzo[e]azapin-5-yl) propanoic acid;

2-{2-[N-(methylethyl)-N-(2-(1,2,3,4-tetrahydropyridino (2,3-b)pyridin-7-yl)ethyl)carbamoyl]-1H,3H,4H,5H-benzo[e]azapin-5-yl}acetic acid;

2-(2-aza-2-cyano-1((1,2,3,4-tetrahydropyridino[2,3-b] pyridin-7-yl)propyl)amino)vinyl)-1H,3H,4H,5H-benzo [e]azapin-5-yl)acetic acid;

2-(2-(((2-(1,2,3,4-tetrahydropyridino(2,3-b)pyridin-7-yl) ethyl)amino)sulfonyl)-1H,3H,4H,5H-benzo[e]azapin-5-yl)acetic acid;

3-(2-(N-(2-(1,2,3,4-tetrahydropyridino(2,3-b)pyridin-7-yl) ethyl)amino)sulfonyl)-1H,3H,4H,5H-benzo[e]azapin-5-yl)propanoic acid;

2-(2-(N-(3-(2-pyridylamino)propyl)carbamoyl)-1H,3H,4H, 5H-benzo[e]azapin-5-yl)acetic acid;

2-((5R)-2-(N-(3-(1,2,3,4-tetrahydropyridino(2,3-b)pyridin-7-yl)prop-1-yl)carbamoyl)-1H,3H,4H,5H-benzo[e] azapin-5-yl)acetic acid;

2-((5R)-2-(N-(3-(1,2,3,4-tetrahydropyridino(2,3-b)pyridin-7-yl)ethyl)carbamoyl)-1H,3H,4H,5H-benzo[e]azapin-5-yl)acetic acid;

2-((5S)-2-(N-(3-(1,2,3,4-tetrahydropyridino(2,3-b)pyridin-7-yl)ethyl)carbamoyl)-1H,3H,4H,5H-benzo[e]azapin-5-yl)acetic acid;

2-((5S)-2-(4-(1,2,3,4-tetrahydropyridino(2,3-b)pyridin-7-yl)butanoyl)carbamoyl)-1H,3H,4H,5H-benzo[e]azapin-5-yl)acetic acid;

2-[2-(4-(1,2,3,4-tetrahydropyridino[2,3-b]pyridin-7-yl) butanoyl)-1H,3H,4H,5H-benzo[e]azapin-5-yl]acetic acid;

2-{2-[N-(2-(1,2,3,4-tetrahydropyridino[2,3-b]pyridin-7-yl) ethyl)carbamoyl]-4H,5H,10H-benzo[d]imidazolo[1,2-a] azepin-5-yl}acetic acid;

2-{2-[N-(methylethyl)-N-(2-(1,2,3,4-tetrahydropyridino[2,3-b]pyridin-7-yl)ethyl)carbamoyl]-4H,5H,10H-benzo[d] imidazolo[1,2-a]azepin-5-yl)acetic acid;

2-{2-[N-(methylethyl)-N-(1,2,3,4tetrahydropyridino[2,3-b]pyridine-6-ylmethyl)carbamoyl]-4H,5H,10H-benzo[d] imidazolo[1,2-a]azepin-5-yl}acetic acid;

2-{2-[N-(1,2,3,4-tetrahydropyridino[2,3-b]pyridin-6-ylmethyl)carbamoyl]-4H,5H,10H-benzo[d]imidazolo[1,2-a]azepin-5-yl}acetic acid;

2-(2-{N-methyl-N-[3-(2-pyridylamino)propyl]carbamoyl}-4H,5H,10H-benzo[d]imidazolo[1,2-a]azepin-5-yl)acetic acid;

2-(8-methoxy-2-(N-(3-(1,2,3,4-tetrahydropyridino[2,3,b] pyridin-7-yl)propyl)carbamoyl)-1H,3H,4H,5H-benzo[e] azaperhydroepin-5-yl)acetic acid;

2-(8-benzyloxy-2-(N-(3-(1,2,3,4-tetrahydropyridino[2,3,b] pyridin-7-yl)propyl)carbamoyl)-1H,3H,4H,5H-benzo[e] azaperhydroepin-5-yl)acetic acid;

2-(8-phenyl-2-(N-(3-(1,2,3,4-tetrahydropyridino[2,3,b] pyridin-7-yl)propyl)carbamoyl)-1H,3H,4H,5H-benzo[e] azaperhydroepin-5-yl)acetic acid;

2-(2-(N-(4-(4,5-dihydroimidazo-2-yl)aminobut-1-yl) carbamoyl)-1H,3H,4H-5H-benzo[e]azapin-5-yl)acetic acid;

2-{8-Chloro-2-[N-(3-(1,2,3,4-tetrahydropyridino[2,3-b] pyridin-7-yl)propyl)carbamoyl]-1H,3H,4H,5H-benzo[e] azepin-5-yl}acetic acid;

2-(8-Bromo-2-[N-(3-(1,2,3,4-tetrahydropyridino[2,3-b] pyridin-7-yl)propyl)carbamoyl]-1H,3H,4H,5H-benzo[e] azepin-5-yl)acetic acid;

2-{7,8-Dibromo-2-[N-(3-(1,2,3,4-tetrahydropyridino[2,3-b] pyridin-7-yl)propyl)carbamoyl]-1H,3H,4H,5H-benzo[e] azepin-5-yl}acetic acid;

2-{8-[(Methylsulfonyl)amino]-2-[N-(3-(1,2,3,4-tetrahydropyridino[2,3-b]pyridin-7-yl)propyl) carbamoyl]-1H,3H,4H,5H-benzo[e]azepin-5-yl}acetic acid;

2-{8-[(phenylsulfonyl)amino]-2-[N-(3-(1,2,3,4-tetrahydropyridino[2,3-b]pyridin-7-yl)propyl) carbamoyl]-1H,3H,4H,5H-benzo[e]azepin-5-yl}acetic acid;

2-{8-Carbonylamino-2-[N-(3-(1,2,3,4-tetrahydropyridino [2,3-b]pyridin-7-yl)propyl)carbamoyl]-1H,3H,4H,5H-benzo[e]azepin-5-yl}acetic acid;

2-{8-(Dimethylamino)-2-[N-(3-(1,2,3,4-tetrahydropyridino [2,3-b]pyridin-7-yl)propyl)carbamoyl]-1H,3H,4H,5H-benzo[e]azepin-5-yl}acetic acid;

2-(2-(N-(3-(6-(methylamino)-2-pyridyl)propyl)carbamoyl)-1H,3H,4H,5H-benzo[e]azapin-5-yl)acetic acid;

2-(2-(N-(2-(1,2,3,4-tetrahydropyridino(2,3-b)pyridin-7-yl) ethyl)carbamoyl)-1H,3H,4H,5H-benzo[e]azapin-5-yl) acetic acid;

2-(3-(N-(2-(1,2,3,4-tetrahydropyridino(2,3-b)pyridin-7-yl) propyl)amino)sulfonyl)-1H,3H,4H,5H-benzo[e]azapin-5-yl)acetic acid;

3-(2-(N-(2-(1,2,3,4-tetrahydropyridino(2,3-b)pyridin-7-yl) ethyl)carbamoyl)-1H,3H,4H,5H-benzo[e]azapin-5-yl) propanoic acid;

3-(2-(N-(3-(1,2,3,4-tetrahydropyridino(2,3-b)pyridin-7-yl) propyl)carbamoyl-1H,3H,4H,5H-benzo[e]azapin-5-yl) propanoic acid;

3-(2-(N-(3-(1,2,3,4-tetrahydropyridino(2,3-b)pyridin-7-yl) propyl)amino)sulfonyl)-1H,3H,4H,5H-benzo[e]azapin-5-yl)propanoic acid;

2-[3-([N-[5-(2-pyridylamino)pentyl]carbamoyl]methyl)-1H,2H,4H,5H-benzo[d]azepinyl}acetic acid;

2-[3-(2-{[4-(2-pyridylamino)butyl]amino}acetyl)-1H,2H, 4H,5H-benzo[d]azepinyl]acetic acid;

2-(2-{N-[3-(5-methyl-1,2,3,4-tetrahydropyridino[2,3-b] pyridin-7-yl)propyl]carbamoyl}-1H,3H,4H,5H-benzo[e] azepin-5-yl)acetic acid;

2-(3-[N-(2-(2-pyridylamino)ethyl)carbamoyl}-1H,2H,4H, 5H-benzo[d]azepinyl)acetic acid;

2-{3-(N-(2-(1,2,3,4-tetrahydropyridino[2,3-b]pyridin-7-yl)ethyl)carbamoyl)-1H,2H,4H,5H-benzo[d]azepin-1-yl}acetic acid;

2-(8-fluoro-2-(N-(2-(1,2,3,4-tetrahydropyridino(2,3-b)pyridin-7-yl)ethyl)carbamoyl)-1H,3H,4H,5H-benzo[e]azapin-5-yl)acetic acid;

2-[2-(N-{4-[(4-methyl-2-pyridyl)amino]butyl}carbamoyl)-1H,3H,4H,5H-benzo[e]azepin-5-yl]acetic acid; and 2-{2-[N-(4-{[benzylamino]carbonylamino}butyl)carbamoyl]-1H,3H,4H,5H-benzo[e]azepin-5-yl}acetic acid.

Compounds of the invention may be shown to inhibit vitronectin $\alpha_v\beta_3$ binding in vitronectin $\alpha_v\beta_3$ binding assays and to inhibit osteoclasts mediated bone resorption in bone resorption pit assays as described in Woo et al. (Eur. J. Pharm. 300:131–5, 1996), EP 528587, WO 97/01540, WO 98/18461 and WO 99/30713 (each of which is incorporated herein by reference in its entirety). Compounds of the invention may be shown to inhibit smooth muscle cell migration in human aortic smooth muscle cell migration assay described in WO 97/01540 and Liaw et al., J. Clin. Invest. 95:713–724, 1995 (each of which is incorporated herein by reference in its entirety).

Compounds of the invention may be shown to inhibit vitronectin $\alpha_v\beta_5$ and/or $\alpha_v\beta_6$ binding in vitronectin $\alpha_v\beta_5$ and $\alpha_v\beta_6$ binding assays as described in WO 99/30709 and WO 99/30713 (each of which are incorporated herein by reference in its entirety). Compounds of the invention may be shown to inhibit $\alpha_5\beta_1$ integrin binding in $\alpha_5\beta_1$ integrin binding assays as described in WO 99/58139 (incorporated herein by reference in its entirety).

Compounds of the invention may be shown to have anti-bone resorption properties in a rat animal models described in WO 97/01540 and Wronski et al., Cells and Mat. 1991:69–74 (each of which is incorporated herein by reference in its entirety). Compounds of the invention may be shown to have anti-angiogenic properties in an animal model described in Passaniti et al., Lab. Invest. 67:519–528, 1992 (incorporated herein by reference in its entirety). Compounds of the invention may be shown to inhibit restenosis in a pig restenosis model described in Schwartz et al., J. Am. College of Cardiology 19:267–274, 1992 (incorporated herein by reference in its entirety). Compounds of the invention may be shown to inhibit retinopathy in a mouse retinopathy model described in Smith et al., Invest. Ophthal. & Vis. Sci. 35:101–111, 1994 (incorporated herein by reference in its entirety).

The foregoing is merely illustrative of the invention and is not intended to limit the invention to the disclosed compounds. Variations and changes which are obvious to one skilled in the art are intended to be within the scope and nature of the invention which are defined in the appended claims.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A compound of the formula

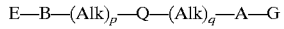

E—B—(Alk)$_p$—Q—(Alk)$_q$—A—G or a pharmaceutically acceptable salt thereof, wherein p and q are each independently 0 or 1;

each Alk is independently an alkyl radical;

A and Q each independently represent a bond, —C(X)—, —S(O)$_t$—, —S—, —O—, —N(R$_1$)—, —C(Y)—N(R$_1$)—, —N(R$_1$)—C(Y)—, —S(O)$_t$—N(R$_1$)—, —N(R$_1$)—S(O)$_t$—, —N(R$_1$)—C(Y)—N(R$_1$)— or —N(R$_1$)—S(O)$_t$—N(R$_1$)—, or a radical of C$_3$–C$_{12}$ cycloalkyl, aryl, heterocyclyl or heteroaryl each of which is optionally substituted by 1–3 radicals of R$_2$; and B represents a bond, —C(Y)—, —S(O)$_t$—, —S—, —O—, —N(R$_1$)—, —C(Y)—N(R$_1$)—, —N(R$_1$)—C(Y)—, —S(O)$_t$—N(R$_1$)—, —N(R$_1$)—S(O)$_t$—, —N(R$_1$)—C(Y)—N(R$_1$)— or —N(R$_1$)—S(O)$_t$—N(R$_1$)—, or a radical of C$_3$–C$_{12}$ cycloalkyl, aryl, heterocyclyl or heteroaryl each of which is optionally substituted by 1–3 radicals of R$_2$; provided the total number of atoms that directly connect E to G via the shortest sequence is 3–12;

each X is independently O or S; and each Y is independently O, S, N(R$_1$) or N(CN); and each t is independently 1 or 2;

each R$_1$ is independently a hydrogen or alkyl radical;

radicals of R$_2$ are each independently a halo, alkyl, alkoxy, alkylthio, haloalkyl, haloalkoxy, hydroxy, carboxy, cyano, azido, amidino, guanidino, nitro, amino, alkylamino or dialkylamino radical or two adjacent R$_2$ radicals represent a methylenedioxy, ethylenedioxy or propylenedioxy radical;

E represents —R$_3$, —NH—R$_3$, —NH—C(Y)—R$_3$, —C(Y)—NH—R$_3$, —NH—S(O)$_t$—R$_3$, —S(O)$_t$—NH—R$_3$, —NH—C(Y)—NH—R$_3$, —NH—C(Y)—O—R$_3$, —NH—S(O)$_t$—NH—R$_3$, —NH-alkyl-C(Y)—R$_3$, —NH-alkyl-S(O)$_t$—R$_3$, —NH-alkyl-C(Y)—NH—R$_3$ or —NH-alkyl-S(O)$_t$—NH—R$_3$ radical;

R$_3$ is a radical of hydrogen, alkyl, aryl, aryl-alkyl, heteroaryl, heteroaryl-alkyl, heterocyclyl or heterocyclyl-alkyl, wherein the aryl, heteroaryl and heterocyclyl radicals are optionally substituted by 1–3 radicals of R$_2$;

G is a radical of formula

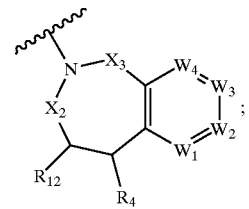

W$_1$ is C—R$_{15}$ or N; W$_2$ is C—R$_{16}$ or N; W$_3$ is C—R$_{17}$ or N; and W$_4$ is C—R$_{18}$ or N; or W$_1$ and W$_2$, W$_2$ and W$_3$, or W$_3$ and W$_4$ taken together represent a fused phenyl, fused C$_5$–C$_7$ cycloalkyl, fused heteroaryl of 5–6 ring members or fused heterocyclyl of 5–7 ring members, each of which is optionally substituted by 1–3 radicals of R$_2$; provided not more than 1 of W$_1$, W$_2$, W$_3$ or W$_4$ represent N;

radicals of R$_{15}$, R$_{16}$, R$_{17}$ and R$_{18}$ are each independently a radical of hydrogen, halo, hydroxy, carboxy, cyano, azido, amidino, nitro, amino, —R$_9$, —C(Y)—R$_9$, —S(O)$_t$—R$_9$, —S—R$_9$, —O—R$_9$, —N(R$_1$)—R$_9$, —C(Y)—N(R$_1$)—R$_9$, —N(R$_1$)—C(Y)—H, —N(R$_1$)—C(Y)—R$_9$, —O—C(Y)—N(R$_1$)—R$_9$, —N(R$_1$)—C(Y)—O—R$_9$, —S(O)$_t$—N(R$_1$)—R$_9$, —N(R$_1$)—S(O)$_t$—R$_9$, —N(R$_1$)—C(Y)—N(R$_1$)—R$_9$ or —N(R$_1$)—S(O)$_t$—N(R$_1$)—R$_9$, or R$_{15}$ and R$_{16}$, R$_{16}$ and R$_{17}$, or R$_{17}$ and R$_{18}$ taken together represent a methylenedioxy, ethylenedioxy or propylenedioxy radical; provided the combined total number of aryl, cycloalkyl, heteroaryl and heterocyclyl radicals in $R_{15}$, $R_{16}$, $R_{17}$ and $R_{18}$ is 0–1;

wherein each $R_9$ is independently a radical of alkyl, haloalkyl, arylalkyl, heteroarylalkyl, heterocyclylalkyl, aryl, $C_3$–$C_{12}$ cycloalkyl, heteroaryl or heterocyclyl, wherein the aryl, $C_3$–$C_{12}$ cycloalkyl, heteroaryl and heterocyclyl radicals are optionally substituted by 1–3 radicals of $R_2$;

$X_2$ and $X_3$ are each independently a —C(X)—, —CHR$_6$— or —CHR$_7$— radical;

$Z_1$ is N or C—$R_6$;

$R_{12}$ is an —$R_6$, —$R_7$ or —O$R_7$ radical;

Heteroaryl is selected from

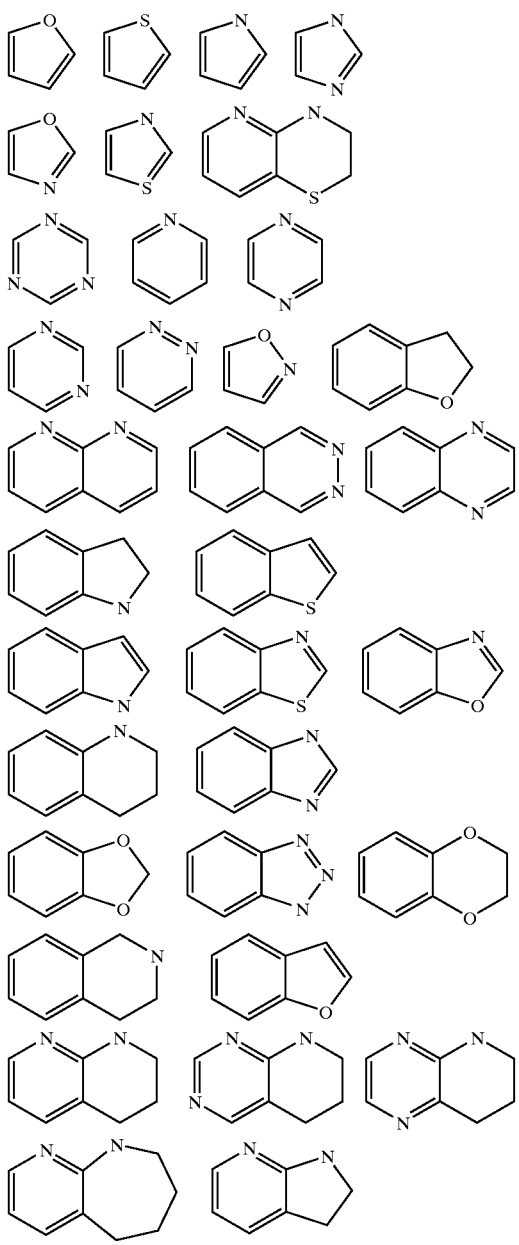
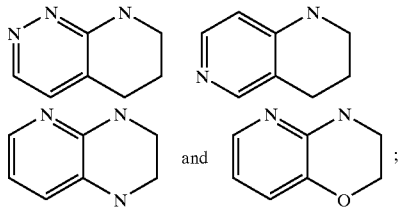

Heterocyclyl is a saturated or partially unsaturated monocyclic or bicyclic heterocycle radical containing 1 to 4 nitrogen, oxygen or sulfur atom ring member and having 3–8 ring members in each ring;

wherein each $R_6$ is independently a hydrogen, hydroxy, alkyl, haloalkyl, alkoxy, haloalkoxy, halo or cyano radical; and each $R_7$ is independently a radical of aryl, aryl-alkyl, heteroaryl, heteroaryl-alkyl, heterocyclyl or heterocyclyl-alkyl, wherein the aryl, heteroaryl and heterocyclyl radicals are optionally substituted by 1–3 radicals of $R_2$; provided the combined total number of aryl, heteroaryl and heterocyclyl radicals in $X_2$, $X_3$ and $R_{12}$ is 0–2; and $R_4$ is an alkyl radical substituted by a radical of carboxy, tetrazolyl, —CO$_2$R$_8$, —C(O)—NH—S(O)$_t$—R$_8$, —C(O)—NH—C(O)—R$_8$ or —C(O)—NH—R$_8$, and optionally substituted by a radical of aryl, heteroaryl or heterocyclyl, each of which is optionally substituted by 1–3 radicals of $R_2$; wherein $R_8$ is an alkyl radical optionally substituted by 1–2 radicals of hydroxy, carboxy, amino, aryl or heteroaryl, wherein the aryl and heteroaryl radicals are optionally substituted by 1–3 radicals of $R_2$.

2. The compound of claim 1 or a pharmaceutically acceptable salt thereof, wherein each Alk is independently a $C_1$–$C_{12}$ alkyl radical;

A and Q each independently represent a bond, —C(X)—, —S(O)$_t$—, —S—, —O—, —N(R$_1$)—, —C(Y)—N(R$_1$)—, —N(R$_1$)—C(Y)—, —S(O)$_t$—N(R$_1$)—, —N(R$_1$)—S(O)$_t$—, —N(R$_1$)—C(Y)—N(R$_1$)— or —N(R$_1$)—S(O)$_t$—N(R$_1$)—, or a radical of $C_3$–$C_8$ cycloalkyl, aryl, heterocyclyl of 5–8 ring members or heteroaryl of 5–10 ring members each of which is optionally substituted by 1–3 radicals of $R_2$; and B represents a bond, —C(Y)—, —S(O)$_t$—, —S—, —O—, —N(R$_1$)—, —C(Y)—N(R$_1$)—, —N(R$_1$)—C(Y)—, —S(O)$_t$—N(R$_1$)—, —N(R$_1$)—S(O)$_t$—, —N(R$_1$)—C(Y)—N(R$_1$)— or —N(R$_1$)—S(O)$_t$—N(R$_1$)—, or a radical of $C_3$–$C_8$ cycloalkyl, aryl, heterocyclyl of 5–8 ring members or heteroaryl of 5–10 ring members each of which is optionally substituted by 1–3 radicals of $R_2$; provided the total number of atoms that directly connect E to G via the shortest sequence is 3–12;

each X is independently O or S; and each Y is independently O, S, N(R$_1$) or N(CN); and each t is independently 1 or 2;

each $R_1$ is independently a hydrogen or $C_1$–$C_4$ alkyl radical;

radicals of $R_2$ are each independently a halo, $C_1$–$C_4$ alkyl, $C_1$–$C_4$ alkoxy, $C_1$–$C_4$ alkylthio, $C_1$–$C_4$ haloalkyl of 1–3 halo radicals, $C_1$–$C_4$ haloalkoxy of 1–3 halo radicals, hydroxy, carboxy, cyano, azido, amidino, guanidino, nitro, amino, $C_1$–$C_4$ alkylamino or di($C_1$–$C_4$ alkyl) amino radical or two adjacent $R_2$ radicals represent a methylenedioxy, ethylenedioxy or propylenedioxy radical;

E represents —$R_3$, —NH—$R_3$, —NH—C(Y)$R_3$, —C(Y)—NH—$R_3$, —NH—S(O)$_t$—$R_3$, —S(O)$_t$—NH—$R_3$, —NH—C(Y)—NH—$R_3$, —NH—C(Y)—O—$R_3$, —NH—S(O)$_t$—NH—$R_3$, —NH—($C_1$-$C_4$ alkyl)—C(Y)—$R_3$, —NH—($C_1$-$C_4$ alkyl)—S(O)$_t$—$R_3$, —NH—($C_1$-$C_4$ alkyl)—C(Y)—NH—$R_3$ or —NH—($C_1$-$C_4$ alkyl)—S(O)$_t$—NH—$R_3$ radical;

$R_3$ is hydrogen, $C_1$-$C_{10}$ alkyl, aryl, aryl-$C_1$-$C_{10}$ alkyl, heteroaryl, heteroaryl-$C_1$-$C_{10}$ alkyl, heterocyclyl or heterocyclyl-$C_1$-$C_{10}$ alkyl radical, wherein the heteroaryl and heterocyclyl radicals have 5–15 ring members and the aryl, heteroaryl and heterocyclyl radicals are optionally substituted by 1–3 radicals of $R_2$;

G is a radical of formula

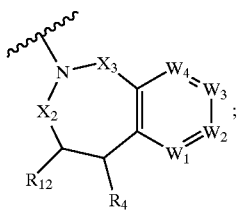

$W_1$ is C—$R_{15}$ or N; $W_2$ is C—$R_{16}$ or N; $W_3$ is C—$R_{17}$ or N; and $W_4$ is C—$R_{18}$ or N; or $W_1$ and $W_2$, $W_2$ and $W_3$, or $W_3$ and $W_4$ taken together represent a fused phenyl, fused $C_5$-$C_7$ cycloalkyl, fused heteroaryl of 5–6 ring members or fused heterocyclyl of 5–7 ring members, each of which is optionally substituted by 1–3 radicals of $R_2$; provided not more than 1 of $W_1$, $W_2$, $W_3$ or $W_4$ represent N;

radicals of $R_{15}$, $R_{16}$, $R_{17}$ and $R_{18}$ are each independently a radical of hydrogen, halo, hydroxy, carboxy, cyano, azido, amidino, nitro, amino, —$R_9$, —C(Y)—$R_9$, —S(O)$_t$—$R_9$, —S—$R_9$, —O—$R_9$, —N($R_1$)—$R_9$, —C(Y)—N($R_1$)—$R_9$, —N($R_1$)—C(Y)—H, —N($R_1$)—C(Y)—$R_9$, —O—C(Y)—N($R_1$)—$R_9$, —N($R_1$)—C(Y)—O—$R_9$, —S(O)$_t$—N($R_1$)—$R_9$, —N($R_1$)—S(O)$_t$—$R_9$, —N($R_1$)—C(Y)—N($R_1$)—$R_9$ or —N($R_1$)—S(O)$_t$—N($R_1$)—$R_9$, or $R_{15}$ and $R_{16}$, $R_{16}$ and $R_{17}$, or $R_{17}$ and $R_{18}$ taken together represent a methylenedioxy, ethylenedioxy or propylenedioxy radical; provided the combined total number of aryl, cycloalkyl, heteroaryl and heterocyclyl radicals in $R_{15}$, $R_{16}$, $R_{17}$ and $R_{18}$ is 0–1;

wherein each $R_9$ is independently a radical of $C_1$-$C_4$ alkyl, $C_1$-$C_4$ haloalkyl of 1–3 halo radicals, aryl-$C_1$-$C_4$ alkyl, heteroaryl-$C_1$-$C_4$ alkyl, heterocyclyl-$C_1$-$C_4$ alkyl, aryl, $C_3$-$C_{12}$ cycloalkyl, heteroaryl or heterocyclyl, wherein the aryl, $C_3$-$C_{12}$ cycloalkyl, heteroaryl and heterocyclyl radicals are optionally substituted by 1–3 radicals of $R_2$;

$X_2$ and $X_3$ are each independently a —C(X)—, —CHR$_6$— or —CHR$_7$— radical;

$Z_1$ is N or C—$R_6$;

$R_{12}$ is an —$R_6$, —$R_7$ or —O$R_7$ radical;

wherein each $R_6$ is independently a hydrogen, hydroxy, $C_1$-$C_4$ alkyl, $C_1$-$C_4$ haloalkyl of 1–3 halo radicals, $C_1$-$C_4$ alkoxy, $C_1$-$C_4$ haloalkoxy, halo or cyano radical; and each $R_7$ is independently a radical of aryl, aryl-$C_1$-$C_4$ alkyl, heteroaryl, heteroaryl-$C_1$-$C_4$ alkyl, heterocyclyl or heterocyclyl-$C_1$-$C_4$ alkyl, wherein the aryl, heteroaryl and heterocyclyl radicals are optionally substituted by 1–3 radicals of $R_2$, and wherein the heteroaryl and heterocyclyl radicals have 5–10 ring members; provided the combined total number of aryl, heteroaryl and heterocyclyl radicals in $X_2$, $X_3$ and $R_{12}$ is 0–2; and $R_4$ is a $C_1$-$C_{10}$ alkyl radical substituted by a radical of carboxy, tetrazolyl, —CO$_2$$R_8$, —C(O)—NH—S(O)$_t$—$R_8$, —C(O)—NH—C(O)—$R_8$ or —C(O)—NH—$R_8$, and optionally substituted by a radical of aryl, heteroaryl or heterocyclyl, each of which is optionally substituted by 1–3 radicals of $R_2$; wherein $R_8$ is a $C_1$-$C_{10}$ alkyl radical optionally substituted by 1–2 radicals of hydroxy, carboxy, amino, aryl or heteroaryl of 5–10 ring members, wherein the aryl and heteroaryl radicals are optionally substituted by 1–3 radicals of $R_2$.

3. The compound of claim 2 or a pharmaceutically acceptable salt thereof, wherein each Alk is independently a $C_1$-$C_8$ alkyl radical;

each X is O; and each Y is independently O, N($R_1$) or N(CN); and each t is 2;

E represents —$R_3$, —NH—$R_3$, —NH—C(Y)—$R_3$, —C(Y)—NH—$R_3$, —S(O)$_t$—NH—$R_3$, —NH—C(Y)—NH—$R_3$, —NH—C(Y)—O—$R_3$ or —NH—($C_1$-$C_4$ alkyl)—C(Y)—NH—$R_3$ radical;

$R_3$ is hydrogen, $C_1$-$C_4$ alkyl, aryl, aryl-$C_1$-$C_4$ alkyl, heteroaryl, heteroaryl-$C_1$-$C_4$ alkyl, heterocyclyl or heterocyclyl-$C_1$-$C_4$ alkyl radical, wherein the heteroaryl and heterocyclyl radicals have 5–15 ring members and the aryl, heteroaryl and heterocyclyl radicals are optionally substituted by 1–3 radicals of $R_2$;

$W_1$ is C—$R_{15}$ or N; $W_2$ is C—$R_{16}$ or N; $W_3$ is C—$R_{17}$ or N; and $W_4$ is C—$R_{18}$ or N; provided not more than 1 of $W_1$, $W_2$, $W_3$ or $W_4$ represent N;

radicals of $R_{15}$, $R_{16}$, $R_{17}$ and $R_{18}$ are each independently a radical of hydrogen, halo, hydroxy, carboxy, cyano, azido, amidino, nitro, amino, —$R_9$, —C(O)—$R_9$, —S(O)$_t$—$R_9$, —S—$R_9$, —O—$R_9$, —N($R_1$)—$R_9$, —C(O)—N($R_1$)—$R_9$, —N($R_1$)—C(O)—H, —N($R_1$)—C(O)—$R_9$, —S(O)$_t$—N($R_1$)—$R_9$ or —N($R_1$)—S(O)$_t$—$R_9$, or $R_{15}$ and $R_{16}$, $R_{16}$ and $R_{17}$, or $R_{17}$ and $R_{18}$ taken together represent a methylenedioxy, ethylenedioxy or propylenedioxy radical; provided the combined total number of aryl, cycloalkyl, heteroaryl and heterocyclyl radicals in $R_{15}$, $R_{16}$, $R_{17}$ and $R_{18}$ is 0–1;

$X_2$ and $X_3$ are each independently a —CHR$_6$— or —CHR$_7$— radical;

$R_{12}$ is a hydrogen, hydroxy or $C_1$-$C_4$ alkyl radical; and $R_4$ is a $C_1$-$C_4$ alkyl radical substituted by a radical of carboxy, tetrazolyl, or —CO$_2$$R_8$, and optionally substituted by a radical of aryl, heteroaryl or heterocyclyl, each of which is optionally substituted by 1–3 radicals of $R_2$; wherein $R_8$ is a $C_1$-$C_4$ alkyl radical optionally substituted by a radical of aryl or heteroaryl of 5–10 ring members, wherein the aryl and heteroaryl radicals are optionally substituted by 1–3 radicals of $R_2$.

4. The compound of claim 3 or a pharmaceutically acceptable salt thereof, wherein each Alk is independently a $C_1$-$C_6$ alkyl radical;

A and Q each independently represent a bond, —C(O)—, —S(O)$_t$—, —O—, —N($R_1$)—, —C(Y)—N($R_1$)—, —N($R_1$)—C(Y)—, —S(O)$_t$—N($R_1$)— or —N($R_1$)—S(O)$_t$—, or a radical of $C_3$-$C_6$ cycloalkyl, phenyl, heterocyclyl of 5–6 ring members or heteroaryl of 5–6 ring members each of which is optionally substituted by 1–3 radicals of $R_2$; and B represents a bond, —C(Y)—, —S(O)$_t$—, —O— or —N(R$_1$)—, or a radical of phenyl, heterocyclyl of 5–6 ring members or heteroaryl of 5–6 ring members each of which is optionally substituted by 1–3 radicals of R$_2$; provided the total number of atoms that directly connect E to G via the shortest sequence is 4–9;

radicals of R$_2$ are each independently a halo, C$_1$–C$_3$ alkyl, C$_1$–C$_3$ alkoxy, C$_1$–C$_3$ alkylthio, —CF$_3$, —OCF$_3$, hydroxy, cyano, nitro, amino, C$_1$–C$_4$ alkylamino or di(C$_1$–C$_4$ alkyl)amino radical;

E represents —R$_3$, —NH—R$_3$, —NH—C(Y)—R$_3$, —C(Y)—NH—R$_3$, —NH—C(Y)—NH—R$_3$ or —NH—C(Y)—O—R$_3$ radical;

R$_3$ is hydrogen, C$_1$–C$_4$ alkyl, aryl, aryl-C$_1$–C$_4$ alkyl, heteroaryl or heteroaryl-C$_1$–C$_4$ alkyl radical, wherein the heteroaryl radical has 5–15 ring members and the aryl and heteroaryl radicals are optionally substituted by 1–3 radicals of R$_2$;

W$_1$ is C—R$_{15}$; W$_2$ is C—R$_{16}$; W$_3$ is C—R$_{17}$; and W$_4$ is C—R$_{18}$;

radicals of R$_{15}$, R$_{17}$ and R$_{18}$ are each independently a radical of hydrogen, halo, hydroxy, cyano, C$_1$–C$_3$ alkyl, C$_1$–C$_3$ alkoxy, —CF$_3$ or —OCF$_3$;

R$_{16}$ is a radical of hydrogen, halo, hydroxy, carboxy, cyano, amino, —R$_9$, —S(O)$_t$—R$_9$, —O—R$_9$, —N(R$_1$)—R$_9$, —C(O)—N(R$_1$)—R$_9$, —N(R$_1$)—C(O)—H, —N(R$_1$)—C(O)—R$_9$, —S(O)$_t$—N(R$_1$)—R$_9$ or —N(R$_1$)—S(O)$_t$—R$_9$;

wherein each R$_9$ is independently a radical of C$_1$–C$_4$ alkyl, —CF$_3$, phenyl-C$_1$–C$_4$ alkyl or phenyl, wherein each phenyl radical is optionally substituted by 1–3 radicals of R$_2$;

X$_2$ and X$_3$ are each independently a —CHR$_6$— radical;

Z$_1$ is C—R$_6$;

R$_{12}$ is a hydrogen, hydroxy or C$_1$–C$_2$ alkyl radical;

wherein each R$_6$ is independently a hydrogen, hydroxy or C$_1$–C$_2$ alkyl radical; and R$_4$ is a C$_1$–C$_4$ alkyl radical substituted by a radical of carboxy or —CO$_2$R$_8$; wherein R$_8$ is a C$_1$–C$_4$ alkyl radical optionally substituted by a phenyl radical, wherein the phenyl radical is optionally substituted by 1–3 radicals of R$_2$.

5. The compound of claim 4 or a pharmaceutically acceptable salt thereof, wherein B represents a bond, —S(O)$_t$—, —O— or —N(R$_1$)—, or a phenyl radical which is optionally substituted by 1–3 radicals of R$_2$; provided the total number of atoms that directly connect E to G via the shortest sequence is 4–7;

each R$_1$ is independently a hydrogen or methyl radical;

radicals of R$_2$ are each independently a halo, methyl, methoxy, —CF$_3$, —OCF$_3$, hydroxy, cyano, nitro, amino, C$_1$–C$_4$ alkylamino or di(C$_1$–C$_2$ alkyl)amino radical;

E represents —R$_3$, —NH—R$_3$, —NH—C(NR$_1$)—R$_1$, —C(NR$_1$)—NH—R$_1$, —NH—C(NR$_1$)—NH—R$_1$ or —NH—C(NR$_1$)—O—CH$_3$ radical;

R$_3$ is a heteroaryl radical of 5–15 ring members and is optionally substituted by 1–3 radicals of R$_2$;

R$_{15}$, R$_{17}$ and R$_{18}$ are each independently a radical of hydrogen, fluoro, chloro, bromo, hydroxy, cyano, methyl, methoxy, —CF$_3$ or —OCF$_3$;

R$_{16}$ is a radical of hydrogen, fluoro, chloro, bromo, hydroxy, cyano, amino, —R$_9$, —S(O)$_t$—R$_9$, —O—R$_9$, —N(R$_1$)—R$_9$, —C(O)—N(R$_1$)—R$_9$, —N(R$_1$)—C(O)—H, —N(R$_1$)—C(O)—R$_9$, —S(O)$_t$—N(R$_1$)—R$_9$ or —N(R$_1$)—S(O)$_t$—R$_9$;

wherein each R$_9$ is independently a radical of C$_1$–C$_4$ alkyl, —CF$_3$, phenyl-C$_1$–C$_2$ alkyl or phenyl, wherein each phenyl radical is optionally substituted by 1–3 radicals of R$_2$;

each R$_6$ is a hydrogen radical; and

R$_4$ is a C$_1$–C$_2$ alkyl radical substituted by a radical of carboxy or —CO$_2$R$_8$; wherein R$_8$ is a C$_1$–C$_2$ alkyl radical.

6. The compound of claim 5 which is 2-(2-(N-(3-(2-pyridylamino)propyl)carbamoyl)-1H,3H,4H,5H-benzo[e]azapin-5-yl)acetic acid;

2-(2-(N-(4-(2-pyridylamino)butyl)carbamoyl)-1H,3H,4H,5H-benzo[e]azapin-5-yl)acetic acid;

2-(2-(N-(5-(2-pyridylamino)pent-1-yl)carbamoyl)-1H,3H,4H,5H-benzo[e]azapin-5-yl)acetic acid;

2-(2-(N-methyl-N-(4-(2-pyridylamino)but-1-yl)carbamoyl)-1H,3H,4H,5H-benzo[e]azapin-5-yl)acetic acid;

2-(2-(N-(4-(2-pyridylamino)-trans-cyclohexyl)carbamoyl)-1H,3H,4H,5H-benzo[e]azapin-5-yl)acetic acid;

2-(2-(((4-(2-pyridylamino)methyl)piperid-1-yl)carbonyl)-1H,3H,4H,5H-benzo[e]azapin-5-yl)acetic acid;

2-(2-(N-(3-(2-pyridylamino)methylphenyl)carbamoyl)-1H,3H,4H,5H-benzo[e]azapin-5-yl)acetic acid;

2-(2-(N-(4-((6-methyl-2-pyridyl)amino)but-1-yl)carbamoyl)-1H,3H,4H,5H-benzo[e]azapin-5-yl)acetic acid;

2-(2-(N-(4-(pyrimidin-2-ylamino)but-1-yl)carbamoyl)-1H,3H,4H,5H-benzo[e]azapin-5-yl)acetic acid;

2-(2-(N-(3-(6-amino-2-pyridyl)prop-1-yl)carbamoyl)-1H,3H,4H,5H-benzo[e]azapin-5-acetic acid;

2-(2-(N-(3-(6-(tert-butoxycarbonylamino)-2-pyridyl)propyl)carbamoyl)-1H,3H,4H,5H-benzo[e]azapin-5-yl)acetic acid;

2-(2-(N-(3-(1,2,3,4-tetrahydropyridino(2,3-b)pyridin-7-yl)prop-1-yl)carbamoyl)-1H,3H,4H,5H,benzo[e]azapin-5-yl)acetic acid;

2-(2-(((4-(2-pyridylamino)but-1-yl)amino)sulfonyl)-1H,3H,5H-benzo[e]azapin-5-yl)acetic acid;

2-(2-(((3-(2-pyridylamino)prop-1-yl)amino)sulfonyl)-1H,3H,4H,5H-benzo[e]azapin-5-yl)acetic acid;

2-(2-(2-((2-(2-pyridylamino)ethyl)amino)acetyl)-1H,3H,4H,5H-benzo[e]azapin-5-yl)acetic acid;

2-(2-(2-((3-(2-pyridylamino)prop-1-yl)amino)acetyl-1H,3H,4H,5H-benzo[e]azapin-5-yl)acetic acid;

2-(2-(2-((4-(2-pyridylamino)but-1-yl)amino)acetyl-1H,3H,4H,5H-benzo[e]azapin-5-yl)acetic acid;

2-(2-((N-(3-(2-pyridylamino)prop-1-yl)carbamoyl)methyl)-1H,3H,4H,5H-benzo[e]azapin-5-yl)acetic acid;

2-(2-(4-(2-pyridylamino)but-1-oxy carbonyl)-1H,3H,4H,5H-benzo[e]azapin-5-yl)acetic acid;

2-(8-methoxy-2-(N-(4-(2-pyridylamino)but-1-yl)carbamoyl)-1H,3H,4H,5H-benzo[e]azaperhydroepin-5-yl)acetic acid;

2-(8-fluoro-2-(N-(3-(1,2,3,4-tetrahydropyridino[2,3,b]pyridin-7-yl)propyl)carbamoyl)-1H,3H,4H,5H-benzo[e]azaperhydroepin-5-yl)acetic acid;.

2-(2-( [N-(4-(2-pyridylamino)prop-1-yl)carbamoyl]methyl)-3-oxo-1H,4H,5H-benzo(e)azepin-5-yl)acetic acid;

2-(2-(N-(3-(1,2,3,4-tetrahydropyridino(2,3-b)pyridin-7-yl)propyl)carbamoyl)-1H,3H,4H,5H,benzo[e]azapin-5-yl)propanoic acid;

2-{2-[N-(methylethyl)-N-(2-(1,2,3,4-tetrahydropyridino[2,3-b]pyridin-7-yl)ethyl)carbamoyl}-1H,3H,4H,5H-benzo[e]azepin-5-yl]acetic acid;

2-(2-aza-2-cyano-1 ((1,2,3,4-tetrahydropyridino[2,3-b]pyridin-7-yl)propyl)amino)vinyl)-1H,3H,4H,5H-benzo[e]azapin-5-yl)acetic acid;

2-(2-(((2-(1,2,3,4-tetrahydropyridino(2,3-b)pyridin-7-yl)ethyl)amino)sulfonyl)-1H,3H,4H,5H,benzo[e]azapin-5-yl)acetic acid;

3-(2-(N-(2-(1,2,3,4-tetrahydropyridino(2,3-b)pyridin-7-yl)ethyl)amino)sulfonyl)-1H,3H,4H,5H-benzo[e]azapin-5-yl)propanoic acid;

2-(2-(N-(3-(2-pyridylamino)propyl)carbamoyl)-1H,3H,4H,5H-benzo[e]azapin-5-yl)acetic acid;

2-((5R)-2-(N-(3-(1,2,3,4-tetrahydropyridino(2,3-b)pyridin-7-yl)prop-1-yl)carbamoyl)-1H,3H,4H,5H-benzo[e]azapin-5-yl)acetic acid;

2-((5R)-2-(N-(3-(1,2,3,4-tetrahydropyridino(2,3-b)pyridin-7-yl)ethyl)carbamoyl)-1H,3H,4H,5H-benzo[e]azapin-5-yl)acetic acid;

2-((5S)-2-(N-(3-(1,2,3,4-tetrahydropyridino(2,3-b)pyridin-7-yl)ethyl)carbamoyl)-1H,3H,4H,5H-benzo[e]azapin-5-yl)acetic acid;

2-((5S)-2-(4-(1,2,3,4-tetrahydropyridino(2,3-b)pyridin-7-yl)butanoyl)carbamoyl)-1H,3H,4H,5H-benzo[e]azapin-5-yl)acetic acid;

2-[2-(4-(1,2,3,4-tetrahydropyridino[2,3-b]pyridin-7-yl)butanoyl)-1H,3H,4H,5H-benzo[e]azapin-5-yl]acetic acid;

2-{2-[N-(2-(1,2,3,4-tetrahydropyridino[2,3-b]pyridin-7-yl)ethyl)carbamoyl]-4H,5H,10H-benzo[d]imidazolo[1,2-a]azepin-5-yl}acetic acid;

2-{2-[N-(methylethyl)-N-(2-(1,2,3,4-tetrahydropyridino[2,3-b]pyridin-7-yl)ethyl)carbamoyl]-4H,5H,10H-benzo[d]imidazolo[1,2-a]azepin-5-yl}acetic acid;

2-{2-[N-(methylethyl)-N-(1,2,3,4tetrahydropyridino[2,3-b]pyridine-6-ylmethyl)carbamoyl]-4H,5H,10H-benzo[d]imidazolo[1,2-a]azepin-5-yl}acetic acid;

2-{2-[N-(1,2,3,4-tetrahydropyridino[2,3-b]pyridin-6-ylmethyl)carbamoyl]-4H,5H,10H-benzo[d]imidazolo[1,2-a]azepin-5-yl}acetic acid;

2-(2-{N-methyl-N-[3-(2-pyridylamino)propyl]carbamoyl}-4H,5H,10H-benzo[d]imidazolo[1,2-a]azepin-5-yl)acetic acid;

2-(8-methoxy-2-(N-(3-(1,2,3,4-tetrahydropyridino[2,3,b]pyridin-7-yl)propyl)carbamoyl)-1H,3H,4H,5H-benzo[e]azaperhydroepin-5-yl)acetic acid;

2-(8-benzyloxy-2-(N-(3-(1,2,3,4-tetrahydropyridino[2,3,b]pyridin-7-yl)propyl)carbamoyl)-1H,3H,4H,5H-benzo[e]azaperhydroepin-5-yl)acetic acid;

2-(8-phenyl-2-(N-(3-(1,2,3,4-tetrahydropyridino[2,3,b]pyridin-7-yl)propyl)carbamoyl)-1H,3H,4H,5H-benzo[e]azaperhydroepin-5-yl)acetic acid;

2-(2-(N-(4-(4,5-dihydroimidazo-2-yl)aminobut-1-yl)carbamoyl)-1H,3H,4H-5H-benzo[e]azapin-5-yl)acetic acid;

2-{8-Chloro-2-[N-(3-(1,2,3,4-tetrahydropyridino[2,3-b]pyridin-7-yl)propyl)carbamoyl]-1H,3H,4H,5H-benzo[e]azepin-5-yl}acetic acid;

2-{8-Bromo-2-[N-(3-(1,2,3,4-tetrahydropyridino[2,3-b]pyridin-7-yl)propyl)carbamoyl]-1H,3H,4H,5H-benzo[e]azepin-5-yl}acetic acid;

2-{7,8-Dibromo-2-[N-(3-(1,2,3,4-tetrahydropyridino[2,3-b]pyridin-7-yl)propyl)carbamoyl]-1H,3H,4H,5H-benzo[e]azepin-5-yl}acetic acid;

2-{8-[(Methylsulfonyl)amino]-2-[N-(3-(1,2,3,4-tetrahydropyridino[2,3-b]pyridin-7-yl)propyl)carbamoyl]-1H,3H,4H,5H-benzo[e]azepin-5-yl}acetic acid;

2-{8-[(Phenylsulfonyl)amino]-2-[N-(3-(1,2,3,4-tetrahydropyridino[2,3-b]pyridin-7-yl)propyl)carbamoyl]-1H,3H,4H,5H-benzo[e]azepin-5-yl}acetic acid;

2-{8-Carbonylamino-2-[N-(3-(1,2,3,4-tetrahydropyridino[2,3-b]pyridin-7-yl)propyl)carbamoyl]-1H,3H,4H,5H-benzo[e]azepin-5-yl}acetic acid;

2-{8-(Dimethylamino)-2-[N-(3-(1,2,3,4-tetrahydro pyridino[2,3-b]pyridin-7-yl)propyl)carbamoyl]-1H,3H,4H,5H-benzo[e]azepin-5-yl}acetic acid;

2-(2-(N-(3-(6-(methylamino)-2-pyridyl)propyl)carbamoyl)-1H,3H,4H,5H-benzo[e]azepin-5-yl)acetic acid;

2-(2-(N-(2-(1,2,3,4-tetrahydropyridino(2,3-b)pyridin-7-yl)ethyl)carbamoyl)-1H,3H,4H,5H-benzo[e]azapin-5-yl)acetic acid;

2-(3-(N-(2-(1,2,3,4-tetrahydropyridino(2,3-b)pyridin-7-yl)propyl)amino)sulfonyl)-1H,3H,4H,5H-benzo[e]azapin-5-yl)acetic acid;

3-(2-(N-(2-(1,2,3,4-tetrahydropyridino(2,3-b)pyridin-7-yl)ethyl)carbamoyl)-1H,3H,4H,5H-benzo[e]azapin-5-yl)propanoic acid;

3-(2-(N-(3-(1,2,3,4-tetrahydropyridino(2,3-b)pyridin-7-yl)propyl)carbamoyl-1H,3H,4H,5H-benzo[e]azapin-5-yl)propanoic acid;

3-(2-(N-(3-(1,2,3,4-tetrahydropyridino(2,3-b)pyridin-7-yl)propyl)amino)sulfonyl)-1H,3H,4H,5H-benzo[e]azapin-5-yl)propanoic acid;

2-(2-{N-[3-(5-methyl-1,2,3,4-tetrahydropyridino[2,3-b]pyridin-7-yl)propyl]carbamoyl}-1H,3H,4H,5H-benzo[e]azepin-5-yl)acetic acid;

2-(8-fluoro-2-(N-(2-(1,2,3,4-tetrahydropyridino(2,3-b)pyridin-7-yl)ethyl)carbamoyl)-1H,3H,4H,5H-benzo[e]azapin-5-yl)acetic acid;

2-[2-(N-{4-[(4-methyl-2-pyridyl)amino]butyl}carbamoyl)-1H,3H,4H,5H-benzo[e]azepin-5-yl]acetic acid; or 2-{2-[N-(4-{[benzylamino]carbonylamino}butyl)carbamoyl]-1H,3H,4H,5H-benzo[e]azepin-5-yl}acetic acid;

or a pharmaceutically acceptable salt thereof.

7. A pharmaceutical composition comprising a compound according to any one of claims 1–6 and a pharmaceutically acceptable carrier.

8. A method of treatment of atherosclerosis, restenosis, inflammation, wound healing, bone resorption related diseases, diabetic retinopathy and macular degeneration comprising administering an effective amount of a compound according to any one of claims 1, 2, 3, 4, 5, or 6.

\* \* \* \* \*

UNITED STATES PATENT AND TRADEMARK OFFICE
CERTIFICATE OF CORRECTION

PATENT NO. : 6,514,964 B1
DATED : February 4, 2003
INVENTOR(S) : Chen et al.

It is certified that error appears in the above-identified patent and that said Letters Patent is hereby corrected as shown below:

Column 5,
Line 58, after "-C(Y)" remove "13".
Line 62, change "-NH-C-(NR$_1$)-NH-R," to -- -NH-C-(NR$_1$)-NH-R$_1$ --.

Column 6,
Row 11, Fig. 2: change to:

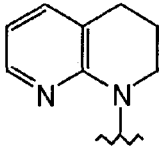

Column 11,
Line 38, change "heteroaryl-C$_3$-C$_4$ alkyl," to -- heteroaryl-C$_1$-C$_4$ alkyl, --.

Column 12,
Line 27, change "-C(O)-NH-C(O)-R$_6$" to -- -C(O)-NH-C(O)-R$_8$ --.

Column 13,
Line 20, change "α$_v$β" to -- α$_v$β$_6$ --.
Line 28, change "pharmacutical" to -- pharmaceutical --.
Line 66, remove "In" between "lesions," and "Behcet's".

Column 19,
Row 1, change "2-yl]" to -- 2-yl --.

Column 19, lines 65-67 through Column 20, lines 1-17,
Change to:

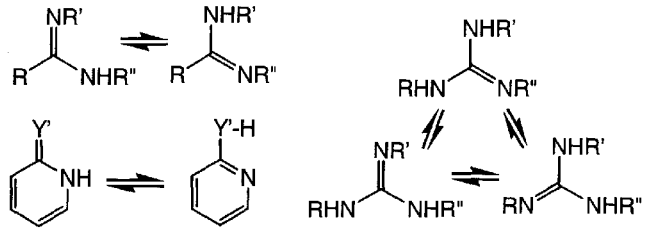

Column 26,
Line 27, change "nmercapto" to -- mercapto --.
Line 32, change "ainclude," to -- include, --.

UNITED STATES PATENT AND TRADEMARK OFFICE
CERTIFICATE OF CORRECTION

PATENT NO. : 6,514,964 B1
DATED : February 4, 2003
INVENTOR(S) : Chen et al.

It is certified that error appears in the above-identified patent and that said Letters Patent is hereby corrected as shown below:

Column 37,
Line 17, change "leu" to -- lieu --.

Column 40,
Line 14, change "bromoohenyl" to -- bromophenyl --.
Line 25, change "bromohenyl" to -- bromophenyl --.
Line 26, change "hydroxyoroyl" to -- hydroxypropyl --.
Line 35, change "bromohenyl" to -- bromophenyl --.
Line 47, change "Asulfate," to -- sulfate, --.
Line 50, change "azaverhydroepin" to -- azaperhydroepin --.
Line 54, change "tetrakis(triphenylphosphine)p alladium" to
-- tetrakis(triphenylphosphine) palladium --.

Column 41,
Lines 25 and 55, change "azain" to -- azapin --.

Column 43,
Line 64, change "d4-D3OD);" to -- d4-D$_3$OD); --.

Column 46,
Line 23, change "-5-y)" to -- -5-yl) --.

Column 48,
Line 59, change "azalin" to -- azapin --.

Column 51,
Line 40, change "H2O (3xg LAH)" to -- H$_2$O (1X g LAH) --.
Line 41, change "a nd" to -- and --.

Column 52,
Line 5, change "methoxyhenyl" to -- methoxphenyl --.
Line 5, change "(3-hydroxwropyl)" to -- (3-hydroxypropyl) --.
Line 58, change "azaTerhydroepin" to -- azaperhydroepin --.

Column 53,
Line 17, change "benzo[e]azaerhydroepin-5-yl)acetic acid" to
-- benzo[e]azaperhydroepin-5-yl)acetic acid --.

UNITED STATES PATENT AND TRADEMARK OFFICE
CERTIFICATE OF CORRECTION

PATENT NO.   : 6,514,964 B1
DATED        : February 4, 2003
INVENTOR(S)  : Chen et al.

It is certified that error appears in the above-identified patent and that said Letters Patent is hereby corrected as shown below:

Column 54,
Line 2, change "5H-benzo[e]azaperhydroeoin-5-yl)acetate" to
-- 5H-benzo[e]azaperhydroepin-5-yl)acetate --.
Line 11, change "hydroxyproNyl" to -- hydroxypropyl --.
Line 36, change "azaperhydroeoin" to -- azaperhydroepin --.
Line 58, change "azaoerhydroeoin" to -- azaperhydroepin --.

Column 55,
Line 48, change "proyl" to -- propyl --.

Column 56,
Line 59, change "azaoerhydroelin" to -- azaperhydroepin --.

Column 58,
Line 6, change "azaerhydroeoin" to -- azaperhydroepin --.

Column 61,
Line 34, change "tetrahydrolyridino[2,3-b]yridin-7-yl)proyyl" to
-- tetrahydropyridino[2,3-b]pyridin-7-yl)propyl --.

Column 62,
Line 45, change "azoerhyroeoin" to -- azaperhydroepin --.
Line 56, change "chramotography" to -- chromotography --.

Column 63,
Line 6, change "azaoerhyroein" to -- azaperhydroepin --.
Line 22, change "tetrahydroyridino" to -- tetrahydropyridino --.

Column 65,
Line 33, delete the second reference to "in".

Column 66,
Lines 1-14, change to:

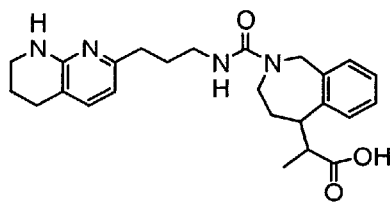

Column 66 cont'd,
Lines 31-43, change to:

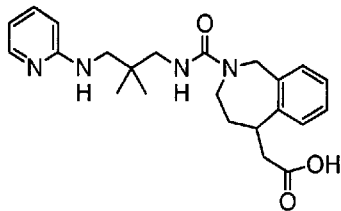

Column 67,
Line 55, change "carbamovyl" to -- carbamoyl --.

Column 68,
Lines 38-39, remove the second reference to "concentrated".
Line 51, change "yridin" to -- pyridin --.
Line 52, change "proyl" to -- propyl --.
Line 60, change "ylproyl)" to -- ylpropyl) --.

Column 69,
Line 17, change "tetrahydroyridino" to -- tetrahydropyridino --.

Column 70,
Line 7, change "tetrahydroyridino" to -- tetrahydropyridino --.
Line 8, change "azain" to -- azapin --.
Line 13, remove the second reference to "and".
Line 54, remove the second reference to "and".
Line 58, change "aminolhenyl" to -- aminophenyl --.

Column 71,
Line 6, change "dy" to -- by --.
Line 8, change "p henyl" to -- phenyl --.

Column 72,
Lines 15 and 36, change "proyl" to -- propyl --.
Line 36, change "carbonylaminol" to -- carbonylamino --.
Line 37, change "azetin" to -- azepin --.
Line 60, change "rN" to -- [N --.

UNITED STATES PATENT AND TRADEMARK OFFICE
CERTIFICATE OF CORRECTION

PATENT NO.    : 6,514,964 B1
DATED         : February 4, 2003
INVENTOR(S)   : Chen et al.

It is certified that error appears in the above-identified patent and that said Letters Patent is hereby corrected as shown below:

Column 73,
Line 8, change "benzore]" to -- benzo[e] --.
Line 13, remove the second reference to "concentrated".
Line 17, change "2.61≧ 2.34" to -- 2.61 - 2.34 --.
Line 36, change "azain" to -- azapin --.
Line 47, change "δ7.11 - 687" to -- δ 7.11 - 6.87 --.

Column 74,
Line 12, change to  -- "benzore] --
Line 33, change "propanotate" to -- propanoate --.
Line 60, change "oropanoic acid" to -- propanoic acid --.

Column 76,
Line 53, change "azeoin" to -- azepin --.
Line 54, change "tetrahydrolyridino" to -- tetrahydropyridino --.

Column 77,
Line 15, change "azaperhydroein" to -- azaperhydroepin --.
Line 47, change "azaperhydroeoin" to -- azaperhydroepin --.
Line 61, change "Hyvdrochloride" to -- Hydrochloride --.

Column 80,
Line 3, remove the second reference to "concentrated".
Line 63, remove the second reference to "concentrated".

Column 81,
Line 29, remove the second reference to "concentrated".
Line 67, remove the second reference to "concentrated".

Column 83,
Line 3, change "ethyl[ ]3-" to -- ethyl][3- --.
Line 21, change "ofor" to -- for --.
Line 41, remove "[benzo".

UNITED STATES PATENT AND TRADEMARK OFFICE
CERTIFICATE OF CORRECTION

PATENT NO. : 6,514,964 B1
DATED : February 4, 2003
INVENTOR(S) : Chen et al.

It is certified that error appears in the above-identified patent and that said Letters Patent is hereby corrected as shown below:

Column 86,
Line 4, change "ander" to -- and --.

Column 87,
Line 32, change "eas" to -- was --.

Column 88,
Line 48, remove the second reference to "concentrated".

Column 90,
Line 27, remove the second reference to "concentrated".

Column 99,
Line 15, change "(10% MeOH/CH$_2$Cl,)." to -- (10% MeOH/CH$_2$Cl$_2$) --.

Column 102,
Line 63, change "ballon" to -- balloon --.

Column 110,
Line 15, change "y)acetic acid" to -- yl)acetic acid --.

Column 112,
Row 28 (W$^4$ column), change "C-" to -- C-H --.

Column 114,
Row 62 (W$^4$ column), insert -- N --.

Column 117,
Row 42, (W$^3$ column): Change "CLH" to -- C-H --.

Column 123,
Line 38, change "[4,5-e]N" to -- [4,5-e] --.

UNITED STATES PATENT AND TRADEMARK OFFICE
CERTIFICATE OF CORRECTION

PATENT NO. : 6,514,964 B1
DATED :February 4, 2003
INVENTOR(S) : Chen et al.

It is certified that error appears in the above-identified patent and that said Letters Patent is hereby corrected as shown below:

Column 143,
Line 32, change "but-2-n-l-yl" to -- but-2-yn-1-yl --.

Signed and Sealed this

Twenty-ninth Day of July, 2003

JAMES E. ROGAN
*Director of the United States Patent and Trademark Office*